US007144581B2

(12) United States Patent
Gaiger et al.

(10) Patent No.: US 7,144,581 B2
(45) Date of Patent: Dec. 5, 2006

(54) COMPOSITIONS AND METHODS FOR WT1 SPECIFIC IMMUNOTHERAPY

(75) Inventors: Alexander Gaiger, Vienna (AT); Martin A. Cheever, Mercer Island, WA (US)

(73) Assignee: Corixa Corporation, Research Triangle Park, NC (US)

( * ) Notice: Subject to any disclaimer, the term of this patent is extended or adjusted under 35 U.S.C. 154(b) by 577 days.

(21) Appl. No.: 09/785,019

(22) Filed: Feb. 15, 2001

(65) Prior Publication Data
US 2003/0082196 A1 May 1, 2003

(51) Int. Cl.
A61K 38/16 (2006.01)
A61K 39/00 (2006.01)
C07K 14/435 (2006.01)

(52) U.S. Cl. .............................. 424/277.1; 424/184.1; 424/185.1; 424/192.1; 424/193.1; 514/2; 514/12; 514/885; 530/358; 530/350; 530/806

(58) Field of Classification Search ................ 530/324, 530/325, 326, 327, 328, 329, 330, 358, 806, 530/403, 350; 424/184.1, 185.1, 277.1, 192.1, 424/193.1; 514/2, 12–18, 885
See application file for complete search history.

(56) References Cited

U.S. PATENT DOCUMENTS

| | | | |
|---|---|---|---|
| 5,350,840 A | 9/1994 | Call et al. | 536/23.1 |
| 5,633,142 A | 5/1997 | Herlyn et al. | 435/7.23 |
| 5,670,317 A | 9/1997 | Ladanyi et al. | 435/6 |
| 5,693,522 A | 12/1997 | Chada et al. | 435/2.402 |
| 5,726,288 A | 3/1998 | Call et al. | 530/350 |
| 6,034,235 A | 3/2000 | Sugiyama et al. | 536/24.5 |
| 6,096,313 A | 8/2000 | Jäger et al. | 424/184.1 |
| 6,277,832 B1 | 8/2001 | Sugiyama et al. | 514/44 |
| 6,316,599 B1 | 11/2001 | Call et al. | 530/387.7 |
| 6,818,751 B1 * | 11/2004 | Xu et al. | 536/23.1 |

FOREIGN PATENT DOCUMENTS

| | | |
|---|---|---|
| EP | 1004319 A1 | 5/2000 |
| EP | 1103564 A1 | 5/2001 |
| JP | 11-89596 A | 4/1999 |
| JP | 11-89599 A | 4/1999 |
| WO | WO 91/07509 | 5/1991 |
| WO | WO 94/21287 | 9/1994 |
| WO | WO95/06725 | 3/1995 |
| WO | WO 95/29995 | 11/1995 |
| WO | WO95/29995 | 11/1995 |
| WO | WO 96/38176 | 12/1996 |
| WO | WO 99/03506 | 1/1999 |
| WO | WO99/58135 | 11/1999 |
| WO | WO 00/06602 | 2/2000 |
| WO | WO 00/18795 | 4/2000 |
| WO | WO 01/60970 | 8/2001 |
| WO | WO 01/94629 | 12/2001 |
| WO | WO 02/00677 | 1/2002 |

OTHER PUBLICATIONS

Boon, T., "Tumor Antigens Recognized By Cytolytic T Lymphocytes: Present Perspectives for Specific Immunotherapy," *Int. J. Cancer* 54: 177-180, 1993.
Oka, Y. et al., "Wilms Tumor Gene Peptide-Based Immunotherapy for Patients with Overt Leukemia from Myelodysplastic Syndrome (MDS) or MDS with Myelofibrosis," *International Journal of Hematology* 78: 56-61, 2003.
Aaronson and Todaro, "Development of 3t3-like lines from Balb/c mouse embryo cultures: transformation susceptibility to SV40," *J. Cell. Physiol.* 72(2):141-148, Oct. 1968.
Adachi et al., "Midkine as novel target gene for the Wilms' tumor suppressor gene (WT1)," *Oncogene* 13: 2197-2203, 1996.
Algar et al., "A WT1 antisense oligonucleotide inhibits proliferation and induces apoptosis in myeloid leukaemia cell lines," *Oncogene* 12: 1005-1014, 1996.
Armstrong et al., "The expression of the Wilms' tumour gene, WT1, in the developing mammalian embryo," *Mechanisms of Development* 40: 85-97, 1992.
Bellantuono et al., "Selective elimination of leukemic progenitors by allorestricted CTL specific for WILMS Tumor Antigen-1 (WT-1)," *Blood*, 94(10):532A-533A, Nov. 15, 1999.
Bergmann et al., "High Levels of Wilms' Tumor Gene (wt1) mRNA in Acute Myeloid Leukemias Are Associated With a Worse Long-Term Outcome," *Blood* 90(3): 1217-1225, 1997.
Bergmann et al., "Wilms Tumor Gene Expression in Acute Myeloid Leukemias," *Leukemia and Lymphoma* 25: 435-443, 1997.
Brenner et al., "RNA polymerase chain reaction detects different levels of four alternatively spliced *WT1* transcripts in Wilms' tumors," *Oncogene* 7: 1431-1433, 1992.
Brieger et al., "The Expression of the Wilms' Tumor Gene in Acute Myelocytic Leukemias as Possible Marker for Leukemic Blast Cells," *Leukemia* 8(12): 2138-2143, 1994.
Brieger et al., "The Wilms' tumor gene is frequently expressed in acute myeloblastic leukemias and may provide a marker for residual blast cells detectable by PCR," *Annals of Oncology* 6: 811-816, 1995.
Buckler et al., "Isolation, Characterization, and Expression of the Murine Wilms' Tumor Gene (WT1) During Kidney Development," *Molecular and Cellular Biology* 11: 1707-1712, 1991.
Call et al., "Isolation and Characterization of a Zinc Finger Polypeptide Gene at the Human Chromosome 11 Wilms' Tumor Locus," *Cell* 60: 509-520, 1990.
Carapeti et al., "Dominant-negative mutations of the Wilms' tumour predisposing gene (WT1) are infrequent in CML blast crisis and de novo acute leukaemia," *Eur. J. Haematol.* 58: 346-349, 1997.

(Continued)

Primary Examiner—Ronald B. Schwadron
(74) Attorney, Agent, or Firm—Seed IP Law Group PLLC

(57) ABSTRACT

Compositions and methods for the therapy of malignant diseases, such as leukemia and cancer, are disclosed. The compositions comprise one or more of a WT1 polynucleotide, a WT1 polypeptide, an antigen-presenting cell presenting a WT1 polypeptide, an antibody that specifically binds to a WT1 polypeptide; or a T cell that specifically reacts with a WT1 polypeptide. Such compositions may be used, for example, for the prevention and treatment of metastatic diseases.

5 Claims, 43 Drawing Sheets

OTHER PUBLICATIONS

Charles et al., "Expression of the Wilms' tumour gene WT1 in the developing human and in paediatric renal tumours: an immunohistochemical study," *J. Clin. Pathol.: Mol. Pathol.* 50: 138-144, 1997.

Charles et al., "Immunohistochemical detection of the Wilms' tumour gene WT1 in desmoplastic small round cell tumour," *Histopathology* 30: 312-314, 1997.

Chen et al., "T-cells for tumor therapy can be obtained from antigen-loaded sponge implants," *Cancer Research* 54(4):1065-1070, Feb. 15, 1994.

Chesebro et al., "Characterization of Ia8 antigen, THY-1.2 antigen, complemnt receptors, and virus production in a group of murine virus-induced leukemia cell lines," *The Journal of Immunology* 117(4):1267-1274, Oct. 1976.

De Bruijn et al., "Peptide loading of empty major histocompatibility complex molecules on RMA-S cells allows the induction of primary cytotoxic T lymphocyte responses," *Eur J Immunol* 21(12):2963-2970, Dec. 1991.

Deavin et al., "Statistical comparison of established T-cell eptiope predictors against a large database of human and murine antigens," *Molecular Immunology*, 33(2):145-155, 1996.

Drummond et al., "Repression of the Insulin-Like Growth Factor Gene by the Wilms Tumor Suppressor WT1," *Science* 257: 674-677, 1992.

Feller and de la Cruz, "Tsites (Version 1.1) A computer program to determine T cell epitopes using four predictive algorithms," *Nature* 349: 720-721, 1991.

Foster et al., "Characterization of prostatic epithelial cell lines derived from transgenic adenocarcinoma of the mouse prostate (TRAMP) model," *Cancer Research* 57(16):3325-3330, Aug. 15, 1997.

Frazier et al., "Expression of the Tumor Suppressor Gene WT1 in Both Human and Mouse Bone Marrow," *Blood* 86: 4704-4706, 1995 (letter).

Gaiger et al., "WT1: A new leukemia and cancer antigen A," *Proceedings of the Annual Meeting of the American Association for Cancer Research*, 40:424, 1999.

Gaiger et al., "Immunity to WT1 in animal models and leukemia pateints," *Blood*, 94(10):78, Nov. 15, 1999.

Gaiger et al., "Immunity to WT1 in the animal model and in patients with acute myeloid leukemia," *Blood* 96(4):1480-1489, Aug. 15, 2000.

Gillis and Smith, "Long term culture of tumour-specific cytotoxic T cells," *Nature* 268:154-156, Jul. 14, 1977.

Glynn et al., "Cross-resistance to the transplantation of syngeneic friend, moloney, and rauscher virus-induced tumors," *Cancer Research* 28(3):434-439, Mar. 1968.

Goodyer et al., "Repression of the retinoic acid receptor-α gene by the Wilms' tumor suppressor gene product, wt1," *Oncogene* 10: 1125-1129, 1995.

Haber et al., "A dominant mutation in the Wilms tumor gene *WT1* cooperates with the viral oncogene *E1A* in transformation of primary kidney cells," *Proc. Natl. Acad. Sci USA* 89: 6010-6014, 1992.

Haber et al., "Alternative splicing and genomic structure of the Wilms tumor gene *WT1*," *Proc. Natl. Acad. Sci USA* 88:9618-9622, 1991.

Haber et al., "An Internal Deletion within an 11p13 Zinc Finger Gene Contributes to the Development of Wilms' Tumor," *Cell* 61: 1257-1269, 1990.

Hamilton et al., "High affinity binding sites for the Wilms' tumour suppressor protein WT1," *Nucleic Acids Research* 23(2): 277-284, 1995.

Harrington et al., "Inhibition of Colony-stimulating Factor-1 Promoter Activity by the Product of the Wilms' Tumor Locus," *The Journal Of Biological Chemistry* 268(28): 21271-21275, 1993.

Harrington et al., "Inhibition of Colony-stimulating Factor-1 Promoter Activity by the Product of the Wilms' Tumor Locus," *The Journal Of Biological Chemistry* 268(28): 21271-21275, 1993.

Horibata and Harris, "Mouse myelomas and lyphomas in culture," *Experimental Cell Research* 60:61-77, 1970.

Huang et al., "Tissue, Developmental, and Tumor-Specific Expression of Divergent Transcripts in Wilms Tumor," *Science* 250: 991-994, 1990.

Inoue et al., "Aberrant Overexpression of the Wilms Tumor Gene (WT1) in Human Leukemia," *Blood* 89(4): 1405-1412, 1997.

Inoue et al., "Long-Term Follow-Up of Minimal Residual Disease in Leukemia Patients by Monitoring WT1 (Wilms Tumor Gene) Expression Levels," *Blood* 88: 2267-2278, 1996.

Inoue et al., "Wilms' Tumor Gene (WT1) Competes With Differentiation-Inducing Signal in Hematopoetic Progenitor Cells," *Blood* 91(8): 2969-2976, 1998.

Inoue et al., "*WT1* as a New Prognostic Factor and a New Marker for the Detection of Minimal Residual Disease in Acute Leukemia," *Blood* 84: 3071-3079, 1994.

King-Underwood and Pritchard-Jones, "Wilms' Tumor (*WT1*) Gene Mutations Occur Mainly in Acute Myeloid Leukemia and May Confer Drug Resistance," *Blood* 91(8): 2961-2968, 1998.

King-Underwood et al., "Mutations in the Wilms' Tumor Gene WT1 in Leukemias," *Blood* 91: 2961-2968, 1998.

Kreidberg et al., "WT-1 Is Required for Early Kidney Development," *Cell* 74: 679-691, 1993.

Kudoh et al., "Constitutive expression of the Wilms tumor suppressor gene WT1 in F9 embryonal carcinoma cells induces apoptotic cell death in response to retinoic acid," *Oncogene* 13: 1431-1439, 1996.

Kudoh et al., "$G_1$ phase arrest induced by Wilms tumor protein WT1 is abrogated by cyclin/CDK complexes," *Proc. Natl. Acad. Sci. USA* 92: 4517-4521, 1995.

Kwok and Higuchi, "Avoiding false positives with PCR," *Nature* 339:237-238, May 18, 1989.

Larsson et al., "Subnuclear Localization of WT1 in Splicing or Transcription Factor Domains Is Regulated by Alternative Splicing," *Cell* 81: 391-401, 1995.

Ljunggren et al., "Empty MHC class I molecules come out in the cold," *Nature* 346:476-480, Aug. 2, 1990.

Lozzio and Lozzio, "Human chronic myelogenous leukemia cell-line with positive Philadelphia chromosome," *Blood* 45(3):321-334, Mar. 1975.

Luo et al., "The tumor suppressor gene WT1 inhibits ras-mediated transformation," *Oncogene* 11: 743-750, 1995.

Madden et al., "Transcriptional Repression Mediated by the WT1 Wilms Tumor Gene Product," *Science* 253: 1550-1552, 1991.

Maurer et al., "The Wilms' tumor gene is expressed in a subset of CD34 progenitors and downregulated early in the course of differentiation in vitro," *Experimental Hematology* 25: 945-950, 1997.

Menke et al., "Wilms' Tumor 1 splice variants have opposite effects on the tumorigenicity of adenovirus-transformed baby-rat kidney cells," *Oncogene* 12: 537-546, 1996.

Menssen et al., "Detection By Monoclonal Antibodies Of The Wilms' Tumor (WT1) Nuclear Protein In Patients With Acute Leukemia," *Int. J. Cancer* 70: 518-523, 1997.

Menssen et al., "Presence of Wilms' tumor gene (*wt1*) transcripts and the WT1 nuclear protein in the majority of human acute leukemias," *Leukemia* 9: 1060-1067, 1995.

Menssen et al., "Wims' Tumor Gene Expression in Human CD34 Hematopoietic Progenitors During Fetal Development and Early Clonogenic Growth," *Blood* 89(9): 3486-3487, 1997 (letter).

Miwa et al., "Expression of the Wilms' Tumor Gene (WT1) in Human Leukemias," *Leukemia* 6(5): 405-409, 1992.

Miyagi et al., "Expression of the Candidate Wilms' Tumor Gene, *WT1*, in Human Leukemia Cells," *Leukemia* 7(7): 970-977, 1993.

Morris et al., "Characterization of the zinc finger protein encoded by the WT1 Wilms' tumor locus," *Oncogene* 6: 2339-2348, 1991.

Mundlos et al., "Nuclear localization of the protein encoded by the Wilms' tumor gene *WT1* in embryonic and adult tissues," *Development* 119: 1329-1341, 1993.

Murata et al., "The Wilms tumor suppressor gene WT1 induces G1 arrest and apoptosis in myeloblastic leukemia M1 cells," *FEBS Letters* 409: 41-45, 1997.

Nakagama et al., "Sequence and Structural Requirements for High-Affinity DNA Binding by the WT1 Gene Product," *Molecular and Cellular Biology* 15(3): 1489-1498, 1995.

Nichols et al., "WT1 Induces Expression of Insulin-like Growth Factor 2 in Wilms' Tumor Cells," *Cancer Research 55*: 4540-4543, 1995.

Ogawa et al., "Successful donor leukocyte transfusion at molecular relapse for a patient with acute myeloid leukemia who was treated with allogeneic bone marrow transplantation: importance of the monitoring of minimal residual disease by WT1 assay," *Bone Marrow Transplantation 21*: 525-527, 1998.

Old et al., "Antigenic properites of chemically induced tumors," *Annals of the New York Academy of Sciences 101*:80-107, Nov. 20, 1962.

Osaka et al., "WT1 Contributes To Leukemogenesis: Expression Patterns In 7,12-Dimethylbenz[a]Anthracene (DMBA)-Induced Leukemia," *International Journal of Cancer 72*: 696-699, 1997.

Parker et al., "Scheme for Ranking Potential HLA-A2 Binding Peptides Based on Independent Binding of Individual Peptide Side-Chains," *Journal of Immunology 152*: 163-175, 1994.

Patek et al., "Transformed cell lines susceptible or resistant to in vivo surveillance against tumorigenesis," *Nature 276*;510-511, Nov. 30, 1978.

Patmasiriwat et al., "Expression pattern of WT1 and GATA-1 in AML with chromosome 16q22 abnormalities," *Leukemia 10*: 1127-1133, 1996.

Pelletier et al., "Expression of the Wilms' tumor gene WT1 in the murine urogenital system," *Genes & Development 5*: 1345-1356, 1991.

Pelletier et al., "Germline Mutations in the Wilms' Tumor Suppressor Gene Are Associated with Abnormal Urogenital Development in Denys-Drash Syndrome," *Cell 67*: 437-447, 1991.

Phelan et al., "Wilms' Tumor Gene, *WT1*, mRNA Is Down-regulated during Induction of Erythroid and Megakaryocytic Differentiation of K562 Cells," *Cell Growth & Differentiation 5*: 677-686, 1994.

Pogue et al., "Amino-terminal alteration of the HLA-A 0201-restricted human immunodeficiency virus pol peptide increases complex stability and *in vitro* immunogenicity," *Proc. Natl. Acad. Sci. USA 92*: 8166-8170, 1995.

Pritchard-Jones et al., "The candidate Wilms' tumour gene is involved in genitourinary development," *Nature 346*: 194-197, 1990.

Pritchard-Jones et al., "The Wilms tumour (WT1) gene is mutated in a secondary leukaemia in a WAGR patient," *Human Molecular Genetics 3*(9): 1633-1637, 1994.

Rackley et al., "Expression of the Wilms' Tumor Suppressor Gene *WT1* during Mouse Embryogenesis," *Cell Growth & Differentiation 4*: 1023-1031, 1993.

Ramani and Cowell, "The Expression Pattern Of Wilms' Tumour Gene (*WT1*) Product In Normal Tissues And Paediatric Renal Tumours," *Journal Of Pathology 179*: 162-168, 1996.

Rauscher et al., "Binding of the Wilms' Tumor Locus Zinc Finger Protein to the EGR-1 Consensus Sequence," *Science 250*: 1259-1262, 1990.

Rauscher, "The WT1 Wilms tumor gene product: a developmentally regulated transcription factor in the kidney that functions as a tumor suppressor," *FASEB J. 7*: 896-903, 1993.

Rauscher et al., "Characterization of monoclonal antibodies directed to the amino-terminus of the WT1, Wilms' tumor suppressor," *Hybridoma*, 17(2):191-198, Apr. 1998.

Reddy et al., "WT1-mediated Transcriptional Activation Is Inhibited by Dominant Negative Mutant Proteins," *The Journal Of Biological Chemistry 270*(18): 10878-10884, 1995.

Rothbard and Taylor, "A sequence pattern common to T cell epitopes," *EMBO Journal*, 7(1):93-100, 1988.

Rupprecht et al., "The Wilms' Tumor Suppressor Gene WT1 Is Negatively Autoregulated," *The Journal Of Biological Chemistry 269*(8): 6198-6206, 1994.

Sadovnikova et al., "Generation of human tumor-reactive cytotoxic T-cells against peptides presented by non-self HLA class I molecules," *Eur.J. Immunol.*, 28:193-200, 1998.

Schmid et al., "Prognostic significance of WT1 gene expression at diagnosis in adult *de novo* acute myeloid leukemia," *Leukemia 11*: 639-643, 1997.

Sekiya et al., "Downregulation of Wilms' Tumor Gene (wt1) During Myelomonocytic Differentiation in HL60 Cells," *Blood 83*(7): 1876-1882, 1994.

Sharma et al., "Molecular Cloning of Rat Wilms' Tumor Complementary DNA and a Study of Messenger RNA Expression in the Urogenital System and the Brain," *Cancer Research 52*: 6407-6412, 1992.

Silberstein et al., "Altered expression of the WT1 Wilms tumor suppressor gene in human breast cancer," *Proc. Natl. Acad. Sci. USA 94*: 8132-8137, 1997.

Skeiky et al., "Cloning, expression, and immunological evaluation of two putative secreted serine protease antigens of *Mycobacterium tuberculosis*," *Infection and Immunity 67*(8):3998-4007, Aug. 1999.

Slavin and Strober, "Spontaneous murine B-cell leukaemia," *Nature 272*:624-626, Apr. 13, 1978.

Svedberg et al., "Constitutive expression of the Wilms' tumor gene (WT1) in the leukemic cell line U937 blocks parts of the differentiation program," *Oncogene 15*: 1-8, 1997.

Tadokoro et al., "Genomic Organization of the Human WT1 Gene," *Jpn. J. Cancer Res. 83*: 1198-1203, 1992.

Tadokoro et al., "Intragenic homozygous deletion of the *WT1* gene in Wilms' tumor," *Oncogene 7*: 1215-1221, 1992.

Tadokoro et al., "PCR Detection of 9 Polymorphisms in the WT1 Gene," *Human Molecular Genetics 2*(12): 2205-2206, 1993.

Tadokoro et al., "Taql RFLPs at the Wilms' tumor gene (WT1)," *Nucleic Acids Research 19*(9): 2514, 1991.

Telerman et al., "Identification of the cellular protein encoded by the human Wilms' tumor (*WT1*) gene," *Oncogene 7*: 2545-2548, 1992.

Toes et al., "Efficient tumor eradication by adoptively transferred cytotoxic T-cell clones in allogeneic hosts," *Int. J. Cancer*, 66:686-691, 1996.

Tsurutani et al., "cDNA cloning and developmental expression of the porcine homologue of *WT1*," *Gene 211*(2): 215-220, 1998.

Wang et al., "A second transcriptionally active DNA-binding site for the Wilms tumor gene product, WT1," *Proc. Natl. Acad. Sci. USA 90*: 8896-8900, 1993.

Wang et al., "The Wilms' Tumor Gene Product WT1 Activates or Suppresses Transcription through Separate Functional Domains," *The Journal Of Biological Chemistry 268*(13): 9172-9175, 1993.

Wang et al., "The Wilms' Tumor Gene Product, WT1, Represses Transcription of the Platelet-derived Growth Factor A-chain Gene," *The Journal Of Biological Chemistry 267*(31): 21999-22002, 1992.

Wang et al., "WT1, the Wilms' tumor suppressor gene product, represses transcription through an interactive nuclear protein," *Oncogene 10*(6): 1243-1247, 1995.

Watson et al., "Leukemia viruses associated with mouse myeloma cells," *Proceeding of the National Academy of Sciences 66*(2):344-351, Jun. 1970.

Werner et al., "Inhibition of Cellular Proliferation by the Wilms' Tumor Suppressor WT1 Is Associated with Suppression of Insulin-Like Growth Factor I Receptor Gene Expression," *Molecular and Cellular Biology 15*: 3516-3522, 1995.

Wu et al., "GATA-1 Transactivates the WT1 Hematopoietic Specific Enhancer," *The Journal Of Biological Chemistry 270*(11): 5944-5949, 1995.

Yamagami et al., "Growth Inhibition of Human Leukemic Cells by WT1 (Wilms Tumor Gene) Antisense Oligodeoxynucleotides: Implications for the Involvement of WT1 in Leukemogenesis," *Blood 87*(7): 2878-2884, 1996.

Ye et al., "Regulation of WT1 by phosphorylation: inhibition of DNA binding, alteration of transcriptional activity and cellular translocation," *The EMBO Journal 15*(20): 5606-5615, 1995.

GenBank Database, Accession No. A39692, Feb. 16, 1997.
GenBank Database, Accession No. AAA36810, Jun. 15, 1990.
GenBank Database, Accession No. AAA62825, Oct. 27, 1994.
GenBank Database, Accession No. AAB33427, May 12, 1995.
GenBank Database, Accession No. AAB33443, Jul. 11, 1995.
GenBank Database, Accession No. AAC60039, Nov. 8, 1996.
GenBank Database, Accession No. BAA94794, Apr. 21, 2000.
GenBank Database, Accession No. CAA35956, May 29, 1991.
GenBank Database, Accession No. CAA43819, Dec. 3, 1993.
GenBank Database, Accession No. CAA59736, Feb. 13, 1996.
GenBank Database, Accession No. 151960, Nov. 5, 1999.

GenBank Database, Accession No. M30393, Jun. 15, 1990.
GenBank Database, Accession No. NM_000378, Nov. 5, 2000.
GenBank Database, Accession No. NM_024424, Mar. 20, 2001.
GenBank Database, Accession No. NM_024426, Mar. 20, 2001.
GenBank Database, Accession No. NP_000369, Nov. 5, 2000.
GenBank Database, Accession No. NP_077742, Mar. 20, 2001.
GenBank Database, Accession No. NP_077743, Mar. 20, 2001.
GenBank Database, Accession No. NP_077744, Mar. 20, 2001.
GenBank Database, Accession No. NP_113722, Apr. 6, 2003.
GenBank Database, Accession No. O62651, Nov. 1, 1998.
GenBank Database, Accession No. P50902, Oct. 1, 1996.
GenBank Database, Accession No. S75264, Jul. 11, 1995.
GenBank Database, Accession No. X51630, May 29, 1991.
Geneseq Database, Accession No. AAT45130, Aug. 19, 1997.
Geneseq Database, Accession No. AAT45131, Aug. 20, 1997.
Geneseq Database, Accession No. AAT45132, Aug. 20, 1997.
Geneseq Database, Accession No. AAT45133, Aug. 20, 1997.
Geneseq Database, Accession No. AAT45134, Aug. 20, 1997.
Geneseq Database, Accession No. AAT45135, Aug. 20, 1997.
Geneseq Database, Accession No. AAT45136, Aug. 20, 1997.
Geneseq Database, Accession No. AAT45137, Aug. 20, 1997.
Geneseq Database, Accession No. AAT45138, Aug. 20, 1997.
Geneseq Database, Accession No. AAT45139, Aug. 20, 1997.
Geneseq Database, Accession No. AAT45140, Aug. 20, 1997.
Geneseq Database, Accession No. AAT45141, Aug. 20, 1997.
Geneseq Database, Accession No. AAT45142, Aug. 20, 1997.
Geneseq Database, Accession No. AAT97855, Mar. 9, 1998.
Geneseq Database, Accession No. AAT97856, Mar. 9, 1998.
Geneseq Database, Accession No. AAT97857, Mar. 9, 1998.
Geneseq Database, Accession No. AAT97858, Mar. 9, 1998.
Geneseq Database, Accession No. AAT97859, Mar. 9, 1998.
Geneseq Database, Accession No. AAT97860, Mar. 9, 1998.
Geneseq Database, Accession No. AAT97861, Mar. 9, 1998.
Geneseq Database, Accession No. AAT97862, Mar. 9, 1998.
Geneseq Database, Accession No. AAT97863, Mar. 9, 1998.
Geneseq Database, Accession No. AAT97864, Mar. 9, 1998.
Geneseq Database, Accession No. AAT97865, Mar. 9, 1998.
Geneseq Database, Accession No. AAT97866, Mar. 9, 1998.
Geneseq Database, Accession No. AAT97867, Mar. 9, 1998.
Geneseq Database, Accession No. AAT97868, Mar. 9, 1998.
Geneseq Database, Accession No. AAX15839, May 11, 1999.
Geneseq Database, Accession No. AAX15840, May 11, 1999.
Geneseq Database, Accession No. AAX15841, May 11, 1999.
Geneseq Database, Accession No. AAX15842, May 11, 1999.
Geneseq Database, Accession No. AAX15843, May 11, 1999.
Geneseq Database, Accession No. AAX15844, May 11, 1999.
Geneseq Database, Accession No. AAX15845, May 11, 1999.
Geneseq Database, Accession No. AAX15846, May 11, 1999.
Geneseq Database, Accession No. AAX15847, May 11, 1999.
Geneseq Database, Accession No. AAX15848, May 11, 1999.
Geneseq Database, Accession No. AAX15849, May 11, 1999.
Geneseq Database, Accession No. AAX15850, May 11, 1999.
Geneseq Database, Accession No. AAX15851, May 11, 1999.
Geneseq Database, Accession No. AAX15852, May 11, 1999.
Geneseq Database, Accession No. AAX15853, May 11, 1999.
Geneseq Database, Accession No. AAX15854, May 11, 1999.
Geneseq Database, Accession No. AAX15855, May 11, 1999.
Geneseq Database, Accession No. AAX23927, Jun. 25, 1999.
Geneseq Database, Accession No. AAX23928, Jun. 25, 1999.
Geneseq Database, Accession No. AAX23929, Jun. 25, 1999.
Geneseq Database, Accession No. AAX23930, Jun. 25, 1999.
Geneseq Database, Accession No. AAX23931, Jun. 25, 1999.
Geneseq Database, Accession No. AAX34315, Jul. 6, 1999.
Geneseq Database, Accession No. AAX34316, Jul. 6, 1999.
Geneseq Database, Accession No. AAX34317, Jul. 6, 1999.
Geneseq Database, Accession No. AAX34318, Jul. 6, 1999.
Geneseq Database, Accession No. AAX34319, Jul. 6, 1999.
Geneseq Database, Accession No. AAX34320, Jul. 6, 1999.
Geneseq Database, Accession No. AAX34321, Jul. 6, 1999.
Genseq Database, Accession No. AAY80196, May 24, 2000.
Genseq Database, Accession No. AAY80197, May 24, 2000.
Genseq Database, Accession No. AAY80198, May 24, 2000.
Genseq Database, Accession No. AAY80199, May 24, 2000.
Genseq Database, Accession No. AAY80200, May 24, 2000.
Genseq Database, Accession No. AAY80201, May 24, 2000.
Genseq Database, Accession No. AAY80202, May 24, 2000.
Genseq Database, Accession No. AAY80203, May 24, 2000.
Genseq Database, Accession No. ABP42234, Aug. 22, 2002.
Gaiger, A. and Cheever, M.A., "Compositions and Methods for WT1 Specific Immunotherapy," U.S. Appl. No. 09/164,223, filed Sep. 30, 1998.
Gaiger, A. and Cheever, M.A., "Compositions and Methods for WT1 Specific Immunotherapy," U.S. Appl. No. 09/276,484, filed Mar. 25, 1999.
Gaiger, A. and Cheever, M.A., "Compositions and Methods for WT1 Specific Immunotherapy," U.S. Appl. No. 09/684,361, filed Oct. 6, 2000.
Gaiger, A. and Cheever, M.A., "Compositions and Methods for WT1 Specific Immunotherapy," U.S. Appl. No. 09/685,830, filed Oct. 9, 2000.

* cited by examiner

HU: MGSDVRDLNALLPAVPSLGGGGGCALPVSGAAQWAPVLDFAPPGASAYGSL
MO: MGSDVRDLNALLPAVSSLGGGGGCGLPVSGAAQWAPVLDFAPPGASAYGSL

HU: GGPAPPPAPPPPPPPPHSFIKQEPSWGGAEPHEEQCLSAFTVHFSGQFTGTAG
MO: GGPAPPPAPPPPPPPPHSFIKQEPSWGGAEPHEEQCLSAFTLHFSGQFTGTAG

HU: ACRYGPFGPPPPSQASSGQARMFPNAPYLPSCLESQPAIRNQGYSTVTFDGTPS
MO: ACRYGPFGPPPPSQASSGQARMFPNAPYLPSCLESQPTIRNQGYSTVTFDGAPS

HU: YGHTPSHHAAQFPNHSFKHEDPMGQQGSLGEQQYSVPPPVYGCHTPTDSCTG
MO: YGHTPSHHAAQFPNHSFKHEDPMGQQGSLGEQQYSVPPPVYGCHTPTDSCTG

HU: SQALLLRTPYSSDNLYQMTSQLECMTWNQMNLGATLKGVAAGSSSSVKWTE
MO: SQALLLRTPYSSDNLYQMTSQLECMTWNQMNLGATLKGMAAGSSSSVKWTE

HU: GQSNHSTGYESDNHTTPILCGAQYRIHTHGVFRGIQDVRRVPGVAPTLVRSAS
MO: GQSNHGIGYESDNHTAPILCGAQYRIHTHGVFRGIQDVRRVSGVAPTLVRSAS

HU: ETSEKRPFMCAYPGCNKRYFKLSHLQMHSRKHTGEKPYQCDFKDCERRFSR
MO: ETSEKRPFMCAYPGCNKRYFKLSHLQMHSRKHTGEKPYQCDFKDCERRFSR

HU: SDQLKRHQRRHTGVKPFQCKTCQRKFSRSDHLKTHTRTHTGKTSEKPFSCR
MO: SDQLKRHQRRHTGVKPFQCKTCQRKFSRSDHLKTHTRTHTGKTSEKPFSCR

HU: WPSCQKKFARSDELVRHHNMHQRNMTKLQLAL
MO: WHSCQKKFARSDELVRHHNMHQRNMTKLHVAL

*Fig. 1*

```
         5   10   15   20   25   30   35   40   45   50   55   60   65   70   75
    MGSDVRDLNALLPAVPSLGGGGGCALPVSGAAQWAPVLDFAPPGASAYGSLGGPAPPPAPPPPPPPPHSFIKQE
    .....AAAAAAAAAAAAAAAAAA......AAAAAA........AAAAAAAAAAAA....................
    ..............................RRRR.........................................
    ............................................................................
    ............................................................................
    ............................................................................

80   85   90   95  100  105  110  115  120  125  130  135  140  145  150
    PSWGGAEPHEEQCLSAFTVHFSGQFTGTAGACRYGPFGPPPPSQASSGQARMFPNAPYLPSCLESQPAIRNQGYS
    ...............AAA......AAAA...................AAA......AAAAAA............
    ............................RRRR....................RRRRR.................
    ...........................................DDDDDDDD........................
    ............................................................................

155  160  165  170  175  180  185  190  195  200  205  210  215  220  225
    TVTFDGTPSYGHTPSHHAAQFPNHSFKHEDPMGQQGSLGEQQYSVPPPVYGCHTPTDSCTGSQALLLRTPYSSDN
    ................AAAAA.........................AAAAAA...............AA
    ................RRRR........................................................
    .........................................................DDDDDDDDDDDDDD...
    ............................................................................

230  235  240  245  250  255  260  265  270  275  280  285  290  295  300
    LYQMTSQLECMTWNQMNLGATLKGVAAGSSSSVKWTEGQSNHSTGYESDNHTTPILCGAQYRIHTHGVFRGIQDV
    AAAAAAAA............AAA.AAA........................................AAAAAAAAAAA
    ............RRRRRRRRRR.....RRRR...........................RRRR.....
    DDDDDD............DDDDDDDDDD................................................
    ...........................................................ddddd........

305  310  315  320  325  330  335  340  345  350  355  360  365  370  375
    RRVPGVAPTLVRSASETSEKRPFMCAYPGCNKRYFKLSHLQMHSRKHTGEKPYQCDFKDCERRFSRSDQLKRHQR
    AAAAA..AAAAAAAAAA..............................AAAA.AAAAAAAAA.
    ....RRRRR.....................RRRR........................................
    .......DDDDDD................................................................
    ............................................................................

380  385  390  395  400  405  410  415  420  425  430  435  440  445  450
    RHTGVKPFQCKTCQRKFSRSDHLKTHTRTHTGKTSEKPFSCRWPSCQKKFARSDELVRHHNMHQRNMTKLQLAL
    .............AAAA.AAAA..AA.....AAAA..........AAA....AAAAAAAA...AAA........
    ...............................................RRRR..RRRR...............
    ............................................................................
    ..............ddddddddddd....................................................

Fig. 8A
```

```
              5   10   15   20   25   30   35   40   45   50   55   60   65   70   75
          MGSDVRDLNALLPAVSSLGGGGGCGLPVSGAAQWAPVLDFAPPGASAYGSLGGPAPPPAPPPPPPPPHSFIKQE
          .....AAAAAAAAAAAAAAAAAAA.......AAAAAA.........AAAAAAAAAAAAA................
          ...............................RRRR.......................................
          ...........................................................................
          ...........................................................................
          ...........................................................................

80   85   90   95  100  105  110  115  120  125  130  135  140  145  150
          PSWGGAEPHEEQCLSAFTLHFSGQFTGTAGACRYGPFGPPPPSQASSGQARMFPNAPYLPSCLESQPTIRNQGYS
          ..........................AAAA........................AAA......AAAAAA.....
          ..........................RRRR........................RRRRR..............
          ..............................................DDDDDDDD....................
          ...........................................................................

155  160  165  170  175  180  185  190  195  200  205  210  215  220  225
          TVTFDGAPSYGHTPSHHAAQFPNHSFKHEDPMGQQGSLGEQQYSVPPPVYGCHTPTDSCTGSQALLLRTPYSSDN
          ................AAAAA........................AAAAAA..............AA
          ................RRRR.......................................................
          ..............................................................DDDDDDDDDDDDDDD...
          ...........................................................................

230  235  240  245  250  255  260  265  270  275  280  285  290  295  300
          LYQMTSQLECMTWNQMNLGATLKGMAAGSSSSVKWTEGQSNHGIGYESDNHTAPILCGAQYRIHTHGVFRGIQDV
          AAAAAAAA............AAA.AAA...........................................AAAAAAAAAA
          ..................RRRRRRRRRR.....RRRR..............................RRRR.....
          DDDDDD..............DDDDDDDDDD.............................................
          ...............................................................ddddd........

305  310  315  320  325  330  335  340  345  350  355  360  365  370  375
          RRVSGVAPTLVRSASETSEKRPFMCAYPGCNKRYFKLSHLQMHSRKHTGEKPYQCDFKDCERRFSRSDQLKRHQR
          AAAAA..AAAAAAAAAAA..................................AAAA.AAAAAAAAA.
          ....RRRRR........................RRRR.....................................
          ..DDDDDDDDDDD..............................................................
          ...........................................................................

380  385  390  395  400  405  410  415  420  425  430  435  440  445  450
          RHTGVKPFQCKTCQRKFSRSDHLKTHTRTHTGKTSEKPFSCRWHSCQKKFARSDELVRHHNMHQRNMTKLHVAL
          .............AAAA.AAAA..AA.....AAAA...........AA....AAAAAAAA...AAAA.......
          ......................................................RRRR..RRRR.............
          ...........................................................................
          ..............ddddddddddd..................................................
```

*Fig. 8B*

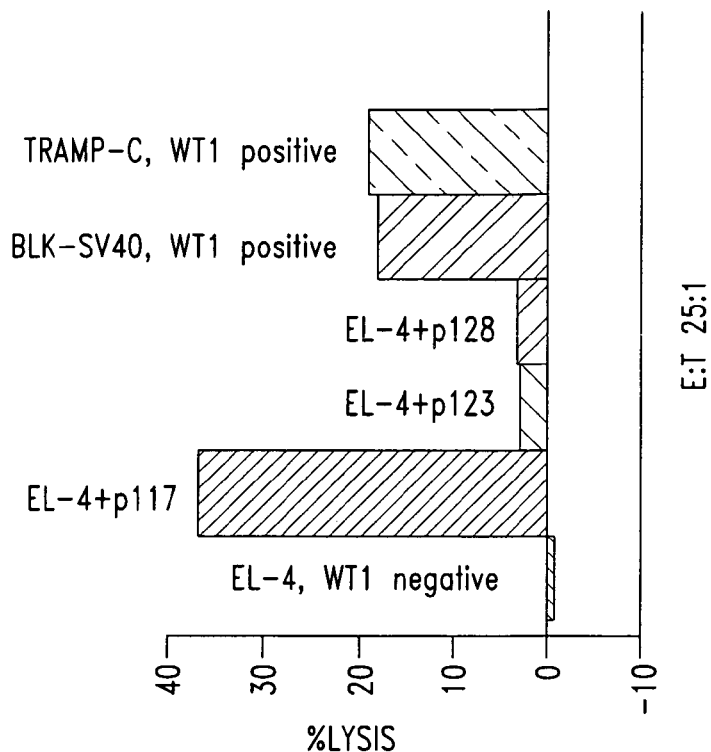
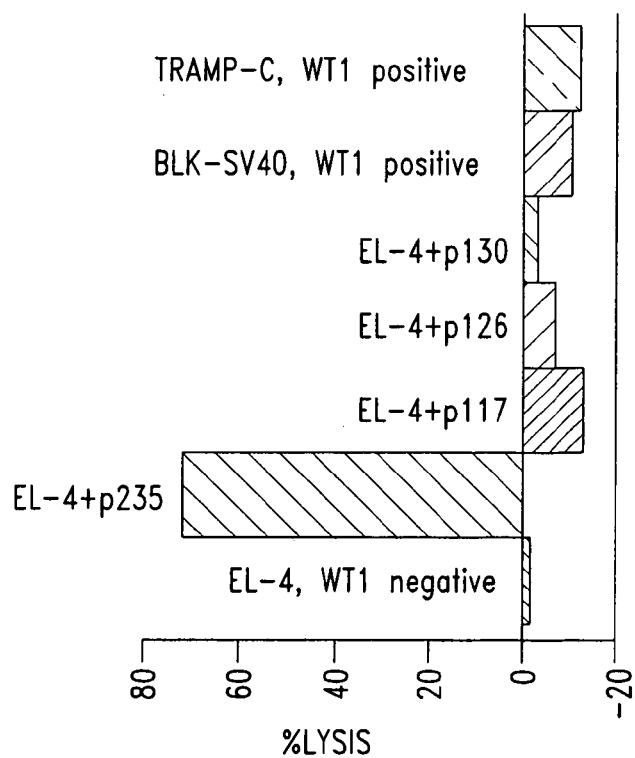

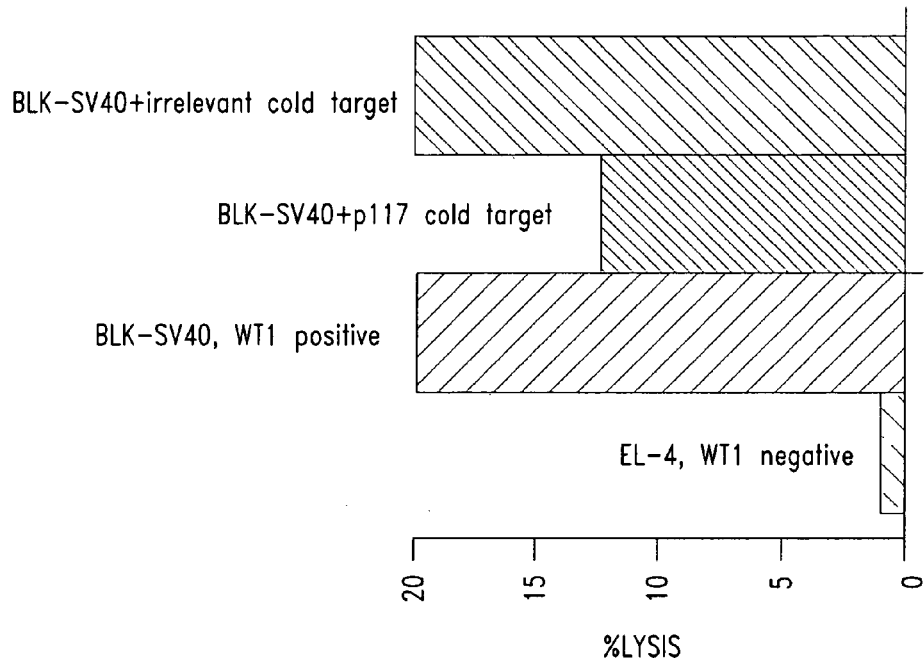
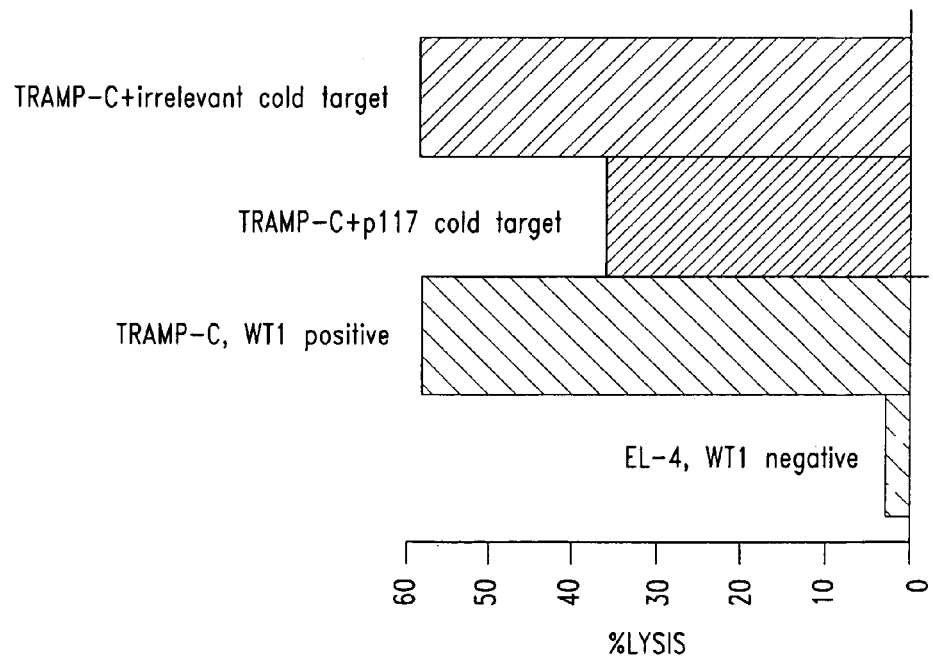

Characteristics of Recombinant WT1 Proteins Used for Serological Analysis

| NAME | Recombinant Protein | WT1 Amino Acid Position | Molecular Weight |
|---|---|---|---|
| WT1/full-length | Ral2-WT1 full length fusion protein | aa 1-449 | 85kDa |
| WT1/N-terminus | TRX-WT1 N-terminus fusion protein | aa 1-249 | 60kDa |
| WT1/C-terminus | WT1 C-terminus protein | aa 267-449 | 50kDa |

*Fig. 18*

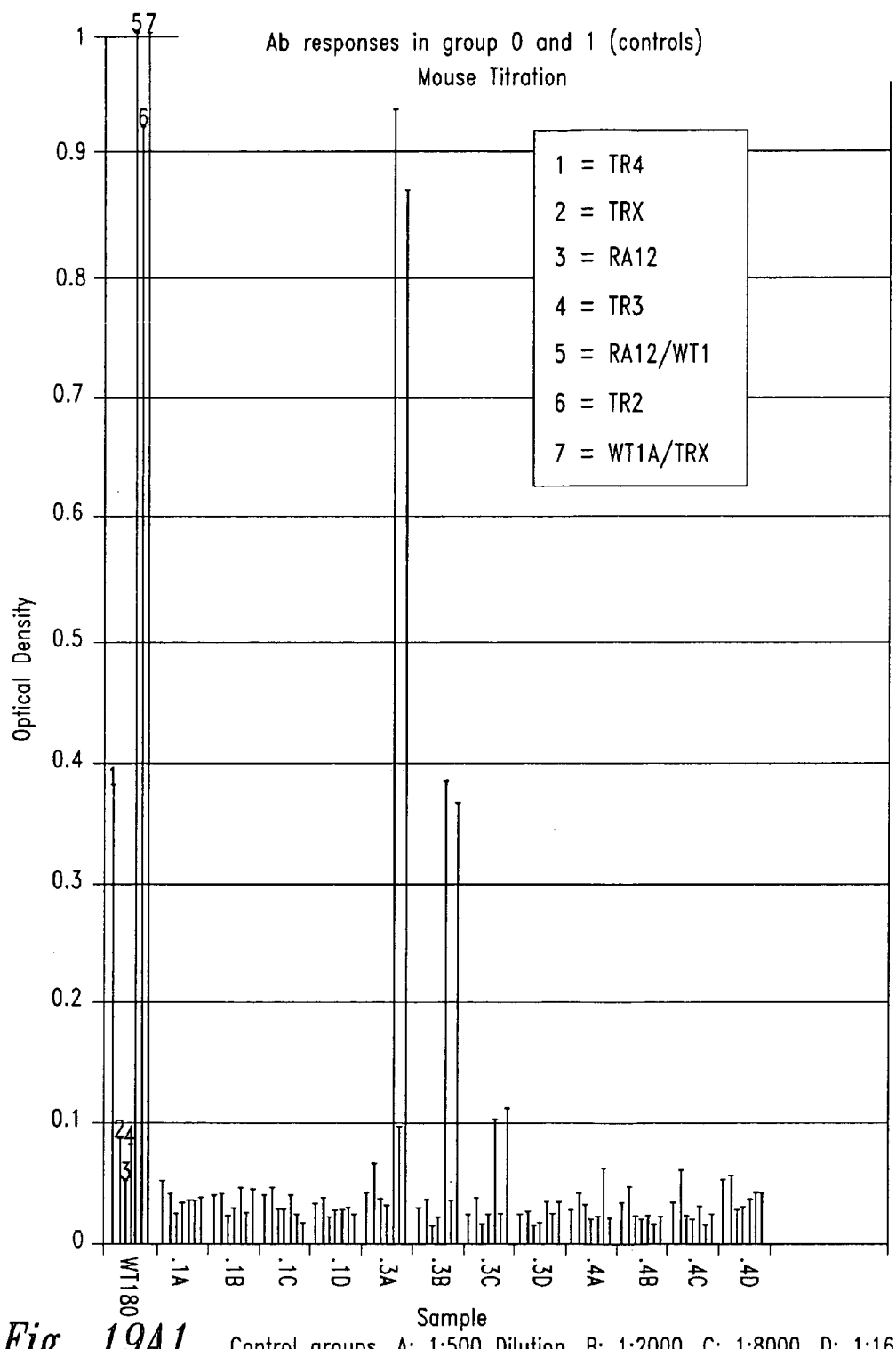
Fig. 19A1 Control groups. A: 1:500 Dilution, B: 1:2000, C: 1:8000, D: 1:16000

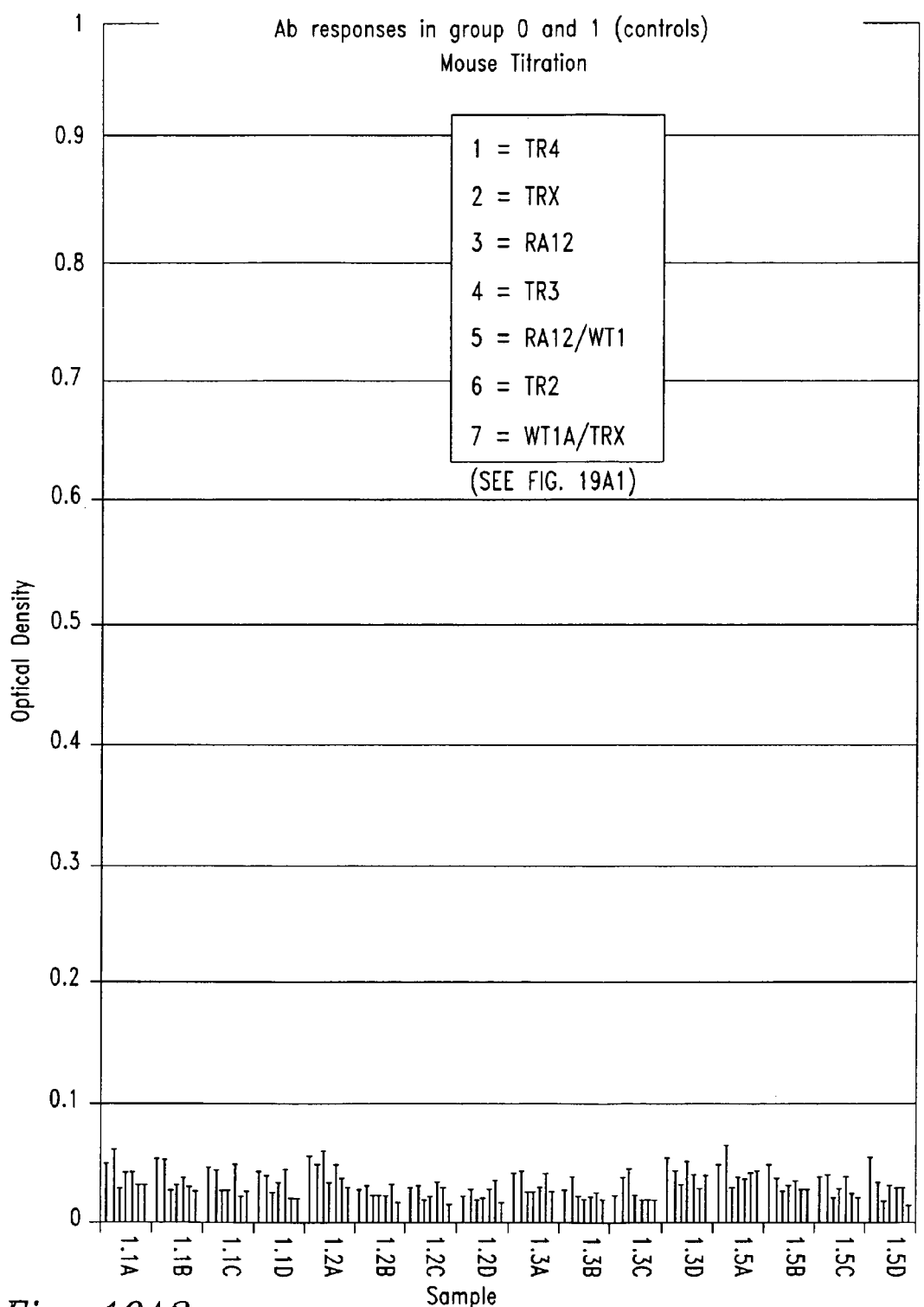
Fig. 19A2  Control groups. A: 1:500 Dilution, B: 1:2000, C: 1:8000, D: 1:16000

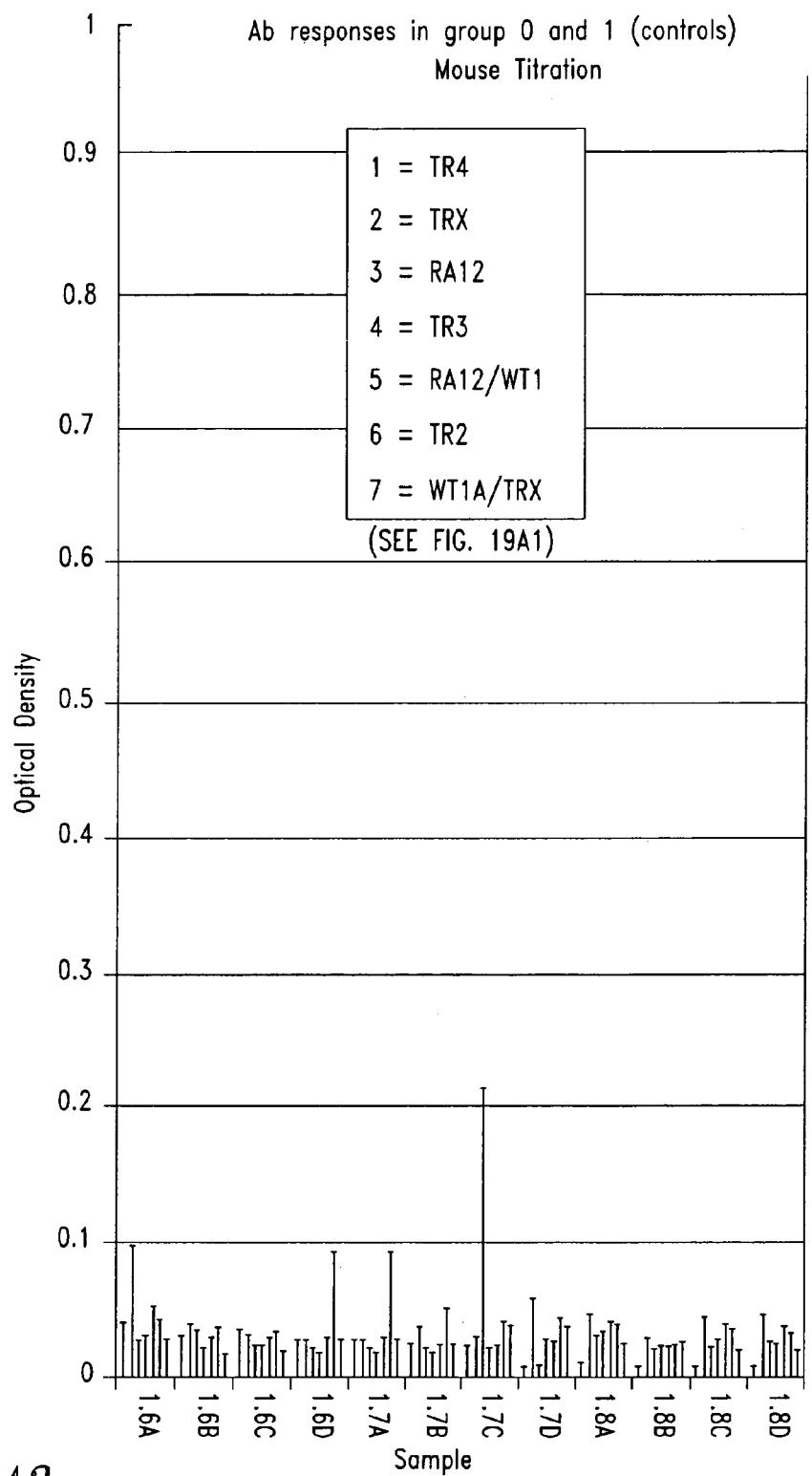
Fig. 19A3  Control groups. A: 1:500 Dilution, B: 1:2000, C: 1:8000, D: 1:16000

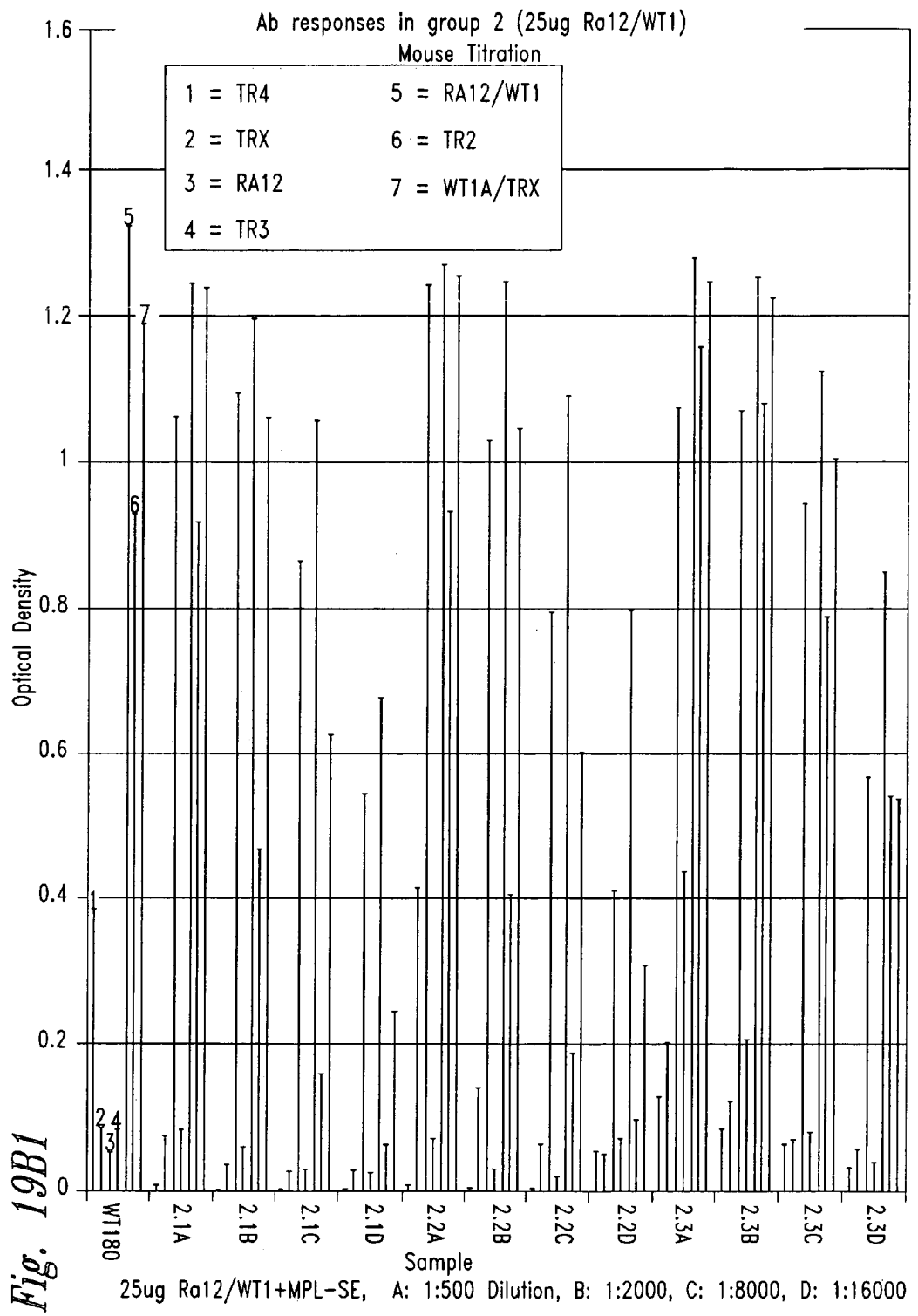
Fig. 19B1

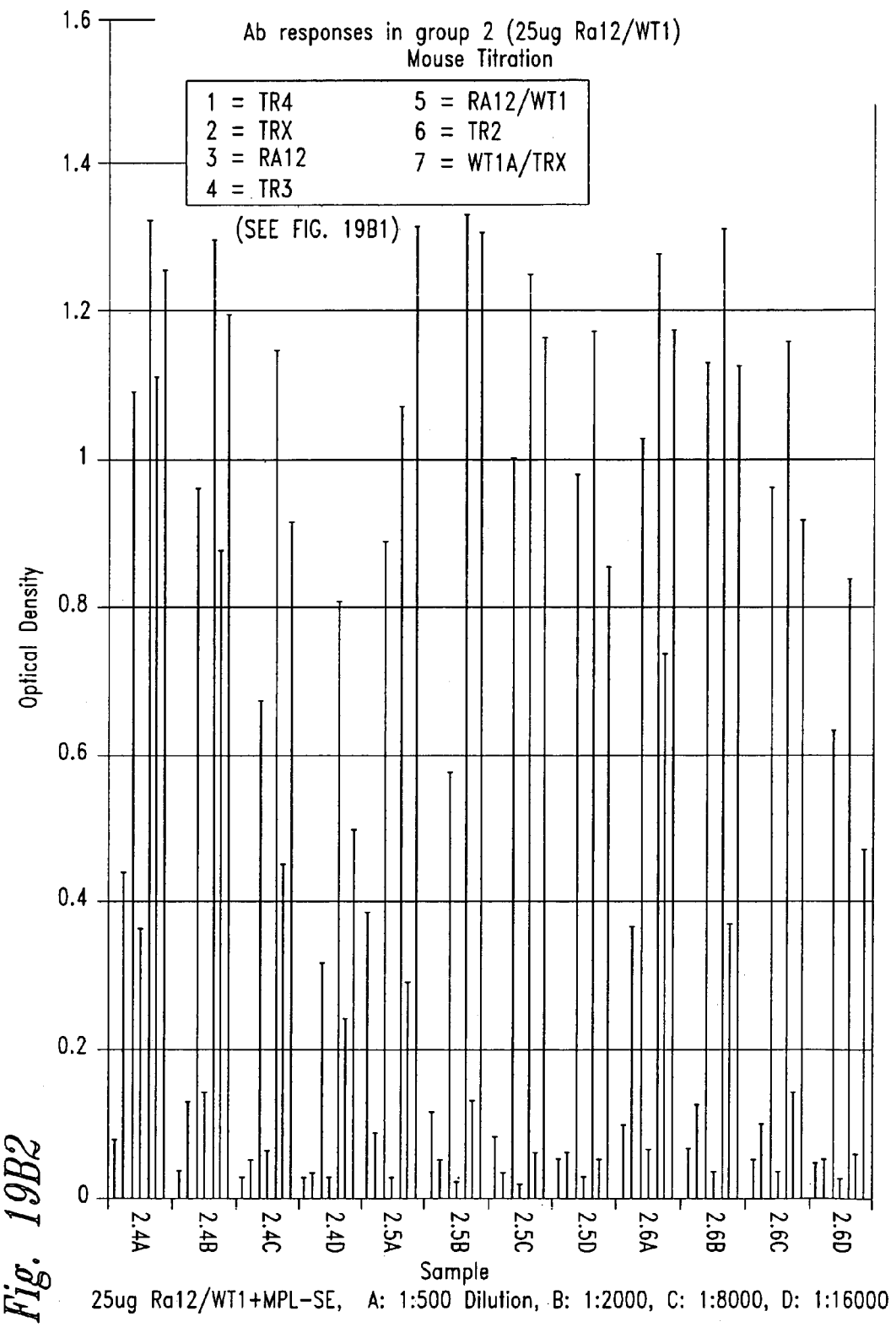
Fig. 19B2

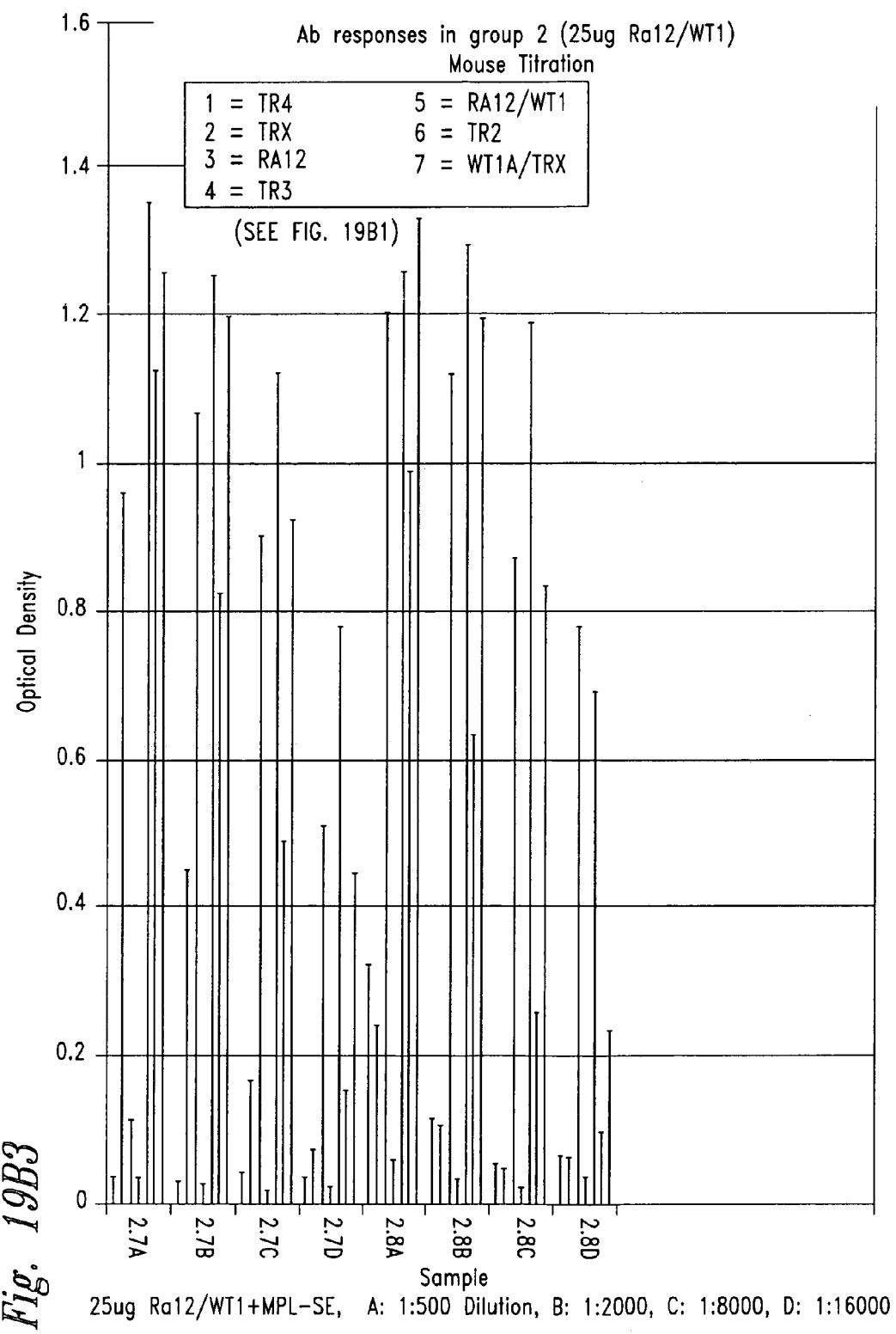
Fig. 19B3

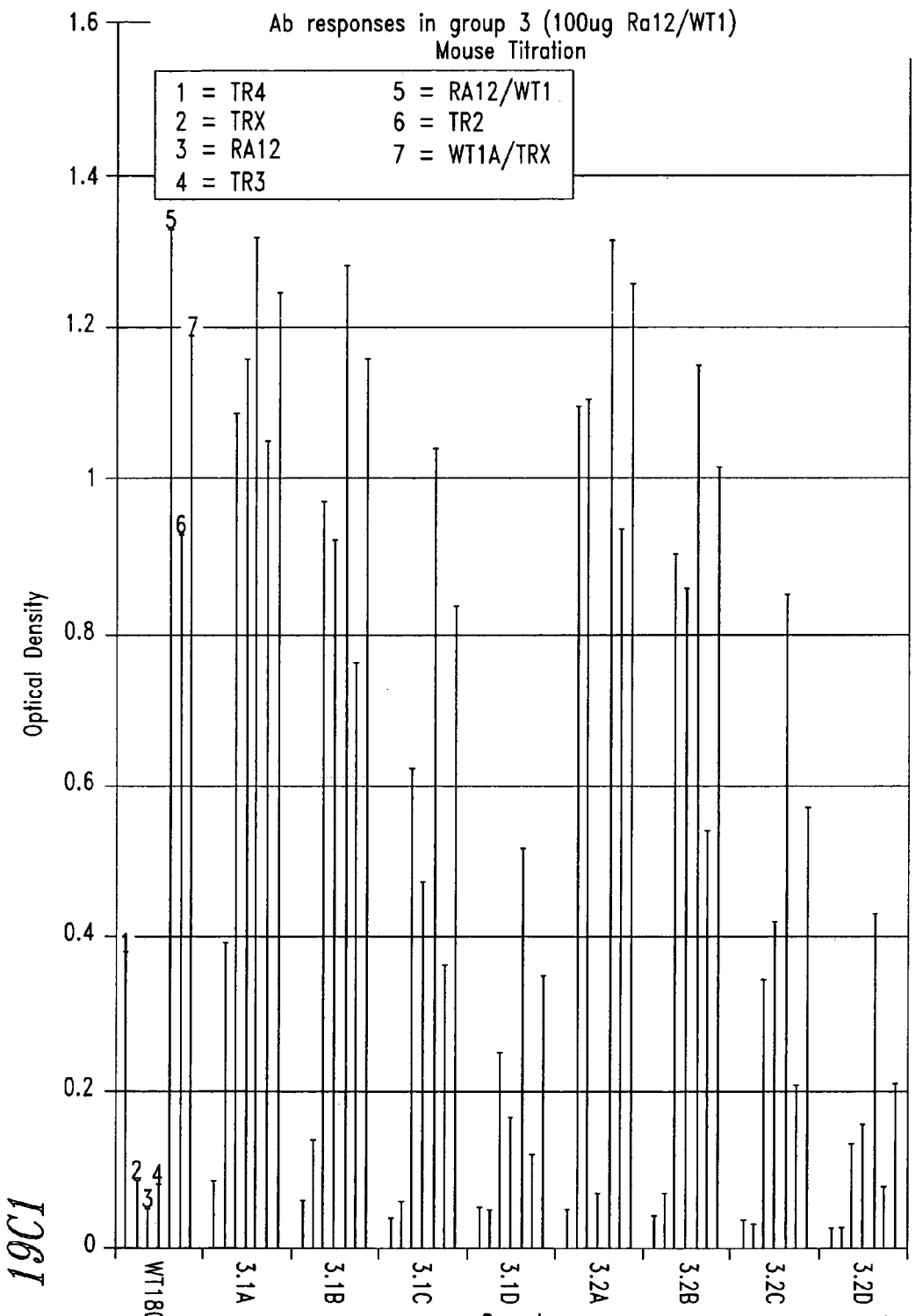
Fig. 19C1

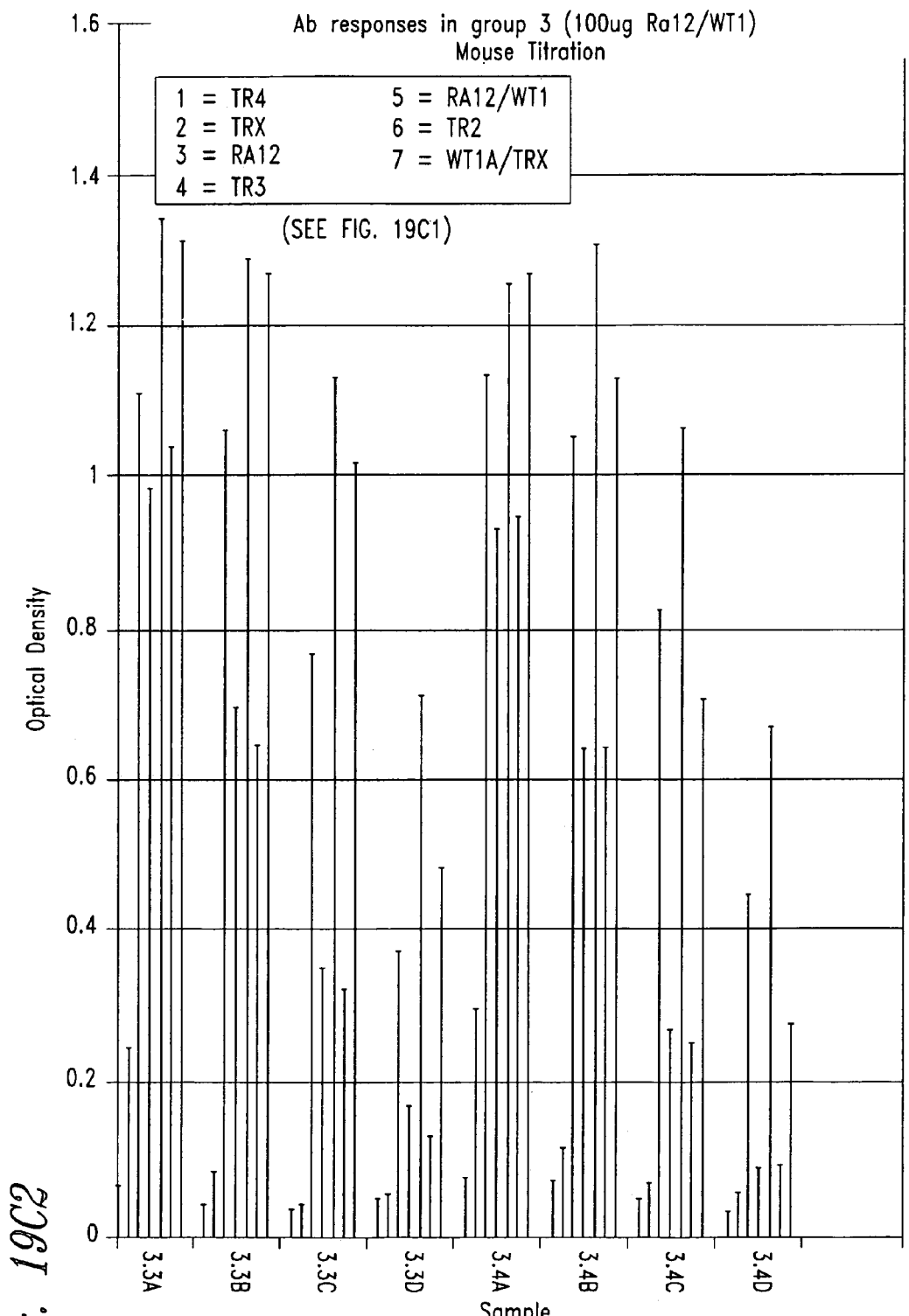
Fig. 19C2

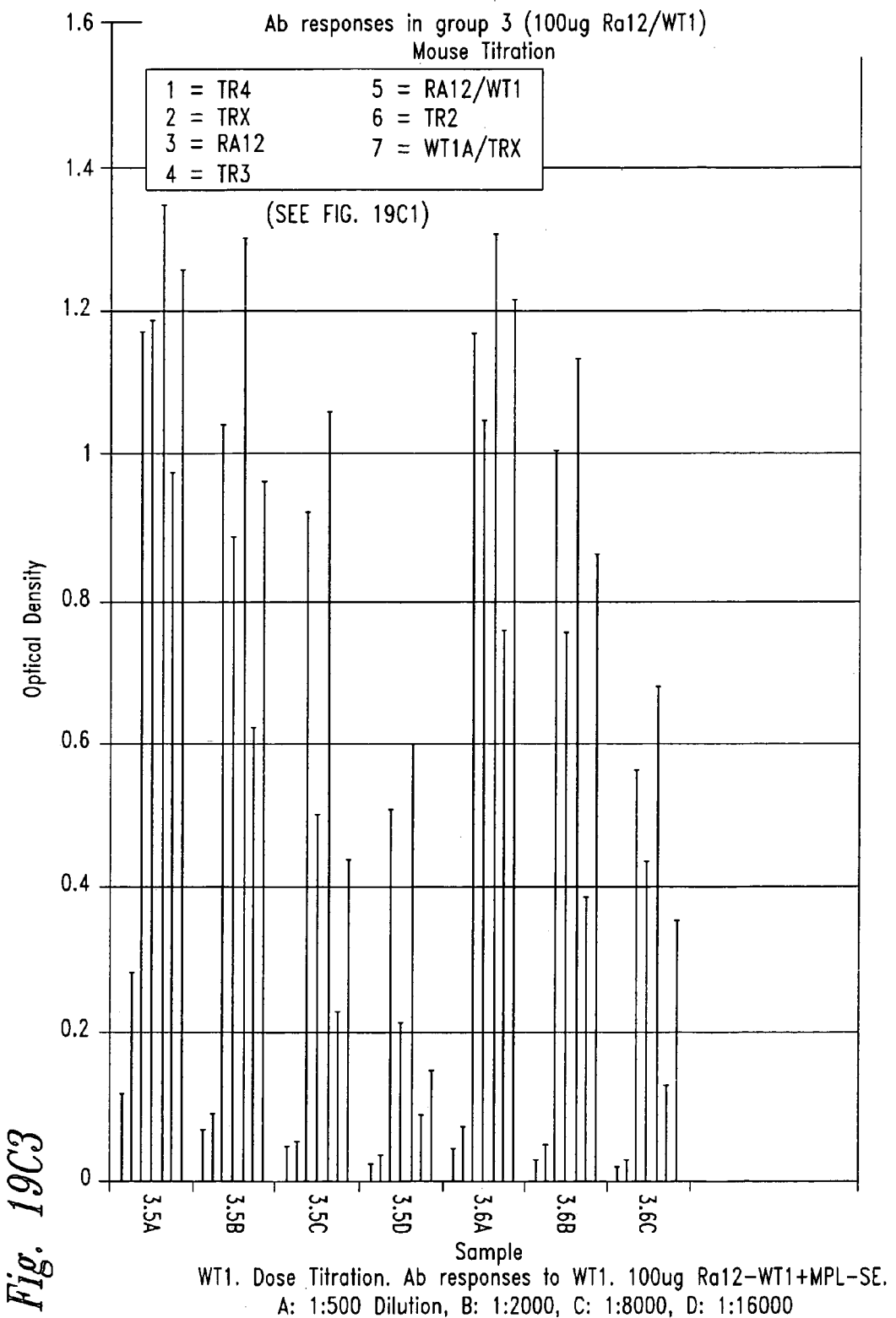
Fig. 19C3

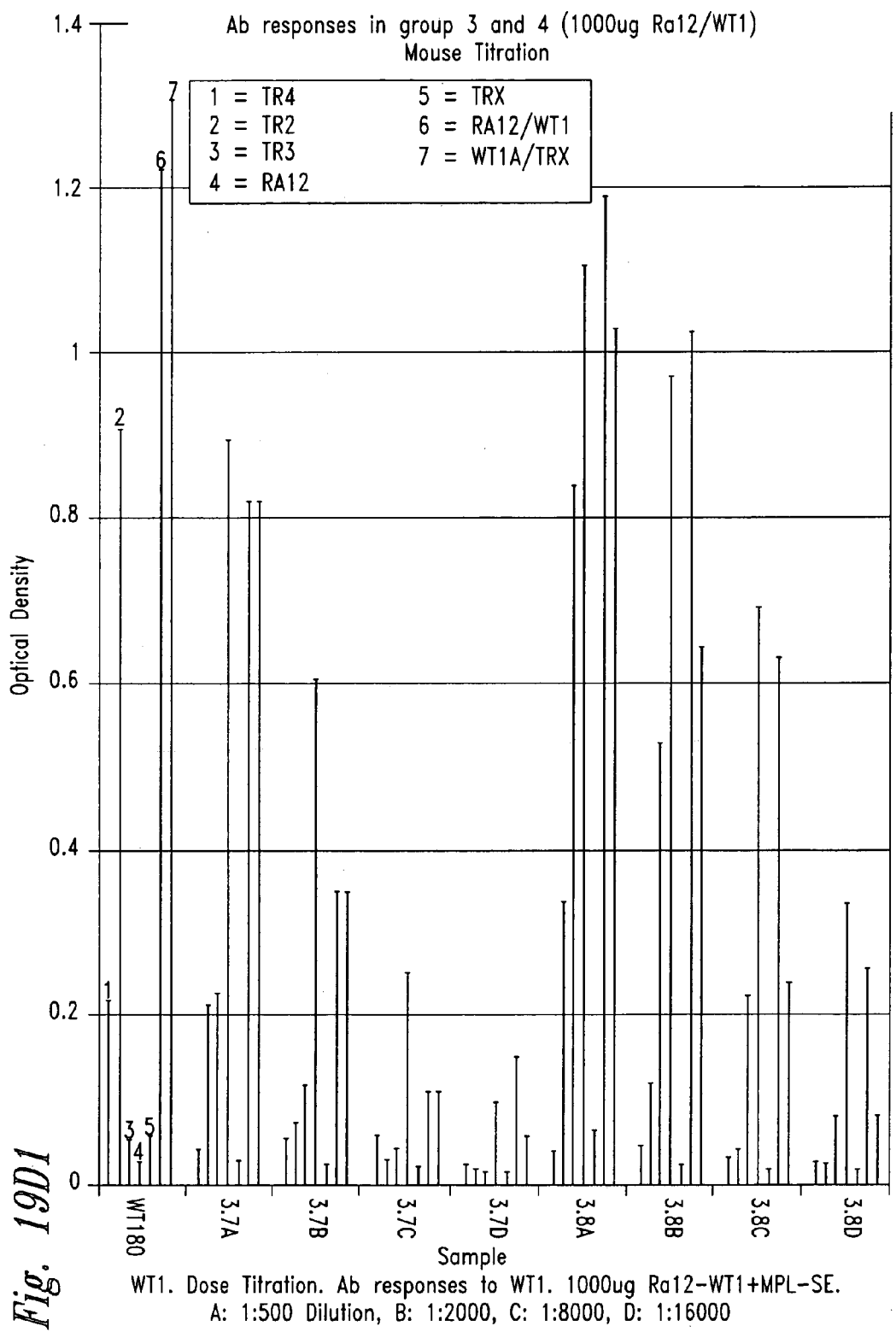
Fig. 19D1

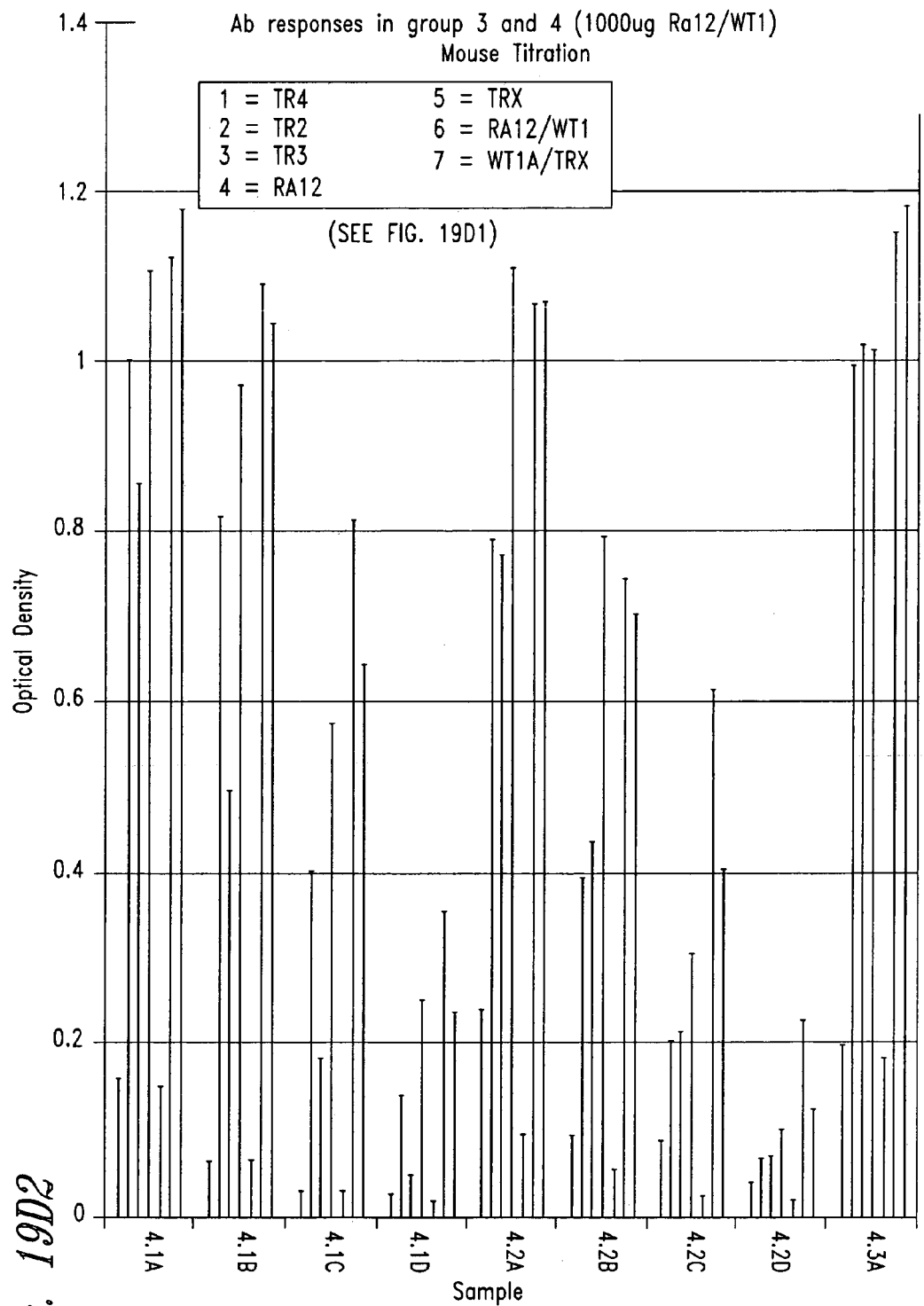

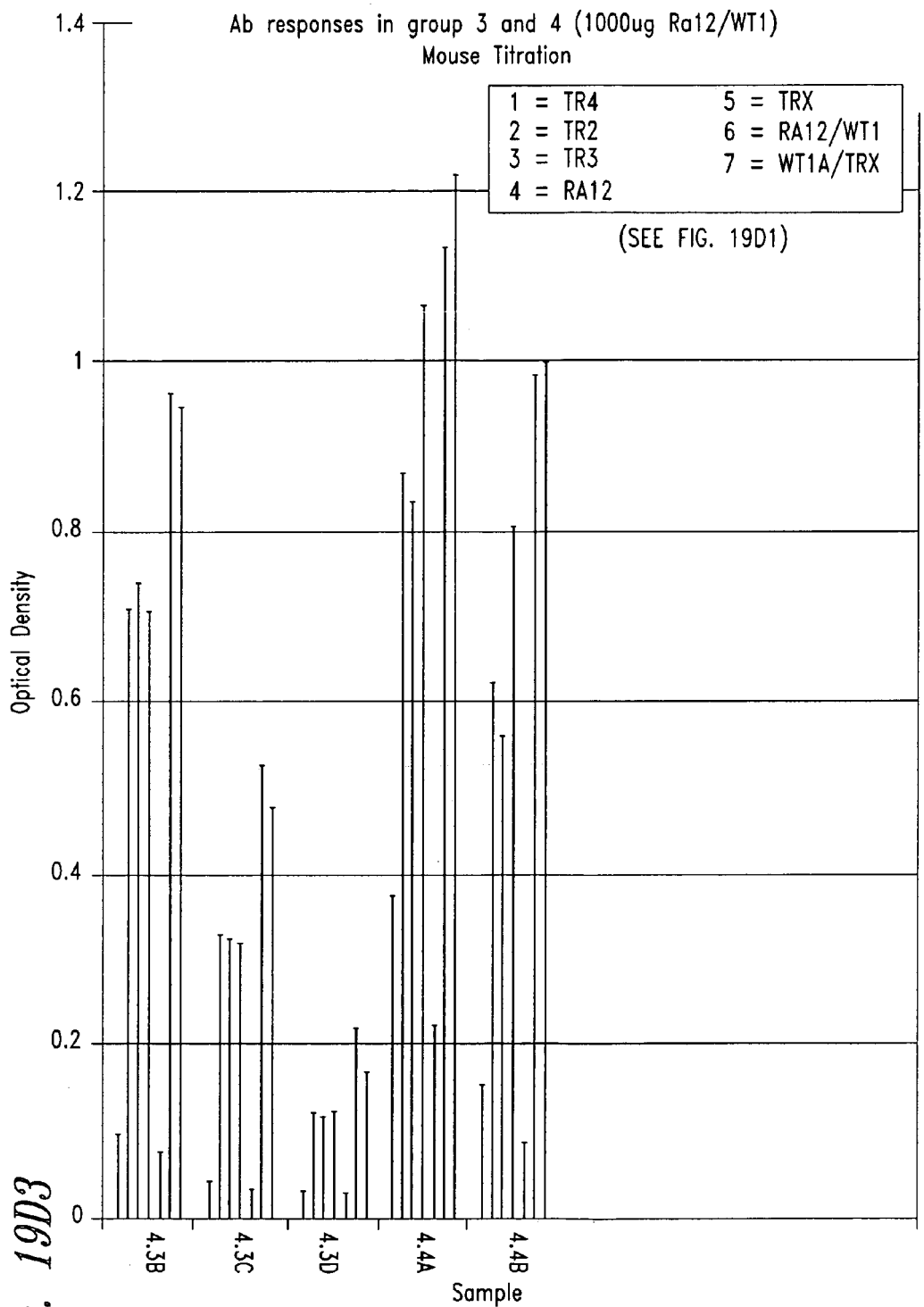
Fig. 19D3

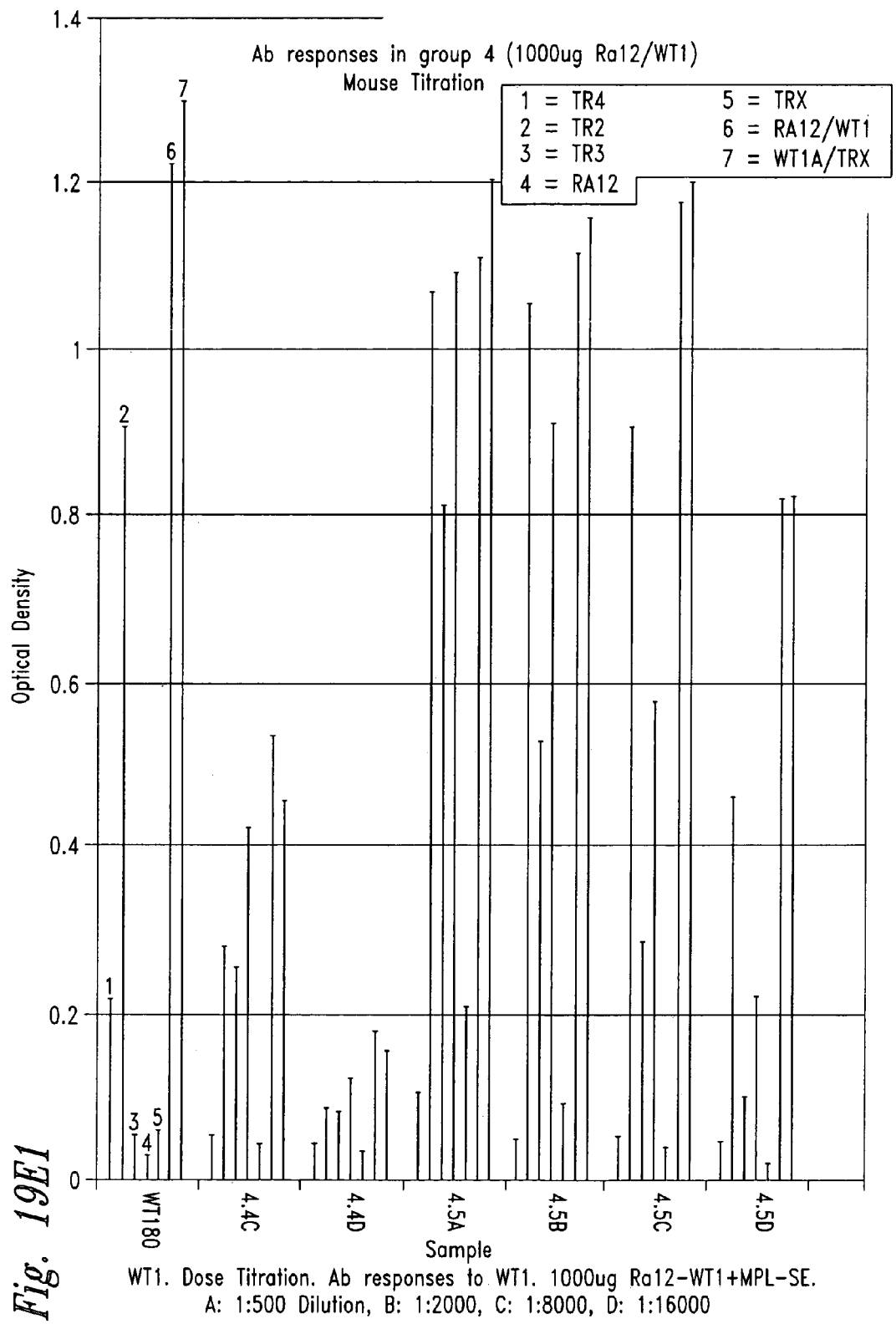
Fig. 19E1  WT1. Dose Titration. Ab responses to WT1. 1000ug Ra12-WT1+MPL-SE.
A: 1:500 Dilution, B: 1:2000, C: 1:8000, D: 1:16000

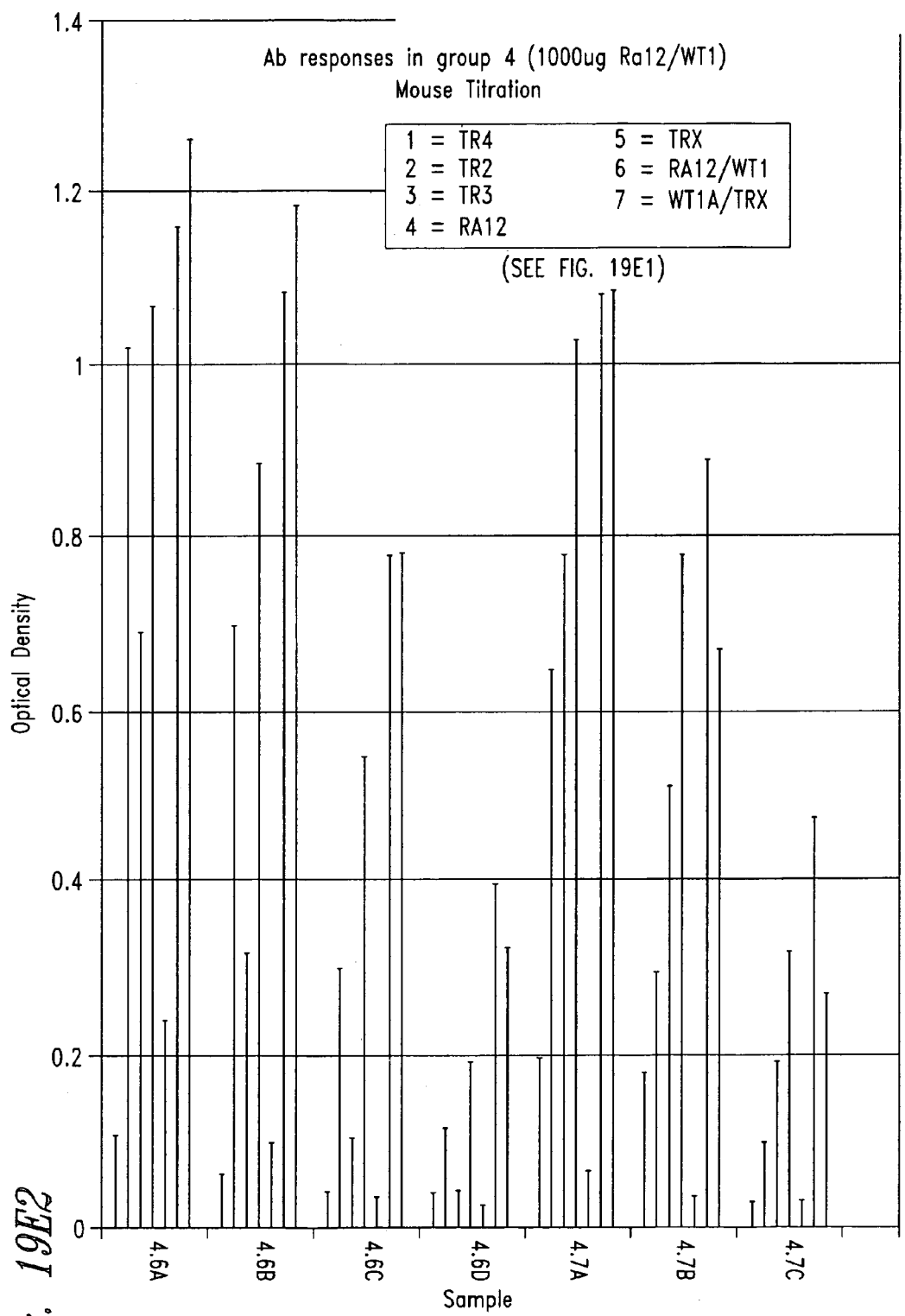
Fig. 19E2

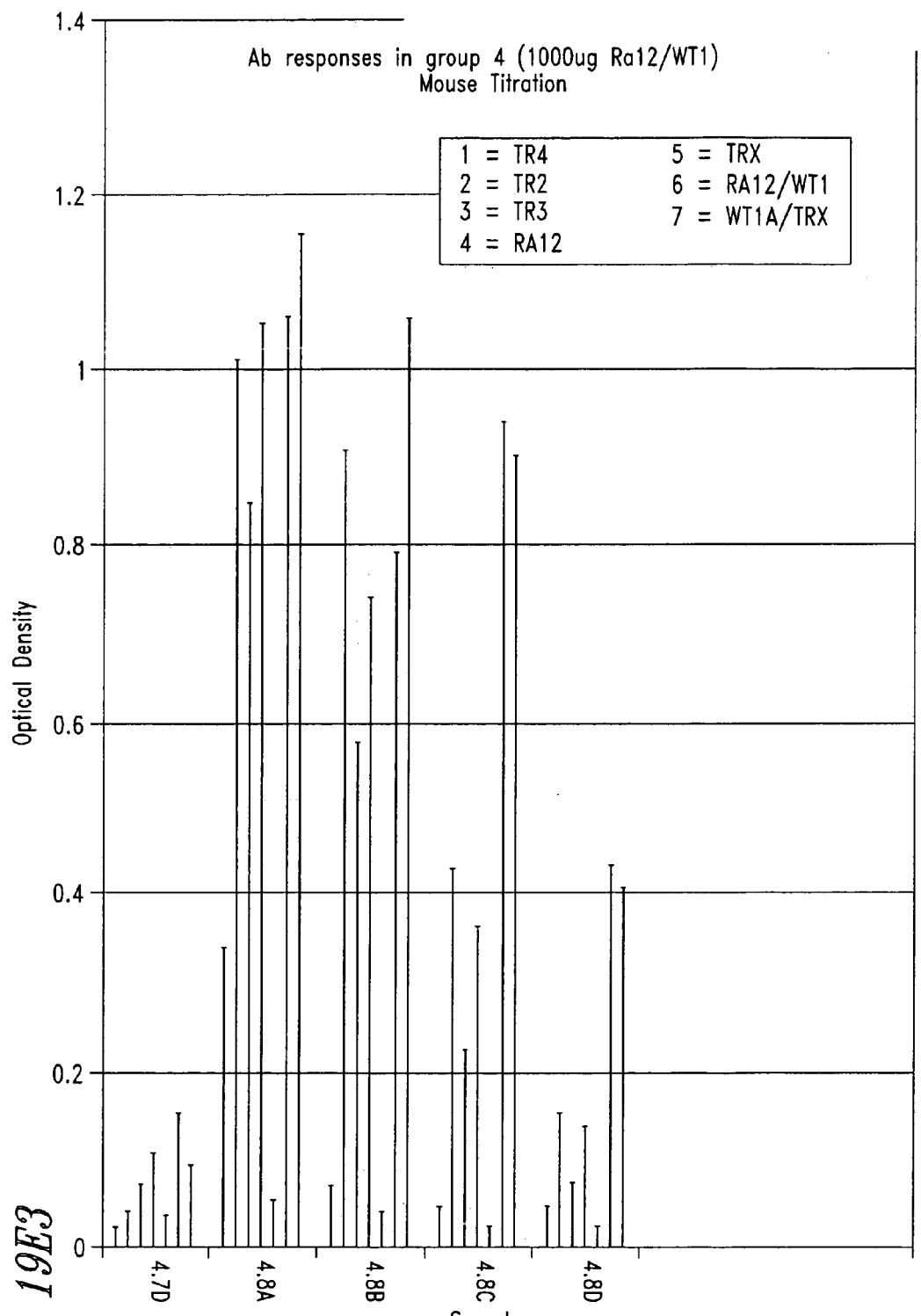
Fig. 19E3 WT1. Dose Titration. Ab responses to WT1. 1000ug Ra12-WT1+MPL-SE. A: 1:500 Dilution, B: 1:2000, C: 1:8000, D: 1:16000

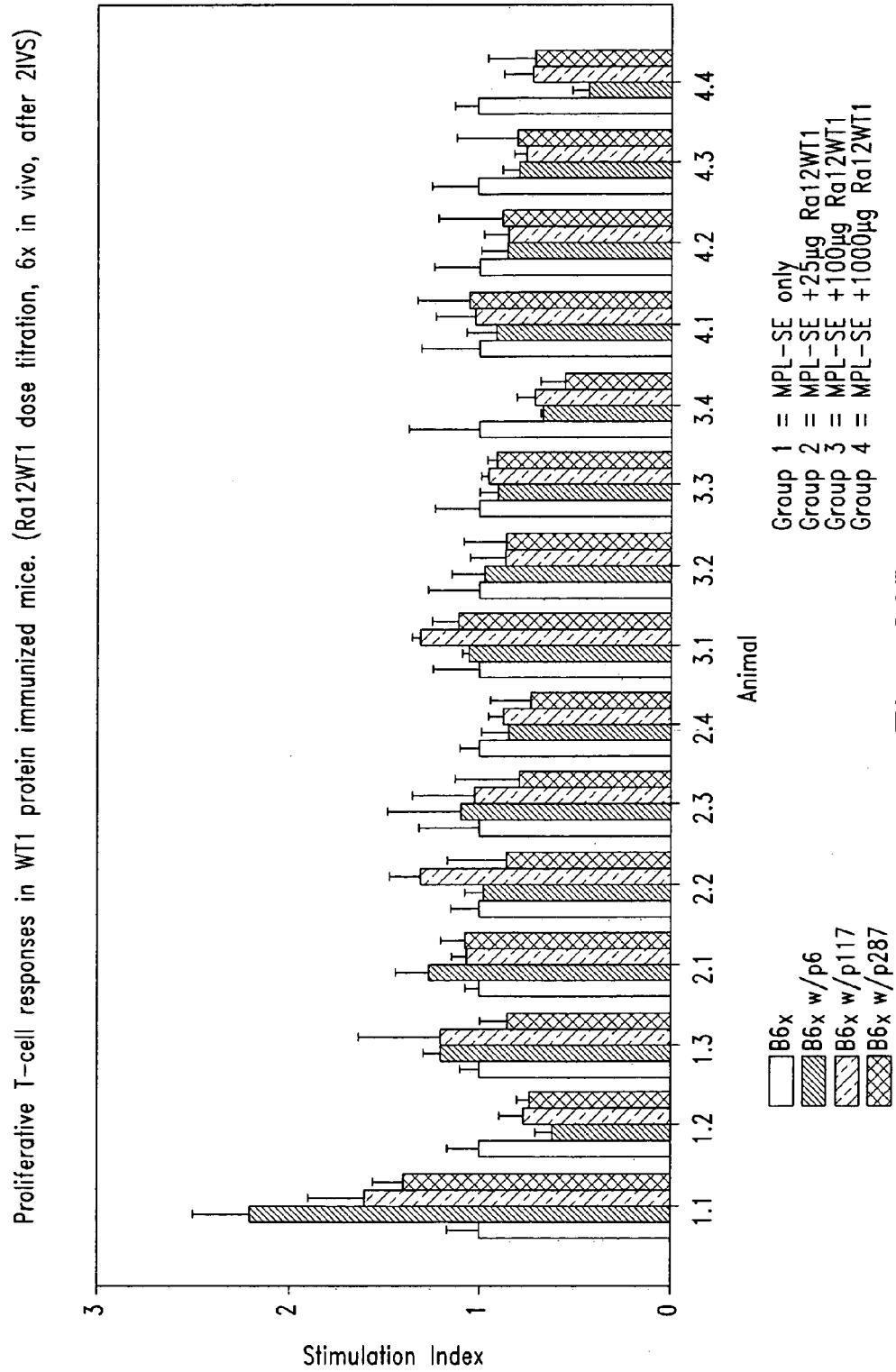

WT1 expression in human DC following adeno WT1 and Vaccinia WT1 infection
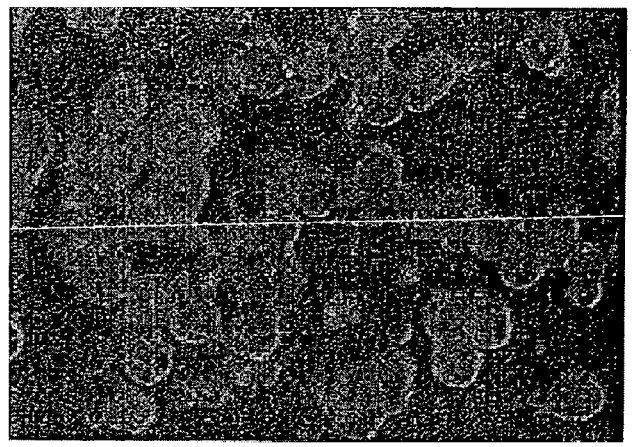
Control
(uninfected human DC)
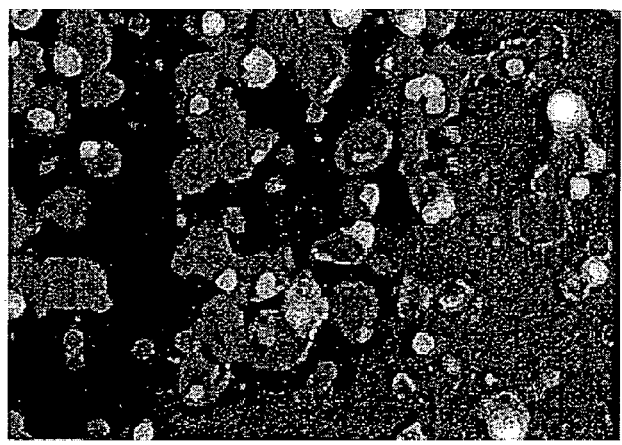
Adeno WT1
(infected human DC)
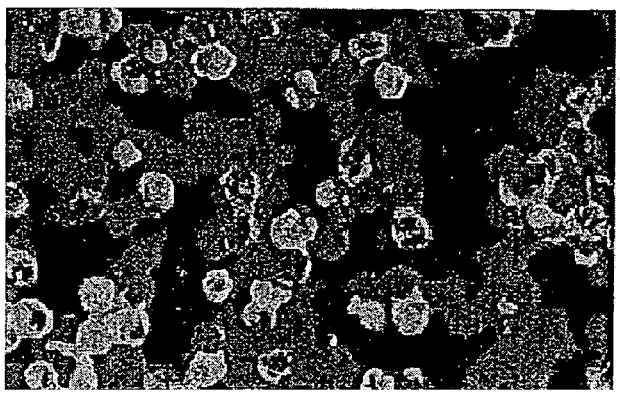
Vaccinia WT1
(infected human DC)
*Fig. 21*

WT1 can be expressed reproducible in human DC
following adeno WT1 infection and is not
induced by a control Adeno infection
Control
(Adeno EGFP
infected human DC)
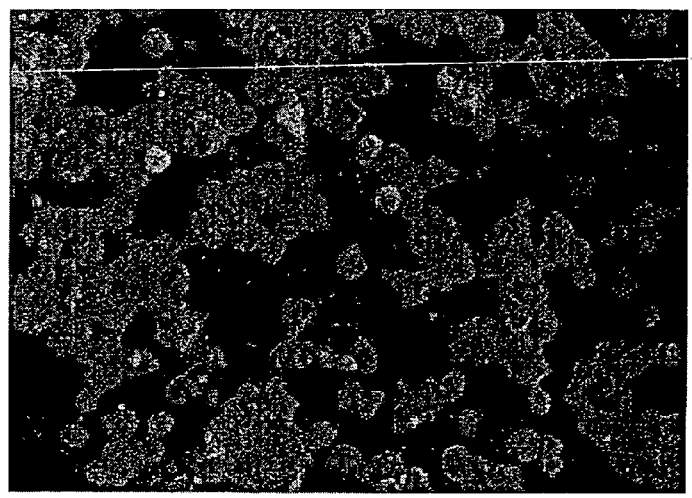
Vaccinia WT1
(infected human
DC)
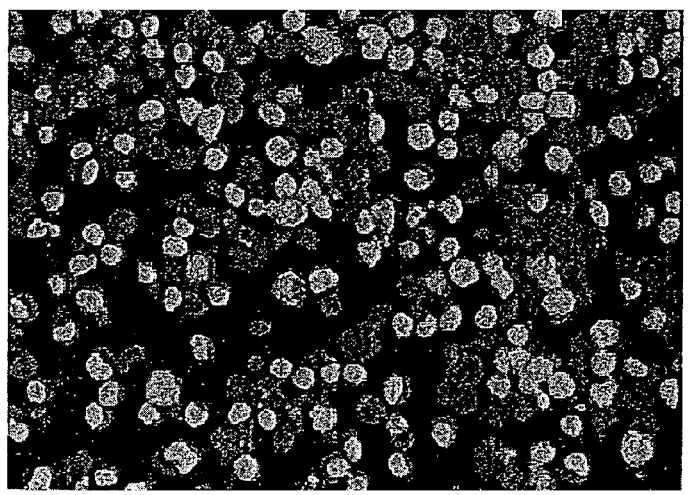
*Fig. 22*

WT-1 F cDNA 2-281

GGCTCCGACGTTCGGGACCTGAACGCACTGCTGCCGGCAGTTCCGTCCCTGGGTGGTGGTGGTGGTTGCGCACTGCCGGTTAGCGGTGCAGCACAGTGGG
CTCCGGTTCTGGACTTCGCACCGCCGGGTGCATCCGCATACGGTTCCCTGGGTGGTCCGGCACCGCCGCCGGCACCGCCGCCGCCGCCGCCGCCGCCGCC
GCACTCCTTCATCAAACAGGAACCGAGCTGGGGTGGTGCAGAACCGCACGAAGAACAGTGCCTGAGCGCATTCACCGTTCACTTCTCCGGCCAGTTCACT
GGCACAGCCGGAGCCTGTCGCTACGGGCCCTTCGGTCCTCCTCCGCCCAGCCAGGCGTCATCCGGCCAGGCCAGGATGTTTCCTAACGCGCCCTACCTGC
CCAGCTGCCTCGAGAGCCAGCCCGCTATTCGCAATCAGGGTTACAGCACGGTCACCTTCGACGGGACGCCCAGCTACGGTCACACGCCCTCGCACCATGC
GGCGCAGTTCCCCAACCACTCATTCAAGCATGAGGATCCCATGGGCCAGCAGGGCTCGCTGGGTGAGCAGCAGTACTCGGTGCCGCCCCCGGTCTATGGC
TGCCACACCCCCACCGACAGCTGCACCGGCAGCCAGGCTTTGCTGCTGAGGACGCCCTACAGCAGTGACAATTTATACCAAATGACATCCCAGCTTGAAT
GCATGACCTGGAATCAGATGAACTTAGGAGCCACCTTAAAGGGCCACAGCACAGGGTACGAGAGCGATAACCACACAACGCCCATCCTCTGCGGAGCCCA
ATACAGAATACACACGCACGGTGTCTTCAGAGGCATTCAGTGA

WT-1 F amino acid 2-281

GSDVRDLNALLPAVPSLGGGGGCALPVSGAAQWAPVLDFAPPGASAYGSLGGPAPPPAPPPPPPPPHSFIKQEPSWGGAEPHEEQCLSAFTVHFSGQFT
GTAGACRYGPFGPPPPSQASSGQARMFPNAPYLPSCLESQPAIRNQGYSTVTFDGTPSYGHTPSHHAAQFPNHSFKHEDPMGQQGSLGEQQYSVPPPVYG
CHTPTDSCTGSQALLLRTPYSSDNLYQMTSQLECMTWNQMNLGATLKGHSTGYESDNHTTPILCGAQYRIHTHGVFRGIQ

*Fig. 24*

SEQUENCE LISTING

```
<160> NUMBER OF SEQ ID NOS: 376

<210> SEQ ID NO 1
<211> LENGTH: 17
<212> TYPE: PRT
<213> ORGANISM: Homo sapien

<400> SEQUENCE: 1

Arg Asp Leu Asn Ala Leu Leu Pro Ala Val Pro Ser Leu Gly Gly Gly
 1               5                  10                  15

Gly

<210> SEQ ID NO 2
<211> LENGTH: 23
<212> TYPE: PRT
<213> ORGANISM: Homo sapien

<400> SEQUENCE: 2
```

```
Pro Ser Gln Ala Ser Ser Gly Gln Ala Arg Met Phe Pro Asn Ala Pro
 1               5                  10                  15

Tyr Leu Pro Ser Cys Leu Glu
            20

<210> SEQ ID NO 3
<211> LENGTH: 23
<212> TYPE: PRT
<213> ORGANISM: Mus musculus

<400> SEQUENCE: 3

Pro Ser Gln Ala Ser Ser Gly Gln Ala Arg Met Phe Pro Asn Ala Pro
 1               5                  10                  15

Tyr Leu Pro Ser Cys Leu Glu
            20

<210> SEQ ID NO 4
<211> LENGTH: 19
<212> TYPE: PRT
<213> ORGANISM: Homo sapien

<400> SEQUENCE: 4

Gly Ala Thr Leu Lys Gly Val Ala Ala Gly Ser Ser Ser Ser Val Lys
 1               5                  10                  15

Trp Thr Glu

<210> SEQ ID NO 5
<211> LENGTH: 22
<212> TYPE: DNA
<213> ORGANISM: Homo sapien

<400> SEQUENCE: 5
gagagtcaga cttgaaagca gt                                              22

<210> SEQ ID NO 6
<211> LENGTH: 20
<212> TYPE: DNA
<213> ORGANISM: Homo sapien

<400> SEQUENCE: 6
ctgagcctca gcaaatgggc                                                 20

<210> SEQ ID NO 7
<211> LENGTH: 27
<212> TYPE: DNA
<213> ORGANISM: Homo sapien

<400> SEQUENCE: 7
gagcatgcat gggctccgac gtgcggg                                         27

<210> SEQ ID NO 8
<211> LENGTH: 25
<212> TYPE: DNA
<213> ORGANISM: Homo sapien

<400> SEQUENCE: 8
ggggtaccca ctgaacggtc cccga                                           25

<210> SEQ ID NO 9
<211> LENGTH: 18
<212> TYPE: DNA
<213> ORGANISM: Mus musculus
```

```
<400> SEQUENCE: 9
tccgagccgc acctcatg                                              18

<210> SEQ ID NO 10
<211> LENGTH: 18
<212> TYPE: DNA
<213> ORGANISM: Mus musculus

<400> SEQUENCE: 10
gcctgggatg ctggactg                                              18

<210> SEQ ID NO 11
<211> LENGTH: 27
<212> TYPE: DNA
<213> ORGANISM: Mus musculus

<400> SEQUENCE: 11
gagcatgcga tgggttccga cgtgcgg                                    27

<210> SEQ ID NO 12
<211> LENGTH: 29
<212> TYPE: DNA
<213> ORGANISM: Mus musculus

<400> SEQUENCE: 12
ggggtacctc aaagcgccac gtggagttt                                  29

<210> SEQ ID NO 13
<211> LENGTH: 17
<212> TYPE: PRT
<213> ORGANISM: Mus musculus

<400> SEQUENCE: 13

Arg Asp Leu Asn Ala Leu Leu Pro Ala Val Ser Ser Leu Gly Gly Gly
 1               5                  10                  15

Gly

<210> SEQ ID NO 14
<211> LENGTH: 19
<212> TYPE: PRT
<213> ORGANISM: Mus musculus

<400> SEQUENCE: 14

Gly Ala Thr Leu Lys Gly Met Ala Ala Gly Ser Ser Ser Ser Val Lys
 1               5                  10                  15

Trp Thr Glu

<210> SEQ ID NO 15
<211> LENGTH: 15
<212> TYPE: PRT
<213> ORGANISM: Homo sapien

<400> SEQUENCE: 15

Arg Ile His Thr His Gly Val Phe Arg Gly Ile Gln Asp Val Arg
 1               5                  10                  15

<210> SEQ ID NO 16
<211> LENGTH: 15
<212> TYPE: PRT
<213> ORGANISM: Mus musculus

<400> SEQUENCE: 16
```

```
Arg Ile His Thr His Gly Val Phe Arg Gly Ile Gln Asp Val Arg
1               5                   10                  15

<210> SEQ ID NO 17
<211> LENGTH: 14
<212> TYPE: PRT
<213> ORGANISM: Mus musculus

<400> SEQUENCE: 17

Val Arg Arg Val Ser Gly Val Ala Pro Thr Leu Val Arg Ser
1               5                   10

<210> SEQ ID NO 18
<211> LENGTH: 14
<212> TYPE: PRT
<213> ORGANISM: Homo sapien

<400> SEQUENCE: 18

Val Arg Arg Val Pro Gly Val Ala Pro Thr Leu Val Arg Ser
1               5                   10

<210> SEQ ID NO 19
<211> LENGTH: 15
<212> TYPE: PRT
<213> ORGANISM: Homo sapien

<400> SEQUENCE: 19

Cys Gln Lys Lys Phe Ala Arg Ser Asp Glu Leu Val Arg His His
1               5                   10                  15

<210> SEQ ID NO 20
<211> LENGTH: 15
<212> TYPE: PRT
<213> ORGANISM: Mus musculus

<400> SEQUENCE: 20

Cys Gln Lys Lys Phe Ala Arg Ser Asp Glu Leu Val Arg His His
1               5                   10                  15

<210> SEQ ID NO 21
<211> LENGTH: 21
<212> TYPE: DNA
<213> ORGANISM: Mus musculus

<400> SEQUENCE: 21
cccaggctgc aataagagat a                                          21

<210> SEQ ID NO 22
<211> LENGTH: 21
<212> TYPE: DNA
<213> ORGANISM: Mus musculus

<400> SEQUENCE: 22
atgttgtgat ggcggaccaa t                                          21

<210> SEQ ID NO 23
<211> LENGTH: 20
<212> TYPE: DNA
<213> ORGANISM: Homo sapien

<400> SEQUENCE: 23
gtggggcgcc ccaggcacca                                            20

<210> SEQ ID NO 24
```

```
<211> LENGTH: 24
<212> TYPE: DNA
<213> ORGANISM: Homo sapien

<400> SEQUENCE: 24
gtccttaatg ctacgcacga tttc                                              24

<210> SEQ ID NO 25
<211> LENGTH: 21
<212> TYPE: DNA
<213> ORGANISM: Homo sapien

<400> SEQUENCE: 25
ggcatctgag accagtgaga a                                                 21

<210> SEQ ID NO 26
<211> LENGTH: 21
<212> TYPE: DNA
<213> ORGANISM: Homo sapien

<400> SEQUENCE: 26
gctgtcccac ttacagatgc a                                                 21

<210> SEQ ID NO 27
<211> LENGTH: 21
<212> TYPE: DNA
<213> ORGANISM: Homo sapien

<400> SEQUENCE: 27
tcaaagcgcc agctggagtt t                                                 21

<210> SEQ ID NO 28
<211> LENGTH: 9
<212> TYPE: PRT
<213> ORGANISM: Homo sapien

<400> SEQUENCE: 28

Ala Ala Gly Ser Ser Ser Ser Val Lys
 1               5

<210> SEQ ID NO 29
<211> LENGTH: 9
<212> TYPE: PRT
<213> ORGANISM: Homo sapien

<400> SEQUENCE: 29

Ala Ala Gln Phe Pro Asn His Ser Phe
 1               5

<210> SEQ ID NO 30
<211> LENGTH: 9
<212> TYPE: PRT
<213> ORGANISM: Homo sapien

<400> SEQUENCE: 30

Ala Glu Pro His Glu Glu Gln Cys Leu
 1               5

<210> SEQ ID NO 31
<211> LENGTH: 9
<212> TYPE: PRT
<213> ORGANISM: Homo sapien

<400> SEQUENCE: 31
```

Ala Gly Ala Cys Arg Tyr Gly Pro Phe
1               5

<210> SEQ ID NO 32
<211> LENGTH: 9
<212> TYPE: PRT
<213> ORGANISM: Homo sapien

<400> SEQUENCE: 32

Ala Gly Ser Ser Ser Val Lys Trp
1               5

<210> SEQ ID NO 33
<211> LENGTH: 9
<212> TYPE: PRT
<213> ORGANISM: Homo sapien

<400> SEQUENCE: 33

Ala Ile Arg Asn Gln Gly Tyr Ser Thr
1               5

<210> SEQ ID NO 34
<211> LENGTH: 9
<212> TYPE: PRT
<213> ORGANISM: Homo sapien

<400> SEQUENCE: 34

Ala Leu Leu Pro Ala Val Pro Ser Leu
1               5

<210> SEQ ID NO 35
<211> LENGTH: 9
<212> TYPE: PRT
<213> ORGANISM: Homo sapien

<400> SEQUENCE: 35

Ala Leu Leu Pro Ala Val Ser Ser Leu
1               5

<210> SEQ ID NO 36
<211> LENGTH: 9
<212> TYPE: PRT
<213> ORGANISM: Homo sapien

<400> SEQUENCE: 36

Ala Gln Phe Pro Asn His Ser Phe Lys
1               5

<210> SEQ ID NO 37
<211> LENGTH: 9
<212> TYPE: PRT
<213> ORGANISM: Homo sapien

<400> SEQUENCE: 37

Ala Gln Trp Ala Pro Val Leu Asp Phe
1               5

<210> SEQ ID NO 38
<211> LENGTH: 9
<212> TYPE: PRT
<213> ORGANISM: Homo sapien

<400> SEQUENCE: 38

Ala Arg Met Phe Pro Asn Ala Pro Tyr
1               5

<210> SEQ ID NO 39
<211> LENGTH: 9
<212> TYPE: PRT
<213> ORGANISM: Homo sapien

<400> SEQUENCE: 39

Ala Arg Ser Asp Glu Leu Val Arg His
1               5

<210> SEQ ID NO 40
<211> LENGTH: 9
<212> TYPE: PRT
<213> ORGANISM: Homo sapien

<400> SEQUENCE: 40

Ala Ser Ser Gly Gln Ala Arg Met Phe
1               5

<210> SEQ ID NO 41
<211> LENGTH: 9
<212> TYPE: PRT
<213> ORGANISM: Homo sapien

<400> SEQUENCE: 41

Ala Tyr Gly Ser Leu Gly Gly Pro Ala
1               5

<210> SEQ ID NO 42
<211> LENGTH: 9
<212> TYPE: PRT
<213> ORGANISM: Homo sapien

<400> SEQUENCE: 42

Ala Tyr Pro Gly Cys Asn Lys Arg Tyr
1               5

<210> SEQ ID NO 43
<211> LENGTH: 9
<212> TYPE: PRT
<213> ORGANISM: Homo sapien

<400> SEQUENCE: 43

Cys Ala Leu Pro Val Ser Gly Ala Ala
1               5

<210> SEQ ID NO 44
<211> LENGTH: 9
<212> TYPE: PRT
<213> ORGANISM: Homo sapien

<400> SEQUENCE: 44

Cys Ala Tyr Pro Gly Cys Asn Lys Arg
1               5

<210> SEQ ID NO 45
<211> LENGTH: 9
<212> TYPE: PRT
<213> ORGANISM: Homo sapien

<400> SEQUENCE: 45

Cys His Thr Pro Thr Asp Ser Cys Thr
1               5

```
<210> SEQ ID NO 46
<211> LENGTH: 9
<212> TYPE: PRT
<213> ORGANISM: Homo sapien

<400> SEQUENCE: 46

Cys Lys Thr Cys Gln Arg Lys Phe Ser
1               5

<210> SEQ ID NO 47
<211> LENGTH: 9
<212> TYPE: PRT
<213> ORGANISM: Homo sapien

<400> SEQUENCE: 47

Cys Leu Glu Ser Gln Pro Ala Ile Arg
1               5

<210> SEQ ID NO 48
<211> LENGTH: 9
<212> TYPE: PRT
<213> ORGANISM: Homo sapien

<400> SEQUENCE: 48

Cys Leu Ser Ala Phe Thr Val His Phe
1               5

<210> SEQ ID NO 49
<211> LENGTH: 9
<212> TYPE: PRT
<213> ORGANISM: Homo sapien

<400> SEQUENCE: 49

Cys Met Thr Trp Asn Gln Met Asn Leu
1               5

<210> SEQ ID NO 50
<211> LENGTH: 9
<212> TYPE: PRT
<213> ORGANISM: Homo sapien

<400> SEQUENCE: 50

Cys Arg Trp Pro Ser Cys Gln Lys Lys
1               5

<210> SEQ ID NO 51
<211> LENGTH: 9
<212> TYPE: PRT
<213> ORGANISM: Homo sapien

<400> SEQUENCE: 51

Cys Arg Tyr Gly Pro Phe Gly Pro Pro
1               5

<210> SEQ ID NO 52
<211> LENGTH: 9
<212> TYPE: PRT
<213> ORGANISM: Homo sapien

<400> SEQUENCE: 52

Cys Thr Gly Ser Gln Ala Leu Leu Leu
1               5

<210> SEQ ID NO 53
<211> LENGTH: 9
```

```
<212> TYPE: PRT
<213> ORGANISM: Homo sapien

<400> SEQUENCE: 53

Asp Glu Leu Val Arg His His Asn Met
1               5

<210> SEQ ID NO 54
<211> LENGTH: 9
<212> TYPE: PRT
<213> ORGANISM: Homo sapien

<400> SEQUENCE: 54

Asp Phe Ala Pro Pro Gly Ala Ser Ala
1               5

<210> SEQ ID NO 55
<211> LENGTH: 9
<212> TYPE: PRT
<213> ORGANISM: Homo sapien

<400> SEQUENCE: 55

Asp Phe Lys Asp Cys Glu Arg Arg Phe
1               5

<210> SEQ ID NO 56
<211> LENGTH: 9
<212> TYPE: PRT
<213> ORGANISM: Homo sapien

<400> SEQUENCE: 56

Asp Gly Thr Pro Ser Tyr Gly His Thr
1               5

<210> SEQ ID NO 57
<211> LENGTH: 9
<212> TYPE: PRT
<213> ORGANISM: Homo sapien

<400> SEQUENCE: 57

Asp His Leu Lys Thr His Thr Arg Thr
1               5

<210> SEQ ID NO 58
<211> LENGTH: 9
<212> TYPE: PRT
<213> ORGANISM: Homo sapien

<400> SEQUENCE: 58

Asp Leu Asn Ala Leu Leu Pro Ala Val
1               5

<210> SEQ ID NO 59
<211> LENGTH: 9
<212> TYPE: PRT
<213> ORGANISM: Homo sapien

<400> SEQUENCE: 59

Asp Pro Met Gly Gln Gln Gly Ser Leu
1               5

<210> SEQ ID NO 60
<211> LENGTH: 9
<212> TYPE: PRT
<213> ORGANISM: Homo sapien
```

```
<400> SEQUENCE: 60

Asp Gln Leu Lys Arg His Gln Arg Arg
1               5

<210> SEQ ID NO 61
<211> LENGTH: 9
<212> TYPE: PRT
<213> ORGANISM: Homo sapien

<400> SEQUENCE: 61

Asp Ser Cys Thr Gly Ser Gln Ala Leu
1               5

<210> SEQ ID NO 62
<211> LENGTH: 9
<212> TYPE: PRT
<213> ORGANISM: Homo sapien

<400> SEQUENCE: 62

Asp Val Arg Asp Leu Asn Ala Leu Leu
1               5

<210> SEQ ID NO 63
<211> LENGTH: 9
<212> TYPE: PRT
<213> ORGANISM: Homo sapien

<400> SEQUENCE: 63

Asp Val Arg Arg Val Pro Gly Val Ala
1               5

<210> SEQ ID NO 64
<211> LENGTH: 9
<212> TYPE: PRT
<213> ORGANISM: Homo sapien

<400> SEQUENCE: 64

Glu Asp Pro Met Gly Gln Gln Gly Ser
1               5

<210> SEQ ID NO 65
<211> LENGTH: 9
<212> TYPE: PRT
<213> ORGANISM: Homo sapien

<400> SEQUENCE: 65

Glu Glu Gln Cys Leu Ser Ala Phe Thr
1               5

<210> SEQ ID NO 66
<211> LENGTH: 9
<212> TYPE: PRT
<213> ORGANISM: Homo sapien

<400> SEQUENCE: 66

Glu Lys Pro Tyr Gln Cys Asp Phe Lys
1               5

<210> SEQ ID NO 67
<211> LENGTH: 9
<212> TYPE: PRT
<213> ORGANISM: Homo sapien

<400> SEQUENCE: 67
```

Glu Lys Arg Pro Phe Met Cys Ala Tyr
1               5

<210> SEQ ID NO 68
<211> LENGTH: 9
<212> TYPE: PRT
<213> ORGANISM: Homo sapien

<400> SEQUENCE: 68

Glu Pro His Glu Glu Gln Cys Leu Ser
1               5

<210> SEQ ID NO 69
<211> LENGTH: 9
<212> TYPE: PRT
<213> ORGANISM: Homo sapien

<400> SEQUENCE: 69

Glu Gln Cys Leu Ser Ala Phe Thr Val
1               5

<210> SEQ ID NO 70
<211> LENGTH: 9
<212> TYPE: PRT
<213> ORGANISM: Homo sapien

<400> SEQUENCE: 70

Glu Ser Asp Asn His Thr Ala Pro Ile
1               5

<210> SEQ ID NO 71
<211> LENGTH: 9
<212> TYPE: PRT
<213> ORGANISM: Homo sapien

<400> SEQUENCE: 71

Glu Ser Asp Asn His Thr Thr Pro Ile
1               5

<210> SEQ ID NO 72
<211> LENGTH: 9
<212> TYPE: PRT
<213> ORGANISM: Homo sapien

<400> SEQUENCE: 72

Glu Ser Gln Pro Ala Ile Arg Asn Gln
1               5

<210> SEQ ID NO 73
<211> LENGTH: 9
<212> TYPE: PRT
<213> ORGANISM: Homo sapien

<400> SEQUENCE: 73

Glu Thr Ser Glu Lys Arg Pro Phe Met
1               5

<210> SEQ ID NO 74
<211> LENGTH: 9
<212> TYPE: PRT
<213> ORGANISM: Homo sapien

<400> SEQUENCE: 74

Phe Ala Pro Pro Gly Ala Ser Ala Tyr

-continued

```
<210> SEQ ID NO 75
<211> LENGTH: 9
<212> TYPE: PRT
<213> ORGANISM: Homo sapien

<400> SEQUENCE: 75

Phe Ala Arg Ser Asp Glu Leu Val Arg
 1               5

<210> SEQ ID NO 76
<211> LENGTH: 9
<212> TYPE: PRT
<213> ORGANISM: Homo sapien

<400> SEQUENCE: 76

Phe Gly Pro Pro Pro Ser Gln Ala
 1               5

<210> SEQ ID NO 77
<211> LENGTH: 9
<212> TYPE: PRT
<213> ORGANISM: Homo sapien

<400> SEQUENCE: 77

Phe Lys Asp Cys Glu Arg Arg Phe Ser
 1               5

<210> SEQ ID NO 78
<211> LENGTH: 9
<212> TYPE: PRT
<213> ORGANISM: Homo sapien

<400> SEQUENCE: 78

Phe Lys Leu Ser His Leu Gln Met His
 1               5

<210> SEQ ID NO 79
<211> LENGTH: 9
<212> TYPE: PRT
<213> ORGANISM: Homo sapien

<400> SEQUENCE: 79

Phe Pro Asn Ala Pro Tyr Leu Pro Ser
 1               5

<210> SEQ ID NO 80
<211> LENGTH: 9
<212> TYPE: PRT
<213> ORGANISM: Homo sapien

<400> SEQUENCE: 80

Phe Gln Cys Lys Thr Cys Gln Arg Lys
 1               5

<210> SEQ ID NO 81
<211> LENGTH: 9
<212> TYPE: PRT
<213> ORGANISM: Homo sapien

<400> SEQUENCE: 81

Phe Arg Gly Ile Gln Asp Val Arg Arg
 1               5
```

<210> SEQ ID NO 82
<211> LENGTH: 9
<212> TYPE: PRT
<213> ORGANISM: Homo sapien

<400> SEQUENCE: 82

Phe Ser Gly Gln Phe Thr Gly Thr Ala
1               5

<210> SEQ ID NO 83
<211> LENGTH: 9
<212> TYPE: PRT
<213> ORGANISM: Homo sapien

<400> SEQUENCE: 83

Phe Ser Arg Ser Asp Gln Leu Lys Arg
1               5

<210> SEQ ID NO 84
<211> LENGTH: 9
<212> TYPE: PRT
<213> ORGANISM: Homo sapien

<400> SEQUENCE: 84

Phe Thr Gly Thr Ala Gly Ala Cys Arg
1               5

<210> SEQ ID NO 85
<211> LENGTH: 9
<212> TYPE: PRT
<213> ORGANISM: Homo sapien

<400> SEQUENCE: 85

Phe Thr Val His Phe Ser Gly Gln Phe
1               5

<210> SEQ ID NO 86
<211> LENGTH: 9
<212> TYPE: PRT
<213> ORGANISM: Homo sapien

<400> SEQUENCE: 86

Gly Ala Ala Gln Trp Ala Pro Val Leu
1               5

<210> SEQ ID NO 87
<211> LENGTH: 9
<212> TYPE: PRT
<213> ORGANISM: Homo sapien

<400> SEQUENCE: 87

Gly Ala Glu Pro His Glu Glu Gln Cys
1               5

<210> SEQ ID NO 88
<211> LENGTH: 9
<212> TYPE: PRT
<213> ORGANISM: Homo sapien

<400> SEQUENCE: 88

Gly Ala Thr Leu Lys Gly Val Ala Ala
1               5

<210> SEQ ID NO 89

```
<211> LENGTH: 9
<212> TYPE: PRT
<213> ORGANISM: Homo sapien

<400> SEQUENCE: 89

Gly Cys Ala Leu Pro Val Ser Gly Ala
1               5

<210> SEQ ID NO 90
<211> LENGTH: 9
<212> TYPE: PRT
<213> ORGANISM: Homo sapien

<400> SEQUENCE: 90

Gly Cys Asn Lys Arg Tyr Phe Lys Leu
1               5

<210> SEQ ID NO 91
<211> LENGTH: 9
<212> TYPE: PRT
<213> ORGANISM: Homo sapien

<400> SEQUENCE: 91

Gly Glu Lys Pro Tyr Gln Cys Asp Phe
1               5

<210> SEQ ID NO 92
<211> LENGTH: 9
<212> TYPE: PRT
<213> ORGANISM: Homo sapien

<400> SEQUENCE: 92

Gly Gly Gly Gly Cys Ala Leu Pro Val
1               5

<210> SEQ ID NO 93
<211> LENGTH: 9
<212> TYPE: PRT
<213> ORGANISM: Homo sapien

<400> SEQUENCE: 93

Gly Gly Pro Ala Pro Pro Pro Ala Pro
1               5

<210> SEQ ID NO 94
<211> LENGTH: 9
<212> TYPE: PRT
<213> ORGANISM: Homo sapien

<400> SEQUENCE: 94

Gly His Thr Pro Ser His His Ala Ala
1               5

<210> SEQ ID NO 95
<211> LENGTH: 9
<212> TYPE: PRT
<213> ORGANISM: Homo sapien

<400> SEQUENCE: 95

Gly Lys Thr Ser Glu Lys Pro Phe Ser
1               5

<210> SEQ ID NO 96
<211> LENGTH: 9
<212> TYPE: PRT
```

```
<213> ORGANISM: Homo sapien

<400> SEQUENCE: 96

Gly Pro Phe Gly Pro Pro Pro Pro Ser
 1               5

<210> SEQ ID NO 97
<211> LENGTH: 9
<212> TYPE: PRT
<213> ORGANISM: Homo sapien

<400> SEQUENCE: 97

Gly Pro Pro Pro Pro Ser Gln Ala Ser
 1               5

<210> SEQ ID NO 98
<211> LENGTH: 9
<212> TYPE: PRT
<213> ORGANISM: Homo sapien

<400> SEQUENCE: 98

Gly Gln Ala Arg Met Phe Pro Asn Ala
 1               5

<210> SEQ ID NO 99
<211> LENGTH: 9
<212> TYPE: PRT
<213> ORGANISM: Homo sapien

<400> SEQUENCE: 99

Gly Gln Phe Thr Gly Thr Ala Gly Ala
 1               5

<210> SEQ ID NO 100
<211> LENGTH: 9
<212> TYPE: PRT
<213> ORGANISM: Homo sapien

<400> SEQUENCE: 100

Gly Gln Ser Asn His Ser Thr Gly Tyr
 1               5

<210> SEQ ID NO 101
<211> LENGTH: 9
<212> TYPE: PRT
<213> ORGANISM: Homo sapien

<400> SEQUENCE: 101

Gly Ser Asp Val Arg Asp Leu Asn Ala
 1               5

<210> SEQ ID NO 102
<211> LENGTH: 9
<212> TYPE: PRT
<213> ORGANISM: Homo sapien

<400> SEQUENCE: 102

Gly Ser Gln Ala Leu Leu Leu Arg Thr
 1               5

<210> SEQ ID NO 103
<211> LENGTH: 9
<212> TYPE: PRT
<213> ORGANISM: Homo sapien
```

```
<400> SEQUENCE: 103

Gly Val Phe Arg Gly Ile Gln Asp Val
 1               5

<210> SEQ ID NO 104
<211> LENGTH: 9
<212> TYPE: PRT
<213> ORGANISM: Homo sapien

<400> SEQUENCE: 104

Gly Val Lys Pro Phe Gln Cys Lys Thr
 1               5

<210> SEQ ID NO 105
<211> LENGTH: 9
<212> TYPE: PRT
<213> ORGANISM: Homo sapien

<400> SEQUENCE: 105

Gly Tyr Glu Ser Asp Asn His Thr Ala
 1               5

<210> SEQ ID NO 106
<211> LENGTH: 9
<212> TYPE: PRT
<213> ORGANISM: Homo sapien

<400> SEQUENCE: 106

Gly Tyr Glu Ser Asp Asn His Thr Thr
 1               5

<210> SEQ ID NO 107
<211> LENGTH: 9
<212> TYPE: PRT
<213> ORGANISM: Homo sapien

<400> SEQUENCE: 107

His Glu Glu Gln Cys Leu Ser Ala Phe
 1               5

<210> SEQ ID NO 108
<211> LENGTH: 9
<212> TYPE: PRT
<213> ORGANISM: Homo sapien

<400> SEQUENCE: 108

His His Asn Met His Gln Arg Asn Met
 1               5

<210> SEQ ID NO 109
<211> LENGTH: 9
<212> TYPE: PRT
<213> ORGANISM: Homo sapien

<400> SEQUENCE: 109

His Gln Arg Arg His Thr Gly Val Lys
 1               5

<210> SEQ ID NO 110
<211> LENGTH: 9
<212> TYPE: PRT
<213> ORGANISM: Homo sapien

<400> SEQUENCE: 110
```

His Ser Phe Lys His Glu Asp Pro Met
1               5

<210> SEQ ID NO 111
<211> LENGTH: 9
<212> TYPE: PRT
<213> ORGANISM: Homo sapien

<400> SEQUENCE: 111

His Ser Arg Lys His Thr Gly Glu Lys
1               5

<210> SEQ ID NO 112
<211> LENGTH: 9
<212> TYPE: PRT
<213> ORGANISM: Homo sapien

<400> SEQUENCE: 112

His Thr Gly Glu Lys Pro Tyr Gln Cys
1               5

<210> SEQ ID NO 113
<211> LENGTH: 9
<212> TYPE: PRT
<213> ORGANISM: Homo sapien

<400> SEQUENCE: 113

His Thr His Gly Val Phe Arg Gly Ile
1               5

<210> SEQ ID NO 114
<211> LENGTH: 9
<212> TYPE: PRT
<213> ORGANISM: Homo sapien

<400> SEQUENCE: 114

His Thr Arg Thr His Thr Gly Lys Thr
1               5

<210> SEQ ID NO 115
<211> LENGTH: 9
<212> TYPE: PRT
<213> ORGANISM: Homo sapien

<400> SEQUENCE: 115

His Thr Thr Pro Ile Leu Cys Gly Ala
1               5

<210> SEQ ID NO 116
<211> LENGTH: 9
<212> TYPE: PRT
<213> ORGANISM: Homo sapien

<400> SEQUENCE: 116

Ile Leu Cys Gly Ala Gln Tyr Arg Ile
1               5

<210> SEQ ID NO 117
<211> LENGTH: 9
<212> TYPE: PRT
<213> ORGANISM: Homo sapien

<400> SEQUENCE: 117

Ile Arg Asn Gln Gly Tyr Ser Thr Val
1               5

<210> SEQ ID NO 118
<211> LENGTH: 9
<212> TYPE: PRT
<213> ORGANISM: Homo sapien

<400> SEQUENCE: 118

Lys Asp Cys Glu Arg Arg Phe Ser Arg
1               5

<210> SEQ ID NO 119
<211> LENGTH: 9
<212> TYPE: PRT
<213> ORGANISM: Homo sapien

<400> SEQUENCE: 119

Lys Phe Ala Arg Ser Asp Glu Leu Val
1               5

<210> SEQ ID NO 120
<211> LENGTH: 9
<212> TYPE: PRT
<213> ORGANISM: Homo sapien

<400> SEQUENCE: 120

Lys Phe Ser Arg Ser Asp His Leu Lys
1               5

<210> SEQ ID NO 121
<211> LENGTH: 9
<212> TYPE: PRT
<213> ORGANISM: Homo sapien

<400> SEQUENCE: 121

Lys His Glu Asp Pro Met Gly Gln Gln
1               5

<210> SEQ ID NO 122
<211> LENGTH: 9
<212> TYPE: PRT
<213> ORGANISM: Homo sapien

<400> SEQUENCE: 122

Lys Lys Phe Ala Arg Ser Asp Glu Leu
1               5

<210> SEQ ID NO 123
<211> LENGTH: 9
<212> TYPE: PRT
<213> ORGANISM: Homo sapien

<400> SEQUENCE: 123

Lys Pro Phe Ser Cys Arg Trp Pro Ser
1               5

<210> SEQ ID NO 124
<211> LENGTH: 9
<212> TYPE: PRT
<213> ORGANISM: Homo sapien

<400> SEQUENCE: 124

Lys Pro Tyr Gln Cys Asp Phe Lys Asp
1               5

```
<210> SEQ ID NO 125
<211> LENGTH: 9
<212> TYPE: PRT
<213> ORGANISM: Homo sapien

<400> SEQUENCE: 125

Lys Gln Glu Pro Ser Trp Gly Gly Ala
1               5

<210> SEQ ID NO 126
<211> LENGTH: 9
<212> TYPE: PRT
<213> ORGANISM: Homo sapien

<400> SEQUENCE: 126

Lys Arg His Gln Arg Arg His Thr Gly
1               5

<210> SEQ ID NO 127
<211> LENGTH: 9
<212> TYPE: PRT
<213> ORGANISM: Homo sapien

<400> SEQUENCE: 127

Lys Arg Tyr Phe Lys Leu Ser His Leu
1               5

<210> SEQ ID NO 128
<211> LENGTH: 9
<212> TYPE: PRT
<213> ORGANISM: Homo sapien

<400> SEQUENCE: 128

Lys Thr Cys Gln Arg Lys Phe Ser Arg
1               5

<210> SEQ ID NO 129
<211> LENGTH: 9
<212> TYPE: PRT
<213> ORGANISM: Homo sapien

<400> SEQUENCE: 129

Lys Thr Ser Glu Lys Pro Phe Ser Cys
1               5

<210> SEQ ID NO 130
<211> LENGTH: 9
<212> TYPE: PRT
<213> ORGANISM: Homo sapien

<400> SEQUENCE: 130

Leu Asp Phe Ala Pro Pro Gly Ala Ser
1               5

<210> SEQ ID NO 131
<211> LENGTH: 9
<212> TYPE: PRT
<213> ORGANISM: Homo sapien

<400> SEQUENCE: 131

Leu Glu Cys Met Thr Trp Asn Gln Met
1               5

<210> SEQ ID NO 132
<211> LENGTH: 9
```

```
<212> TYPE: PRT
<213> ORGANISM: Homo sapien

<400> SEQUENCE: 132

Leu Glu Ser Gln Pro Ala Ile Arg Asn
 1               5

<210> SEQ ID NO 133
<211> LENGTH: 9
<212> TYPE: PRT
<213> ORGANISM: Homo sapien

<400> SEQUENCE: 133

Leu Gly Ala Thr Leu Lys Gly Val Ala
 1               5

<210> SEQ ID NO 134
<211> LENGTH: 9
<212> TYPE: PRT
<213> ORGANISM: Homo sapien

<400> SEQUENCE: 134

Leu Gly Gly Gly Gly Gly Cys Ala Leu
 1               5

<210> SEQ ID NO 135
<211> LENGTH: 9
<212> TYPE: PRT
<213> ORGANISM: Homo sapien

<400> SEQUENCE: 135

Leu Lys Gly Val Ala Ala Gly Ser Ser
 1               5

<210> SEQ ID NO 136
<211> LENGTH: 9
<212> TYPE: PRT
<213> ORGANISM: Homo sapien

<400> SEQUENCE: 136

Leu Lys Arg His Gln Arg Arg His Thr
 1               5

<210> SEQ ID NO 137
<211> LENGTH: 9
<212> TYPE: PRT
<213> ORGANISM: Homo sapien

<400> SEQUENCE: 137

Leu Lys Thr His Thr Arg Thr His Thr
 1               5

<210> SEQ ID NO 138
<211> LENGTH: 9
<212> TYPE: PRT
<213> ORGANISM: Homo sapien

<400> SEQUENCE: 138

Leu Pro Val Ser Gly Ala Ala Gln Trp
 1               5

<210> SEQ ID NO 139
<211> LENGTH: 9
<212> TYPE: PRT
<213> ORGANISM: Homo sapien
```

```
<400> SEQUENCE: 139

Leu Gln Met His Ser Arg Lys His Thr
1               5

<210> SEQ ID NO 140
<211> LENGTH: 9
<212> TYPE: PRT
<213> ORGANISM: Homo sapien

<400> SEQUENCE: 140

Leu Arg Thr Pro Tyr Ser Ser Asp Asn
1               5

<210> SEQ ID NO 141
<211> LENGTH: 9
<212> TYPE: PRT
<213> ORGANISM: Homo sapien

<400> SEQUENCE: 141

Leu Ser His Leu Gln Met His Ser Arg
1               5

<210> SEQ ID NO 142
<211> LENGTH: 9
<212> TYPE: PRT
<213> ORGANISM: Homo sapien

<400> SEQUENCE: 142

Met Cys Ala Tyr Pro Gly Cys Asn Lys
1               5

<210> SEQ ID NO 143
<211> LENGTH: 9
<212> TYPE: PRT
<213> ORGANISM: Homo sapien

<400> SEQUENCE: 143

Met His Gln Arg Asn Met Thr Lys Leu
1               5

<210> SEQ ID NO 144
<211> LENGTH: 9
<212> TYPE: PRT
<213> ORGANISM: Homo sapien

<400> SEQUENCE: 144

Asn Ala Pro Tyr Leu Pro Ser Cys Leu
1               5

<210> SEQ ID NO 145
<211> LENGTH: 9
<212> TYPE: PRT
<213> ORGANISM: Homo sapien

<400> SEQUENCE: 145

Asn Lys Arg Tyr Phe Lys Leu Ser His
1               5

<210> SEQ ID NO 146
<211> LENGTH: 9
<212> TYPE: PRT
<213> ORGANISM: Homo sapien

<400> SEQUENCE: 146
```

Asn Leu Gly Ala Thr Leu Lys Gly Val
1               5

<210> SEQ ID NO 147
<211> LENGTH: 9
<212> TYPE: PRT
<213> ORGANISM: Homo sapien

<400> SEQUENCE: 147

Asn Leu Tyr Gln Met Thr Ser Gln Leu
1               5

<210> SEQ ID NO 148
<211> LENGTH: 9
<212> TYPE: PRT
<213> ORGANISM: Homo sapien

<400> SEQUENCE: 148

Asn Met His Gln Arg Asn Met Thr Lys
1               5

<210> SEQ ID NO 149
<211> LENGTH: 9
<212> TYPE: PRT
<213> ORGANISM: Homo sapien

<400> SEQUENCE: 149

Asn Met Thr Lys Leu Gln Leu Ala Leu
1               5

<210> SEQ ID NO 150
<211> LENGTH: 9
<212> TYPE: PRT
<213> ORGANISM: Homo sapien

<400> SEQUENCE: 150

Asn Gln Gly Tyr Ser Thr Val Thr Phe
1               5

<210> SEQ ID NO 151
<211> LENGTH: 9
<212> TYPE: PRT
<213> ORGANISM: Homo sapien

<400> SEQUENCE: 151

Asn Gln Met Asn Leu Gly Ala Thr Leu
1               5

<210> SEQ ID NO 152
<211> LENGTH: 9
<212> TYPE: PRT
<213> ORGANISM: Homo sapien

<400> SEQUENCE: 152

Pro Ala Ile Arg Asn Gln Gly Tyr Ser
1               5

<210> SEQ ID NO 153
<211> LENGTH: 9
<212> TYPE: PRT
<213> ORGANISM: Homo sapien

<400> SEQUENCE: 153

Pro Gly Ala Ser Ala Tyr Gly Ser Leu

```
1               5
```

<210> SEQ ID NO 154
<211> LENGTH: 9
<212> TYPE: PRT
<213> ORGANISM: Homo sapien

<400> SEQUENCE: 154

```
Pro His Glu Glu Gln Cys Leu Ser Ala
1               5
```

<210> SEQ ID NO 155
<211> LENGTH: 9
<212> TYPE: PRT
<213> ORGANISM: Homo sapien

<400> SEQUENCE: 155

```
Pro Ile Leu Cys Gly Ala Gln Tyr Arg
1               5
```

<210> SEQ ID NO 156
<211> LENGTH: 9
<212> TYPE: PRT
<213> ORGANISM: Homo sapien

<400> SEQUENCE: 156

```
Pro Pro Pro Pro His Ser Phe Ile Lys
1               5
```

<210> SEQ ID NO 157
<211> LENGTH: 9
<212> TYPE: PRT
<213> ORGANISM: Homo sapien

<400> SEQUENCE: 157

```
Pro Pro Pro Pro Pro His Ser Phe Ile
1               5
```

<210> SEQ ID NO 158
<211> LENGTH: 9
<212> TYPE: PRT
<213> ORGANISM: Homo sapien

<400> SEQUENCE: 158

```
Pro Pro Pro Pro Pro Pro His Ser Phe
1               5
```

<210> SEQ ID NO 159
<211> LENGTH: 9
<212> TYPE: PRT
<213> ORGANISM: Homo sapien

<400> SEQUENCE: 159

```
Pro Ser Cys Gln Lys Lys Phe Ala Arg
1               5
```

<210> SEQ ID NO 160
<211> LENGTH: 9
<212> TYPE: PRT
<213> ORGANISM: Homo sapien

<400> SEQUENCE: 160

```
Gln Ala Leu Leu Leu Arg Thr Pro Tyr
1               5
```

```
<210> SEQ ID NO 161
<211> LENGTH: 9
<212> TYPE: PRT
<213> ORGANISM: Homo sapien

<400> SEQUENCE: 161

Gln Ala Ser Ser Gly Gln Ala Arg Met
1               5

<210> SEQ ID NO 162
<211> LENGTH: 9
<212> TYPE: PRT
<213> ORGANISM: Homo sapien

<400> SEQUENCE: 162

Gln Cys Asp Phe Lys Asp Cys Glu Arg
1               5

<210> SEQ ID NO 163
<211> LENGTH: 9
<212> TYPE: PRT
<213> ORGANISM: Homo sapien

<400> SEQUENCE: 163

Gln Cys Lys Thr Cys Gln Arg Lys Phe
1               5

<210> SEQ ID NO 164
<211> LENGTH: 9
<212> TYPE: PRT
<213> ORGANISM: Homo sapien

<400> SEQUENCE: 164

Gln Asp Val Arg Arg Val Pro Gly Val
1               5

<210> SEQ ID NO 165
<211> LENGTH: 9
<212> TYPE: PRT
<213> ORGANISM: Homo sapien

<400> SEQUENCE: 165

Gln Phe Thr Gly Thr Ala Gly Ala Cys
1               5

<210> SEQ ID NO 166
<211> LENGTH: 9
<212> TYPE: PRT
<213> ORGANISM: Homo sapien

<400> SEQUENCE: 166

Gln Gly Ser Leu Gly Glu Gln Gln Tyr
1               5

<210> SEQ ID NO 167
<211> LENGTH: 9
<212> TYPE: PRT
<213> ORGANISM: Homo sapien

<400> SEQUENCE: 167

Gln Leu Glu Cys Met Thr Trp Asn Gln
1               5

<210> SEQ ID NO 168
```

```
<211> LENGTH: 9
<212> TYPE: PRT
<213> ORGANISM: Homo sapien

<400> SEQUENCE: 168

Gln Met Asn Leu Gly Ala Thr Leu Lys
1               5

<210> SEQ ID NO 169
<211> LENGTH: 9
<212> TYPE: PRT
<213> ORGANISM: Homo sapien

<400> SEQUENCE: 169

Gln Met Thr Ser Gln Leu Glu Cys Met
1               5

<210> SEQ ID NO 170
<211> LENGTH: 9
<212> TYPE: PRT
<213> ORGANISM: Homo sapien

<400> SEQUENCE: 170

Gln Pro Ala Ile Arg Asn Gln Gly Tyr
1               5

<210> SEQ ID NO 171
<211> LENGTH: 9
<212> TYPE: PRT
<213> ORGANISM: Homo sapien

<400> SEQUENCE: 171

Gln Gln Tyr Ser Val Pro Pro Pro Val
1               5

<210> SEQ ID NO 172
<211> LENGTH: 9
<212> TYPE: PRT
<213> ORGANISM: Homo sapien

<400> SEQUENCE: 172

Gln Arg Lys Phe Ser Arg Ser Asp His
1               5

<210> SEQ ID NO 173
<211> LENGTH: 9
<212> TYPE: PRT
<213> ORGANISM: Homo sapien

<400> SEQUENCE: 173

Gln Arg Asn Met Thr Lys Leu Gln Leu
1               5

<210> SEQ ID NO 174
<211> LENGTH: 9
<212> TYPE: PRT
<213> ORGANISM: Homo sapien

<400> SEQUENCE: 174

Gln Trp Ala Pro Val Leu Asp Phe Ala
1               5

<210> SEQ ID NO 175
<211> LENGTH: 9
<212> TYPE: PRT
```

```
<213> ORGANISM: Homo sapien

<400> SEQUENCE: 175

Gln Tyr Arg Ile His Thr His Gly Val
 1               5

<210> SEQ ID NO 176
<211> LENGTH: 9
<212> TYPE: PRT
<213> ORGANISM: Homo sapien

<400> SEQUENCE: 176

Gln Tyr Ser Val Pro Pro Pro Val Tyr
 1               5

<210> SEQ ID NO 177
<211> LENGTH: 9
<212> TYPE: PRT
<213> ORGANISM: Homo sapien

<400> SEQUENCE: 177

Arg Asp Leu Asn Ala Leu Leu Pro Ala
 1               5

<210> SEQ ID NO 178
<211> LENGTH: 9
<212> TYPE: PRT
<213> ORGANISM: Homo sapien

<400> SEQUENCE: 178

Arg Phe Ser Arg Ser Asp Gln Leu Lys
 1               5

<210> SEQ ID NO 179
<211> LENGTH: 9
<212> TYPE: PRT
<213> ORGANISM: Homo sapien

<400> SEQUENCE: 179

Arg Gly Ile Gln Asp Val Arg Arg Val
 1               5

<210> SEQ ID NO 180
<211> LENGTH: 9
<212> TYPE: PRT
<213> ORGANISM: Homo sapien

<400> SEQUENCE: 180

Arg His His Asn Met His Gln Arg Asn
 1               5

<210> SEQ ID NO 181
<211> LENGTH: 9
<212> TYPE: PRT
<213> ORGANISM: Homo sapien

<400> SEQUENCE: 181

Arg His Gln Arg Arg His Thr Gly Val
 1               5

<210> SEQ ID NO 182
<211> LENGTH: 9
<212> TYPE: PRT
<213> ORGANISM: Homo sapien
```

```
<400> SEQUENCE: 182

Arg Ile His Thr His Gly Val Phe Arg
1               5

<210> SEQ ID NO 183
<211> LENGTH: 9
<212> TYPE: PRT
<213> ORGANISM: Homo sapien

<400> SEQUENCE: 183

Arg Lys Phe Ser Arg Ser Asp His Leu
1               5

<210> SEQ ID NO 184
<211> LENGTH: 9
<212> TYPE: PRT
<213> ORGANISM: Homo sapien

<400> SEQUENCE: 184

Arg Lys His Thr Gly Glu Lys Pro Tyr
1               5

<210> SEQ ID NO 185
<211> LENGTH: 9
<212> TYPE: PRT
<213> ORGANISM: Homo sapien

<400> SEQUENCE: 185

Arg Met Phe Pro Asn Ala Pro Tyr Leu
1               5

<210> SEQ ID NO 186
<211> LENGTH: 9
<212> TYPE: PRT
<213> ORGANISM: Homo sapien

<400> SEQUENCE: 186

Arg Asn Met Thr Lys Leu Gln Leu Ala
1               5

<210> SEQ ID NO 187
<211> LENGTH: 9
<212> TYPE: PRT
<213> ORGANISM: Homo sapien

<400> SEQUENCE: 187

Arg Arg Phe Ser Arg Ser Asp Gln Leu
1               5

<210> SEQ ID NO 188
<211> LENGTH: 9
<212> TYPE: PRT
<213> ORGANISM: Homo sapien

<400> SEQUENCE: 188

Arg Arg His Thr Gly Val Lys Pro Phe
1               5

<210> SEQ ID NO 189
<211> LENGTH: 9
<212> TYPE: PRT
<213> ORGANISM: Homo sapien

<400> SEQUENCE: 189
```

Arg Arg Val Pro Gly Val Ala Pro Thr
1               5

<210> SEQ ID NO 190
<211> LENGTH: 9
<212> TYPE: PRT
<213> ORGANISM: Homo sapien

<400> SEQUENCE: 190

Arg Ser Ala Ser Glu Thr Ser Glu Lys
1               5

<210> SEQ ID NO 191
<211> LENGTH: 9
<212> TYPE: PRT
<213> ORGANISM: Homo sapien

<400> SEQUENCE: 191

Arg Ser Asp Glu Leu Val Arg His His
1               5

<210> SEQ ID NO 192
<211> LENGTH: 9
<212> TYPE: PRT
<213> ORGANISM: Homo sapien

<400> SEQUENCE: 192

Arg Ser Asp His Leu Lys Thr His Thr
1               5

<210> SEQ ID NO 193
<211> LENGTH: 9
<212> TYPE: PRT
<213> ORGANISM: Homo sapien

<400> SEQUENCE: 193

Arg Ser Asp Gln Leu Lys Arg His Gln
1               5

<210> SEQ ID NO 194
<211> LENGTH: 9
<212> TYPE: PRT
<213> ORGANISM: Homo sapien

<400> SEQUENCE: 194

Arg Thr Pro Tyr Ser Ser Asp Asn Leu
1               5

<210> SEQ ID NO 195
<211> LENGTH: 9
<212> TYPE: PRT
<213> ORGANISM: Homo sapien

<400> SEQUENCE: 195

Arg Val Pro Gly Val Ala Pro Thr Leu
1               5

<210> SEQ ID NO 196
<211> LENGTH: 9
<212> TYPE: PRT
<213> ORGANISM: Homo sapien

<400> SEQUENCE: 196

Arg Trp Pro Ser Cys Gln Lys Lys Phe
1               5

```
<210> SEQ ID NO 197
<211> LENGTH: 9
<212> TYPE: PRT
<213> ORGANISM: Homo sapien

<400> SEQUENCE: 197

Ser Ala Ser Glu Thr Ser Glu Lys Arg
1               5

<210> SEQ ID NO 198
<211> LENGTH: 9
<212> TYPE: PRT
<213> ORGANISM: Homo sapien

<400> SEQUENCE: 198

Ser Cys Leu Glu Ser Gln Pro Ala Ile
1               5

<210> SEQ ID NO 199
<211> LENGTH: 9
<212> TYPE: PRT
<213> ORGANISM: Homo sapien

<400> SEQUENCE: 199

Ser Cys Leu Glu Ser Gln Pro Thr Ile
1               5

<210> SEQ ID NO 200
<211> LENGTH: 9
<212> TYPE: PRT
<213> ORGANISM: Homo sapien

<400> SEQUENCE: 200

Ser Cys Gln Lys Lys Phe Ala Arg Ser
1               5

<210> SEQ ID NO 201
<211> LENGTH: 9
<212> TYPE: PRT
<213> ORGANISM: Homo sapien

<400> SEQUENCE: 201

Ser Cys Arg Trp Pro Ser Cys Gln Lys
1               5

<210> SEQ ID NO 202
<211> LENGTH: 9
<212> TYPE: PRT
<213> ORGANISM: Homo sapien

<400> SEQUENCE: 202

Ser Cys Thr Gly Ser Gln Ala Leu Leu
1               5

<210> SEQ ID NO 203
<211> LENGTH: 9
<212> TYPE: PRT
<213> ORGANISM: Homo sapien

<400> SEQUENCE: 203

Ser Asp Glu Leu Val Arg His His Asn
1               5
```

```
<210> SEQ ID NO 204
<211> LENGTH: 9
<212> TYPE: PRT
<213> ORGANISM: Homo sapien

<400> SEQUENCE: 204

Ser Asp Asn His Thr Thr Pro Ile Leu
1               5

<210> SEQ ID NO 205
<211> LENGTH: 9
<212> TYPE: PRT
<213> ORGANISM: Homo sapien

<400> SEQUENCE: 205

Ser Asp Asn Leu Tyr Gln Met Thr Ser
1               5

<210> SEQ ID NO 206
<211> LENGTH: 9
<212> TYPE: PRT
<213> ORGANISM: Homo sapien

<400> SEQUENCE: 206

Ser Asp Val Arg Asp Leu Asn Ala Leu
1               5

<210> SEQ ID NO 207
<211> LENGTH: 9
<212> TYPE: PRT
<213> ORGANISM: Homo sapien

<400> SEQUENCE: 207

Ser Glu Lys Pro Phe Ser Cys Arg Trp
1               5

<210> SEQ ID NO 208
<211> LENGTH: 9
<212> TYPE: PRT
<213> ORGANISM: Homo sapien

<400> SEQUENCE: 208

Ser Glu Lys Arg Pro Phe Met Cys Ala
1               5

<210> SEQ ID NO 209
<211> LENGTH: 9
<212> TYPE: PRT
<213> ORGANISM: Homo sapien

<400> SEQUENCE: 209

Ser Glu Thr Ser Glu Lys Arg Pro Phe
1               5

<210> SEQ ID NO 210
<211> LENGTH: 9
<212> TYPE: PRT
<213> ORGANISM: Homo sapien

<400> SEQUENCE: 210

Ser Phe Ile Lys Gln Glu Pro Ser Trp
1               5

<210> SEQ ID NO 211
<211> LENGTH: 9
```

```
<212> TYPE: PRT
<213> ORGANISM: Homo sapien

<400> SEQUENCE: 211

Ser Gly Ala Ala Gln Trp Ala Pro Val
1               5

<210> SEQ ID NO 212
<211> LENGTH: 9
<212> TYPE: PRT
<213> ORGANISM: Homo sapien

<400> SEQUENCE: 212

Ser Gly Gln Ala Arg Met Phe Pro Asn
1               5

<210> SEQ ID NO 213
<211> LENGTH: 9
<212> TYPE: PRT
<213> ORGANISM: Homo sapien

<400> SEQUENCE: 213

Ser His His Ala Ala Gln Phe Pro Asn
1               5

<210> SEQ ID NO 214
<211> LENGTH: 9
<212> TYPE: PRT
<213> ORGANISM: Homo sapien

<400> SEQUENCE: 214

Ser Leu Gly Glu Gln Gln Tyr Ser Val
1               5

<210> SEQ ID NO 215
<211> LENGTH: 9
<212> TYPE: PRT
<213> ORGANISM: Homo sapien

<400> SEQUENCE: 215

Ser Leu Gly Gly Gly Gly Gly Cys Ala
1               5

<210> SEQ ID NO 216
<211> LENGTH: 9
<212> TYPE: PRT
<213> ORGANISM: Homo sapien

<400> SEQUENCE: 216

Ser Gln Ala Ser Ser Gly Gln Ala Arg
1               5

<210> SEQ ID NO 217
<211> LENGTH: 9
<212> TYPE: PRT
<213> ORGANISM: Homo sapien

<400> SEQUENCE: 217

Ser Ser Asp Asn Leu Tyr Gln Met Thr
1               5

<210> SEQ ID NO 218
<211> LENGTH: 9
<212> TYPE: PRT
<213> ORGANISM: Homo sapien
```

```
<400> SEQUENCE: 218

Ser Val Pro Pro Val Tyr Gly Cys
1               5

<210> SEQ ID NO 219
<211> LENGTH: 9
<212> TYPE: PRT
<213> ORGANISM: Homo sapien

<400> SEQUENCE: 219

Thr Cys Gln Arg Lys Phe Ser Arg Ser
1               5

<210> SEQ ID NO 220
<211> LENGTH: 9
<212> TYPE: PRT
<213> ORGANISM: Homo sapien

<400> SEQUENCE: 220

Thr Asp Ser Cys Thr Gly Ser Gln Ala
1               5

<210> SEQ ID NO 221
<211> LENGTH: 9
<212> TYPE: PRT
<213> ORGANISM: Homo sapien

<400> SEQUENCE: 221

Thr Glu Gly Gln Ser Asn His Ser Thr
1               5

<210> SEQ ID NO 222
<211> LENGTH: 9
<212> TYPE: PRT
<213> ORGANISM: Homo sapien

<400> SEQUENCE: 222

Thr Gly Lys Thr Ser Glu Lys Pro Phe
1               5

<210> SEQ ID NO 223
<211> LENGTH: 9
<212> TYPE: PRT
<213> ORGANISM: Homo sapien

<400> SEQUENCE: 223

Thr Gly Ser Gln Ala Leu Leu Leu Arg
1               5

<210> SEQ ID NO 224
<211> LENGTH: 9
<212> TYPE: PRT
<213> ORGANISM: Homo sapien

<400> SEQUENCE: 224

Thr Gly Thr Ala Gly Ala Cys Arg Tyr
1               5

<210> SEQ ID NO 225
<211> LENGTH: 9
<212> TYPE: PRT
<213> ORGANISM: Homo sapien

<400> SEQUENCE: 225
```

```
Thr Gly Tyr Glu Ser Asp Asn His Thr
 1               5

<210> SEQ ID NO 226
<211> LENGTH: 9
<212> TYPE: PRT
<213> ORGANISM: Homo sapien

<400> SEQUENCE: 226

Thr Leu Val Arg Ser Ala Ser Glu Thr
 1               5

<210> SEQ ID NO 227
<211> LENGTH: 9
<212> TYPE: PRT
<213> ORGANISM: Homo sapien

<400> SEQUENCE: 227

Thr Pro Ile Leu Cys Gly Ala Gln Tyr
 1               5

<210> SEQ ID NO 228
<211> LENGTH: 9
<212> TYPE: PRT
<213> ORGANISM: Homo sapien

<400> SEQUENCE: 228

Thr Pro Ser His His Ala Ala Gln Phe
 1               5

<210> SEQ ID NO 229
<211> LENGTH: 9
<212> TYPE: PRT
<213> ORGANISM: Homo sapien

<400> SEQUENCE: 229

Thr Pro Ser Tyr Gly His Thr Pro Ser
 1               5

<210> SEQ ID NO 230
<211> LENGTH: 9
<212> TYPE: PRT
<213> ORGANISM: Homo sapien

<400> SEQUENCE: 230

Thr Pro Thr Asp Ser Cys Thr Gly Ser
 1               5

<210> SEQ ID NO 231
<211> LENGTH: 9
<212> TYPE: PRT
<213> ORGANISM: Homo sapien

<400> SEQUENCE: 231

Thr Pro Tyr Ser Ser Asp Asn Leu Tyr
 1               5

<210> SEQ ID NO 232
<211> LENGTH: 9
<212> TYPE: PRT
<213> ORGANISM: Homo sapien

<400> SEQUENCE: 232

Thr Ser Glu Lys Pro Phe Ser Cys Arg
```

```
<210> SEQ ID NO 233
<211> LENGTH: 9
<212> TYPE: PRT
<213> ORGANISM: Homo sapien

<400> SEQUENCE: 233

Thr Ser Glu Lys Arg Pro Phe Met Cys
 1               5

<210> SEQ ID NO 234
<211> LENGTH: 9
<212> TYPE: PRT
<213> ORGANISM: Homo sapien

<400> SEQUENCE: 234

Thr Ser Gln Leu Glu Cys Met Thr Trp
 1               5

<210> SEQ ID NO 235
<211> LENGTH: 9
<212> TYPE: PRT
<213> ORGANISM: Homo sapien

<400> SEQUENCE: 235

Thr Val His Phe Ser Gly Gln Phe Thr
 1               5

<210> SEQ ID NO 236
<211> LENGTH: 9
<212> TYPE: PRT
<213> ORGANISM: Homo sapien

<400> SEQUENCE: 236

Val Ala Ala Gly Ser Ser Ser Ser Val
 1               5

<210> SEQ ID NO 237
<211> LENGTH: 9
<212> TYPE: PRT
<213> ORGANISM: Homo sapien

<400> SEQUENCE: 237

Val Ala Pro Thr Leu Val Arg Ser Ala
 1               5

<210> SEQ ID NO 238
<211> LENGTH: 9
<212> TYPE: PRT
<213> ORGANISM: Homo sapien

<400> SEQUENCE: 238

Val Phe Arg Gly Ile Gln Asp Val Arg
 1               5

<210> SEQ ID NO 239
<211> LENGTH: 9
<212> TYPE: PRT
<213> ORGANISM: Homo sapien

<400> SEQUENCE: 239

Val Lys Pro Phe Gln Cys Lys Thr Cys
 1               5
```

```
<210> SEQ ID NO 240
<211> LENGTH: 9
<212> TYPE: PRT
<213> ORGANISM: Homo sapien

<400> SEQUENCE: 240

Val Lys Trp Thr Glu Gly Gln Ser Asn
1               5

<210> SEQ ID NO 241
<211> LENGTH: 9
<212> TYPE: PRT
<213> ORGANISM: Homo sapien

<400> SEQUENCE: 241

Val Leu Asp Phe Ala Pro Pro Gly Ala
1               5

<210> SEQ ID NO 242
<211> LENGTH: 9
<212> TYPE: PRT
<213> ORGANISM: Homo sapien

<400> SEQUENCE: 242

Val Pro Gly Val Ala Pro Thr Leu Val
1               5

<210> SEQ ID NO 243
<211> LENGTH: 9
<212> TYPE: PRT
<213> ORGANISM: Homo sapien

<400> SEQUENCE: 243

Val Arg His His Asn Met His Gln Arg
1               5

<210> SEQ ID NO 244
<211> LENGTH: 9
<212> TYPE: PRT
<213> ORGANISM: Homo sapien

<400> SEQUENCE: 244

Val Thr Phe Asp Gly Thr Pro Ser Tyr
1               5

<210> SEQ ID NO 245
<211> LENGTH: 9
<212> TYPE: PRT
<213> ORGANISM: Homo sapien

<400> SEQUENCE: 245

Trp Asn Gln Met Asn Leu Gly Ala Thr
1               5

<210> SEQ ID NO 246
<211> LENGTH: 9
<212> TYPE: PRT
<213> ORGANISM: Homo sapien

<400> SEQUENCE: 246

Trp Pro Ser Cys Gln Lys Lys Phe Ala
1               5

<210> SEQ ID NO 247
```

```
<211> LENGTH: 9
<212> TYPE: PRT
<213> ORGANISM: Homo sapien

<400> SEQUENCE: 247

Trp Thr Glu Gly Gln Ser Asn His Ser
1               5

<210> SEQ ID NO 248
<211> LENGTH: 9
<212> TYPE: PRT
<213> ORGANISM: Homo sapien

<400> SEQUENCE: 248

Tyr Phe Lys Leu Ser His Leu Gln Met
1               5

<210> SEQ ID NO 249
<211> LENGTH: 9
<212> TYPE: PRT
<213> ORGANISM: Homo sapien

<400> SEQUENCE: 249

Tyr Gly His Thr Pro Ser His His Ala
1               5

<210> SEQ ID NO 250
<211> LENGTH: 9
<212> TYPE: PRT
<213> ORGANISM: Homo sapien

<400> SEQUENCE: 250

Tyr Pro Gly Cys Asn Lys Arg Tyr Phe
1               5

<210> SEQ ID NO 251
<211> LENGTH: 9
<212> TYPE: PRT
<213> ORGANISM: Homo sapien

<400> SEQUENCE: 251

Tyr Gln Met Thr Ser Gln Leu Glu Cys
1               5

<210> SEQ ID NO 252
<211> LENGTH: 9
<212> TYPE: PRT
<213> ORGANISM: Homo sapien

<400> SEQUENCE: 252

Tyr Arg Ile His Thr His Gly Val Phe
1               5

<210> SEQ ID NO 253
<211> LENGTH: 9
<212> TYPE: PRT
<213> ORGANISM: Homo sapien

<400> SEQUENCE: 253

Tyr Ser Ser Asp Asn Leu Tyr Gln Met
1               5

<210> SEQ ID NO 254
<211> LENGTH: 9
<212> TYPE: PRT
```

-continued

```
<213> ORGANISM: Mus musculus

<400> SEQUENCE: 254

Ala Glu Pro His Glu Glu Gln Cys Leu
 1               5

<210> SEQ ID NO 255
<211> LENGTH: 9
<212> TYPE: PRT
<213> ORGANISM: Mus musculus

<400> SEQUENCE: 255

Ala Leu Leu Pro Ala Val Ser Ser Leu
 1               5

<210> SEQ ID NO 256
<211> LENGTH: 9
<212> TYPE: PRT
<213> ORGANISM: Mus musculus

<400> SEQUENCE: 256

Ala Tyr Gly Ser Leu Gly Gly Pro Ala
 1               5

<210> SEQ ID NO 257
<211> LENGTH: 9
<212> TYPE: PRT
<213> ORGANISM: Mus musculus

<400> SEQUENCE: 257

Ala Tyr Pro Gly Cys Asn Lys Arg Tyr
 1               5

<210> SEQ ID NO 258
<211> LENGTH: 9
<212> TYPE: PRT
<213> ORGANISM: Mus musculus

<400> SEQUENCE: 258

Cys Met Thr Trp Asn Gln Met Asn Leu
 1               5

<210> SEQ ID NO 259
<211> LENGTH: 9
<212> TYPE: PRT
<213> ORGANISM: Mus musculus

<400> SEQUENCE: 259

Cys Thr Gly Ser Gln Ala Leu Leu Leu
 1               5

<210> SEQ ID NO 260
<211> LENGTH: 9
<212> TYPE: PRT
<213> ORGANISM: Mus musculus

<400> SEQUENCE: 260

Asp Gly Ala Pro Ser Tyr Gly His Thr
 1               5

<210> SEQ ID NO 261
<211> LENGTH: 9
<212> TYPE: PRT
<213> ORGANISM: Mus musculus
```

```
<400> SEQUENCE: 261

Asp Leu Asn Ala Leu Leu Pro Ala Val
1               5

<210> SEQ ID NO 262
<211> LENGTH: 9
<212> TYPE: PRT
<213> ORGANISM: Mus musculus

<400> SEQUENCE: 262

Asp Pro Met Gly Gln Gln Gly Ser Leu
1               5

<210> SEQ ID NO 263
<211> LENGTH: 9
<212> TYPE: PRT
<213> ORGANISM: Mus musculus

<400> SEQUENCE: 263

Asp Ser Cys Thr Gly Ser Gln Ala Leu
1               5

<210> SEQ ID NO 264
<211> LENGTH: 9
<212> TYPE: PRT
<213> ORGANISM: Mus musculus

<400> SEQUENCE: 264

Asp Val Arg Asp Leu Asn Ala Leu Leu
1               5

<210> SEQ ID NO 265
<211> LENGTH: 9
<212> TYPE: PRT
<213> ORGANISM: Mus musculus

<400> SEQUENCE: 265

Glu Gln Cys Leu Ser Ala Phe Thr Leu
1               5

<210> SEQ ID NO 266
<211> LENGTH: 9
<212> TYPE: PRT
<213> ORGANISM: Mus musculus

<400> SEQUENCE: 266

Glu Ser Asp Asn His Thr Ala Pro Ile
1               5

<210> SEQ ID NO 267
<211> LENGTH: 9
<212> TYPE: PRT
<213> ORGANISM: Mus musculus

<400> SEQUENCE: 267

Phe Pro Asn Ala Pro Tyr Leu Pro Ser
1               5

<210> SEQ ID NO 268
<211> LENGTH: 9
<212> TYPE: PRT
<213> ORGANISM: Mus musculus

<400> SEQUENCE: 268
```

Gly Cys Asn Lys Arg Tyr Phe Lys Leu
1               5

<210> SEQ ID NO 269
<211> LENGTH: 9
<212> TYPE: PRT
<213> ORGANISM: Mus musculus

<400> SEQUENCE: 269

Gly Gln Ala Arg Met Phe Pro Asn Ala
1               5

<210> SEQ ID NO 270
<211> LENGTH: 9
<212> TYPE: PRT
<213> ORGANISM: Mus musculus

<400> SEQUENCE: 270

Gly Val Phe Arg Gly Ile Gln Asp Val
1               5

<210> SEQ ID NO 271
<211> LENGTH: 9
<212> TYPE: PRT
<213> ORGANISM: Mus musculus

<400> SEQUENCE: 271

Gly Tyr Glu Ser Asp Asn His Thr Ala
1               5

<210> SEQ ID NO 272
<211> LENGTH: 9
<212> TYPE: PRT
<213> ORGANISM: Mus musculus

<400> SEQUENCE: 272

His Ser Phe Lys His Glu Asp Pro Met
1               5

<210> SEQ ID NO 273
<211> LENGTH: 9
<212> TYPE: PRT
<213> ORGANISM: Mus musculus

<400> SEQUENCE: 273

His Thr His Gly Val Phe Arg Gly Ile
1               5

<210> SEQ ID NO 274
<211> LENGTH: 9
<212> TYPE: PRT
<213> ORGANISM: Mus musculus

<400> SEQUENCE: 274

Ile Leu Cys Gly Ala Gln Tyr Arg Ile
1               5

<210> SEQ ID NO 275
<211> LENGTH: 9
<212> TYPE: PRT
<213> ORGANISM: Mus musculus

<400> SEQUENCE: 275

Lys Phe Ala Arg Ser Asp Glu Leu Val
1               5

<210> SEQ ID NO 276
<211> LENGTH: 9
<212> TYPE: PRT
<213> ORGANISM: Mus musculus

<400> SEQUENCE: 276

Lys Arg Tyr Phe Lys Leu Ser His Leu
1               5

<210> SEQ ID NO 277
<211> LENGTH: 9
<212> TYPE: PRT
<213> ORGANISM: Mus musculus

<400> SEQUENCE: 277

Lys Thr Ser Glu Lys Pro Phe Ser Cys
1               5

<210> SEQ ID NO 278
<211> LENGTH: 9
<212> TYPE: PRT
<213> ORGANISM: Mus musculus

<400> SEQUENCE: 278

Leu Glu Cys Met Thr Trp Asn Gln Met
1               5

<210> SEQ ID NO 279
<211> LENGTH: 9
<212> TYPE: PRT
<213> ORGANISM: Mus musculus

<400> SEQUENCE: 279

Leu Gly Gly Gly Gly Cys Gly Leu
1               5

<210> SEQ ID NO 280
<211> LENGTH: 9
<212> TYPE: PRT
<213> ORGANISM: Mus musculus

<400> SEQUENCE: 280

Leu Gln Met His Ser Arg Lys His Thr
1               5

<210> SEQ ID NO 281
<211> LENGTH: 9
<212> TYPE: PRT
<213> ORGANISM: Mus musculus

<400> SEQUENCE: 281

Met His Gln Arg Asn Met Thr Lys Leu
1               5

<210> SEQ ID NO 282
<211> LENGTH: 9
<212> TYPE: PRT
<213> ORGANISM: Mus musculus

<400> SEQUENCE: 282

Asn Ala Pro Tyr Leu Pro Ser Cys Leu
1               5

```
<210> SEQ ID NO 283
<211> LENGTH: 9
<212> TYPE: PRT
<213> ORGANISM: Mus musculus

<400> SEQUENCE: 283

Asn Leu Gly Ala Thr Leu Lys Gly Met
1               5

<210> SEQ ID NO 284
<211> LENGTH: 9
<212> TYPE: PRT
<213> ORGANISM: Mus musculus

<400> SEQUENCE: 284

Asn Leu Tyr Gln Met Thr Ser Gln Leu
1               5

<210> SEQ ID NO 285
<211> LENGTH: 9
<212> TYPE: PRT
<213> ORGANISM: Mus musculus

<400> SEQUENCE: 285

Asn Met Thr Lys Leu His Val Ala Leu
1               5

<210> SEQ ID NO 286
<211> LENGTH: 9
<212> TYPE: PRT
<213> ORGANISM: Mus musculus

<400> SEQUENCE: 286

Asn Gln Met Asn Leu Gly Ala Thr Leu
1               5

<210> SEQ ID NO 287
<211> LENGTH: 9
<212> TYPE: PRT
<213> ORGANISM: Mus musculus

<400> SEQUENCE: 287

Pro Gly Ala Ser Ala Tyr Gly Ser Leu
1               5

<210> SEQ ID NO 288
<211> LENGTH: 9
<212> TYPE: PRT
<213> ORGANISM: Mus musculus

<400> SEQUENCE: 288

Gln Ala Ser Ser Gly Gln Ala Arg Met
1               5

<210> SEQ ID NO 289
<211> LENGTH: 9
<212> TYPE: PRT
<213> ORGANISM: Mus musculus

<400> SEQUENCE: 289

Gln Met Thr Ser Gln Leu Glu Cys Met
1               5

<210> SEQ ID NO 290
<211> LENGTH: 9
```

```
<212> TYPE: PRT
<213> ORGANISM: Mus musculus

<400> SEQUENCE: 290

Gln Gln Tyr Ser Val Pro Pro Val
 1               5

<210> SEQ ID NO 291
<211> LENGTH: 9
<212> TYPE: PRT
<213> ORGANISM: Mus musculus

<400> SEQUENCE: 291

Gln Tyr Arg Ile His Thr His Gly Val
 1               5

<210> SEQ ID NO 292
<211> LENGTH: 9
<212> TYPE: PRT
<213> ORGANISM: Mus musculus

<400> SEQUENCE: 292

Gln Tyr Ser Val Pro Pro Val Tyr
 1               5

<210> SEQ ID NO 293
<211> LENGTH: 9
<212> TYPE: PRT
<213> ORGANISM: Mus musculus

<400> SEQUENCE: 293

Arg Met Phe Pro Asn Ala Pro Tyr Leu
 1               5

<210> SEQ ID NO 294
<211> LENGTH: 9
<212> TYPE: PRT
<213> ORGANISM: Mus musculus

<400> SEQUENCE: 294

Arg Thr Pro Tyr Ser Ser Asp Asn Leu
 1               5

<210> SEQ ID NO 295
<211> LENGTH: 9
<212> TYPE: PRT
<213> ORGANISM: Mus musculus

<400> SEQUENCE: 295

Arg Val Ser Gly Val Ala Pro Thr Leu
 1               5

<210> SEQ ID NO 296
<211> LENGTH: 9
<212> TYPE: PRT
<213> ORGANISM: Mus musculus

<400> SEQUENCE: 296

Ser Cys Leu Glu Ser Gln Pro Thr Ile
 1               5

<210> SEQ ID NO 297
<211> LENGTH: 9
<212> TYPE: PRT
<213> ORGANISM: Mus musculus
```

<400> SEQUENCE: 297

Ser Cys Gln Lys Lys Phe Ala Arg Ser
1               5

<210> SEQ ID NO 298
<211> LENGTH: 9
<212> TYPE: PRT
<213> ORGANISM: Mus musculus

<400> SEQUENCE: 298

Ser Asp Val Arg Asp Leu Asn Ala Leu
1               5

<210> SEQ ID NO 299
<211> LENGTH: 9
<212> TYPE: PRT
<213> ORGANISM: Mus musculus

<400> SEQUENCE: 299

Ser Leu Gly Glu Gln Gln Tyr Ser Val
1               5

<210> SEQ ID NO 300
<211> LENGTH: 9
<212> TYPE: PRT
<213> ORGANISM: Mus musculus

<400> SEQUENCE: 300

Thr Cys Gln Arg Lys Phe Ser Arg Ser
1               5

<210> SEQ ID NO 301
<211> LENGTH: 9
<212> TYPE: PRT
<213> ORGANISM: Mus musculus

<400> SEQUENCE: 301

Thr Glu Gly Gln Ser Asn His Gly Ile
1               5

<210> SEQ ID NO 302
<211> LENGTH: 9
<212> TYPE: PRT
<213> ORGANISM: Mus musculus

<400> SEQUENCE: 302

Thr Leu His Phe Ser Gly Gln Phe Thr
1               5

<210> SEQ ID NO 303
<211> LENGTH: 9
<212> TYPE: PRT
<213> ORGANISM: Mus musculus

<400> SEQUENCE: 303

Thr Leu Val Arg Ser Ala Ser Glu Thr
1               5

<210> SEQ ID NO 304
<211> LENGTH: 9
<212> TYPE: PRT
<213> ORGANISM: Mus musculus

<400> SEQUENCE: 304

Val Leu Asp Phe Ala Pro Pro Gly Ala
1               5

<210> SEQ ID NO 305
<211> LENGTH: 9
<212> TYPE: PRT
<213> ORGANISM: Mus musculus

<400> SEQUENCE: 305

Trp Asn Gln Met Asn Leu Gly Ala Thr
1               5

<210> SEQ ID NO 306
<211> LENGTH: 9
<212> TYPE: PRT
<213> ORGANISM: Mus musculus

<400> SEQUENCE: 306

Tyr Phe Lys Leu Ser His Leu Gln Met
1               5

<210> SEQ ID NO 307
<211> LENGTH: 9
<212> TYPE: PRT
<213> ORGANISM: Mus musculus

<400> SEQUENCE: 307

Tyr Gln Met Thr Ser Gln Leu Glu Cys
1               5

<210> SEQ ID NO 308
<211> LENGTH: 9
<212> TYPE: PRT
<213> ORGANISM: Mus musculus

<400> SEQUENCE: 308

Tyr Ser Ser Asp Asn Leu Tyr Gln Met
1               5

<210> SEQ ID NO 309
<211> LENGTH: 6
<212> TYPE: PRT
<213> ORGANISM: Homo sapien

<400> SEQUENCE: 309

Gly Ala Ala Gln Trp Ala
1               5

<210> SEQ ID NO 310
<211> LENGTH: 12
<212> TYPE: PRT
<213> ORGANISM: Homo sapien

<400> SEQUENCE: 310

Ala Ser Ala Tyr Gly Ser Leu Gly Gly Pro Ala Pro
1               5                   10

<210> SEQ ID NO 311
<211> LENGTH: 15
<212> TYPE: PRT
<213> ORGANISM: Homo sapien

<400> SEQUENCE: 311

Ala Phe Thr Val His Phe Ser Gly Gln Phe Thr Gly Thr Ala Gly

-continued

```
1               5               10              15

<210> SEQ ID NO 312
<211> LENGTH: 5
<212> TYPE: PRT
<213> ORGANISM: Homo sapien

<400> SEQUENCE: 312

His Ala Ala Gln Phe
 1               5

<210> SEQ ID NO 313
<211> LENGTH: 32
<212> TYPE: PRT
<213> ORGANISM: Homo sapien

<400> SEQUENCE: 313

Cys His Thr Pro Thr Asp Ser Cys Thr Gly Ser Gln Ala Leu Leu Leu
 1               5                   10                  15

Arg Thr Pro Tyr Ser Ser Asp Asn Leu Tyr Gln Met Thr Ser Gln Leu
                20                  25                  30

<210> SEQ ID NO 314
<211> LENGTH: 32
<212> TYPE: PRT
<213> ORGANISM: Homo sapien

<400> SEQUENCE: 314

Arg Ile His Thr His Gly Val Phe Arg Gly Ile Gln Asp Val Arg Arg
 1               5                   10                  15

Val Pro Gly Val Ala Pro Thr Leu Val Arg Ser Ala Ser Glu Thr Ser
                20                  25                  30

<210> SEQ ID NO 315
<211> LENGTH: 4
<212> TYPE: PRT
<213> ORGANISM: Homo sapien

<400> SEQUENCE: 315

Arg Tyr Phe Lys
 1

<210> SEQ ID NO 316
<211> LENGTH: 14
<212> TYPE: PRT
<213> ORGANISM: Homo sapien

<400> SEQUENCE: 316

Glu Arg Arg Phe Ser Arg Ser Asp Gln Leu Lys Arg His Gln
 1               5                   10

<210> SEQ ID NO 317
<211> LENGTH: 22
<212> TYPE: PRT
<213> ORGANISM: Homo sapien

<400> SEQUENCE: 317

Gln Arg Lys Phe Ser Arg Ser Asp His Leu Lys Thr His Thr Arg Thr
 1               5                   10                  15

His Thr Gly Lys Thr Ser
                20

<210> SEQ ID NO 318
```

-continued

```
<211> LENGTH: 21
<212> TYPE: PRT
<213> ORGANISM: Homo sapien

<400> SEQUENCE: 318

Cys Gln Lys Lys Phe Ala Arg Ser Asp Glu Leu Val Arg His His Asn
 1               5                  10                  15

Met His Gln Arg Asn
             20

<210> SEQ ID NO 319
<211> LENGTH: 449
<212> TYPE: PRT
<213> ORGANISM: Homo sapien

<400> SEQUENCE: 319

Met Gly Ser Asp Val Arg Asp Leu Asn Ala Leu Leu Pro Ala Val Pro
 1               5                  10                  15

Ser Leu Gly Gly Gly Gly Cys Ala Leu Pro Val Ser Gly Ala Ala
             20                  25                  30

Gln Trp Ala Pro Val Leu Asp Phe Ala Pro Pro Gly Ala Ser Ala Tyr
             35                  40                  45

Gly Ser Leu Gly Gly Pro Ala Pro Pro Ala Pro Pro Pro Pro
 50                  55                  60

Pro Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Val His Phe
                 85                  90                  95

Ser Gly Gln Phe Thr Gly Thr Ala Gly Ala Cys Arg Tyr Gly Pro Phe
                100                 105                 110

Gly Pro Pro Pro Pro Ser Gln Ala Ser Ser Gly Gln Ala Arg Met Phe
                115                 120                 125

Pro Asn Ala Pro Tyr Leu Pro Ser Cys Leu Glu Ser Gln Pro Ala Ile
130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
                165                 170                 175

Lys His Glu Asp Pro Met Gly Gln Gln Gly Ser Leu Gly Glu Gln Gln
                180                 185                 190

Tyr Ser Val Pro Pro Val Tyr Gly Cys His Thr Pro Thr Asp Ser
                195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
                260                 265                 270

Ser Asp Asn His Thr Thr Pro Ile Leu Cys Gly Ala Gln Tyr Arg Ile
                275                 280                 285

His Thr His Gly Val Phe Arg Gly Ile Gln Asp Val Arg Arg Val Pro
                290                 295                 300

Gly Val Ala Pro Thr Leu Val Arg Ser Ala Ser Glu Thr Ser Glu Lys
305                 310                 315                 320
```

```
Arg Pro Phe Met Cys Ala Tyr Pro Gly Cys Asn Lys Arg Tyr Phe Lys
            325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
            355                 360                 365

Gln Leu Lys Arg His Gln Arg Arg His Thr Gly Val Lys Pro Phe Gln
            370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
            405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
            435                 440                 445

Leu

<210> SEQ ID NO 320
<211> LENGTH: 449
<212> TYPE: PRT
<213> ORGANISM: Mus musculus

<400> SEQUENCE: 320

Met Gly Ser Asp Val Arg Asp Leu Asn Ala Leu Leu Pro Ala Val Ser
1               5                   10                  15

Ser Leu Gly Gly Gly Gly Gly Cys Gly Leu Pro Val Ser Gly Ala Ala
            20                  25                  30

Gln Trp Ala Pro Val Leu Asp Phe Ala Pro Pro Gly Ala Ser Ala Tyr
            35                  40                  45

Gly Ser Leu Gly Gly Pro Ala Pro Pro Ala Pro Pro Pro Pro Pro Pro
        50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Leu His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
            115                 120                 125

Pro Asn Ala Pro Tyr Leu Pro Ser Cys Leu Glu Ser Gln Pro Thr Ile
130                 135                 140

Arg Asn Gln Gly Tyr Ser Thr Val Thr Phe Asp Gly Ala Pro Ser Tyr
145                 150                 155                 160

Gly His Thr Pro Ser His His Ala Ala Gln Phe Pro Asn His Ser Phe
            165                 170                 175

Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
            195                 200                 205

Cys Thr Gly Ser Gln Ala Leu Leu Leu Arg Thr Pro Tyr Ser Ser Asp
    210                 215                 220

Asn Leu Tyr Gln Met Thr Ser Gln Leu Glu Cys Met Thr Trp Asn Gln
225                 230                 235                 240
```

-continued

```
Met Asn Leu Gly Ala Thr Leu Lys Gly Met Ala Gly Ser Ser Ser
                245                 250                 255

Ser Val Lys Trp Thr Glu Gly Gln Ser Asn His Gly Ile Gly Tyr Glu
            260                 265                 270

Ser Asp Asn His Thr Ala Pro Ile Leu Cys Gly Ala Gln Tyr Arg Ile
        275                 280                 285

His Thr His Gly Val Phe Arg Gly Ile Gln Asp Val Arg Arg Val Ser
    290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
        355                 360                 365

Gln Leu Lys Arg His Gln Arg Arg His Thr Gly Val Lys Pro Phe Gln
    370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp His Ser Cys Gln Lys Lys Phe Ala Arg Ser Asp Glu Leu Val
            420                 425                 430

Arg His His Asn Met His Gln Arg Asn Met Thr Lys Leu His Val Ala
        435                 440                 445
Leu

<210> SEQ ID NO 321
<211> LENGTH: 9
<212> TYPE: PRT
<213> ORGANISM: Homo sapien and Mus musculus

<400> SEQUENCE: 321

Pro Ser Gln Ala Ser Ser Gly Gln Ala
1               5

<210> SEQ ID NO 322
<211> LENGTH: 9
<212> TYPE: PRT
<213> ORGANISM: Homo sapien and Mus musculus

<400> SEQUENCE: 322

Ser Ser Gly Gln Ala Arg Met Phe Pro
1               5

<210> SEQ ID NO 323
<211> LENGTH: 9
<212> TYPE: PRT
<213> ORGANISM: Homo sapien and Mus musculus

<400> SEQUENCE: 323

Gln Ala Arg Met Phe Pro Asn Ala Pro
1               5

<210> SEQ ID NO 324
<211> LENGTH: 9
<212> TYPE: PRT
<213> ORGANISM: Homo sapien and Mus musculus
```

-continued

```
<400> SEQUENCE: 324

Met Phe Pro Asn Ala Pro Tyr Leu Pro
1               5

<210> SEQ ID NO 325
<211> LENGTH: 9
<212> TYPE: PRT
<213> ORGANISM: Homo sapien and Mus musculus

<400> SEQUENCE: 325

Pro Asn Ala Pro Tyr Leu Pro Ser Cys
1               5

<210> SEQ ID NO 326
<211> LENGTH: 9
<212> TYPE: PRT
<213> ORGANISM: Homo sapien and Mus musculus

<400> SEQUENCE: 326

Ala Pro Tyr Leu Pro Ser Cys Leu Glu
1               5

<210> SEQ ID NO 327
<211> LENGTH: 1029
<212> TYPE: DNA
<213> ORGANISM: Homo sapiens

<400> SEQUENCE: 327
atgcagcatc accaccatca ccacatgagc gataaaatta ttcacctgac tgacgacagt      60
tttgacacgg atgtactcaa agcggacggg gcgatcctcg tcgatttctg ggcagagtgg     120
tgcggtccgt gcaaaatgat cgccccgatt ctggatgaaa tcgctgacga atatcagggc     180
aaactgaccg ttgcaaaact gaacatcgat caaaaccctg gcactgcgcc gaaatatggc     240
atccgtggta tcccgactct gctgctgttc aaaaacggtg aagtggcggc aaccaaagtg     300
ggtgcactgt ctaaaggtca gttgaaagag ttcctcgacg ctaacctggc cggttctggt     360
tctggccata tgcagcatca ccaccatcac cacgtgtcta tcgaaggtcg tgctagctct     420
ggtggcagcg gtctggttcc gcgtggtagc tctggttcgg gggacgacga cgacaaatct     480
agtaggcaca gcacagggta cgagagcgat aaccacacaa cgcccatcct ctgcggagcc     540
caatacagaa tacacacgca cggtgtcttc agaggcattc aggatgtgcg acgtgtgcct     600
ggagtagccc cgactcttgt acggtcggca tctgagacca gtgagaaacg ccccttcatg     660
tgtgcttacc caggctgcaa taagagatat tttaagctgt cccacttaca gatgcacagc     720
aggaagcaca ctggtgagaa accataccag tgtgacttca aggactgtga acgaaggttt     780
tttcgttcag accagctcaa aagacaccaa aggagacata caggtgtgaa accattccag     840
tgtaaaactt gtcagcgaaa gttctcccgg tccgaccacc tgaagaccca caccaggact     900
catacaggtg aaaagccctt cagctgtcgg tggccaagtt gtcagaaaaa gtttgcccgg     960
tcagatgaat tagtccgcca tcacaacatg catcagagaa acatgaccaa actccagctg    1020
gcgctttga                                                           1029

<210> SEQ ID NO 328
<211> LENGTH: 1233
<212> TYPE: DNA
<213> ORGANISM: Homo sapiens

<400> SEQUENCE: 328
```

```
atgcagcatc accaccatca ccacatgagc gataaaatta ttcacctgac tgacgacagt      60
tttgacacgg atgtactcaa agcggacggg gcgatcctcg tcgatttctg ggcagagtgg     120
tgcggtccgt gcaaaatgat cgccccgatt ctggatgaaa tcgctgacga atatcagggc     180
aaactgaccg ttgcaaaact gaacatcgat caaaaccctg gcactgcgcc gaaatatggc     240
atccgtggta tcccgactct gctgctgttc aaaaacggtg aagtggcggc aaccaaagtg     300
ggtgcactgt ctaaaggtca gttgaaagag ttcctcgacg ctaacctggc cggttctggt     360
tctggccata tgcagcatca ccaccatcac cacgtgtcta tcgaaggtcg tgctagctct     420
ggtggcagcg gtctggttcc gcgtggtagc tctggttcgg gggacgacga cgacaaatct     480
agtaggggct ccgacgttcg tgacctgaac gcactgctgc cggcagttcc gtccctgggt     540
ggtggtggtg gttgcgcact gccggttagc ggtgcagcac agtgggctcc ggttctggac     600
ttcgcaccgc cgggtgcatc cgcatacggt tccctgggtg gtccggcacc gccgccggca     660
ccgccgccgc cgccgccgcc gccgccgcac tccttcatca acaggaacc gagctggggt     720
ggtgcagaac gcacgaaga acagtgcctg agcgcattca ccgttcactt ctccggccag     780
ttcactggca cagccggagc ctgtcgctac gggcccttcg gtcctcctcc gcccagccag     840
gcgtcatccg gccaggccag gatgtttcct aacgcgccct acctgcccag ctgcctcgag     900
agccagcccg ctattcgcaa tcaggttac agcacgtca ccttcgacgg gacgcccagc      960
tacggtcaca cgccctcgca ccatgcggcg cagttcccca ccactcatt caagcatgag    1020
gatcccatgg gccagcaggg ctcgctgggt gagcagcagt actcggtgcc gccccggtc    1080
tatggctgcc acaccccac cgacagctgc accggcagcc aggctttgct gctgaggacg    1140
ccctacagca gtgacaattt ataccaaatg acatcccagc ttgaatgcat gacctggaat    1200
cagatgaact aggagccac cttaaagggc tga                                  1233
```

<210> SEQ ID NO 329
<211> LENGTH: 1776
<212> TYPE: DNA
<213> ORGANISM: Homo sapiens

<400> SEQUENCE: 329

```
atgcagcatc accaccatca ccacatgagc gataaaatta ttcacctgac tgacgacagt      60
tttgacacgg atgtactcaa agcggacggg gcgatcctcg tcgatttctg ggcagagtgg     120
tgcggtccgt gcaaaatgat cgccccgatt ctggatgaaa tcgctgacga atatcagggc     180
aaactgaccg ttgcaaaact gaacatcgat caaaaccctg gcactgcgcc gaaatatggc     240
atccgtggta tcccgactct gctgctgttc aaaaacggtg aagtggcggc aaccaaagtg     300
ggtgcactgt ctaaaggtca gttgaaagag ttcctcgacg ctaacctggc cggttctggt     360
tctggccata tgcagcatca ccaccatcac cacgtgtcta tcgaaggtcg tgctagctct     420
ggtggcagcg gtctggttcc gcgtggtagc tctggttcgg gggacgacga cgacaaatct     480
agtaggatgg ctccgacgt tcgtgacctg aacgcactgc tgccggcagt tccgtccctg     540
ggtggtggtg gtggttgcgc actgccggtt agcggtgcag cacagtgggc tccggttctg     600
gacttcgcac cgccgggtgc atccgcatac ggttccctgg gtggtccggc accgccgccg     660
gcaccgccgc cgccgccgcc gccgccgccg cactccttca tcaaacagga accgagctgg     720
ggtggtgcag aaccgcacga agaacagtgc ctgagcgcat tcaccgttca cttctccggc     780
cagttcactg gcacagccgg agcctgtcgc tacgggccct cggtcctcc tccgcccagc      840
```

```
caggcgtcat ccggccaggc caggatgttt cctaacgcgc cctacctgcc cagctgcctc      900
gagagccagc ccgctattcg caatcagggt tacagcacgg tcaccttcga cgggacgccc      960
agctacggtc acacgccctc gcaccatgcg gcgcagttcc ccaaccactc attcaagcat     1020
gaggatccca tgggccagca gggctcgctg gtgagcagc agtactcggt gccgcccccg      1080
gtctatggct gccacacccc caccgacagc tgcaccggca gccaggcttt gctgctgagg     1140
acgccctaca gcagtgacaa tttataccaa atgcatcccc agcttgaatg catgacctgg     1200
aatcagatga acttaggagc caccttaaag ggccacagca cagggtacga gagcgataac     1260
cacacaacgc ccatcctctg cggagcccaa tacagaatac acacgcacgg tgtcttcaga     1320
ggcattcagg atgtgcgacg tgtgcctgga gtagccccga ctcttgtacg gtcggcatct     1380
gagaccagtg agaaacgccc cttcatgtgt gcttacccag gctgcaataa gagatatttt     1440
aagctgtccc acttacagat gcacagcagg aagcacactg gtgagaaacc ataccagtgt     1500
gacttcaagg actgtgaacg aaggtttttt cgttcagacc agctcaaaag acaccaaagg     1560
agacatacag gtgtgaaacc attccagtgt aaaacttgtc agcgaaagtt ctcccggtcc     1620
gaccacctga agacccacac caggactcat acaggtgaaa agcccttcag ctgtcggtgg     1680
ccaagttgtc agaaaaagtt tgcccggtca gatgaattag tccgccatca caacatgcat     1740
cagagaaaca tgaccaaact ccagctggcg ctttga                                1776

<210> SEQ ID NO 330
<211> LENGTH: 771
<212> TYPE: DNA
<213> ORGANISM: Homo sapiens

<400> SEQUENCE: 330
atgcagcatc accaccatca ccacggctcc gacgttcgtg acctgaacgc actgctgccg       60
gcagttccgt ccctgggtgg tggtggtggt tgcgcactgc cggttagcgg tgcagcacag      120
tgggctccgg ttctggactt cgcaccgccg ggtgcatccg catacggttc cctgggtggt      180
ccggcaccgc cgccggcacc gccgccgccg ccgccgccgc cgccgcactc cttcatcaaa      240
caggaaccga gctggggtgg tgcagaaccg cacgaagaac agtgcctgag cgcattcacc      300
gttcacttct ccggccagtt cactggcaca gccggagcct gtcgctacgg gcccttcgtg      360
cctcctccgc ccagccaggc gtcatccggc caggccagga tgtttcctaa cgcgccctac      420
ctgcccagct gcctcgagag ccagcccgct attcgcaatc agggttacag cacggtcacc      480
ttcgacggga cgcccagcta cggtcacacg ccctcgcacc atgcggcgca gttccccaac      540
cactcattca gcatgaggat cccatgggc cagcagggct cgctgggtga gcagcagtac      600
tcggtgccgc ccccggtcta tggctgccac accccaccg acagctgcac cggcagccag      660
gctttgctgc tgaggacgcc ctacagcagt gacaatttat accaaatgac atcccagctt      720
gaatgcatga cctggaatca gatgaactta ggagccacct taaagggctg a                771

<210> SEQ ID NO 331
<211> LENGTH: 567
<212> TYPE: DNA
<213> ORGANISM: Homo sapiens

<400> SEQUENCE: 331
atgcagcatc accaccatca ccaccacagc acagggtacg agagcgataa ccacacaacg       60
cccatcctct gcggagccca atacagaata cacacgcacg gtgtcttcag aggcattcag      120
gatgtgcgac gtgtgcctgg agtagccccg actcttgtac ggtcggcatc tgagaccagt      180
```

| | | |
|---|---|---|
| gagaaacgcc ccttcatgtg tgcttaccca ggctgcaata agagatattt taagctgtcc | 240 |
| cacttacaga tgcacagcag gaagcacact ggtgagaaac cataccagtg tgacttcaag | 300 |
| gactgtgaac gaaggttttt tcgttcagac cagctcaaaa gacaccaaag gagacataca | 360 |
| ggtgtgaaac cattccagtg taaaacttgt cagcgaaagt tctcccggtc cgaccacctg | 420 |
| aagacccaca ccaggactca tacaggtgaa aagcccttca gctgtcggtg gccaagttgt | 480 |
| cagaaaaagt ttgcccggtc agatgaatta gtccgccatc acaacatgca tcagagaaac | 540 |
| atgaccaaac tccagctggc gctttga | 567 |

<210> SEQ ID NO 332
<211> LENGTH: 342
<212> TYPE: PRT
<213> ORGANISM: Homo sapiens

<400> SEQUENCE: 332

```
Met Gln His His His His His His Met Ser Asp Lys Ile Ile His Leu
  1               5                  10                  15
Thr Asp Ser Phe Asp Thr Asp Val Leu Lys Ala Asp Gly Ala Ile
         20                  25                  30
Leu Val Asp Phe Trp Ala Glu Trp Cys Gly Pro Cys Lys Met Ile Ala
     35                  40                  45
Pro Ile Leu Asp Glu Ile Ala Asp Glu Tyr Gln Gly Lys Leu Thr Val
 50                  55                  60
Ala Lys Leu Asn Ile Asp Gln Asn Pro Gly Thr Ala Pro Lys Tyr Gly
 65                  70                  75                  80
Ile Arg Gly Ile Pro Thr Leu Leu Leu Phe Lys Asn Gly Glu Val Ala
                 85                  90                  95
Ala Thr Lys Val Gly Ala Leu Ser Lys Gly Gln Leu Lys Glu Phe Leu
            100                 105                 110
Asp Ala Asn Leu Ala Gly Ser Gly Ser Gly His Met Gln His His His
        115                 120                 125
His His His Val Ser Ile Glu Gly Arg Ala Ser Ser Gly Gly Ser Gly
    130                 135                 140
Leu Val Pro Arg Gly Ser Gly Ser Gly Asp Asp Asp Lys Ser
145                 150                 155                 160
Ser Arg His Ser Thr Gly Tyr Glu Ser Asp Asn His Thr Thr Pro Ile
                165                 170                 175
Leu Cys Gly Ala Gln Tyr Arg Ile His Thr His Gly Val Phe Arg Gly
            180                 185                 190
Ile Gln Asp Val Arg Arg Val Pro Gly Val Ala Pro Thr Leu Val Arg
        195                 200                 205
Ser Ala Ser Glu Thr Ser Glu Lys Arg Pro Phe Met Cys Ala Tyr Pro
    210                 215                 220
Gly Cys Asn Lys Arg Tyr Phe Lys Leu Ser His Leu Gln Met His Ser
225                 230                 235                 240
Arg Lys His Thr Gly Glu Lys Pro Tyr Gln Cys Asp Phe Lys Asp Cys
                245                 250                 255
Glu Arg Arg Phe Phe Arg Ser Asp Gln Leu Lys Arg His Gln Arg Arg
            260                 265                 270
His Thr Gly Val Lys Pro Phe Gln Cys Lys Thr Cys Gln Arg Lys Phe
        275                 280                 285
Ser Arg Ser Asp His Leu Lys Thr His Thr Arg Thr His Thr Gly Glu
    290                 295                 300
```

-continued

Lys Pro Phe Ser Cys Arg Trp Pro Ser Cys Gln Lys Lys Phe Ala Arg
305                 310                 315                 320

Ser Asp Glu Leu Val Arg His His Asn Met His Gln Arg Asn Met Thr
                325                 330                 335

Lys Leu Gln Leu Ala Leu
            340

<210> SEQ ID NO 333
<211> LENGTH: 410
<212> TYPE: PRT
<213> ORGANISM: Homo sapiens

<400> SEQUENCE: 333

Met Gln His His His His His Met Ser Asp Lys Ile Ile His Leu
                5                   10                  15

Thr Asp Ser Phe Asp Thr Asp Val Leu Lys Ala Asp Gly Ala Ile
            20                  25                  30

Leu Val Asp Phe Trp Ala Glu Trp Cys Gly Pro Cys Lys Met Ile Ala
            35                  40                  45

Pro Ile Leu Asp Glu Ile Ala Asp Glu Tyr Gln Gly Lys Leu Thr Val
50                  55                  60

Ala Lys Leu Asn Ile Asp Gln Asn Pro Gly Thr Ala Pro Lys Tyr Gly
65                  70                  75                  80

Ile Arg Gly Ile Pro Thr Leu Leu Leu Phe Lys Asn Gly Glu Val Ala
                85                  90                  95

Ala Thr Lys Val Gly Ala Leu Ser Lys Gly Gln Leu Lys Glu Phe Leu
            100                 105                 110

Asp Ala Asn Leu Ala Gly Ser Gly Ser Gly His Met Gln His His His
            115                 120                 125

His His His Val Ser Ile Glu Gly Arg Ala Ser Ser Gly Gly Ser Gly
130                 135                 140

Leu Val Pro Arg Gly Ser Gly Ser Gly Asp Asp Asp Lys Ser
145                 150                 155                 160

Ser Arg Gly Ser Asp Val Arg Asp Leu Asn Ala Leu Leu Pro Ala Val
                165                 170                 175

Pro Ser Leu Gly Gly Gly Gly Cys Ala Leu Pro Val Ser Gly Ala
            180                 185                 190

Ala Gln Trp Ala Pro Val Leu Asp Phe Ala Pro Pro Gly Ala Ser Ala
            195                 200                 205

Tyr Gly Ser Leu Gly Gly Pro Ala Pro Pro Ala Pro Pro Pro
210                 215                 220

Pro Pro Pro Pro His Ser Phe Ile Lys Gln Glu Pro Ser Trp Gly
225                 230                 235                 240

Gly Ala Glu Pro His Glu Glu Gln Cys Leu Ser Ala Phe Thr Val His
                245                 250                 255

Phe Ser Gly Gln Phe Thr Gly Thr Ala Gly Ala Cys Arg Tyr Gly Pro
            260                 265                 270

Phe Gly Pro Pro Pro Ser Gln Ala Ser Ser Gly Gln Ala Arg Met
            275                 280                 285

Phe Pro Asn Ala Pro Tyr Leu Pro Ser Cys Leu Glu Ser Gln Pro Ala
290                 295                 300

Ile Arg Asn Gln Gly Tyr Ser Thr Val Thr Phe Asp Gly Thr Pro Ser
305                 310                 315                 320

Tyr Gly His Thr Pro Ser His His Ala Ala Gln Phe Pro Asn His Ser

```
                      325                 330                 335

Phe Lys His Glu Asp Pro Met Gly Gln Gln Gly Ser Leu Gly Glu Gln
                340                 345                 350

Gln Tyr Ser Val Pro Pro Val Tyr Gly Cys His Thr Pro Thr Asp
            355                 360                 365

Ser Cys Thr Gly Ser Gln Ala Leu Leu Leu Arg Thr Pro Tyr Ser Ser
    370                 375                 380

Asp Asn Leu Tyr Gln Met Thr Ser Gln Leu Glu Cys Met Thr Trp Asn
385                 390                 395                 400

Gln Met Asn Leu Gly Ala Thr Leu Lys Gly
                405                 410

<210> SEQ ID NO 334
<211> LENGTH: 591
<212> TYPE: PRT
<213> ORGANISM: Homo sapiens

<400> SEQUENCE: 334

Met Gln His His His His His His Met Ser Asp Lys Ile Ile His Leu
                  5                  10                  15

Thr Asp Asp Ser Phe Asp Thr Asp Val Leu Lys Ala Asp Gly Ala Ile
             20                  25                  30

Leu Val Asp Phe Trp Ala Glu Trp Cys Gly Pro Cys Lys Met Ile Ala
         35                  40                  45

Pro Ile Leu Asp Glu Ile Ala Asp Glu Tyr Gln Gly Lys Leu Thr Val
     50                  55                  60

Ala Lys Leu Asn Ile Asp Gln Asn Pro Gly Thr Ala Pro Lys Tyr Gly
 65                  70                  75                  80

Ile Arg Gly Ile Pro Thr Leu Leu Leu Phe Lys Asn Gly Glu Val Ala
                 85                  90                  95

Ala Thr Lys Val Gly Ala Leu Ser Lys Gly Gln Leu Lys Glu Phe Leu
            100                 105                 110

Asp Ala Asn Leu Ala Gly Ser Gly Ser Gly His Met Gln His His His
        115                 120                 125

His His His Val Ser Ile Glu Gly Arg Ala Ser Ser Gly Gly Ser Gly
    130                 135                 140

Leu Val Pro Arg Gly Ser Ser Gly Ser Gly Asp Asp Asp Lys Ser
145                 150                 155                 160

Ser Arg Met Gly Ser Asp Val Arg Asp Leu Asn Ala Leu Leu Pro Ala
                165                 170                 175

Val Pro Ser Leu Gly Gly Gly Gly Cys Ala Leu Pro Val Ser Gly
            180                 185                 190

Ala Ala Gln Trp Ala Pro Val Leu Asp Phe Ala Pro Pro Gly Ala Ser
        195                 200                 205

Ala Tyr Gly Ser Leu Gly Gly Pro Ala Pro Pro Ala Pro Pro
    210                 215                 220

Pro Pro Pro Pro Pro His Ser Phe Ile Lys Gln Glu Pro Ser Trp
225                 230                 235                 240

Gly Gly Ala Glu Pro His Glu Glu Gln Cys Leu Ser Ala Phe Thr Val
                245                 250                 255

His Phe Ser Gly Gln Phe Thr Gly Thr Ala Gly Ala Cys Arg Tyr Gly
            260                 265                 270

Pro Phe Gly Pro Pro Pro Ser Gln Ala Ser Ser Gly Gln Ala Arg
        275                 280                 285
```

```
Met Phe Pro Asn Ala Pro Tyr Leu Pro Ser Cys Leu Glu Ser Gln Pro
    290                 295                 300

Ala Ile Arg Asn Gln Gly Tyr Ser Thr Val Thr Phe Asp Gly Thr Pro
305                 310                 315                 320

Ser Tyr Gly His Thr Pro Ser His His Ala Ala Gln Phe Pro Asn His
                325                 330                 335

Ser Phe Lys His Glu Asp Pro Met Gly Gln Gln Gly Ser Leu Gly Glu
            340                 345                 350

Gln Gln Tyr Ser Val Pro Pro Val Tyr Gly Cys His Thr Pro Thr
        355                 360                 365

Asp Ser Cys Thr Gly Ser Gln Ala Leu Leu Arg Thr Pro Tyr Ser
    370                 375                 380

Ser Asp Asn Leu Tyr Gln Met Thr Ser Gln Leu Glu Cys Met Thr Trp
385                 390                 395                 400

Asn Gln Met Asn Leu Gly Ala Thr Leu Lys Gly His Ser Thr Gly Tyr
                405                 410                 415

Glu Ser Asp Asn His Thr Thr Pro Ile Leu Cys Gly Ala Gln Tyr Arg
                420                 425                 430

Ile His Thr His Gly Val Phe Arg Gly Ile Gln Asp Val Arg Arg Val
            435                 440                 445

Pro Gly Val Ala Pro Thr Leu Val Arg Ser Ala Ser Glu Thr Ser Glu
    450                 455                 460

Lys Arg Pro Phe Met Cys Ala Tyr Pro Gly Cys Asn Lys Arg Tyr Phe
465                 470                 475                 480

Lys Leu Ser His Leu Gln Met His Ser Arg Lys His Thr Gly Glu Lys
                485                 490                 495

Pro Tyr Gln Cys Asp Phe Lys Asp Cys Glu Arg Arg Phe Phe Arg Ser
            500                 505                 510

Asp Gln Leu Lys Arg His Gln Arg Arg His Thr Gly Val Lys Pro Phe
    515                 520                 525

Gln Cys Lys Thr Cys Gln Arg Lys Phe Ser Arg Ser Asp His Leu Lys
    530                 535                 540

Thr His Thr Arg Thr His Thr Gly Glu Lys Pro Phe Ser Cys Arg Trp
545                 550                 555                 560

Pro Ser Cys Gln Lys Lys Phe Ala Arg Ser Asp Glu Leu Val Arg His
                565                 570                 575

His Asn Met His Gln Arg Asn Met Thr Lys Leu Gln Leu Ala Leu
                580                 585                 590

<210> SEQ ID NO 335
<211> LENGTH: 256
<212> TYPE: PRT
<213> ORGANISM: Homo sapiens

<400> SEQUENCE: 335

Met Gln His His His His His His Gly Ser Asp Val Arg Asp Leu Asn
                5                   10                  15

Ala Leu Leu Pro Ala Val Pro Ser Leu Gly Gly Gly Gly Gly Cys Ala
            20                  25                  30

Leu Pro Val Ser Gly Ala Ala Gln Trp Ala Pro Val Leu Asp Phe Ala
        35                  40                  45

Pro Pro Gly Ala Ser Ala Tyr Gly Ser Leu Gly Gly Pro Ala Pro Pro
    50                  55                  60

Pro Ala Pro Pro Pro Pro Pro Pro Pro Pro His Ser Phe Ile Lys
65                  70                  75                  80
```

-continued

Gln Glu Pro Ser Trp Gly Gly Ala Glu Pro His Glu Gln Cys Leu
                85                  90                  95

Ser Ala Phe Thr Val His Phe Ser Gly Gln Phe Thr Gly Thr Ala Gly
                100                 105                 110

Ala Cys Arg Tyr Gly Pro Phe Gly Pro Pro Pro Ser Gln Ala Ser
                115                 120                 125

Ser Gly Gln Ala Arg Met Phe Pro Asn Ala Pro Tyr Leu Pro Ser Cys
    130                 135                 140

Leu Glu Ser Gln Pro Ala Ile Arg Asn Gln Gly Tyr Ser Thr Val Thr
145                 150                 155                 160

Phe Asp Gly Thr Pro Ser Tyr Gly His Thr Pro Ser His His Ala Ala
                165                 170                 175

Gln Phe Pro Asn His Ser Phe Lys His Glu Asp Pro Met Gly Gln Gln
                180                 185                 190

Gly Ser Leu Gly Glu Gln Gln Tyr Ser Val Pro Pro Val Tyr Gly
    195                 200                 205

Cys His Thr Pro Thr Asp Ser Cys Thr Gly Ser Gln Ala Leu Leu Leu
    210                 215                 220

Arg Thr Pro Tyr Ser Ser Asp Asn Leu Tyr Gln Met Thr Ser Gln Leu
225                 230                 235                 240

Glu Cys Met Thr Trp Asn Gln Met Asn Leu Gly Ala Thr Leu Lys Gly
                245                 250                 255

<210> SEQ ID NO 336
<211> LENGTH: 188
<212> TYPE: PRT
<213> ORGANISM: Homo sapiens

<400> SEQUENCE: 336

Met Gln His His His His His His Ser Thr Gly Tyr Glu Ser Asp
                5                   10                  15

Asn His Thr Thr Pro Ile Leu Cys Gly Ala Gln Tyr Arg Ile His Thr
                20                  25                  30

His Gly Val Phe Arg Gly Ile Gln Asp Val Arg Arg Val Pro Gly Val
            35                  40                  45

Ala Pro Thr Leu Val Arg Ser Ala Ser Glu Thr Ser Glu Lys Arg Pro
    50                  55                  60

Phe Met Cys Ala Tyr Pro Gly Cys Asn Lys Arg Tyr Phe Lys Leu Ser
65                  70                  75                  80

His Leu Gln Met His Ser Arg Lys His Thr Gly Glu Lys Pro Tyr Gln
                85                  90                  95

Cys Asp Phe Lys Asp Cys Glu Arg Arg Phe Phe Arg Ser Asp Gln Leu
                100                 105                 110

Lys Arg His Gln Arg Arg His Thr Gly Val Lys Pro Phe Gln Cys Lys
            115                 120                 125

Thr Cys Gln Arg Lys Phe Ser Arg Ser Asp His Leu Lys Thr His Thr
    130                 135                 140

Arg Thr His Thr Gly Glu Lys Pro Phe Ser Cys Arg Trp Pro Ser Cys
145                 150                 155                 160

Gln Lys Lys Phe Ala Arg Ser Asp Glu Leu Val Arg His His Asn Met
                165                 170                 175

His Gln Arg Asn Met Thr Lys Leu Gln Leu Ala Leu
                180                 185

<210> SEQ ID NO 337
<211> LENGTH: 324
<212> TYPE: DNA
<213> ORGANISM: Homo sapiens

<400> SEQUENCE: 337

| | | | | | |
|---|---|---|---|---|---|
| atgcagcatc | accaccatca | ccacggttcc | gacgtgcggg | acctgaacgc | actgctgccg | 60 |
| gcagttccat | ccctgggtgg | cggtggaggc | tgcgcactgc | cggttagcgg | tgcagcacag | 120 |
| tgggctccag | ttctggactt | cgcaccgcct | ggtgcatccg | catacggttc | cctgggtggt | 180 |
| ccagcacctc | cgcccgcaac | gcccccaccg | cctccaccgc | cccgcactc | cttcatcaaa | 240 |
| caggaaccta | gctggggtgg | tgcagaaccg | cacgaagaac | agtgcctgag | cgcattctga | 300 |
| gaattctgca | gatatccatc | acac | | | | 324 |

<210> SEQ ID NO 338
<211> LENGTH: 462
<212> TYPE: DNA
<213> ORGANISM: Homo sapiens

<400> SEQUENCE: 338

| | | | | | |
|---|---|---|---|---|---|
| atgcagcatc | accaccatca | ccaccacgaa | gaacagtgcc | tgagcgcatt | caccgttcac | 60 |
| ttctccggcc | agttcactgg | cacagccgga | gcctgtcgct | acgggcccctt | cggtcctcct | 120 |
| ccgcccagcc | aggcgtcatc | cggccaggcc | aggatgtttc | ctaacgcgcc | ctacctgccc | 180 |
| agctgcctcg | agagccagcc | cgctattcgc | aatcagggtt | acagcacggt | caccttcgac | 240 |
| gggacgccca | gctacggtca | cacgccctcg | caccatgcgg | cgcagttccc | caaccactca | 300 |
| ttcaagcatg | aggatcccat | gggccagcag | ggctcgctgg | gtgagcagca | gtactcggtg | 360 |
| ccgcccccgg | tctatggctg | ccacaccccc | accgacagct | gcaccggcag | ccaggctttg | 420 |
| ctgctgagga | cgccctacag | cagtgacaat | ttatactgat | ga | | 462 |

<210> SEQ ID NO 339
<211> LENGTH: 405
<212> TYPE: DNA
<213> ORGANISM: Homo sapiens

<400> SEQUENCE: 339

| | | | | | |
|---|---|---|---|---|---|
| atgcagcatc | accaccatca | ccaccaggct | ttgctgctga | ggacgcccta | cagcagtgac | 60 |
| aatttatacc | aaatgacatc | ccagcttgaa | tgcatgacct | ggaatcagat | gaacttagga | 120 |
| gccaccttaa | agggccacag | cacagggtac | gagagcgata | accacacaac | gcccatcctc | 180 |
| tgcggagccc | aatacagaat | acacacgcac | ggtgtcttca | gaggcattca | ggatgtgcga | 240 |
| cgtgtgcctg | gagtagcccc | gactcttgta | cggtcggcat | ctgagaccag | tgagaaacgc | 300 |
| cccttcatgt | gtgcttaccc | aggctgcaat | aagagatatt | ttaagctgtc | ccacttacag | 360 |
| atgcacagca | ggaagcacac | tggtgagaaa | ccataccagt | gatga | | 405 |

<210> SEQ ID NO 340
<211> LENGTH: 339
<212> TYPE: DNA
<213> ORGANISM: Homo sapiens

<400> SEQUENCE: 340

| | | | | | |
|---|---|---|---|---|---|
| atgcagcatc | accaccatca | ccaccacagc | aggaagcaca | ctggtgagaa | accataccag | 60 |
| tgtgacttca | aggactgtga | acgaaggttt | tttcgttcag | accagctcaa | agacaccaa | 120 |
| aggagacata | caggtgtgaa | accattccag | tgtaaaactt | gtcagcgaaa | gttctcccgg | 180 |

| | | | | |
|---|---|---|---|---|
| tccgaccacc | tgaagaccca | caccaggact | catacaggtg | aaaagccctt cagctgtcgg | 240 |
| tggccaagtt | gtcagaaaaa | gtttgcccgg | tcagatgaat | tagtccgcca tcacaacatg | 300 |
| catcagagaa | acatgaccaa | actccagctg | gcgctttga | | 339 |

<210> SEQ ID NO 341
<211> LENGTH: 1110
<212> TYPE: DNA
<213> ORGANISM: Homo sapiens

<400> SEQUENCE: 341

| | | | | |
|---|---|---|---|---|
| atgcagcatc | accaccatca | ccaccactcc | ttcatcaaac | aggaaccgag ctggggtggt | 60 |
| gcagaaccgc | acgaagaaca | gtgcctgagc | gcattcaccg | ttcacttctc cggccagttc | 120 |
| actggcacag | ccggagcctg | tcgctacggg | cccttcggtc | ctcctccgcc cagccaggcg | 180 |
| tcatccggcc | aggccaggat | gtttcctaac | gcgccctacc | tgcccagctg cctcgagagc | 240 |
| cagcccgcta | ttcgcaatca | gggttacagc | acggtcacct | cgacgggac gcccagctac | 300 |
| ggtcacacgc | cctcgcacca | tgcggcgcag | ttccccaacc | actcattcaa gcatgaggat | 360 |
| cccatgggcc | agcagggctc | gctgggtgag | cagcagtact | cggtgccgcc cccggtctat | 420 |
| ggctgccaca | cccccaccga | cagctgcacc | ggcagccagg | ctttgctgct gaggacgccc | 480 |
| tacagcagtg | acaatttata | ccaaatgaca | tcccagcttg | aatgcatgac ctggaatcag | 540 |
| atgaacttag | gagccacctt | aaagggccac | agcacagggt | acgagagcga taaccacaca | 600 |
| acgcccatcc | tctgcggagc | ccaatacaga | atacacacgc | acggtgtctt cagaggcatt | 660 |
| caggatgtgc | gacgtgtgcc | tggagtagcc | ccgactcttg | tacggtcggc atctgagacc | 720 |
| agtgagaaac | gcccttcat | gtgtgcttac | ccaggctgca | ataagagata ttttaagctg | 780 |
| tcccacttac | agatgcacag | caggaagcac | actggtgaga | accatacca gtgtgacttc | 840 |
| aaggactgtg | aacgaaggtt | ttttcgttca | gaccagctca | aaagacacca aaggagacat | 900 |
| acaggtgtga | aaccattcca | gtgtaaaact | tgtcagcgaa | agttctcccg gtccgaccac | 960 |
| ctgaagaccc | acaccaggac | tcatacaggt | gaaaagccct | tcagctgtcg gtggccaagt | 1020 |
| tgtcagaaaa | agtttgcccg | gtcagatgaa | ttagtccgcc | atcacaacat gcatcagaga | 1080 |
| aacatgacca | aactccagct | ggcgctttga | | | 1110 |

<210> SEQ ID NO 342
<211> LENGTH: 99
<212> TYPE: PRT
<213> ORGANISM: Homo sapiens

<400> SEQUENCE: 342

Met Gln His His His His His His Gly Ser Asp Val Arg Asp Leu Asn
1               5                   10                  15

Ala Leu Leu Pro Ala Val Pro Ser Leu Gly Gly Gly Gly Cys Ala
            20                  25                  30

Leu Pro Val Ser Gly Ala Ala Gln Trp Ala Pro Val Leu Asp Phe Ala
        35                  40                  45

Pro Pro Gly Ala Ser Ala Tyr Gly Ser Leu Gly Gly Pro Ala Pro Pro
    50                  55                  60

Pro Ala Pro Pro Pro Pro Pro Pro Pro His Ser Phe Ile Lys
65                  70                  75                  80

Gln Glu Pro Ser Trp Gly Gly Ala Glu Pro His Glu Glu Gln Cys Leu
                85                  90                  95

Ser Ala Phe

<210> SEQ ID NO 343
<211> LENGTH: 152
<212> TYPE: PRT
<213> ORGANISM: Homo sapiens

<400> SEQUENCE: 343

Met Gln His His His His His His Glu Glu Gln Cys Leu Ser Ala
1               5                   10                  15

Phe Thr Val His Phe Ser Gly Gln Phe Thr Gly Thr Ala Gly Ala Cys
            20                  25                  30

Arg Tyr Gly Pro Phe Gly Pro Pro Pro Ser Gln Ala Ser Ser Gly
        35                  40                  45

Gln Ala Arg Met Phe Pro Asn Ala Pro Tyr Leu Pro Ser Cys Leu Glu
    50                  55                  60

Ser Gln Pro Ala Ile Arg Asn Gln Gly Tyr Ser Thr Val Thr Phe Asp
65                  70                  75                  80

Gly Thr Pro Ser Tyr Gly His Thr Pro Ser His His Ala Ala Gln Phe
                85                  90                  95

Pro Asn His Ser Phe Lys His Glu Asp Pro Met Gly Gln Gln Gly Ser
            100                 105                 110

Leu Gly Glu Gln Gln Tyr Ser Val Pro Pro Val Tyr Gly Cys His
        115                 120                 125

Thr Pro Thr Asp Ser Cys Thr Gly Ser Gln Ala Leu Leu Leu Arg Thr
    130                 135                 140

Pro Tyr Ser Ser Asp Asn Leu Tyr
145                 150

<210> SEQ ID NO 344
<211> LENGTH: 133
<212> TYPE: PRT
<213> ORGANISM: Homo sapiens

<400> SEQUENCE: 344

Met Gln His His His His His His Gln Ala Leu Leu Leu Arg Thr Pro
1               5                   10                  15

Tyr Ser Ser Asp Asn Leu Tyr Gln Met Thr Ser Gln Leu Glu Cys Met
            20                  25                  30

Thr Trp Asn Gln Met Asn Leu Gly Ala Thr Leu Lys Gly His Ser Thr
        35                  40                  45

Gly Tyr Glu Ser Asp Asn His Thr Thr Pro Ile Leu Cys Gly Ala Gln
    50                  55                  60

Tyr Arg Ile His Thr His Gly Val Phe Arg Gly Ile Gln Asp Val Arg
65                  70                  75                  80

Arg Val Pro Gly Val Ala Pro Thr Leu Val Arg Ser Ala Ser Glu Thr
                85                  90                  95

Ser Glu Lys Arg Pro Phe Met Cys Ala Tyr Pro Gly Cys Asn Lys Arg
            100                 105                 110

Tyr Phe Lys Leu Ser His Leu Gln Met His Ser Arg Lys His Thr Gly
        115                 120                 125

Glu Lys Pro Tyr Gln
    130

<210> SEQ ID NO 345
<211> LENGTH: 112
<212> TYPE: PRT
<213> ORGANISM: Homo sapiens

<400> SEQUENCE: 345

```
Met Gln His His His His His His Ser Arg Lys His Thr Gly Glu
                5                  10                 15

Lys Pro Tyr Gln Cys Asp Phe Lys Asp Cys Glu Arg Arg Phe Arg
           20                   25                  30

Ser Asp Gln Leu Lys Arg His Gln Arg Arg His Thr Gly Val Lys Pro
           35                  40                  45

Phe Gln Cys Lys Thr Cys Gln Arg Lys Phe Ser Arg Ser Asp His Leu
           50                  55                  60

Lys Thr His Thr Arg Thr His Thr Gly Glu Lys Pro Phe Ser Cys Arg
 65                  70                  75                  80

Trp Pro Ser Cys Gln Lys Lys Phe Ala Arg Ser Asp Glu Leu Val Arg
                85                  90                  95

His His Asn Met His Gln Arg Asn Met Thr Lys Leu Gln Leu Ala Leu
               100                 105                 110
```

<210> SEQ ID NO 346
<211> LENGTH: 369
<212> TYPE: PRT
<213> ORGANISM: Homo sapiens

<400> SEQUENCE: 346

```
Met Gln His His His His His His Ser Phe Ile Lys Gln Glu Pro
                5                  10                 15

Ser Trp Gly Gly Ala Glu Pro His Glu Glu Gln Cys Leu Ser Ala Phe
           20                  25                  30

Thr Val His Phe Ser Gly Gln Phe Thr Gly Thr Ala Gly Ala Cys Arg
           35                  40                  45

Tyr Gly Pro Phe Gly Pro Pro Pro Ser Gln Ala Ser Ser Gly Gln
 50                  55                  60

Ala Arg Met Phe Pro Asn Ala Pro Tyr Leu Pro Ser Cys Leu Glu Ser
 65                  70                  75                  80

Gln Pro Ala Ile Arg Asn Gln Gly Tyr Ser Thr Val Thr Phe Asp Gly
                85                  90                  95

Thr Pro Ser Tyr Gly His Thr Pro Ser His His Ala Ala Gln Phe Pro
               100                 105                 110

Asn His Ser Phe Lys His Glu Asp Pro Met Gly Gln Gln Gly Ser Leu
               115                 120                 125

Gly Glu Gln Gln Tyr Ser Val Pro Pro Val Tyr Gly Cys His Thr
130                 135                 140

Pro Thr Asp Ser Cys Thr Gly Ser Gln Ala Leu Leu Leu Arg Thr Pro
145                 150                 155                 160

Tyr Ser Ser Asp Asn Leu Tyr Gln Met Thr Ser Gln Leu Glu Cys Met
                165                 170                 175

Thr Trp Asn Gln Met Asn Leu Gly Ala Thr Leu Lys Gly His Ser Thr
               180                 185                 190

Gly Tyr Glu Ser Asp Asn His Thr Thr Pro Ile Leu Cys Gly Ala Gln
               195                 200                 205

Tyr Arg Ile His Thr His Gly Val Phe Arg Gly Ile Gln Asp Val Arg
       210                 215                 220

Arg Val Pro Gly Val Ala Pro Thr Leu Val Arg Ser Ala Ser Glu Thr
225                 230                 235                 240

Ser Glu Lys Arg Pro Phe Met Cys Ala Tyr Pro Gly Cys Asn Lys Arg
                245                 250                 255
```

-continued

```
Tyr Phe Lys Leu Ser His Leu Gln Met His Ser Arg Lys His Thr Gly
            260                 265                 270

Glu Lys Pro Tyr Gln Cys Asp Phe Lys Asp Cys Glu Arg Arg Phe Phe
        275                 280                 285

Arg Ser Asp Gln Leu Lys Arg His Gln Arg Arg His Thr Gly Val Lys
    290                 295                 300

Pro Phe Gln Cys Lys Thr Cys Gln Arg Lys Phe Ser Arg Ser Asp His
305                 310                 315                 320

Leu Lys Thr His Thr Arg Thr His Thr Gly Glu Lys Pro Phe Ser Cys
            325                 330                 335

Arg Trp Pro Ser Cys Gln Lys Lys Phe Ala Arg Ser Asp Glu Leu Val
        340                 345                 350

Arg His His Asn Met His Gln Arg Asn Met Thr Lys Leu Gln Leu Ala
    355                 360                 365

Leu

<210> SEQ ID NO 347
<211> LENGTH: 21
<212> TYPE: DNA
<213> ORGANISM: Artificial Sequence
<220> FEATURE:
<223> OTHER INFORMATION: Primer

<400> SEQUENCE: 347
ggctccgacg tgcgggacct g                                           21

<210> SEQ ID NO 348
<211> LENGTH: 30
<212> TYPE: DNA
<213> ORGANISM: Artificial Sequence
<220> FEATURE:
<223> OTHER INFORMATION: Primer

<400> SEQUENCE: 348
gaattctcaa agcgccagct ggagtttggt                                  30

<210> SEQ ID NO 349
<211> LENGTH: 21
<212> TYPE: DNA
<213> ORGANISM: Artificial Sequence
<220> FEATURE:
<223> OTHER INFORMATION: Primer

<400> SEQUENCE: 349
ggctccgacg tgcgggacct g                                           21

<210> SEQ ID NO 350
<211> LENGTH: 30
<212> TYPE: DNA
<213> ORGANISM: Artificial Sequence
<220> FEATURE:
<223> OTHER INFORMATION: Primer

<400> SEQUENCE: 350
gaattctcaa agcgccagct ggagtttggt                                  30

<210> SEQ ID NO 351
<211> LENGTH: 21
<212> TYPE: DNA
<213> ORGANISM: Artificial Sequence
<220> FEATURE:
<223> OTHER INFORMATION: Primer
```

<400> SEQUENCE: 351
cacagcacag ggtacgagag c                                          21

<210> SEQ ID NO 352
<211> LENGTH: 30
<212> TYPE: DNA
<213> ORGANISM: Artificial Sequence
<220> FEATURE:
<223> OTHER INFORMATION: Primer

<400> SEQUENCE: 352
gaattctcaa agcgccagct ggagtttggt                                 30

<210> SEQ ID NO 353
<211> LENGTH: 29
<212> TYPE: DNA
<213> ORGANISM: Artificial Sequence
<220> FEATURE:
<223> OTHER INFORMATION: Primer

<400> SEQUENCE: 353
cacgaagaac agtgcctgag cgcattcac                                  29

<210> SEQ ID NO 354
<211> LENGTH: 32
<212> TYPE: DNA
<213> ORGANISM: Artificial Sequence
<220> FEATURE:
<223> OTHER INFORMATION: Primer

<400> SEQUENCE: 354
ccggcgaatt catcagtata aattgtcact gc                              32

<210> SEQ ID NO 355
<211> LENGTH: 24
<212> TYPE: DNA
<213> ORGANISM: Artificial Sequence
<220> FEATURE:
<223> OTHER INFORMATION: Primer

<400> SEQUENCE: 355
caggctttgc tgctgaggac gccc                                       24

<210> SEQ ID NO 356
<211> LENGTH: 34
<212> TYPE: DNA
<213> ORGANISM: Artificial Sequence
<220> FEATURE:
<223> OTHER INFORMATION: Primer

<400> SEQUENCE: 356
cacggagaat tcatcactgg tatggtttct cacc                            34

<210> SEQ ID NO 357
<211> LENGTH: 28
<212> TYPE: DNA
<213> ORGANISM: Artificial Sequence
<220> FEATURE:
<223> OTHER INFORMATION: Primer

<400> SEQUENCE: 357
cacagcagga agcacactgg tgagaaac                                   28

<210> SEQ ID NO 358

```
<211> LENGTH: 30
<212> TYPE: DNA
<213> ORGANISM: Artificial Sequence
<220> FEATURE:
<223> OTHER INFORMATION: Primer

<400> SEQUENCE: 358
ggatatctgc agaattctca aagcgccagc                                    30

<210> SEQ ID NO 359
<211> LENGTH: 22
<212> TYPE: DNA
<213> ORGANISM: Artificial Sequence
<220> FEATURE:
<223> OTHER INFORMATION: Primer

<400> SEQUENCE: 359
cactccttca tcaaacagga ac                                            22

<210> SEQ ID NO 360
<211> LENGTH: 30
<212> TYPE: DNA
<213> ORGANISM: Artificial Sequence
<220> FEATURE:
<223> OTHER INFORMATION: Primer

<400> SEQUENCE: 360
ggatatctgc agaattctca aagcgccagc                                    30

<210> SEQ ID NO 361
<211> LENGTH: 33
<212> TYPE: DNA
<213> ORGANISM: Artificial Sequence
<220> FEATURE:
<223> OTHER INFORMATION: Primer

<400> SEQUENCE: 361
ggttccgacg tgcgggacct gaacgcactg ctg                                33

<210> SEQ ID NO 362
<211> LENGTH: 40
<212> TYPE: DNA
<213> ORGANISM: Artificial Sequence
<220> FEATURE:
<223> OTHER INFORMATION: Primer

<400> SEQUENCE: 362
ctgccggcag cagtgcgttc aggtcccgca cgtcggaacc                         40

<210> SEQ ID NO 363
<211> LENGTH: 35
<212> TYPE: DNA
<213> ORGANISM: Artificial Sequence
<220> FEATURE:
<223> OTHER INFORMATION: Primer

<400> SEQUENCE: 363
ccggcagttc catccctggg tggcggtgga ggctg                              35

<210> SEQ ID NO 364
<211> LENGTH: 38
<212> TYPE: DNA
<213> ORGANISM: Artificial Sequence
<220> FEATURE:
<223> OTHER INFORMATION: Primer

<400> SEQUENCE: 364
```
cggcagtgcg cagcctccac cgccacccag ggatggaa    38

<210> SEQ ID NO 365
<211> LENGTH: 35
<212> TYPE: DNA
<213> ORGANISM: Artificial Sequence
<220> FEATURE:
<223> OTHER INFORMATION: Primer

<400> SEQUENCE: 365
cgcactgccg gttagcggtg cagcacagtg ggctc    35

<210> SEQ ID NO 366
<211> LENGTH: 33
<212> TYPE: DNA
<213> ORGANISM: Artificial Sequence
<220> FEATURE:
<223> OTHER INFORMATION: Primer

<400> SEQUENCE: 366
cagaactgga gcccactgtg ctgcaccgct aac    33

<210> SEQ ID NO 367
<211> LENGTH: 38
<212> TYPE: DNA
<213> ORGANISM: Artificial Sequence
<220> FEATURE:
<223> OTHER INFORMATION: Primer

<400> SEQUENCE: 367
cagttctgga cttcgcaccg cctggtgcat ccgcatac    38

<210> SEQ ID NO 368
<211> LENGTH: 39
<212> TYPE: DNA
<213> ORGANISM: Artificial Sequence
<220> FEATURE:
<223> OTHER INFORMATION: Primer

<400> SEQUENCE: 368
cagggaaccg tatgcggatg caccaggcgg tgcgaagtc    39

<210> SEQ ID NO 369
<211> LENGTH: 38
<212> TYPE: DNA
<213> ORGANISM: Artificial Sequence
<220> FEATURE:
<223> OTHER INFORMATION: Primer

<400> SEQUENCE: 369
ggttccctgg gtggtccagc acctccgccc gcaacgcc    38

<210> SEQ ID NO 370
<211> LENGTH: 38
<212> TYPE: DNA
<213> ORGANISM: Artificial Sequence
<220> FEATURE:
<223> OTHER INFORMATION: Primer

<400> SEQUENCE: 370
ggcggtgggg gcgttgcggg cggaggtgct ggaccacc    38

<210> SEQ ID NO 371
<211> LENGTH: 40
<212> TYPE: DNA

```
<213> ORGANISM: Artificial Sequence
<220> FEATURE:
<223> OTHER INFORMATION: Primer

<400> SEQUENCE: 371
cccaccgcct ccaccgcccc cgcactcctt catcaaacag                    40

<210> SEQ ID NO 372
<211> LENGTH: 39
<212> TYPE: DNA
<213> ORGANISM: Artificial Sequence
<220> FEATURE:
<223> OTHER INFORMATION: Primer

<400> SEQUENCE: 372
ctaggttcct gtttgatgaa ggagtgcggg ggcggtgga                     39

<210> SEQ ID NO 373
<211> LENGTH: 38
<212> TYPE: DNA
<213> ORGANISM: Artificial Sequence
<220> FEATURE:
<223> OTHER INFORMATION: Primer

<400> SEQUENCE: 373
gaacctagct ggggtggtgc agaaccgcac gaagaaca                      38

<210> SEQ ID NO 374
<211> LENGTH: 39
<212> TYPE: DNA
<213> ORGANISM: Artificial Sequence
<220> FEATURE:
<223> OTHER INFORMATION: Primer

<400> SEQUENCE: 374
ctcaggcact gttcttcgtg cggttctgca ccaccccag                     39

<210> SEQ ID NO 375
<211> LENGTH: 32
<212> TYPE: DNA
<213> ORGANISM: Artificial Sequence
<220> FEATURE:
<223> OTHER INFORMATION: Primer

<400> SEQUENCE: 375
gtgcctgagc gcattctgag aattctgcag at                            32

<210> SEQ ID NO 376
<211> LENGTH: 34
<212> TYPE: DNA
<213> ORGANISM: Artificial Sequence
<220> FEATURE:
<223> OTHER INFORMATION: Primer

<400> SEQUENCE: 376
gtgtgatgga tatctgcaga attctcagaa tgcg                          34
```

COMPOSITIONS AND METHODS FOR WT1 SPECIFIC IMMUNOTHERAPY

This invention was made in part with government support under NIH SBIR Phase I grant number IR43 CA81752-01A1. The Government may have certain rights in this invention.

TECHNICAL FIELD

The present invention relates generally to the immunotherapy of malignant diseases such as leukemia and cancers. The invention is more specifically related to compositions for generating or enhancing an immune response to WT1, and to the use of such compositions for preventing and/or treating malignant diseases.

BACKGROUND OF THE INVENTION

Cancer and leukemia are significant health problems in the United States and throughout the world. Although advances have been made in detection and treatment of such diseases, no vaccine or other universally successful method for prevention or treatment of cancer and leukemia is currently available. Management of the diseases currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and the high mortality continues to be observed in many cancer patients.

Immunotherapies have the potential to substantially improve cancer and leukemia treatment and survival. Recent data demonstrate that leukemia can be cured by immunotherapy in the context of bone marrow transplantation (e.g., donor lymphocyte infusions). Such therapies may involve the generation or enhancement of an immune response to a tumor-associated antigen (TAA). However, to date relatively few TAAs are known and the generation of an immune response against such antigens has, with rare exception, not been shown to be therapeutically beneficial.

Accordingly, there is a need in the art for improved methods for leukemia and cancer prevention and therapy. The present invention fulfills these needs and further provides other related advantages.

SUMMARY OF THE INVENTION

Briefly stated, this invention provides compositions and methods for the diagnosis and therapy of diseases such as leukemia and cancer. In one aspect, the present invention provides polypeptides comprising an immunogenic portion of a native WT1, or a variant thereof that differs in one or more substitutions, deletions, additions and/or insertions such that the ability of the variant to react with antigen-specific antisera and/or T-cell lines or clones is not substantially diminished. Within certain embodiments, the polypeptide comprises no more than 16 consecutive amino acid residues of a native WT1 polypeptide. Within other embodiments, the polypeptide comprises an immunogenic portion of amino acid residues 1–174 of a native WT1 polypeptide or a variant thereof, wherein the polypeptide comprises no more than 16 consecutive amino acid residues present within amino acids 175 to 449 of the native WT1 polypeptide. The immunogenic portion preferably binds to an MHC class I and/or class II molecule. Within certain embodiments, the polypeptide comprises a sequence selected from the group consisting of (a) sequences recited in any one or more of Tables II–XLVI, (b) variants of the foregoing sequences that differ in one or more substitutions, deletions, additions and/or insertions such that the ability of the variant to react with antigen-specific antisera and/or T-cell lines or clones is not substantially diminished and (c) mimetics of the polypeptides recited above, such that the ability of the mimetic to react with antigen-specific antisera and/or T cell lines or clones is not substantially diminished.

Within other embodiments, the polypeptide comprises a sequence selected from the group consisting of (a) ALLPAVPSL (SEQ ID NO:34), GATLKGVAA (SEQ ID NO:88), CMTWNQMNL (SEQ ID NOs: 49 and 258), SCLESQPTI (SEQ ID NOs: 199 and 296), SCLESQPAI (SEQ ID NO:198), NLYQMTSQL (SEQ ID NOs: 147 and 284), ALLPAVSSL (SEQ ID NOs: 35 and 255), RMFP-NAPYL (SEQ ID NOs: 185 and 293), (b) variants of the foregoing sequences that differ in one or more substitutions, deletions, additions and/or insertions such that the ability of the variant to react with antigen-specific antisera and/or T-cell lines or clones is not substantially diminished and (c) mimetics of the polypeptides recited above, such that the ability of the mimetic to react with antigen-specific antisera and/or T cell lines or clones is not substantially diminished. Mimetics may comprises amino acids in combination with one or more amino acid mimetics or may be entirely nonpeptide mimetics.

Within further aspects, the present invention provides polypeptides comprising a variant of an immunogenic portion of a WT1 protein, wherein the variant differs from the immunogenic portion due to substitutions at between 1 and 3 amino acid positions within the immunogenic portion such that the ability of the variant to react with antigen-specific antisera and/or T-cell lines or clones is enhanced relative to a native WT1 protein.

The present invention further provides WT1 polynucleotides that encode a WT1 polypeptide as described above.

Within other aspects, the present invention provides pharmaceutical compositions and vaccines. Pharmaceutical compositions may comprise a polypeptide or mimetic as described above and/or one or more of (i) a WT1 polynucleotide; (ii) an antibody or antigen-binding fragment thereof that specifically binds to a WT1 polypeptide; (iii) a T cell that specifically reacts with a WT1 polypeptide or (iv) an antigen-presenting cell that expresses a WT1 polypeptide, in combination with a pharmaceutically acceptable carrier or excipient. Vaccines comprise a polypeptide as described above and/or one or more of (i) a WT1 polynucleotide, (ii) an antigen-presenting cell that expresses a WT1 polypeptide or (iii) an anti-idiotypic antibody, and a non-specific immune response enhancer. Within certain embodiments, less than 23 consecutive amino acid residues, preferably less than 17 amino acid residues, of a native WT1 polypeptide are present within a WT1 polypeptide employed within such pharmaceutical compositions and vaccines. The immune response enhancer may be an adjuvant. Preferably, an immune response enhancer enhances a T cell response.

The present invention further provides methods for enhancing or inducing an immune response in a patient, comprising administering to a patient a pharmaceutical composition or vaccine as described above. In certain embodiments, the patient is a human.

The present invention further provides methods for inhibiting the development of a malignant disease in a patient, comprising administering to a patient a pharmaceutical composition or vaccine as described above. Malignant diseases include, but are not limited to leukemias (e.g., acute myeloid, acute lymphocytic and chronic myeloid) and cancers (e.g., breast, lung, thyroid or gastrointestinal cancer or a melanoma). The patient may, but need not, be afflicted with the malignant disease, and the administration of the pharmaceutical composition or vaccine may inhibit the onset of such a disease, or may inhibit progression and/or metastasis of an existing disease.

The present invention further provides, within other aspects, methods for removing cells expressing WT1 from bone marrow and/or peripheral blood or fractions thereof, comprising contacting bone marrow, peripheral blood or a fraction of bone marrow or peripheral blood with T cells that specifically react with a WT1 polypeptide, wherein the step of contacting is performed under conditions and for a time sufficient to permit the removal of WT1 positive cells to less than 10%, preferably less than 5% and more preferably less than 1%, of the number of myeloid or lymphatic cells in the bone marrow, peripheral blood or fraction. Bone marrow, peripheral blood and fractions may be obtained from a patient afflicted with a disease associated with WT1 expression, or may be obtained from a human or non-human mammal not afflicted with such a disease.

Within related aspects, the present invention provides methods for inhibiting the development of a malignant disease in a patient, comprising administering to a patient bone marrow, peripheral blood or a fraction of bone marrow or peripheral blood prepared as described above. Such bone marrow, peripheral blood or fractions may be autologous, or may be derived from a related or unrelated human or non-human animal (e.g., syngeneic or allogeneic).

In other aspects, the present invention provides methods for stimulating (or priming) and/or expanding T cells, comprising contacting T cells with a WT1 polypeptide under conditions and for a time sufficient to permit the stimulation and/or expansion of T cells. Such T cells may be autologous, allogeneic, syngeneic or unrelated WT1-specific T cells, and may be stimulated in vitro or in vivo. Expanded T cells may, within certain embodiments, be present within bone marrow, peripheral blood or a fraction of bone marrow or peripheral blood, and may (but need not) be clonal. Within certain embodiments, T cells may be present in a mammal during stimulation and/or expansion. WT1-specific T cells may be used, for example, within donor lymphocyte infusions.

Within related aspects, methods are provided for inhibiting the development of a malignant disease in a patient, comprising administering to a patient T cells prepared as described above. Such T cells may, within certain embodiments, be autologous, syngeneic or allogeneic.

The present invention further provides, within other aspects, methods for monitoring the effectiveness of an immunization or therapy for a malignant disease associated with WT1 expression in a patient. Such methods are based on monitoring antibody, CD4+ T cell and/or CD8+ T cell responses in the patient. Within certain such aspects, a method may comprise the steps of: (a) incubating a first biological sample with one or more of: (i) a WT1 polypeptide; (ii) a polynucleotide encoding a WT1 polypeptide; or (iii) an antigen presenting cell that expresses a WT1 polypeptide, wherein the first biological sample is obtained from a patient prior to a therapy or immunization, and wherein the incubation is performed under conditions and for a time sufficient to allow immunocomplexes to form; (b) detecting immunocomplexes formed between the WT1 polypeptide and antibodies in the biological sample that specifically bind to the WT1 polypeptide; (c) repeating steps (a) and (b) using a second biological sample obtained from the same patient following therapy or immunization; and (d) comparing the number of immunocomplexes detected in the first and second biological samples, and therefrom monitoring the effectiveness of the therapy or immunization in the patient.

Within certain embodiments of the above methods, the step of detecting comprises (a) incubating the immunocomplexes with a detection reagent that is capable of binding to the immunocomplexes, wherein the detection reagent comprises a reporter group, (b) removing unbound detection reagent, and (c) detecting the presence or absence of the reporter group. The detection reagent may comprise, for example, a second antibody, or antigen-binding fragment thereof, capable of binding to the antibodies that specifically bind to the WT1 polypeptide or a molecule such as Protein A. Within other embodiments, a reporter group is bound to the WT1 polypeptide, and the step of detecting comprises removing unbound WT1 polypeptide and subsequently detecting the presence or absence of the reporter group.

Within further aspects, methods for monitoring the effectiveness of an immunization or therapy for a malignant disease associated with WT1 expression in a patient may comprise the steps of: (a) incubating a first biological sample with one or more of: (i) a WT1 polypeptide; (ii) a polynucleotide encoding a WT1 polypeptide; or (iii) an antigen presenting cell that expresses a WT1 polypeptide, wherein the biological sample comprises CD4+ and/or CD8+ T cells and is obtained from a patient prior to a therapy or immunization, and wherein the incubation is performed under conditions and for a time sufficient to allow specific activation, proliferation and/or lysis of T cells; (b) detecting an amount of activation, proliferation and/or lysis of the T cells; (c) repeating steps (a) and (b) using a second biological sample comprising CD4+ and/or CD8+ T cells, wherein the second biological sample is obtained from the same patient following therapy or immunization; and (d) comparing the amount of activation, proliferation and/or lysis of T cells in the first and second biological samples, and therefrom monitoring the effectiveness of the therapy or immunization in the patient.

The present invention further provides methods for inhibiting the development of a malignant disease associated with WT1 expression in a patient, comprising the steps of: (a) incubating $CD4^+$ and/or CD8+ T cells isolated from a patient with one or more of: (i) a WT1 polypeptide; (ii) a polynucleotide encoding a WT1 polypeptide; or (iii) an antigen presenting cell that expresses a WT1 polypeptide, such that the T cells proliferate; and (b) administering to the patient an effective amount of the proliferated T cells, and therefrom inhibiting the development of a malignant disease in the patient. Within certain embodiments, the step of incubating the T cells may be repeated one or more times.

Within other aspects, the present invention provides methods for inhibiting the development of a malignant disease associated with WT1 expression in a patient, comprising the steps of: (a) incubating $CD4^+$ and/or CD8+ T cells isolated from a patient with one or more of: (i) a WT1 polypeptide; (ii) a polynucleotide encoding a WT1 polypeptide; or (iii) an antigen presenting cell that expresses a WT1 polypeptide, such that the T cells proliferate; (b) cloning one or more cells that proliferated; and (c) administering to the patient an effective amount of the cloned T cells.

Within other aspects, methods are provided for determining the presence or absence of a malignant disease associated with WT1 expression in a patient, comprising the steps of: (a) incubating CD4+ and/or CD8+ T cells isolated from a patient with one or more of: (i) a WT1 polypeptide; (ii) a polynucleotide encoding a WT1 polypeptide; or (iii) an antigen presenting cell that expresses a WT1 polypeptide; and (b) detecting the presence or absence of specific activation of the T cells, therefrom determining the presence or absence of a malignant disease associated with WT1 expression. Within certain embodiments, the step of detecting comprises detecting the presence or absence of proliferation of the T cells.

Within further aspects, the present invention provides methods for determining the presence or absence of a malignant disease associated with WT1 expression in a patient, comprising the steps of: (a) incubating a biological sample obtained from a patient with one or more of: (i) a WT1 polypeptide; (ii) a polynucleotide encoding a WT1 polypeptide; or (iii) an antigen presenting cell that expresses a WT1 polypeptide, wherein the incubation is performed under conditions and for a time sufficient to allow immunocomplexes to form; and (b) detecting immunocomplexes formed between the WT1 polypeptide and antibodies in the biological sample that specifically bind to the WT1 polypeptide; and therefrom determining the presence or absence of a malignant disease associated with WT1 expression.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 depicts a comparison of the mouse (MO) and human (HU) WT1 protein sequences (SEQ ID NOS: 320 and 319 respectively).

FIG. 6A) or p287–301 (p287), p299–313 (p299), p421–435 (p421) (Vaccine B; FIG. 6B) and spleen cells pulsed with an irrelevant control peptide (irrelevant peptide) at 25 ug/ml and were assayed after 96 hr for proliferation by ($^3$H) thymidine incorporation. Bars represent the stimulation index (SI), which is calculated as the mean of the experimental wells divided by the mean of the control (B6 spleen cells with no antigen).

FIGS. 8A and 8B present the results of TSITES Analysis of human WT1 (SEQ ID NO:319) for peptides that have the potential to elicit Th responses. Regions indicated by "A" are AMPHI midpoints of blocks, "R" indicates residues matching the Rothbard/'Taylor motif, "D" indicates residues matching the IAd motif, and 'd' indicates residues matching the IEd motif.

FIG. 9A illustrates the lysis of target cells by allogeneic cell lines and FIG. 9B shows the lysis of peptide coated cell lines. In each case, the % lysis (as determined by standard chromium release assays) is shown at three indicated effector:target ratios. Results are provided for lymphoma cells (LSTRA and E10), as well as E10+p235–243 (E10+P235). E10 cells are also referred to herein as EL-4 cells.

FIG. 10A illustrates that T-cells of non-immunized B6 mice do not kill WT1 positive tumor cell lines. FIG. 10B illustrates the lysis of target cells by allogeneic cell lines. FIGS. 10C and 10D demonstrate the lysis of WT1 positive tumor cell lines, as compared to WT1 negative cell lines in two different experiments. In addition, FIGS. 10C and 10D show the lysis of peptide-coated cell lines (WT1 negative cell line E10 coated with the relevant WT1 peptide P117) In each case, the % lysis (as determined by standard chromium release assays) is shown at three indicated effector:target ratios. Results are provided for lymphoma cells (E10), prostate cancer cells (TRAMP-C), a transformed fibroblast cell line (BLK-SV40), as well as E10+p117.

FIGS. 11A and 11B are histograms illustrating the ability of representative peptide P117–139 specific CTL to lyse WT1 positive tumor cells. Three weeks after the third immunization, spleen cells of mice that had been inoculated with the peptides p235–243 or p117–139 were stimulated in vitro with the relevant peptide and tested for ability to lyse targets incubated with WT1 peptides as well as WT1 positive and negative tumor cells. The bars represent the mean % specific lysis in chromium release assays performed in triplicate with an E:T ratio of 25:1. FIG. 11A shows the cytotoxic activity of the p235–243 specific T cell line against the WT 1 negative cell line EL-4 (EL-4, WT1 negative); EL-4 pulsed with the relevant (used for immunization as well as for restimulation) peptide p235–243 (EL-4+p235); EL-4 pulsed with the irrelevant peptides p117–139 (EL-4+p117) p126–134 (EL-4+p126) or p130–138 (EL-4+p130) and the WT1 positive tumor cells BLK-SV40 (BLK-SV40, WT1 positive) and TRAMP-C (TRAMP-C, WT1 positive), as indicated. FIG. 11B shows cytotoxic activity of the p117–139 specific T cell line against EL-4; EL-4 pulsed with the relevant peptide P117–139 (EL-4+p117) and EL-4 pulsed with the irrelevant peptides p123–131 (EL-4+p123), or p128–136 (EL-4+p128); BLK-SV40 and TRAMP-C, as indicated.

FIGS. 12A and 12B are histograms illustrating the specificity of lysis of WT1 positive tumor cells, as demonstrated by cold target inhibition. The bars represent the mean % specific lysis in chromium release assays performed in triplicate with an E:T ratio of 25:1. FIG. 12A shows the cytotoxic activity of the p117–139 specific T cell line against the WT1 negative cell line EL-4 (EL-4, WT1 negative); the WT1 positive tumor cell line TRAMP-C (TRAMP-C, WT1 positive); TRAMP-C cells incubated with a ten-fold excess (compared to the hot target) of EL-4 cells pulsed with the relevant peptide p117–139 (TRAMP-C+p117 cold target) without $^{51}$Cr labeling and TRAMP-C cells incubated with EL-4 pulsed with an irrelevant peptide without $^{51}$Cr labeling (TRAMP-C+irrelevant cold target), as indicated. FIG. 12B shows the cytotoxic activity of the p117–139 specific T cell line against the WT1 negative cell line EL-4 (EL-4, WT1 negative); the WT1 positive tumor cell line BLK-SV40 (BLK-SV40, WT1 positive); BLK-SV40 cells incubated with the relevant cold target (BLK-SV40+p117 cold target) and BLK-SV40 cells incubated with the irrelevant cold target (BLK-SV40+irrelevant cold target), as indicated.

FIG. 13A shows the cytotoxic activity of the p117–139 specific T cell line against the WT1 negative cell line EL-4 (EL-4, WT1 negative) and EL-4 cells pulsed with the peptides p117–139 (EL-4+p117), p119–127 (EL-4+p119), p120–128 (EL-4+p120(EL-4+p123), p126–134 (EL-4+p126), p128–136 (EL-4+p128), and p130–138 (EL-4+p130). FIG. 13B shows the cytotoxic activity of the CTL line after restimulation with p126–134 against the WT1 negative cell line EL-4, EL-4 cells pulsed with p117–139 (EL-4+p117), p126–134 (EL-4+p126) and the WT1 positive tumor cell line TRAMP-C. FIG. 13C shows the cytotoxic activity of the CTL line after restimulation with p130–138 against EL-4, EL-4 cells pulsed with p117–139 (EL-4+p117), p130–138 (EL-4+p130) and the WT1 positive tumor cell line TRAMP-C.

FIG. 18 provides the characteristics of the recombinant WT1 proteins used for serological analysis.

FIG. 19A–19E is a bar graph depicting the antibody responses in mice elicited by vaccination with different doses of WT1 protein.

FIG. 21 is a photograph of human DC, examined by fluorescent microscopy, expressing WT1 following adeno WT1 and Vaccinia WT1 infection.

FIG. 22 is a photograph that demonstrates that WT1 expression in human DC is reproducible following adeno WT1 infection and is not induced by a control Adeno infection.

DETAILED DESCRIPTION OF THE INVENTION

Figure 2:
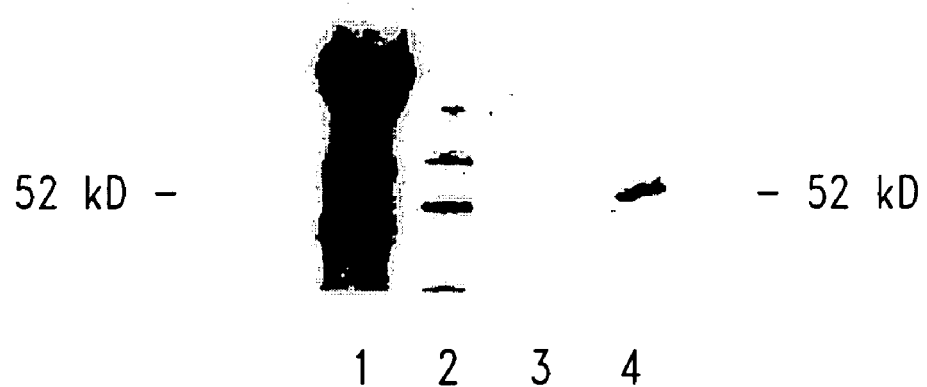
FIG. 2 is a Western blot illustrating the detection of WT1 specific antibodies in patients with hematological malignancy (AML). Lane 1 shows molecular weight markers; lane 2 shows a positive control (WT1 positive human leukemia cell line immunoprecipitated with a WT1 specific antibody); lane 3 shows a negative control (WT1 positive cell line immunoprecipitated with mouse sera); and lane 4 shows a WT1 positive cell line immunoprecipitated with sera of a patient with AML. For lanes 2–4, the immunoprecipitate was separated by gel electrophoresis and probed with a WT1 specific antibody.

As noted above, the present invention is generally directed to compositions and methods for the immunotherapy and diagnosis of malignant diseases. The compositions described herein may include WT1 polypeptides, WT1 polynucleotides, antigen-presenting cells (APC, e.g., dendritic cells) that express a WT1 polypeptide, agents such as antibodies that bind to a WT1 polypeptide and/or immune system cells (e.g., T cells) specific for WT1. WT1 Polypeptides of the present invention generally comprise at least a portion of a Wilms Tumor gene product (WT1) or a variant thereof. Nucleic acid sequences of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a portion of a WT1 polypeptide. T cells that may be employed within such compositions are generally T cells (e.g., CD4$^+$ and/or CD8$^+$) that are specific for a WT1 polypeptide. Certain methods described herein further employ antigen-presenting cells that express a WT1 polypeptide as provided herein.

The present invention is based on the discovery that an immune response raised against a Wilms Tumor (WT) gene product (e.g., WT1) can provide prophylactic and/or therapeutic benefit for patients afflicted with malignant diseases characterized by increased WT1 gene expression. Such diseases include, but are not limited to, leukemias (e.g., acute myeloid leukemia (AML), chronic myeloid leukemia (CML), acute lymphocytic leukemia (ALL) and childhood ALL), as well as many cancers such as lung, breast, thyroid and gastrointestinal cancers and melanomas. The WT1 gene was originally identified and isolated on the basis of a cytogenetic deletion at chromosome 11p13 in patients with Wilms' tumor (see Call et al., U.S. Pat. No. 5,350,840). The gene consists of 10 exons and encodes a zinc finger transcription factor, and sequences of mouse and human WT1 proteins are provided in FIG. 1 and SEQ ID NOs: 319 and 320.

WT1 Polypeptides

Within the context of the present invention, a WT1 polypeptide is a polypeptide that comprises at least an immunogenic portion of a native WT1 (i.e., a WT1 protein expressed by an organism that is not genetically modified), or a variant thereof, as described herein. A WT1 polypeptide may be of any length, provided that it comprises at least an immunogenic portion of a native protein or a variant thereof. In other words, a WT1 polypeptide may be an oligopeptide (i.e., consisting of a relatively small number of amino acid residues, such as 8–10 residues, joined by peptide bonds), a full length WT1 protein (e.g., present within a human or non-human animal, such as a mouse) or a polypeptide of intermediate size. Within certain embodiments, the use of WT1 polypeptides that contain a small number of consecutive amino acid residues of a native WT1 polypeptide is preferred. Such polypeptides are preferred for certain uses in which the generation of a T cell response is desired. For example, such a WT1 polypeptide may contain less than 23, preferably no more than 18, and more preferably no more than 15 consecutive amino acid residues, of a native WT1 polypeptide. Polypeptides comprising nine consecutive amino acid residues of a native WT1 polypeptide are generally suitable for such purposes. Additional sequences derived from the native protein and/or heterologous sequences may be present within any WT1 polypeptide, and such sequences may (but need not) possess further immunogenic or antigenic properties. Polypeptides as provided herein may further be associated (covalently or noncovalently) with other polypeptide or non-polypeptide compounds.

An "immunogenic portion," as used herein is a portion of a polypeptide that is recognized (i.e., specifically bound) by a B-cell and/or T-cell surface antigen receptor. Certain preferred immunogenic portions bind to an MHC class I or class II molecule. As used herein, an immunogenic portion is said to "bind to" an MHC class I or class II molecule if such binding is detectable using any assay known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., *J. Immunol.* 152:163, 1994). Alternatively, functional peptide competition assays that are known in the art may be employed. Certain immunogenic portions have one or more of the sequences recited within one or more of Tables II–XIV. Representative immunogenic portions include, but are not limited to, RDLNALL-PAVPSLGGGG (human WT1 residues 6–22; SEQ ID NO: 1), PSQASSGQARMFPNAPYLPSCLE (human and mouse WT1 residues 117–139; SEQ ID NOs: 2 and 3 respectively), GATLKGVAAGSSSSVKWTE (human WT1 residues 244–262; SEQ ID NO:4), GATLKGVAA (human WT1 residues 244–252; SEQ ID NO:88), CMTWNQMNL (human and mouse WT1 residues 235–243; SEQ ID NOs: 49 and 258 respectively), SCLESQPTI (mouse WT1 residues 136–144; SEQ ID NO:296), SCLESQPAI (human WT1 residues 136–144; SEQ ID NO:198), NLYQMTSQL (human and mouse WT1 residues 225–233; SEQ ID NOs: 147 and 284 respectively); ALLPAVSSL (mouse WT1 residues 10–18; SEQ ID NO:255); or RMFPNAPYL (human and mouse WT1 residues 126–134; SEQ ID NOs: 185 and 293 respectively). Further immunogenic portions are provided herein, and others may generally be identified using well known techniques, such as those summarized in Paul, *Fundamental Immunology*, 3rd ed., 243–247 (Raven Press, 1993) and references cited therein. Representative techniques for identifying immunogenic portions include screening polypeptides for the ability to react with antigen-specific antisera and/or T-cell lines or clones. An immunogenic portion of a native WT1 polypeptide is a portion that reacts with such antisera and/or T-cells at a level that is not substantially less than the reactivity of the full length WT1 (e.g., in an ELISA and/or T-cell reactivity assay). In other words, an immunogenic portion may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988.

Alternatively, immunogenic portions may be identified using computer analysis, such as the Tsites program (see Rothbard and Taylor, *EMBO J.* 7:93–100, 1988; Deavin et al., *Mol. Immunol.* 33:145–155, 1996), which searches for peptide motifs that have the potential to elicit Th responses. CTL peptides with motifs appropriate for binding to murine and human class I or class II MHC may be identified according to BIMAS (Parker et al., *J. Immunol.* 152:163, 1994) and other HLA peptide binding prediction analyses. To confirm immunogenicity, a peptide may be tested using an HLA A2 transgenic mouse model and/or an in vitro stimulation assay using dendritic cells, fibroblasts or peripheral blood cells.

As noted above, a composition may comprise a variant of a native WT1 protein. A polypeptide "variant," as used herein, is a polypeptide that differs from a native polypeptide in one or more substitutions, deletions, additions and/or insertions, such that the immunogenicity of the polypeptide is retained (i.e., the ability of the variant to react with antigen-specific antisera and/or T-cell lines or clones is not substantially diminished relative to the native polypeptide). In other words, the ability of a variant to react with antigen-specific antisera and/or T-cell lines or clones may be enhanced or unchanged, relative to the native polypeptide, or may be diminished by less than 50%, and preferably less than 20%, relative to the native polypeptide. Such variants may generally be identified by modifying one of the above polypeptide sequences and evaluating the reactivity of the modified polypeptide with antisera and/or T-cells as described herein. It has been found, within the context of the present invention, that a relatively small number of substitutions (e.g., 1 to 3) within an immunogenic portion of a WT1 polypeptide may serve to enhance the ability of the polypeptide to elicit an immune response. Suitable substitutions may generally be identified by using computer programs, as described above, and the effect confirmed based on the reactivity of the modified polypeptide with antisera and/or T-cells as described herein. Accordingly, within certain preferred embodiments, a WT1 polypeptide comprises a variant in which 1 to 3 amino acid resides within an immunogenic portion are substituted such that the ability to react with antigen-specific antisera and/or T-cell lines or clones is statistically greater than that for the unmodified polypeptide. Such substitutions are preferably located within an MHC binding site of the polypeptide, which may be identified as described above. Preferred substitutions allow increased binding to MHC class I or class II molecules.

Certain variants contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants may also (or alternatively) be modified by, for example, the deletion or addition of amino acids that have minimal influence on the immunogenicity, secondary structure and hydropathic nature of the polypeptide.

In a preferred embodiment, a variant polypeptide of the WT1 N-terminus (amino acids 1–249) is constructed, wherein the variant polypeptide is capable of binding to an antibody that recognizes full-length WT1 and/or WT1 N-terminus polypeptide. A non-limiting example of an antibody is anti WT-1 antibody WT180 (Santa Cruz Biotechnology, Inc., Santa Cruz, Calif.).

As noted above, WT1 polypeptides may be conjugated to a signal (or leader) sequence at the N-terminal end of the protein which co-translationally or post-translationally directs transfer of the protein. A polypeptide may also, or alternatively, be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

WT1 polypeptides may be prepared using any of a variety of well known techniques. Recombinant polypeptides encoded by a WT1 polynucleotide as described herein may be readily prepared from the polynucleotide. In general, any of a variety of expression vectors known to those of ordinary skill in the art may be employed to express recombinant WT1 polypeptides. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli,* yeast or a mammalian cell line such as COS or CHO. Supernatants from suitable host/vector systems which secrete recombinant protein or polypeptide into culture media may be first concentrated using a commercially available filter. The concentrate may then be applied to a suitable purification matrix such as an affinity matrix or an ion exchange resin. Finally, one or more reverse phase HPLC steps can be employed to further purify a recombinant polypeptide. Such techniques may be used to prepare native polypeptides or variants thereof. For example, polynucleotides that encode a variant of a native polypeptide may generally be prepared using standard mutagenesis techniques, such as oligonucleotide-directed site-specific mutagenesis, and sections of the DNA sequence may be removed to permit preparation of truncated polypeptides.

Certain portions and other variants may also be generated by synthetic means, using techniques well known to those of ordinary skill in the art. For example, polypeptides having fewer than about 500 amino acids, preferably fewer than about 100 amino acids, and more preferably fewer than about 50 amino acids, may be synthesized. Polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc. (Foster City, Calif.), and may be operated according to the manufacturer's instructions.

In general, polypeptides and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Within further aspects, the present invention provides mimetics of WT1 polypeptides. Such mimetics may comprise amino acids linked to one or more amino acid mimetics (i.e., one or more amino acids within the WT1 protein may be replaced by an amino acid mimetic) or may be entirely nonpeptide mimetics. An amino acid mimetic is a compound that is conformationally similar to an amino acid such that it can be substituted for an amino acid within a WT1 polypeptide without substantially diminishing the ability to react with antigen-specific antisera and/or T cell lines or clones. A nonpeptide mimetic is a compound that does not contain amino acids, and that has an overall conformation that is similar to a WT1 polypeptide such that the ability of the mimetic to react with WT1-specific antisera and/or T cell lines or clones is not substantially diminished relative to the ability of a WT1 polypeptide. Such mimetics may be designed based on standard techniques (e.g., nuclear magnetic resonance and computational techniques) that evaluate the three dimensional structure of a peptide sequence. Mimetics may be designed where one or more of the side chain functionalities of the WT1 polypeptide are replaced by groups that do not necessarily have the same size or volume, but have similar chemical and/or physical properties which produce similar biological responses. It should be understood that, within embodiments described herein, a mimetic may be substituted for a WT1 polypeptide.

Within other illustrative embodiments, a polypeptide may be a fusion polypeptide that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the polypeptide or to enable the polypeptide to be targeted to desired intracellular compartments. Still further fusion partners include affinity tags, which facilitate purification of the polypeptide.

Fusion polypeptides may generally be prepared using standard techniques, including chemical conjugation. Preferably, a fusion polypeptide is expressed as a recombinant polypeptide, allowing the production of increased levels, relative to a non-fused polypeptide, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion polypeptide that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion polypeptide using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

The fusion polypeptide can comprise a polypeptide as described herein together with an unrelated immunogenic protein, such as an immunogenic protein capable of eliciting a recall response. Examples of such proteins include tetanus, tuberculosis and hepatitis proteins (see, for example, Stoute et al. *New Engl. J. Med.*, 336:86–91, 1997).

In one preferred embodiment, the immunological fusion partner is derived from a *Mycobacterium sp.*, such as a *Mycobacterium tuberculosis*-derived Ra12 fragment. Ra12 compositions and methods for their use in enhancing the expression and/or immunogenicity of heterologous polynucleotide/polypeptide sequences is described in U.S. patent application Ser. No. 60/158,585, the disclosure of which is incorporated herein by reference in its entirety. Briefly, Ra12 refers to a polynucleotide region that is a subsequence of a *Mycobacterium tuberculosis* MTB32A nucleic acid. MTB32A is a serine protease of 32 KD molecular weight encoded by a gene in virulent and avirulent strains of *M. tuberculosis*. The nucleotide sequence and amino acid sequence of MTB32A have been described (for example, U.S. patent application Ser. No. 60/158,585; see also, Skeiky et al., *Infection and Immun.* (1999) 67:3998–4007, incorporated herein by reference). C-terminal fragments of the MTB32A coding sequence express at high levels and remain as soluble polypeptides throughout the purification process. Moreover, Ra12 may enhance the immunogenicity of heterologous immunogenic polypeptides with which it is fused. One preferred Ra12 fusion polypeptide comprises a 14 KD C-terminal fragment corresponding to amino acid residues 192 to 323 of MTB32A. Other preferred Ra12 polynucleotides generally comprise at least about 15 consecutive nucleotides, at least about 30 nucleotides, at least about 60 nucleotides, at least about 100 nucleotides, at least about 200 nucleotides, or at least about 300 nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants preferably exhibit at least about 70% identity, more preferably at least about 80% identity and most preferably at least about 90% identity to a polynucleotide sequence that encodes a native Ra12 polypeptide or a portion thereof.

Within other preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in E. coli (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of E. coli C-LYTA expressing plasmids useful for expression of fusion proteins. Purification of hybrid proteins containing the C-LYTA fragment at the amino terminus has been described (see Biotechnology 10:795–798, 1992). Within a preferred embodiment, a repeat portion of LYTA may be incorporated into a fusion polypeptide. A repeat portion is found in the C-terminal region starting at residue 178. A particularly preferred repeat portion incorporates residues 188–305.

Yet another illustrative embodiment involves fusion polypeptides, and the polynucleotides encoding them, wherein the fusion partner comprises a targeting signal capable of directing a polypeptide to the endosomal/lysosomal compartment, as described in U.S. Pat. No. 5,633,234. An immunogenic polypeptide of the invention, when fused with this targeting signal, will associate more efficiently with MHC class II molecules and thereby provide enhanced in vivo stimulation of CD4+ T-cells specific for the polypeptide.

The invention provides truncated forms of WT-1 polypeptides that can be recombinantly expressed in E. coli without the addition of a fusion partner. Examples of these truncated forms are shown in SEQ ID NOs:342–346, and are encoded by polynucleotides shown in SEQ ID NOs:337–341. In variations of these truncations, the first 76 amino acids of WT-1 can be fused to the C-terminus of the protein, creating a recombinant protein that is easier to express in E. coli. Other hosts in addition to E. coli can also be used, such as, for example, B. megaterium. The protein can further be prepared without a histidine tag.

In other embodiments, different subunits can be made and fused together in an order which differs from that of native WT-1. In addition, fusions can be made with, for example, Ra12. Exemplary fusion proteins are shown in SEQ ID NOs: 332–336 and can be encoded by polynucleotides shown in SEQ ID NOs: 327–331.

WT1 Polynucleotides

Any polynucleotide that encodes a WT1 polypeptide as described herein is a WT1 polynucleotide encompassed by the present invention. Such polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

WT1 polynucleotides may encode a native WT1 protein, or may encode a variant of WT1 as described herein. Polynucleotide variants may contain one or more substitutions, additions, deletions and/or insertions such that the immunogenicity of the encoded polypeptide is not diminished, relative to a native WT1 protein. The effect on the immunogenicity of the encoded polypeptide may generally be assessed as described herein. Preferred variants contain nucleotide substitutions, deletions, insertions and/or additions at no more than 20%, preferably at no more than 10%, of the nucleotide positions that encode an immunogenic portion of a native WT1 sequence. Certain variants are substantially homologous to a native gene, or a portion thereof. Such polynucleotide variants are capable of hybridizing under moderately stringent conditions to a naturally occurring DNA sequence encoding a WT1 polypeptide (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS). Such hybridizing DNA sequences are also within the scope of this invention.

It will be appreciated by those of ordinary skill in the art that, as a result of the degeneracy of the genetic code, there are many nucleotide sequences that encode a WT1 polypeptide. Some of these polynucleotides bear minimal homology to the nucleotide sequence of any native gene. Nonetheless, polynucleotides that vary due to differences in codon usage are specifically contemplated by the present invention.

Once an immunogenic portion of WT1 is identified, as described above, a WT1 polynucleotide may be prepared using any of a variety of techniques. For example, a WT1 polynucleotide may be amplified from cDNA prepared from cells that express WT1. Such polynucleotides may be amplified via polymerase chain reaction (PCR). For this approach, sequence-specific primers may be designed based on the sequence of the immunogenic portion and may be purchased or synthesized. For example, suitable primers for PCR amplification of a human WT1 gene include: first step—P118: 1434–1414: 5' GAG AGT CAG ACT TGA AAG CAGT 3' (SEQ ID NO:5) and P135: 5° CTG AGC CTC AGC AAA TGG GC 3' (SEQ ID NO:6); second step—P136: 5' GAG CAT GCA TGG GCT CCG ACG TGC GGG 3' (SEQ ID NO:7) and P137: 5' GGG GTA CCC ACT GAA CGG TCC CCG A 3' (SEQ ID NO:8). Primers for PCR amplification of a mouse WT1 gene include: first step—P138: 5' TCC GAG CCG CAC CTC ATG 3' (SEQ ID NO:9) and P139: 5' GCC TGG GAT GCT GGA CTG 3' (SEQ ID NO:10), second step—P140: 5' GAG CAT GCG ATG GGT TCC GAC GTG CGG 3' (SEQ ID NO:11) and P141: 5' GGG GTA CCT CAA AGC GCC ACG TGG AGT TT 3' (SEQ ID NO:12).

An amplified portion may then be used to isolate a full length gene from a human genomic DNA library or from a suitable cDNA library, using well known techniques. Alternatively, a full length gene can be constructed from multiple PCR fragments. WT1 polynucleotides may also be prepared by synthesizing oligonucleotide components, and ligating components together to generate the complete polynucleotide.

WT1 polynucleotides may also be synthesized by any method known in the art, including chemical synthesis (e.g., solid phase phosphoramidite chemical synthesis). Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a WT1 polypeptide, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells such as dendritic cells with a cDNA construct encoding a WT1 polypeptide, and administering the transfected cells to the patient).

Polynucleotides that encode a WT1 polypeptide may generally be used for production of the polypeptide, in vitro or in vivo. WT1 polynucleotides that are complementary to a coding sequence (i.e., antisense polynucleotides) may also be used as a probe or to inhibit WT1 expression. cDNA constructs that can be transcribed into antisense RNA may also be introduced into cells of tissues to facilitate the production of antisense RNA.

Any polynucleotide may be further modified to increase stability in vivo. Possible modifications include, but are not limited to, the addition of flanking sequences at the 5' and/or 3' ends; the use of phosphorothioate or 2'O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art. cDNA constructs within such a vector may be used, for example, to transfect human or animal cell lines for use in establishing WT1 positive tumor models which may be used to perform tumor protection and adoptive immunotherapy experiments to demonstrate tumor or leukemia-growth inhibition or lysis of such cells.

Other therapeutic formulations for polynucleotides include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Antibodies and Fragments Thereof

The present invention further provides binding agents, such as antibodies and antigen-binding fragments thereof, that specifically bind to a WT1 polypeptide. As used herein, an agent is said to "specifically bind" to a WT1 polypeptide if it reacts at a detectable level (within, for example, an ELISA) with a WT1 polypeptide, and does not react detectably with unrelated proteins under similar conditions. As used herein, "binding" refers to a noncovalent association between two separate molecules such that a "complex" is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant maybe determined using methods well known in the art.

Any agent that satisfies the above requirements may be a binding agent. In a preferred embodiment, a binding agent is an antibody or an antigen-binding fragment thereof. Certain antibodies are commercially available from, for example, Santa Cruz Biotechnology (Santa Cruz, Calif.). Alternatively, antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual,* Cold Spring Harbor Laboratory, 1988) and digested by papain to yield Fab and Fc fragments. The Fab and Fc fragments may be separated by affinity chromatography on protein A bead columns.

Monoclonal antibodies and fragments thereof may be coupled to one or more therapeutic agents. Suitable agents in this regard include radioactive tracers and chemotherapeutic agents, which may be used, for example, to purge autologous bone marrow in vitro). Representative therapeutic agents include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein. For diagnostic purposes, coupling of radioactive agents may be used to facilitate tracing of metastases or to determine the location of WT1-positive tumors.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used. A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Also provided herein are anti-idiotypic antibodies that mimic an immunogenic portion of WT1. Such antibodies may be raised against an antibody, or antigen-binding fragment thereof, that specifically binds to an immunogenic portion of WT1, using well known techniques. Anti-idiotypic antibodies that mimic an immunogenic portion of WT1 are those antibodies that bind to an antibody, or antigen-binding fragment thereof, that specifically binds to an immunogenic portion of WT1, as described herein.

T Cells

Immunotherapeutic compositions may also, or alternatively, comprise T cells specific for WT1. Such cells may generally be prepared in vitro or ex vivo, using standard procedures. For example, T cells may be present within (or isolated from) bone marrow, peripheral blood or a fraction of bone marrow or peripheral blood of a mammal, such as a patient, using a commercially available cell separation system, such as the CEPRATE™ system, available from CellPro Inc., Bothell, Wash. (see also U.S. Pat. No. 5,240, 856; U.S. Pat. No. 5,215,926; WO 89/06280; WO 91/16116 and WO 92/07243). Alternatively, T cells may be derived from related or unrelated humans, non-human animals, cell lines or cultures.

T cells may be stimulated with WT1 polypeptide, polynucleotide encoding a WT1 polypeptide and/or an antigen presenting cell (APC) that expresses a WT1 polypeptide. Such stimulation is performed under conditions and for a time sufficient to permit the generation of T cells that are specific for the WT1 polypeptide. Preferably, a WT1 polypeptide or polynucleotide is present within a delivery vehicle, such as a microsphere, to facilitate the generation of antigen-specific T cells. Briefly, T cells, which may be isolated from a patient or a related or unrelated donor by routine techniques (such as by Ficoll/Hypaque density gradient centrifugation of peripheral blood lymphocytes), are incubated with WT1 polypeptide. For example, T cells may be incubated in vitro for 2–9 days (typically 4 days) at 37° C. with WT1 polypeptide (e.g., 5 to 25 µg/ml) or cells synthesizing a comparable amount of WT1 polypeptide. It may be desirable to incubate a separate aliquot of a T cell sample in the absence of WT1 polypeptide to serve as a control.

T cells are considered to be specific for a WT1 polypeptide if the T cells kill target cells coated with a WT1 polypeptide or expressing a gene encoding such a polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to a WT1 polypeptide may be quantified. Contact with a WT1 polypeptide (200 ng/ml–100 µg/ml, preferably 100 ng/ml–25 µg/ml) for 3–7 days should result in at least a two fold increase in proliferation of the T cells and/or contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998). WT1 specific T cells may be expanded using standard techniques. Within preferred embodiments, the T cells are derived from a patient or a related or unrelated donor and are administered to the patient following stimulation and expansion.

T cells that have been activated in response to a WT1 polypeptide, polynucleotide or WT1-expressing APC may be $CD4^+$ and/or $CD8^+$. Specific activation of $CD4^+$ or $CD8^+$ T cells may be detected in a variety of ways. Methods for detecting specific T cell activation include detecting the proliferation of T cells, the production of cytokines (e.g., lymphokines), or the generation of cytolytic activity (i.e., generation of cytotoxic T cells specific for WT1). For $CD4^+$ T cells, a preferred method for detecting specific T cell activation is the detection of the proliferation of T cells. For $CD8^+$ T cells, a preferred method for detecting specific T cell activation is the detection of the generation of cytolytic activity.

For therapeutic purposes, $CD4^+$ or $CD8^+$ T cells that proliferate in response to the WT1 polypeptide, polynucleotide or APC can be expanded in number either in vitro or in vivo. Proliferation of such T cells in vitro may be accomplished in a variety of ways. For example, the T cells can be re-exposed to WT1 polypeptide, with or without the addition of T cell growth factors, such as interleukin-2, and/or stimulator cells that synthesize a WT1 polypeptide. The addition of stimulator cells is preferred where generating $CD8^+$ T cell responses. T cells can be grown to large numbers in vitro with retention of specificity in response to intermittent restimulation with WT1 polypeptide. Briefly, for the primary in vitro stimulation (IVS), large numbers of lymphocytes (e.g., greater than $4\times10^7$) may be placed in flasks with media containing human serum. WT1 polypeptide (e.g., peptide at 10 µg/ml) may be added directly, along with tetanus toxoid (e.g., 5 µg/ml). The flasks may then be incubated (e.g., 37° C. for 7 days). For a second IVS, T cells are then harvested and placed in new flasks with $2–3\times10^7$ irradiated peripheral blood mononuclear cells. WT1 polypeptide (e.g., 10 µg/ml) is added directly. The flasks are incubated at 37° C. for 7 days. On day 2 and day 4 after the second IVS, 2–5 units of interleukin-2 (IL-2) may be added. For a third IVS, the T cells may be placed in wells and stimulated with the individual's own EBV transformed B cells coated with the peptide. IL-2 may be added on days 2 and 4 of each cycle. As soon as the cells are shown to be specific cytotoxic T cells, they may be expanded using a 10 day stimulation cycle with higher IL-2 (20 units) on days 2, 4 and 6.

Alternatively, one or more T cells that proliferate in the presence of WT1 polypeptide can be expanded in number by cloning. Methods for cloning cells are well known in the art, and include limiting dilution. Responder T cells may be purified from the peripheral blood of sensitized patients by density gradient centrifugation and sheep red cell resetting and established in culture by stimulating with the nominal antigen in the presence of irradiated autologous filler cells. In order to generate CD4+ T cell lines, WT1 polypeptide is used as the antigenic stimulus and autologous peripheral blood lymphocytes (PBL) or lymphoblastoid cell lines (LCL) immortalized by infection with Epstein Barr virus are used as antigen presenting cells. In order to generate CD8+ T cell lines, autologous antigen-presenting cells transfected with an expression vector which produces WT1 polypeptide may be used as stimulator cells. Established T cell lines may be cloned 2–4 days following antigen stimulation by plating stimulated T cells at a frequency of 0.5 cells per well in 96-well flat-bottom plates with $1 \times 10^6$ irradiated PBL or LCL cells and recombinant interleukin-2 (rIL2) (50 U/ml). Wells with established clonal growth may be identified at approximately 2–3 weeks after initial plating and restimulated with appropriate antigen in the presence of autologous antigen-presenting cells, then subsequently expanded by the addition of low doses of rIL2 (10 U/ml) 2–3 days following antigen stimulation. T cell clones may be maintained in 24-well plates by periodic restimulation with antigen and rIL2 approximately every two weeks.

Within certain embodiments, allogeneic T-cells may be primed (i.e., sensitized to WT1) in vivo and/or in vitro. Such priming may be achieved by contacting T cells with a WT1 polypeptide, a polynucleotide encoding such a polypeptide or a cell producing such a polypeptide under conditions and for a time sufficient to permit the priming of T cells. In general, T cells are considered to be primed if, for example, contact with a WT1 polypeptide results in proliferation and/or activation of the T cells, as measured by standard proliferation, chromium release and/or cytokine release assays as described herein. A stimulation index of more than two fold increase in proliferation or lysis, and more than three fold increase in the level of cytokine, compared to negative controls, indicates T-cell specificity. Cells primed in vitro may be employed, for example, within a bone marrow transplantation or as donor lymphocyte infusion.

T cells specific for WT1 can kill cells that express WT1 protein. Introduction of genes encoding T-cell receptor (TCR) chains for WT1 are used as a means to quantitatively and qualitatively improve responses to WT1 bearing leukemia and cancer cells. Vaccines to increase the number of T cells that can react to WT1 positive cells are one method of targeting WT1 bearing cells. T cell therapy with T cells specific for WT1 is another method. An alternative method is to introduce the TCR chains specific for WT1 into T cells or other cells with lytic potential. In a suitable embodiment, the TCR alpha and beta chains are cloned out from a WT1 specific T cell line and used for adoptive T cell therapy, such as described in WO96/30516, incorporated herein by reference.

Pharmaceutical Compositions and Vaccines

Within certain aspects, polypeptides, polynucleotides, antibodies and/or T cells may be incorporated into pharmaceutical compositions or vaccines. Alternatively, a pharmaceutical composition may comprise an antigen-presenting cell (e.g., a dendritic cell) transfected with a WT1 polynucleotide such that the antigen presenting cell expresses a WT1 polypeptide. Pharmaceutical compositions comprise one or more such compounds or cells and a physiologically acceptable carrier or excipient. Certain vaccines may comprise one or more such compounds or cells and a non-specific immune response enhancer, such as an adjuvant or a liposome (into which the compound is incorporated).

Pharmaceutical compositions and vaccines may additionally contain a delivery system, such as biodegradable microspheres which are disclosed, for example, in U.S. Pat. Nos. 4,897,268 and 5,075,109. Pharmaceutical compositions and vaccines within the scope of the present invention may also contain other compounds, which may be biologically active or inactive.

Within certain embodiments, pharmaceutical compositions and vaccines are designed to elicit T cell responses specific for a WT1 polypeptide in a patient, such as a human. In general, T cell responses may be favored through the use of relatively short polypeptides (e.g., comprising less than 23 consecutive amino acid residues of a native WT1 polypeptide, preferably 4–16 consecutive residues, more preferably 8–16 consecutive residues and still more preferably 8–10 consecutive residues. Alternatively, or in addition, a vaccine may comprise a non-specific immune response enhancer that preferentially enhances a T cell response. In other words, the immune response enhancer may enhance the level of a T cell response to a WT1 polypeptide by an amount that is proportionally greater than the amount by which an antibody response is enhanced. For example, when compared to a standard oil based adjuvant, such as CFA, an immune response enhancer that preferentially enhances a T cell response may enhance a proliferative T cell response by at least two fold, a lytic response by at least 10%, and/or T cell activation by at least two fold compared to WT1-megative control cell lines, while not detectably enhancing an antibody response. The amount by which a T cell or antibody response to a WT1 polypeptide is enhanced may generally be determined using any representative technique known in the art, such as the techniques provided herein.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacterial and viral expression systems and mammalian expression systems. Appropriate nucleic acid expression systems contain the necessary DNA, cDNA or RNA sequences for expression in the patient (such as a suitable promoter and terminating signal). Bacterial delivery systems involve the administration of a bacterium (such as *Bacillus-Calmette-Guerrin*) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

As noted above, a pharmaceutical composition or vaccine may comprise an antigen-presenting cell that expresses a WT1 polypeptide. For therapeutic purposes, as described herein, the antigen presenting cell is preferably an autologous dendritic cell. Such cells may be prepared and transfected using standard techniques, such as those described by Reeves et al., *Cancer Res.* 56:5672–5677, 1996; Tuting et al., *J. Immunol.* 160:1139–1147, 1998; and Nair et al., *Nature Biotechnol.* 16:364–369, 1998). Expression of a WT1 polypeptide on the surface of an antigen-presenting cell may be confirmed by in vitro stimulation and standard proliferation as well as chromium release assays, as described herein.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. For certain topical applications, formulation as a cream or lotion, using well known components, is preferred.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers, such as adjuvants, may be employed in the vaccines of this invention. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable non-specific immune response enhancers include alum-based adjuvants (e.g., Alhydrogel, Rehydragel, aluminum phosphate, Algammulin, aluminum hydroxide); oil based adjuvants (Freund's adjuvant (FA), Specol, RIBI, TiterMax, Montanide ISA50 or Seppic MONTANIDE ISA 720; cytokines (e.g., GM-CSF or Flat3-ligand); microspheres; nonionic block copolymer-based adjuvants; dimethyl dioctadecyl ammoniumbromide (DDA) based adjuvants AS-1, AS-2 (Smith Kline Beecham); Ribi Adjuvant system based adjuvants; QS21 (Aquila); saponin based adjuvants (crude saponin, the saponin Quil A ); muramyl dipeptide (MDP) based adjuvants such as SAF (Syntex adjuvant in its microfluidized form (SAF-m)); dimethyl-dioctadecyl ammonium bromide (DDA); human complement based adjuvants *m. vaccae* and derivatives; immune stimulating complex (iscom) based adjuvants; inactivated toxins; and attenuated infectious agents (such as *M. tuberculosis*).

As noted above, within certain embodiments, immune response enhancers are chosen for their ability to preferentially elicit or enhance a T cell response (e.g., CD4$^+$ and/or CD8$^+$) to a WT1 polypeptide. Such immune response enhancers are well known in the art, and include (but are not limited to) Montanide ISA50, Seppic MONTANIDE ISA 720, cytokines (e.g., GM-CSF, Flat3-ligand), microspheres, dimethyl dioctadecyl ammoniumbromide (DDA) based adjuvants, AS-1 (Smith Kline Beecham), AS-2 (Smith Kline Beecham), Ribi Adjuvant system based adjuvants, QS21 (Aquila), saponin based adjuvants (crude saponin, the sapo-nin Quil A), Syntex adjuvant in its microfluidized form (SAF-m), MV, ddMV (Genesis), immune stimulating complex (iscom) based adjuvants and inactivated toxins.

The compositions and vaccines described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide, antibody or cell dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Therapy of Malignant Diseases

In further aspects of the present invention, the compositions and vaccines described herein may be used to inhibit the development of malignant diseases (e.g., progressive or metastatic diseases or diseases characterized by small tumor burden such as minimal residual disease). In general, such methods may be used to prevent, delay or treat a disease associated with WT1 expression. In other words, therapeutic methods provided herein may be used to treat an existing WT1-associated disease, or may be used to prevent or delay the onset of such a disease in a patient who is free of disease or who is afflicted with a disease that is not yet associated with WT1 expression.

As used herein, a disease is "associated with WT1 expression" if diseased cells (e.g., tumor cells) at some time during the course of the disease generate detectably higher levels of a WT1 polypeptide than normal cells of the same tissue. Association of WT1 expression with a malignant disease does not require that WT1 be present on a tumor. For example, overexpression of WT1 may be involved with initiation of a tumor, but the protein expression may subsequently be lost. Alternatively, a malignant disease that is not characterized by an increase in WT1 expression may, at a later time, progress to a disease that is characterized by increased WT1 expression. Accordingly, any malignant disease in which diseased cells formerly expressed, currently express or are expected to subsequently express increased levels of WT1 is considered to be "associated with WT1 expression."

Immunotherapy may be performed using any of a variety of techniques, in which compounds or cells provided herein function to remove WT1-expressing cells from a patient. Such removal may take place as a result of enhancing or inducing an immune response in a patient specific for WT1 or a cell expressing WT1. Alternatively, WT1-expressing cells may be removed ex vivo (e.g., by treatment of autologous bone marrow, peripheral blood or a fraction of bone marrow or peripheral blood). Fractions of bone marrow or peripheral blood may be obtained using any standard technique in the art.

Within such methods, pharmaceutical compositions and vaccines may be administered to a patient. As used herein, a "patient" refers to any warm-blooded animal, preferably a human. A patient may or may not be afflicted with a malignant disease. Accordingly, the above pharmaceutical compositions and vaccines may be used to prevent the onset of a disease (i.e., prophylactically) or to treat a patient afflicted with a disease (e.g., to prevent or delay progression and/or metastasis of an existing disease). A patient afflicted with a disease may have a minimal residual disease (e.g., a low tumor burden in a leukemia patient in complete or partial remission or a cancer patient following reduction of the tumor burden after surgery radiotherapy and/or chemotherapy). Such a patient may be immunized to inhibit a relapse (i.e., prevent or delay the relapse, or decrease the severity of a relapse). Within certain preferred embodiments, the patient is afflicted with a leukemia (e.g., AML, CML, ALL or childhood ALL), a myelodysplastic syndrome (MDS) or a cancer (e.g., gastrointestinal, lung, thyroid or breast cancer or a melanoma), where the cancer or leukemia is WT1 positive (i.e., reacts detectably with an anti-WT1 antibody, as provided herein or expresses WT1 mRNA at a level detectable by RT-PCR, as described herein) or suffers from an autoimmune disease directed against WT1-expressing cells.

Other diseases associated with WT1 overexpression include kidney cancer (such as renal cell carcinoma, or Wilms tumor), as described in Satoh F., et al., *Pathol. Int.* 50(6):458–71(2000), and Campbell C. E. et al., *Int. J. Cancer* 78(2):182–8 (1998) mesothelioma, as described in Amin, K. M. et al., *Am. J. Pathol.* 146(2):344–56 (1995). Harada et al. (*Mol. Urol.* 3(4):357–364 (1999) describe WT1 gene expression in human testicular germ-cell tumors. Nonomura et al. *Hinyokika Kiyo* 45(8):593–7 (1999) describe molecular staging of testicular cancer using polymerase chain reaction of the testicular cancer-specific genes. Shimizu et al., *Int. J. Gynecol. Pathol.* 19(2):158–63 (2000) describe the immunohistochemical detection of the Wilms' tumor gene (WT1) in epithelial ovarian tumors.

WT1 overexpression was also described in desmoplastic small round cell tumors, by Bamoud, R. et al., *Am. J. Surg. Pathol.* 24(6):830–6 (2000); and *Pathol. Res. Pract.* 194 (10):693–700 (1998). WT1 overexpression in glioblastoma and other cancer was described by Menssen, H. D. et al., *J. Cancer Res. Clin. Oncol.* 126(4):226–32 (2000), "Wilms' tumor gene (WT1) expression in lung cancer, colon cancer and glioblastoma cell lines compared to freshly isolated tumor specimens." Other diseases showing WT1 overexpression include EBV associated diseases, such as Burkitt's lymphoma and nasopharyngeal cancer (Spinsanti P. et al., *Leuk. Lymphoma* 38(5–6):611–9 (2000), "Wilms' tumor gene expression by normal and malignant human B lymphocytes."

In *Leukemia* 14(9):1634–4 (2000), Pan et al., describe in vitro IL-12 treatment of peripheral blood mononuclear cells from patients with leukemia or myelodysplastic syndromes, and reported an increase in cytotoxicity and reduction in WT1 gene expression. In *Leukemia* 13(6):891–900 (1999), Patmasiriwat et al. reported WT1 and GATA1 expression in myelodysplastic syndrome and acute leukemia. In *Leukemia* 13(3):393–9 (1999), Tamaki et al. reported that the Wilms' tumor gene WT1 is a good marker for diagnosis of disease progression of myelodysplastic syndromes. Expression of the Wilms' tumor gene WT1 in solid tumors, and its involvement in tumor cell growth, was discussed in relation to gastric cancer, colon cancer, lung cancer, breast cancer cell lines, germ cell tumor cell line, ovarian cancer, the uterine cancer, thyroid cancer cell line, hepatocellular carcinoma, in Oji et al., *Jpn. J. Cancer Res.* 90(2):194–204 (1999).

The compositions provided herein may be used alone or in combination with conventional therapeutic regimens such as surgery, irradiation, chemotherapy and/or bone marrow transplantation (autologous, syngeneic, allogeneic or unrelated). As discussed in greater detail below, binding agents and T cells as provided herein may be used for purging of autologous stem cells. Such purging may be beneficial prior to, for example, bone marrow transplantation or transfusion of blood or components thereof. Binding agents, T cells, antigen presenting cells (APC) and compositions provided herein may further be used for expanding and stimulating (or priming) autologous, allogeneic, syngeneic or unrelated WT1-specific T-cells in vitro and/or in vivo. Such WT1-specific T cells may be used, for example, within donor lymphocyte infusions.

Routes and frequency of administration, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. In some tumors, pharmaceutical compositions or vaccines may be administered locally (by, for example, rectocoloscopy, gastroscopy, videoendoscopy, angiography or other methods known in the art). Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response that is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent complete or partial remissions, or longer disease-free and/or overall survival) in vaccinated patients as compared to non-vaccinated patients. In general, for pharmaceutical compositions and vaccines comprising one or more polypeptides, the amount of each polypeptide present in a dose ranges from about 100 µg to 5 mg. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent complete or partial remissions, or longer disease-free and/or overall survival) in treated patients as compared to non-treated patients. Increases in preexisting immune responses to WT1 generally correlate with an improved clinical outcome. Such immune responses may generally be evaluated using standard proliferation, cytotoxicity or cytokine assays, which may be performed using samples obtained from a patient before and after treatment.

Within further aspects, methods for inhibiting the development of a malignant disease associated with WT1 expression involve the administration of autologous T cells that have been activated in response to a WT1 polypeptide or WT1-expressing APC, as described above. Such T cells may be $CD4^+$ and/or $CD8^+$, and may be proliferated as described above. The T cells may be administered to the individual in an amount effective to inhibit the development of a malignant disease. Typically, about $1 \times 10^9$ to $1 \times 10^{11}$ T cells/$M^2$ are administered intravenously, intracavitary or in the bed of a resected tumor. It will be evident to those skilled in the art that the number of cells and the frequency of administration will be dependent upon the response of the patient.

Within certain embodiments, T cells may be stimulated prior to an autologous bone marrow transplantation. Such stimulation may take place in vivo or in vitro. For in vitro stimulation, bone marrow and/or peripheral blood (or a fraction of bone marrow or peripheral blood) obtained from a patient may be contacted with a WT1 polypeptide, a polynucleotide encoding a WT1 polypeptide and/or an APC that expresses a WT1 polypeptide under conditions and for a time sufficient to permit the stimulation of T cells as described above. Bone marrow, peripheral blood stem cells and/or WT1-specific T cells may then be administered to a patient using standard techniques.

Within related embodiments, T cells of a related or unrelated donor may be stimulated prior to a syngeneic or allogeneic (related or unrelated) bone marrow transplantation. Such stimulation may take place in vivo or in vitro. For in vitro stimulation, bone marrow and/or peripheral blood (or a fraction of bone marrow or peripheral blood) obtained from a related or unrelated donor may be contacted with a WT1 polypeptide, WT1 polynucleotide and/or APC that expresses a WT1 polypeptide under conditions and for a time sufficient to permit the stimulation of T cells as described above. Bone marrow, peripheral blood stem cells and/or WT1-specific T cells may then be administered to a patient using standard techniques.

Within other embodiments, WT1-specific T cells as described herein may be used to remove cells expressing WT1 from autologous bone marrow, peripheral blood or a fraction of bone marrow or peripheral blood (e.g., $CD34^+$ enriched peripheral blood (PB) prior to administration to a patient). Such methods may be performed by contacting bone marrow or PB with such T cells under conditions and for a time sufficient to permit the reduction of WT1 expressing cells to less than 10%, preferably less than 5% and more preferably less than 1%, of the total number of myeloid or lymphatic cells in the bone marrow or peripheral blood. The extent to which such cells have been removed may be readily determined by standard methods such as, for example, qualitative and quantitative PCR analysis, morphology, immunohistochemistry and FACS analysis. Bone marrow or PB (or a fraction thereof) may then be administered to a patient using standard techniques.

Diagnostic Methods

The present invention further provides methods for detecting a malignant disease associated with WT1 expression, and for monitoring the effectiveness of an immunization or therapy for such a disease. Such methods are based on the discovery, within the present invention, that an immune response specific for WT1 protein can be detected in patients afflicted with such diseases, and that methods which enhance such immune responses may provide a preventive or therapeutic benefit.

To determine the presence or absence of a malignant disease associated with WT1 expression, a patient may be tested for the level of T cells specific for WT1. Within certain methods, a biological sample comprising $CD4^+$ and/or $CD8^+$ T cells isolated from a patient is incubated with a WT1 polypeptide, a polynucleotide encoding a WT1 polypeptide and/or an APC that expresses a WT1 polypeptide, and the presence or absence of specific activation of the T cells is detected, as described herein. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with WT1 polypeptide (e.g., 5–25 µg/ml). It may be desirable to incubate another aliquot of a T cell sample in the absence of WT1 polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a malignant disease associated with WT1 expression. Further correlation may be made, using methods well known in the art, between the level of proliferation and/or cytolytic activity and the predicted response to therapy. In particular, patients that display a higher antibody, proliferative and/or lytic response may be expected to show a greater response to therapy.

Within other methods, a biological sample obtained from a patient is tested for the level of antibody specific for WT1. The biological sample is incubated with a WT1 polypeptide, a polynucleotide encoding a WT1 polypeptide and/or an APC that expresses a WT1 polypeptide under conditions and for a time sufficient to allow immunocomplexes to form. Immunocomplexes formed between the WT1 polypeptide and antibodies in the biological sample that specifically bind to the WT1 polypeptide are then detected. A biological sample for use within such methods may be any sample obtained from a patient that would be expected to contain antibodies. Suitable biological samples include blood, sera, ascites, bone marrow, pleural effusion, and cerebrospinal fluid.

The biological sample is incubated with the WT1 polypeptide in a reaction mixture under conditions and for a time sufficient to permit immunocomplexes to form between the polypeptide and antibodies specific for WT1. For example, a biological sample and WT1 polypeptide may be incubated at 4° C. for 24–48 hours.

Following the incubation, the reaction mixture is tested for the presence of immunocomplexes. Detection of immunocomplexes formed between the WT1 polypeptide and antibodies present in the biological sample may be accomplished by a variety of known techniques, such as radioimmunoassays (RIA) and enzyme linked immunosorbent assays (ELISA). Suitable assays are well known in the art and are amply described in the scientific and Patent literature (e.g., Harlow and Lane, *Antibodies: A Laboratory Manual*, Cold Spring Harbor Laboratory, 1988). Assays that may be used include, but are not limited to, the double monoclonal antibody sandwich immunoassay technique of David et al. (U.S. Pat. No. 4,376,110); monoclonal-polyclonal antibody sandwich assays (Wide et al., in Kirkham and Hunter, eds., *Radioimmunoassay Methods*, E. and S. Livingstone, Edinburgh, 1970); the "western blot" method of Gordon et al. (U.S. Pat. No. 4,452,901); immunoprecipitation of labeled ligand (Brown et al., *J. Biol. Chem.* 255:4980–4983, 1980); enzyme-linked immunosorbent assays as described by, for example, Raines and Ross (*J. Biol. Chem.* 257:5154–5160, 1982); immunocytochemical techniques, including the use of fluorochromes (Brooks et al., *Clin. Exp. Immunol.* 39: 477, 1980); and neutralization of activity (Bowen-Pope et al., *Proc. Natl. Acad. Sci. USA* 81:2396–2400, 1984). Other immunoassays include, but are not limited to, those described in U.S. Pat. Nos.: 3,817,827; 3,850,752; 3,901,654; 3,935,074; 3,984,533; 3,996,345; 4,034,074; and 4,098,876.

For detection purposes, WT1 polypeptide may either be labeled or unlabeled. Unlabeled WT1 polypeptide may be used in agglutination assays or in combination with labeled detection reagents that bind to the immunocomplexes (e.g., anti-immunoglobulin, protein G, protein A or a lectin and secondary antibodies, or antigen-binding fragments thereof, capable of binding to the antibodies that specifically bind to the WT1 polypeptide). If the WT1 polypeptide is labeled, the reporter group may be any suitable reporter group known in the art, including radioisotopes, fluorescent groups, luminescent groups, enzymes, biotin and dye particles.

Within certain assays, unlabeled WT1 polypeptide is immobilized on a solid support. The solid support may be any material known to those of ordinary skill in the art to which the polypeptide may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The polypeptide may be immobilized on the solid support using a variety of techniques known to those of skill in the art, which are amply described in the Patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the WT1 polypeptide, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of polypeptide ranging from about 10 ng to about 10 μg, and preferably about 100 ng to about 1 μg, is sufficient to immobilize an adequate amount of polypeptide.

Following immobilization, the remaining protein binding sites on the support are typically blocked. Any suitable blocking agent known to those of ordinary skill in the art, such as bovine serum albumin, Tween 20™ (Sigma Chemical Co., St. Louis, Mo.), heat-inactivated normal goat serum (NGS), or BLOTTO (buffered solution of nonfat dry milk which also contains a preservative, salts, and an antifoaming agent). The support is then incubated with a biological sample suspected of containing specific antibody. The sample can be applied neat, or, more often, it can be diluted, usually in a buffered solution which contains a small amount (0.1%–5.0% by weight) of protein, such as BSA, NGS, or BLOTTO. In general, an appropriate contact time (i.e., incubation time) is a period of time that is sufficient to detect the presence of antibody that specifically binds WT1 within a sample containing such an antibody. Preferably, the contact time is sufficient to achieve a level of binding that is at least about 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. A detection reagent that binds to the immunocomplexes and that comprises a reporter group may then be added. The detection reagent is incubated with the immunocomplex for an amount of time sufficient to detect the bound antibody. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups (e.g., horseradish peroxidase, beta-galactosidase, alkaline phosphatase and glucose oxidase) may generally be detected by the addition of substrate (generally for a specific period of time), followed by spectroscopic or other analysis of the reaction products. Regardless of the specific method employed, a level of bound detection reagent that is at least two fold greater than background (i.e., the level observed for a biological sample obtained from a disease-free individual) indicates the presence of a malignant disease associated with WT1 expression.

In general, methods for monitoring the effectiveness of an immunization or therapy involve monitoring changes in the level of antibodies or T cells specific for WT1 in the patient. Methods in which antibody levels are monitored may comprise the steps of: (a) incubating a first biological sample, obtained from a patient prior to a therapy or immunization, with a WT1 polypeptide, wherein the incubation is performed under conditions and for a time sufficient to allow immunocomplexes to form; (b) detecting immunocomplexes formed between the WT1 polypeptide and antibodies in the biological sample that specifically bind to the WT1 polypeptide; (c) repeating steps (a) and (b) using a second biological sample taken from the patient following therapy or immunization; and (d) comparing the number of immunocomplexes detected in the first and second biological samples. Alternatively, a polynucleotide encoding a WT1 polypeptide, or an APC expressing a WT1 polypeptide may be employed in place of the WT1 polypeptide. Within such methods, immunocomplexes between the WT1 polypeptide encoded by the polynucleotide, or expressed by the APC, and antibodies in the biological sample are detected.

Methods in which T cell activation and/or the number of WT1 specific precursors are monitored may comprise the steps of: (a) incubating a first biological sample comprising CD4+ and/or CD8+ cells (e.g., bone marrow, peripheral blood or a fraction thereof), obtained from a patient prior to a therapy or immunization, with a WT1 polypeptide, wherein the incubation is performed under conditions and for a time sufficient to allow specific activation, proliferation and/or lysis of T cells; (b) detecting an amount of activation, proliferation and/or lysis of the T cells; (c) repeating steps (a) and (b) using a second biological sample comprising CD4+ and/or CD8+ T cells, and taken from the same patient following therapy or immunization; and (d) comparing the amount of activation, proliferation and/or lysis of T cells in the first and second biological samples. Alternatively, a polynucleotide encoding a WT1 polypeptide, or an APC expressing a WT1 polypeptide may be employed in place of the WT1 polypeptide.

A biological sample for use within such methods may be any sample obtained from a patient that would be expected to contain antibodies, CD4+ T cells and/or CD8+ T cells. Suitable biological samples include blood, sera, ascites, bone marrow, pleural effusion and cerebrospinal fluid. A first biological sample may be obtained prior to initiation of therapy or immunization or part way through a therapy or vaccination regime. The second biological sample should be obtained in a similar manner, but at a time following additional therapy or immunization. The second biological sample may be obtained at the completion of, or part way through, therapy or immunization, provided that at least a portion of therapy or immunization takes place between the isolation of the first and second biological samples.

Incubation and detection steps for both samples may generally be performed as described above. A statistically significant increase in the number of immunocomplexes in the second sample relative to the first sample reflects successful therapy or immunization.

The following Examples are offered by way of illustration and not by way of limitation.

EXAMPLES

Example 1

Identification of an Immune Response to WT1 in Patients with Hematological Malignancies This Example illustrates the identification of an existent immune response in patients with a hematological malignancy.

To evaluate the presence of preexisting WT1 specific antibody responses in patients, sera of patients with acute myelogenous leukemia (AML), acute lymphocytic leukemia (ALL), chronic myelogenous leukemia (CML) and severe aplastic anemia were analyzed using Western blot analysis. Sera were tested for the ability to immunoprecipitate WT1 from the human leukemic cell line K562 (American Type Culture Collection, Manassas, Va.). In each case, immunoprecipitates were separated by gel electrophoresis, transferred to membrane and probed with the anti WT-1 antibody WT180 (Santa Cruz Biotechnology, Inc., Santa Cruz, Calif.). This Western blot analysis identified potential WT1 specific antibodies in patients with hematological malignancy. A representative Western blot showing the results for a patient with AML is shown in FIG. 2. A 52 kD protein in the immunoprecipitate generated using the patient sera was recognized by the WT1 specific antibody. The 52 kD protein migrated at the same size as the positive control.

Additional studies analyzed the sera of patients with AML and CML for the presence of antibodies to full-length and truncated WT1 proteins. CDNA constructs representing the human WT1/full-length (aa 1–449), the N-terminus (aa 1–249) (WT1/N-terminus) and C-terminuis (aa 267–449) (WT1/C-terminus) region were subcloned into modified pET28 vectors. The WT1/full-length and WT1/N-terminus proteins were expressed as Ra12 fusion proteins. Ra12 is the C-terminal fragment of a secreted Mycobacterium tuberculosis protein, denoted as MTB32B. (Skeiky et al., *Infect Immun.* 67;3998, 1999). The Ra12-WT1/full-length fusion region was cloned 3' to a histidine-tag in a histidine-tag modified pET28 vector. The WT1/N-terminus region was subcloned into a modified pET28 vector that has a 5' histidine-tag followed by the thioredoxin (TRX)-WT1/N-terminus fusion region followed by a 3' histidine-tag. The WT1/C-terminus coding region was subcloned into a modified pET28 vector without a fusion partner containing only the 5' and 3' histidine-tag, followed by a Thrombin and EK site.

BL21 pLysS *E. coli* (Stratagene, La Jolla, Calif.) were transformed with the three WT1 expression constructs, grown overnight and induced with isopropyl-β-D-thiogalactoside (IPTG). WT1 proteins were purified as follows: Cells were harvested and lysed by incubation in 10 mM Tris, pH 8.0 with Complete Protease Inhibitor Tablets (Boehringer Mannheim Biochemicals, Indianapolis, Ind.) at 37° C. followed by repeated rounds of sonication. Inclusion bodies were washed twice with 10 mM Tris, pH 8.0. Proteins were then purified by metal chelate affinity chromatography over nickel-nitrilotriacetic acid resin (QIAGEN Inc., Valencia, Calif.; Hochuli et al., *Biologically Active Molecules:* 217, 1989) followed by chromatography on a Source Q anion exchange resin (Amersham Pharmacia Biotech, Upsala, Sweden). The identity of the WT1 proteins was confirmed by N-terminal sequencing.

Sera from adult patients with de nova AML or CML were studied for the presence of WT1 specific Ab. Recombinant proteins were adsorbed to TC microwell plates (Nunc, Roskilde, Denmark). Plates were washed with PBS/0.5% Tween 20 and blocked with 1% BSA/PBS/0.1% Tween 20. After washing, serum dilutions were added and incubated overnight at 4° C. Plates were washed and Donkey anti-human IgG-HRP secondary antibody was added (Jackson-Immunochem, West Grove, Pa.) and incubated for 2h at room temperature. Plates were washed, incubated with TMB Peroxidase substrate solution (Kirkegaard and Perry Laboratories, Mass.), quenched with 1N $H_2SO_4$, and immediately read (Cyto-Fluor 2350; Millipore, Bedford, Mass.).

For the serological survey, human sera were tested by ELISA over a range of serial dilutions from 1:50 to 1:20,000. A positive reaction was defined as an OD value of a 1:500 diluted serum that exceeded the mean OD value of sera from normal donors (n=96) by three (WT1/full-length, WT1C-terminus) standard deviations. Due to a higher background in normal donors to the WT1/N-terminus protein a positive reaction to WT1/N-terninus was defined as an OD value of 1:500 diluted serum that exceeded the mean OD value of sera from normal donors by four standard deviations. To verify that the patient Ab response was directed against WT1 and not to the Ra12 or TRX fusion part of the protein or possible *E. coli* contaminant proteins, controls included the Ra12 and TRX protein alone purified in a similar manner. Samples that showed reactivity against the Ra12 and/or TRX proteins were excluded from the analysis.

To evaluate for the presence of immunity to WT1, Ab to recombinant full-length and truncated WT1 proteins in the sera of normal individuals and patients with leukemia were determined. Antibody reactivity was analyzed by ELISA reactivity to WT1/full-length protein, WT1/N-terminus protein and WT1/C-terminus protein.

Figure 16:
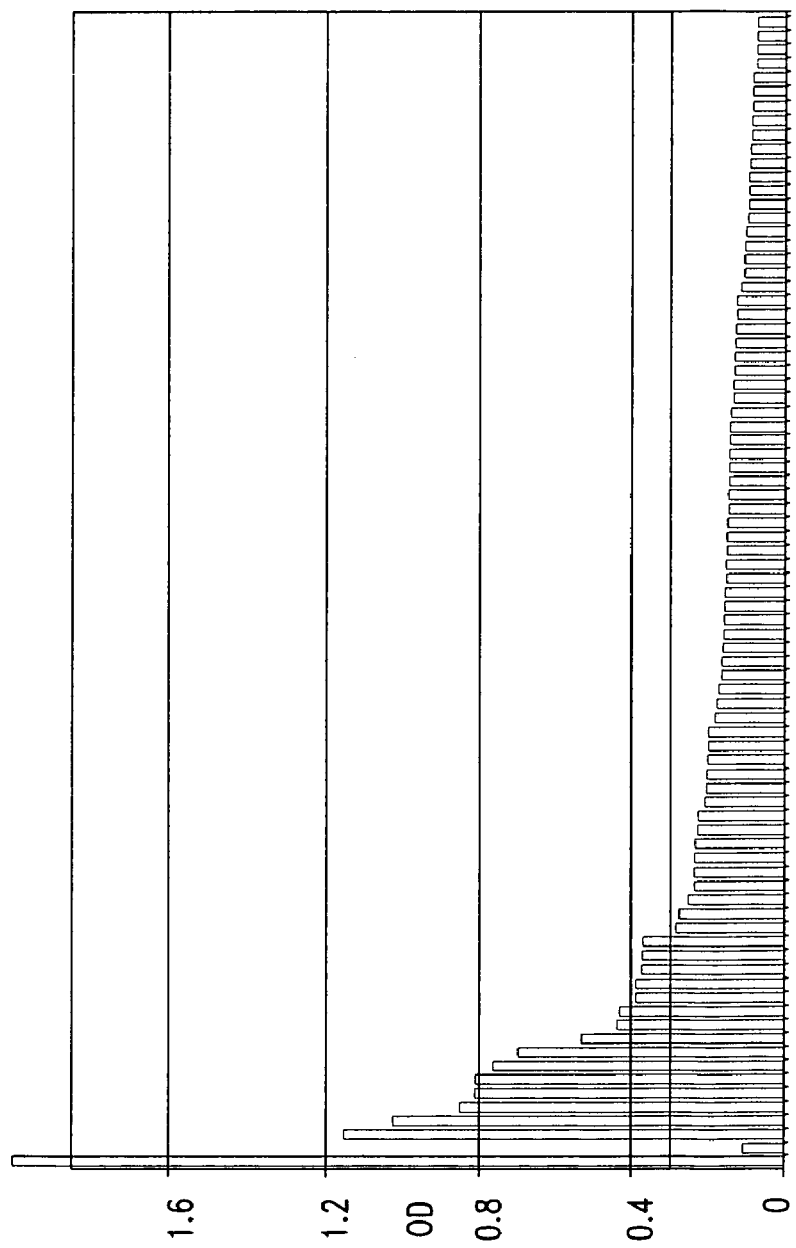
FIG. 16 depicts serum antibody reactivity to WT1 in 81 patients with CML. Reactivity of serum antibody to WT1/full-length protein was evaluated by ELISA in patients with AML. The first and second lanes represent the positive and negative controls, respectively. Commercially obtained WT1 specific antibody WT180 was used for the positive control. The next 81 lanes represent results using sera from each individual patient. The OD values depicted were from ELISA using a 1:500 serum dilution. The figure includes cumulative data from 3 separate experiments.
Figure 17:
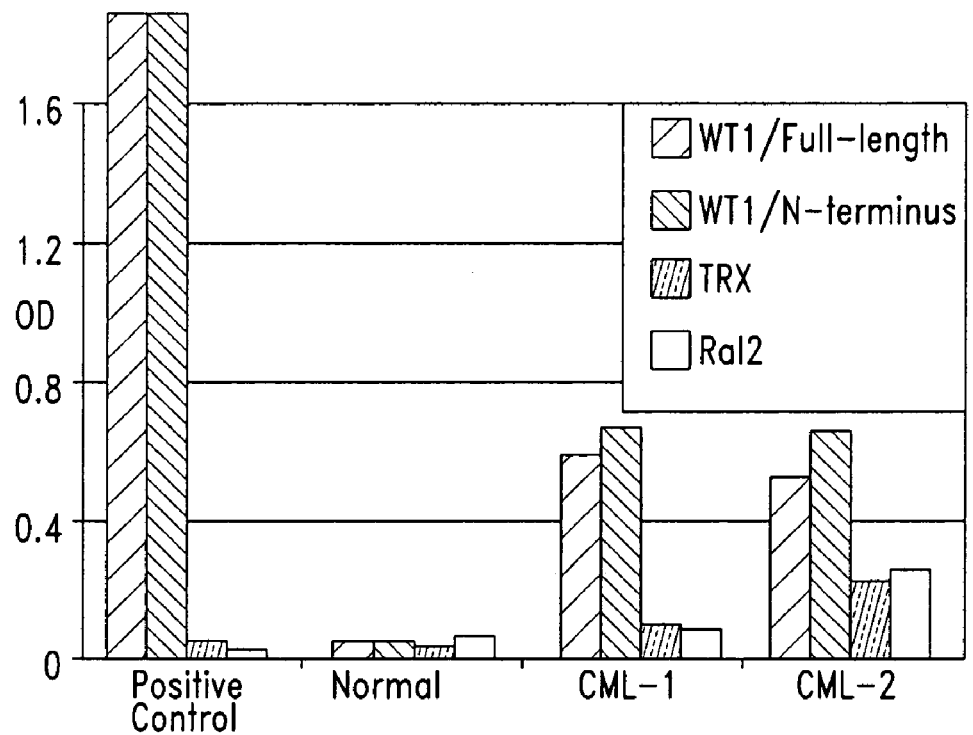
FIG. 17 depicts serum antibody reactivity to WT1 proteins and control proteins in 2 patients with CML. Reactivity of serum antibody to WT1/full-length, WT1/N-terminus, TRX and Ra12 proteins was evaluated by ELISA in 2 patients with CML. The OD values depicted were from ELISA using a 1:500 serum dilution. CML-1 and CML-2 denote serum from 2 of the individual patients in FIG. 3 with demonstrated antibody reactivity to WT1/full-length. The WT1/full-length protein was expressed as a fusion protein with Ra12. The WT1/N-terminus protein was expressed as a fusion protein with TRX. The control Ra12 and TRX proteins were purified in a similar manner. The results confirm that the serum antibody reactivity against the WT1 fusion proteins is directed against the WT1 portions of the protein.

Only 2 of 96 normal donors had serum antibodies reactive with WT1/full-length protein (FIG. 18). One of those individuals had antibody to WT1/N-terminus protein and one had antibody to WT1/C-terminus protein. In contrast, 16 of 63 patients (25%) with AML had serum antibodies reactive with WT1/full-length protein. By marked contrast, only 2 of 63 patients (3%) had reactivity to WT1/C-terminus protein. Fifteen of 81 patients (19%) with CML had serum antibodies reactive with WT1/full-length protein and 12 of 81 patients (15%) had serum antibodies reactive with WT1/N-terminus. Only 3 of 81 patients (3%) had reactivity to WT1/C-terminus protein. (FIGS. 16 and 17.)

These data demonstrate that Ab responses to WT1 are detectable in some patients with AML and CML. The greater incidence of antibody in leukemia patients provides strong evidence that immunization to the WT1 protein occurred as a result of patients bearing malignancy that expresses or at some time expressed WT1. Without being limited to a specific theory, it is believed that the observed antibody responses to WT1 most probably result from patients becoming immune to WT1 on their own leukemia cells and provide direct evidence that WT1 can be immunogenic despite being a "self" protein.

The presence of antibody to WT1 strongly implies that concurrent helper T cell responses are also present in the same patients. WT1 is an internal protein. Thus, CTL responses are likely to be the most effective in terms of leukemia therapy and the most toxic arm of immunity. Thus, these data provide evidence that therapeutic vaccines directed against WT1 will be able to elicit an immune response to WT1.

The majority of the antibodies detected were reactive with epitopes within the N-terminus while only a small subgroup of patients showed a weak antibody response to the C-terminus. This is consistent with observations in the animal model, where immunization with peptides derived from the N-terminus elicited antibody, helper T cell and CTL responses, whereas none of the peptides tested from the C-terminus elicited antibody or T cell responses (Gaiger et al., *Blood* 96:1334, 2000).

Example 2

Induction of Antibodies to WT1 in Mice Immunized with Cell Lines Expressing WT1

This Example illustrates the use of cells expressing WT1 to induce a WT1 specific antibody response in vivo.

Detection of existent antibodies to WT1 in patients with leukemia strongly implied that it is possible to immunize to WT1 protein to elicit immunity to WT1. To test whether immunity to WT1 can be generated by vaccination, mice were injected with TRAMP-C, a WT1 positive tumor cell line of B6 origin. Briefly, male B6 mice were immunized with $5 \times 10^6$ TRAMP-C cells subcutaneously and boosted twice with $5 \times 10^6$ cells at three week intervals. Three weeks after the final immunization, sera were obtained and single cell suspensions of spleens were prepared in RPMI 1640 medium (GIBCO) with 25 μM β-2-mercaptoethanol, 200 units of penicillin per ml, 10 mM L-glutamine, and 10% fetal bovine serum.

Figure 3:
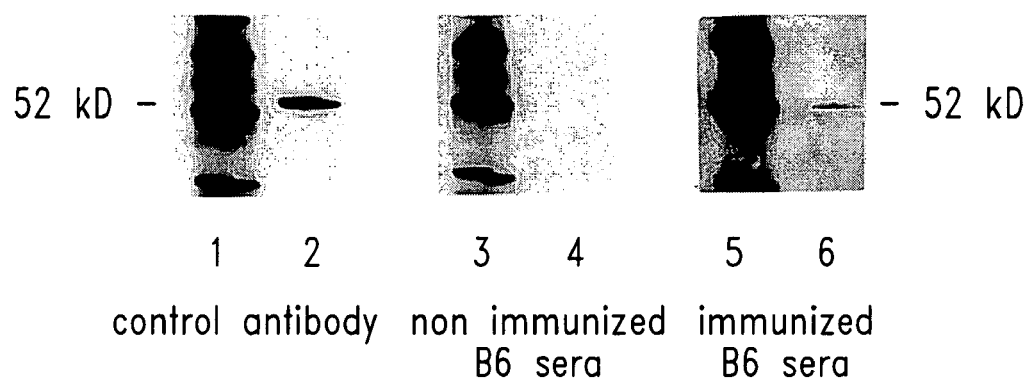
FIG. 3 is a Western blot illustrating the detection of a WT1 specific antibody response in B6 mice immunized with TRAMP-C, a WT1 positive tumor cell line. Lanes 1, 3 and 5 show molecular weight markers, and lanes 2, 4 and 6 show a WT1 specific positive control (N180, Santa Cruz Biotechnology, polypeptide spanning 180 amino acids of the N-terminal region of the WT1 protein, migrating on the Western blot at 52 kD). The primary antibody used was WT180 in lane 2, sera of non-immunized B6 mice in lane 4 and sera of the immunized B6 mice in lane 6.

Following immunization to TRAMP-C, a WT1 specific antibody response in the immunized animals was detectable. A representative Western blot is shown in FIG. 3. These results show that immunization to WT1 protein can elicit an immune response to WT1 protein.

Example 3

Induction of Th and Antibody Responses in Mice Immunized with WT1 Peptides

This Example illustrates the ability of immunization with WT1 peptides to elicit an immune response specific for WT1.

Peptides suitable for eliciting Ab and proliferative T cell responses were identified according to the Tsites program (Rothbard and Taylor, *EMBO J.* 7:93–100, 1988; Deavin et al., *Mol. Immunol.* 33:145–155, 1996), which searches for peptide motifs that have the potential to elicit Th responses. Peptides shown in Table I were synthesized and sequenced.

TABLE I

WT1 Peptides

| Peptide | Sequence | Comments |
|---|---|---|
| Mouse: p6–22 | RDLNALLPAVSSLGGGG (SEQ ID NO:13) | 1 mismatch relative to human WT1 sequence |
| Human: p6–22 | RDLNALLPAVPSLGGGG (SEQ ID NO:1) | |
| Human/mouse p117–139 | PSQASSGQARMFPNAPYLPSCLE (SEQ ID NOs: 2 and 3) | |
| Mouse: p244–262 | GATLKGMAAGSSSSVKWTE (SEQ ID NO:14) | 1 mismatch relative to human WT1 sequence |
| Human: p244–262 | GATLKGVAAGSSSSVKWTE (SEQ ID NO:4) | |
| Human/mouse: p287–301 | RIHTHGVFRGIQDVR (SEQ ID NOs: 15 and 16) | |
| Mouse: p299–313 | VRRVSGVAPTLVRS (SEQ ID NO:17) | 1 mismatch relative to human WT1 sequence |
| Human/mouse: p421–435 | CQKKFARSDELVRHH (SEQ ID NOs: 19 and 20) | |

For immunization, peptides were grouped as follows:
Group A: p6–22 human: 10.9 mg in 1 ml (10 μl = 100 μg)
p117–139 human/mouse: 7.6 mg in 1 ml (14 μl = 100 μg)
p244–262 human: 4.6. mg in 1 ml (22 μl = 100 μg)
Group B: p287–301 human/mouse: 7.2 mg in 1 ml (14 μl = 100 μg)
mouse p299–313: 6.6. mg in 1 ml (15 μl = 100 μg)
p421–435 human/mouse: 3.3 mg in 1 ml (30 μl = 100 μg)
Control: (FBL peptide 100 μg) + CFA/IFA
Control: (CD45 peptide 100 μg) + CFA/IFA Group A contained peptides present within the amino terminus portion of WT1 (exon 1) and Group B contained peptides present within the carboxy terminus, which contains a four zinc finger region with sequence homology to other DNA-binding proteins. Within group B, p287–301 and p299–313 were derived from exon 7, zinc finger 1, and p421–435 was derived from exon 10, zinc finger IV.

B6 mice were immunized with a group of WT1 peptides or with a control peptide. Peptides were dissolved in 1 ml sterile water for injection, and B6 mice were immunized 3 times at time intervals of three weeks. Adjuvants used were CFA/IFA, GM-CSF, and Montinide. The presence of antibodies specific for WT1 was then determined as described in Examples 1 and 2, and proliferative T cell responses were evaluated using a standard thymidine incorporation assay, in which cells were cultured in the presence of antigen and proliferation was evaluated by measuring incorporated radioactivity (Chen et al., Cancer Res. 54:1065–1070, 1994). In particular, lymphocytes were cultured in 96-well plates at $2 \times 10^5$ cells per well with $4 \times 10^5$ irradiated (3000 rads) syngeneic spleen cells and the designated peptide.

Figure 4:
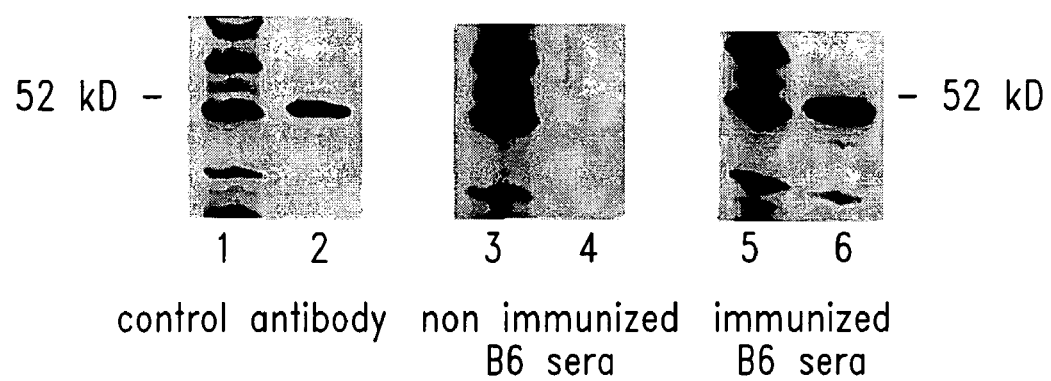
FIG. 4 is a Western blot illustrating the detection of WT1 specific antibodies in mice immunized with representative WT1 peptides. Lanes 1, 3 and 5 show molecular weight markers and lanes 2, 4 and 6 show a WT1 specific positive control (N180, Santa Cruz Biotechnology, polypeptide spanning 180 amino acids of the N-terminal region of the WT1 protein, migrating on the Western blot at 52 kD). The primary antibody used was WT180 in lane 2, sera of non-immunized B6 mice in lane 4 and sera of the immunized B6 mice in lane 6.
Figure 5A:
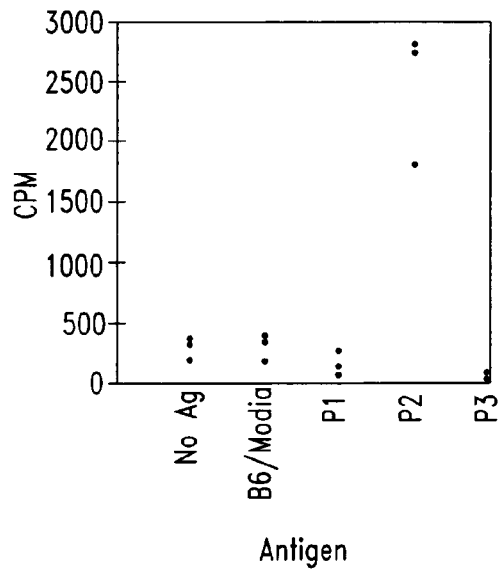
FIGS. 5A to 5C are graphs illustrating the stimulation of proliferative T cell responses in mice immunized with representative WT1 peptides. Thymidine incorporation assays were performed using one T cell line and two different clones, as indicated, and results were expressed as cpm. Controls indicated on the x axis were no antigen (No Ag) and B6/media; antigens used were p6–22 human (p1), p117–139 (p2) or p244–262 human (p3).
Figure 5B:
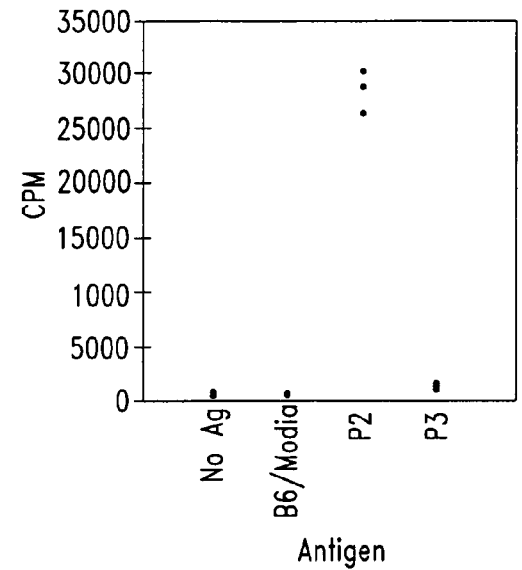
Figure 5C:
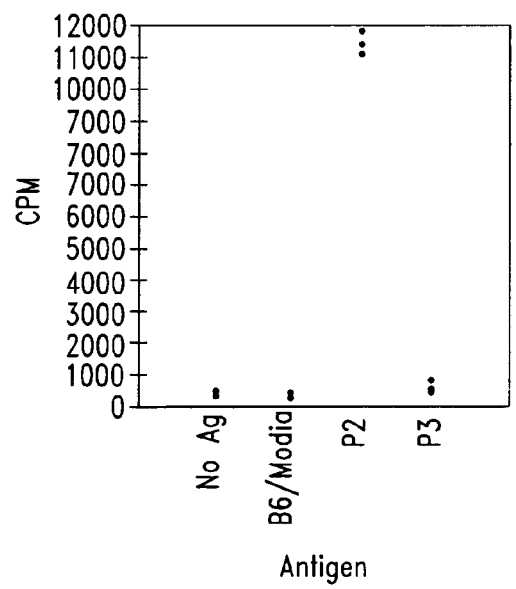

Immunization of mice with the group of peptides designated as Group A elicited an antibody response to WT1 (FIG. 4). No antibodies were detected following immunization to Vaccine B, which is consistent with a lack of helper T cell response from immunization with Vaccine B. P117–139 elicited proliferative T cell responses (FIGS. 5A–5C). The stimulation indices (SI) varied between 8 and 72. Other peptides (P6–22 and P299–313) also were shown to elicit proliferative T cell responses. Immunization with P6–22 resulted in a stimulation index (SI) of 2.3 and immunization with P299–313 resulted in a SI of 3.3. Positive controls included ConA stimulated T cells, as well as T cells stimulated with known antigens, such as CD45 and FBL, and allogeneic T cell lines (DeBruijn et al., Eur. J. Immunol. 21:2963–2970, 1991).

Figures 6A, 6B:
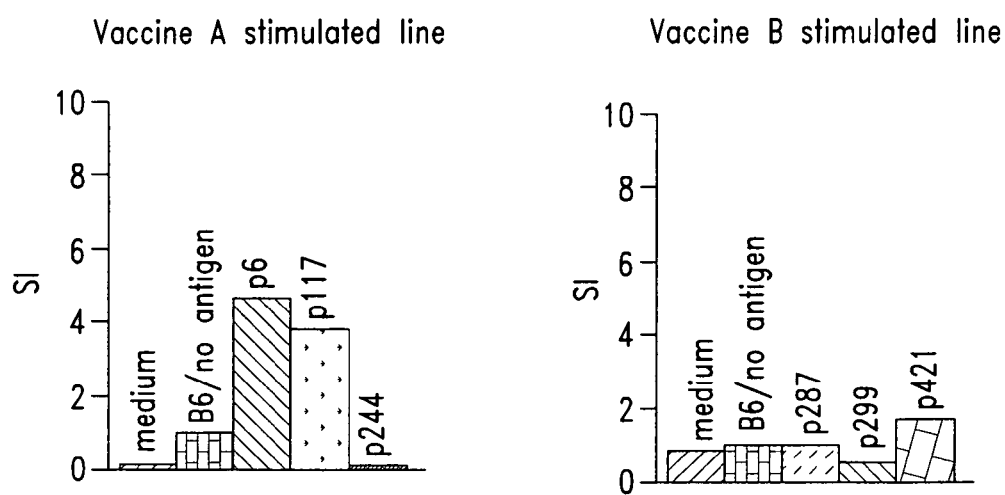
FIGS. 6A and 6B are histograms illustrating the stimulation of proliferative T cell responses in mice immunized with representative WT1 peptides. Three weeks after the third immunization, spleen cells of mice that had been inoculated with Vaccine A or Vaccine B were cultured with medium alone (medium) or spleen cells and medium (B6/no antigen), B6 spleen cells pulsed with the peptides p6–22 (p6), p117–139 (p117), p244–262 (p244) (Vaccine A.

FIGS. 6A and 6B show the proliferative response observed for each of the three peptides within vaccine A (FIG. 6A) and vaccine B (FIG. 6B). Vaccine A elicited proliferative T cell responses to the immunizing peptides p6-22 and p117–139, with stimulation indices (SI) varying between 3 and 8 (bulk lines). No proliferative response to p244–262 was detected (FIG. 6A).

Figure 7A:
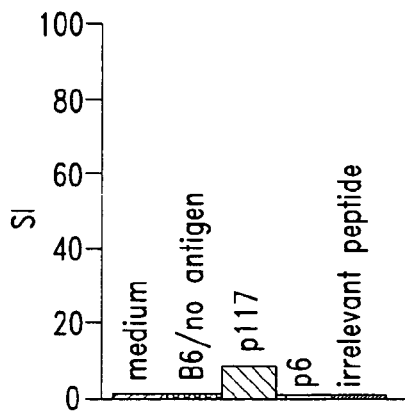
FIGS. 7A–7D are histograms illustrating the generation of proliferative T-cell lines and clones specific for p 117–139 and p6–22. Following in vivo immunization, the initial three in vitro stimulations (IVS) were carried out using all three peptides of Vaccine A or B, respectively. Subsequent IVS were carried out as single peptide stimulations using only the two relevant peptides p117–139 and p6-22. Clones were derived from both the p6–22 and p117–139 specific T cell lines, as indicated. T cells were cultured with medium alone (medium) or spleen cells and medium (B6/no antigen), B6 spleen cells pulsed with the peptides p6-22 (p6), p117–139 (p117) or an irrelevant control peptide (irrelevant peptide) at 25 ug/ml and were assayed after 96 hr for proliferation by ($^3$H) thymidine incorporation. Bars represent the stimulation index (SI), which is calculated as the mean of the experimental wells divided by the mean of the control (B6 spleen cells with no antigen).
Figure 7B:
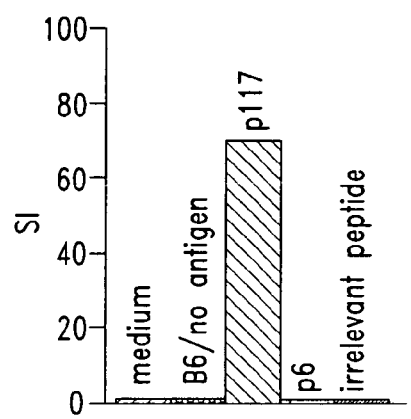
Figure 7C:
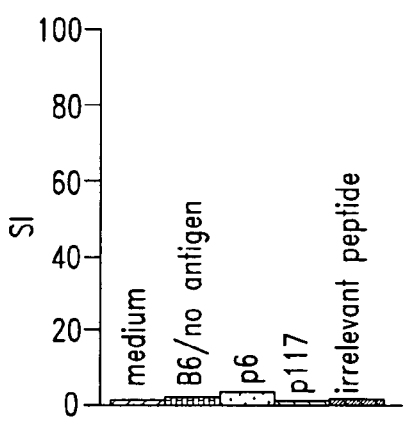
Figure 7D:
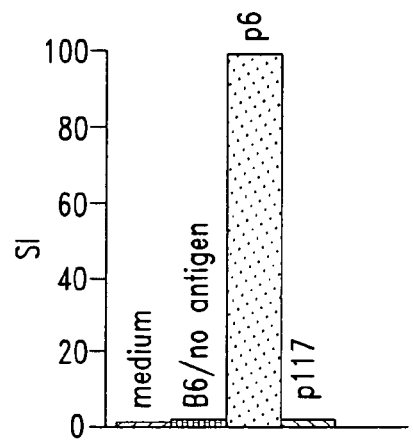

Subsequent in vitro stimulations were carried out as single peptide stimulations using only p6-22 and p117–139. Stimulation of the Vaccine A specific T cell line with p117–139 resulted in proliferation to p117–139 with no response to p6-22 (FIG. 7A). Clones derived from the line were specific for p117–139 (FIG. 7B). By contrast, stimulation of the Vaccine A specific T cell line with p6–22 resulted in proliferation to p6-22 with no response to p117–139 (FIG. 7C). Clones derived from the line were specific for p6-22 (FIG. 7D).

These results show that vaccination with WT1 peptides can elicit antibody responses to WT1 protein and proliferative T cell responses to the immunizing peptides.

Example 4

Induction of CTL Responses in Mice Immunized with WT1 Peptides

This Example illustrates the ability of WT1 peptides to elicit CTL immunity.

Peptides (9-mers) with motifs appropriate for binding to class I MHC were identified using a BIMAS HLA peptide binding prediction analysis (Parker et al., J. Immunol. 152: 163, 1994). Peptides identified within such analyses are shown in Tables II–XLIV. In each of these tables, the score reflects the theoretical binding affinity (half-time of dissociation) of the peptide to the MHC molecule indicated.

Peptides identified using the Tsites program (Rothbard and Taylor, EMBO J. 7:93–100, 1988; Deavin et al., Mol. Immunol. 33:145–155, 1996), which searches for peptide motifs that have the potential to elicit Th responses are further shown in FIGS. 8A and 8B, and Table XLV.

TABLE II

Results of BIMAS HLA Peptide Binding Prediction Analysis for Binding of Human WT1 Peptides to Human HLA A1

| Rank | Start Position | Subsequence | Residue Listing | Score (Estimate of Half Time of Disassociation of a Molecule Containing This Subsequence) |
|---|---|---|---|---|
| 1 | 137 | CLESQPAIR | (SEQ ID NO:47) | 18.000 |
| 2 | 80 | GAEPHEEQC | (SEQ ID NO:87) | 9.000 |
| 3 | 40 | FAPPGASAY | (SEQ ID NO:74) | 5.000 |
| 4 | 354 | QCDFKDCER | (SEQ ID NO:162) | 5.000 |
| 5 | 2 | GSDVRDLNA | (SEQ ID NO:101) | 3.750 |
| 6 | 152 | VTFDGTPSY | (SEQ ID NO:244) | 2.500 |
| 7 | 260 | WTEGQSNHS | (SEQ ID NO:247) | 2.250 |
| 8 | 409 | TSEKPFSCR | (SEQ ID NO:232) | 1.350 |
| 9 | 73 | KQEPSWGGA | (SEQ ID NO:125) | 1.350 |
| 10 | 386 | KTCQRKFSR | (SEQ ID NO:128) | 1.250 |
| 11 | 37 | VLDFAPPGA | (SEQ ID NO:241) | 1.000 |
| 12 | 325 | CAYPGCNKR | (SEQ ID NO:44) | 1.000 |
| 13 | 232 | QLECMTWNQ | (SEQ ID NO:167) | 0.900 |
| 14 | 272 | ESDNHTTPI | (SEQ ID NO:71) | 0.750 |
| 15 | 366 | RSDQLKRHQ | (SEQ ID NO:193) | 0.750 |
| 16 | 222 | SSDNLYQMT | (SEQ ID NO:217) | 0.750 |
| 17 | 427 | RSDELVRHH | (SEQ ID NO:191) | 0.750 |
| 18 | 394 | RSDHLKTHT | (SEQ ID NO:192) | 0.750 |
| 19 | 317 | TSEKRPFMC | (SEQ ID NO:233) | 0.675 |
| 20 | 213 | QALLLRTPY | (SEQ ID NO:160) | 0.500 |

TABLE III

Results of BIMAS HLA Peptide Binding Prediction Analysis for Binding of Human WT1 Peptides to Human HLA A 0201

| Rank | Start Position | Subsequence Residue Listing | Score (Estimate of Half Time of Disassociation of a Molecule Containing This Subsequence) |
|---|---|---|---|
| 1 | 126 | RMFPNAPYL (SEQ ID NO:185) | 313.968 |
| 2 | 187 | SLGEQQYSV (SEQ ID NO:214) | 285.163 |
| 3 | 10 | ALLPAVPSL (SEQ ID NO:34) | 181.794 |
| 4 | 242 | NLGATLKGV (SEQ ID NO:146) | 159.970 |
| 5 | 225 | NLYQMTSQL (SEQ ID NO:147) | 68.360 |
| 6 | 292 | GVFRGIQDV (SEQ ID NO:103) | 51.790 |
| 7 | 191 | QQYSVPPPV (SEQ ID NO:171) | 22.566 |
| 8 | 280 | ILCGAQYRI (SEQ ID NO:116) | 17.736 |
| 9 | 235 | CMTWNQMNL (SEQ ID NO:49) | 15.428 |
| 10 | 441 | NMTKLQLAL (SEQ ID NO:149) | 15.428 |
| 11 | 7 | DLNALLPAV (SEQ ID NO:58) | 11.998 |
| 12 | 227 | YQMTSQLEC (SEQ ID NO:251) | 8.573 |
| 13 | 239 | NQMNLGATL (SEQ ID NO:151) | 8.014 |
| 14 | 309 | TLVRSASET (SEQ ID NO:226) | 7.452 |
| 15 | 408 | KTSEKPFSC (SEQ ID NO:129) | 5.743 |
| 16 | 340 | LQMHSRKHT (SEQ ID NO:139) | 4.752 |
| 17 | 228 | QMTSQLECM (SEQ ID NO:169) | 4.044 |
| 18 | 93 | TVHFSGQFT (SEQ ID NO:235) | 3.586 |
| 19 | 37 | VLDFAPPGA (SEQ ID NO:241) | 3.378 |
| 20 | 86 | EQCLSAFTV (SEQ ID NO:69) | 3.068 |

TABLE IV

Results of BIMAS HLA Peptide Binding Prediction Analysis for Binding of Human WT1 Peptides to Human HLA A 0205

| Rank | Start Position | Subsequence Residue Listing | Score (Estimate of Half Time of Disassociation of a Molecule Containing This Subsequence) |
|---|---|---|---|
| 1 | 10 | ALLPAVPSL (SEQ ID NO:34) | 42.000 |
| 2 | 292 | GVFRGIQDV (SEQ ID NO:103) | 24.000 |
| 3 | 126 | RMFPNAPYL (SEQ ID NO:185) | 21.000 |
| 4 | 225 | NLYQMTSQL (SEQ ID NO:147) | 21.000 |
| 5 | 239 | NQMNLGATL (SEQ ID NO:151) | 16.800 |
| 6 | 302 | RVPGVAPTL (SEQ ID NO:195) | 14.000 |
| 7 | 441 | NMTKLQLAL (SEQ ID NO:149) | 7.000 |
| 8 | 235 | CMTWNQMNL (SEQ ID NO:49) | 7.000 |
| 9 | 187 | SLGEQQYSV (SEQ ID NO:214) | 6.000 |
| 10 | 191 | QQYSVPPPV (SEQ ID NO:171) | 4.800 |
| 11 | 340 | LQMHSRKHT (SEQ ID NO:139) | 4.080 |
| 12 | 242 | NLGATLKGV (SEQ ID NO:146) | 4.000 |
| 13 | 227 | YQMTSQLEC (SEQ ID NO:251) | 3.600 |
| 14 | 194 | SVPPPVYGC (SEQ ID NO:218) | 2.000 |
| 15 | 93 | TVHFSGQFT (SEQ ID NO:235) | 2.000 |
| 16 | 280 | ILCGAQYRI (SEQ ID NO:116) | 1.700 |
| 17 | 98 | GQFTGTAGA (SEQ ID NO:99) | 1.200 |
| 18 | 309 | TLVRSASET (SEQ ID NO:226) | 1.000 |
| 19 | 81 | AEPHEEQCL (SEQ ID NO:30) | 0.980 |
| 20 | 73 | KQEPSWGGA (SEQ ID NO:125) | 0.960 |

TABLE V

Results of BIMAS HLA Peptide Binding Prediction Analysis for Binding of Human WT1 Peptides to Human HLA A24

| Rank | Start Position | Subsequence Residue Listing | Score (Estimate of Half Time of Disassociation of a Molecule Containing This Subsequence) |
|---|---|---|---|
| 1 | 302 | RVPGVAPTL (SEQ ID NO:195) | 16.800 |
| 2 | 218 | RTPYSSDNL (SEQ ID NO:194) | 12.000 |
| 3 | 356 | DFKDCERRF (SEQ ID NO:55) | 12.000 |
| 4 | 126 | RMFPNAPYL (SEQ ID NO:185) | 9.600 |

TABLE V-continued

Results of BIMAS HLA Peptide Binding Prediction Analysis for Binding of Human WT1 Peptides to Human HLA A24

| Rank | Start Position | Subsequence Residue Listing | Score (Estimate of Half Time of Disassociation of a Molecule Containing This Subsequence) |
|---|---|---|---|
| 5 | 326 | AYPGCNKRY (SEQ ID NO:42) | 7.500 |
| 6 | 270 | GYESDNHT (SEQ ID NO:106)T | 7.500 |
| 7 | 239 | NQMNLGATL (SEQ ID NO:151) | 7.200 |
| 8 | 10 | ALLPAVPSL (SEQ ID NO:34) | 7.200 |
| 9 | 130 | NAPYLPSCL (SEQ ID NO:144) | 7.200 |
| 10 | 329 | GCNKRYFKL (SEQ ID NO:90) | 6.600 |
| 11 | 417 | RWPSCQKKF (SEQ ID NO:196) | 6.600 |
| 12 | 47 | AYGSLGGPA (SEQ ID NO:41) | 6.000 |
| 13 | 180 | DPMGQQGSL (SEQ ID NO:59) | 6.000 |
| 14 | 4 | DVRDLNALL (SEQ ID NO:62) | 5.760 |
| 15 | 285 | QYRIHTHGV (SEQ ID NO:175) | 5.000 |
| 16 | 192 | QYSVPPPVY (SEQ ID NO:176) | 5.000 |
| 17 | 207 | DSCTGSQAL (SEQ ID NO:61) | 4.800 |
| 18 | 441 | NMTKLQLAL (SEQ ID NO:149) | 4.800 |
| 19 | 225 | NLYQMTSQL (SEQ ID NO:147) | 4.000 |
| 20 | 235 | CMTWNQMNL (SEQ ID NO:49) | 4.000 |

TABLE VI

Results of BIMAS HLA Peptide Binding Prediction Analysis for Binding of Human WT1 Peptides to Human HLA A3

| Rank | Start Position | Subsequence Residue Listing | Score (Estimate of Half Time of Disassociation of a Molecule Containing This Subsequence) |
|---|---|---|---|
| 1 | 436 | NMHQRNMTK (SEQ ID NO:148) | 40.000 |
| 2 | 240 | QMNLGATLK (SEQ ID NO:168) | 20.000 |
| 3 | 88 | CLSAFTVHF (SEQ ID NO:48) | 6.000 |
| 4 | 126 | RMFPNAPYL (SEQ ID NO:185) | 4.500 |
| 5 | 169 | AQFPNHSFK (SEQ ID NO:36) | 4.500 |
| 6 | 10 | ALLPAVPSL (SEQ ID NO:34) | 4.050 |
| 7 | 137 | CLESQPAIR (SEQ ID NO:47) | 4.000 |
| 8 | 225 | NLYQMTSQL (SEQ ID NO:147) | 3.000 |
| 9 | 32 | AQWAPVLDF (SEQ ID NO:37) | 2.700 |
| 10 | 280 | ILCGAQYRI (SEQ ID NO:116) | 2.700 |
| 11 | 386 | KTCQRKFSR (SEQ ID NO:128) | 1.800 |
| 12 | 235 | CMTWNQMNL (SEQ ID NO:49) | 1.200 |
| 13 | 441 | NMTKLQLAL (SEQ ID NO:149) | 1.200 |
| 14 | 152 | VTFDGTPSY (SEQ ID NO:244) | 1.000 |
| 15 | 187 | SLGEQQYSV (SEQ ID NO:214) | 0.900 |
| 16 | 383 | FQCKTCQRK (SEQ ID NO:80) | 0.600 |
| 17 | 292 | GVFRGIQDV (SEQ ID NO:103) | 0.450 |
| 18 | 194 | SVPPPVYGC (SEQ ID NO:218) | 0.405 |
| 19 | 287 | RIHTHGVFR (SEQ ID NO:182) | 0.400 |
| 20 | 263 | GQSNHSTGY (SEQ ID NO:100) | 0.360 |

TABLE VII

Results of BIIMAS HLA Peptide Binding Prediction Analysis for Binding of Human WT1 Peptides to Human HLA A68.1

| Rank | Start Position | Subsequence Residue Listing | Score (Estimate of Half Time of Disassociation of a Molecule Containing This Subsequence) |
|---|---|---|---|
| 1 | 100 | FTGTAGACR (SEQ ID NO:84) | 100.000 |
| 2 | 386 | KTCQRKFSR (SEQ ID NO:128) | 50.000 |
| 3 | 368 | DQLKRHQRR (SEQ ID NO:60) | 30.000 |
| 4 | 312 | RSASETSEK (SEQ ID NO:190) | 18.000 |
| 5 | 337 | LSHLQMHSR (SEQ ID NO:141) | 15.000 |
| 6 | 364 | FSRSDQLKR (SEQ ID NO:83) | 15.000 |
| 7 | 409 | TSEKPFSCR (SEQ ID NO:232) | 15.000 |
| 8 | 299 | DVRRVPGVA (SEQ ID NO:63) | 12.000 |

TABLE VII-continued

Results of BIIMAS HLA Peptide Binding Prediction Analysis for Binding of Human WT1 Peptides to Human HLA A68.1

| Rank | Start Position | Subsequence Residue Listing | Score (Estimate of Half Time of Disassociation of a Molecule Containing This Subsequence) |
|---|---|---|---|
| 9  | 4   | DVRDLNALL (SEQ ID NO:62)  | 12.000 |
| 10 | 118 | SQASSGQAR (SEQ ID NO:216) | 10.000 |
| 11 | 343 | HSRKHTGEK (SEQ ID NO:111) | 9.000 |
| 12 | 169 | AQFPNHSFK (SEQ ID NO:36)  | 9.000 |
| 13 | 292 | GVFRGIQDV (SEQ ID NO:103) | 8.000 |
| 14 | 325 | CAYPGCNKR (SEQ ID NO:44)  | 7.500 |
| 15 | 425 | FARSDELVR (SEQ ID NO:75)  | 7.500 |
| 16 | 354 | QCDFKDCER (SEQ ID NO:162) | 7.500 |
| 17 | 324 | MCAYPGCNK (SEQ ID NO:142) | 6.000 |
| 18 | 251 | AAGSSSSVK (SEQ ID NO:28)  | 6.000 |
| 19 | 379 | GVKPFQCKT (SEQ ID NO:104) | 6.000 |
| 20 | 137 | CLESQPAIR (SEQ ID NO:47)  | 5.000 |

TABLE VIII

Results of BIMAS HLA Peptide Binding Prediction Analysis for Binding of Human WT1 Peptides to Human HLA A 1101

| Rank | Start Position | Subsequence Residue Listing | Score (Estimate of Half Time of Disassociation of a Molecule Containing This Subsequence) |
|---|---|---|---|
| 1  | 386 | KTCQRKFSR (SEQ ID NO:128) | 1.800 |
| 2  | 169 | AQFPNHSFK (SEQ ID NO:36)  | 1.200 |
| 3  | 436 | NMHQRNMTK (SEQ ID NO:148) | 0.800 |
| 4  | 391 | KFSRSDHLK (SEQ ID NO:120) | 0.600 |
| 5  | 373 | HQRRHTGVK (SEQ ID NO:109) | 0.600 |
| 6  | 383 | FQCKTCQRK (SEQ ID NO:80)  | 0.600 |
| 7  | 363 | RFSRSDQLK (SEQ ID NO:178) | 0.600 |
| 8  | 240 | QMNLGATLK (SEQ ID NO:168) | 0.400 |
| 9  | 287 | RIHTHGVFR (SEQ ID NO:182) | 0.240 |
| 10 | 100 | FTGTAGACR (SEQ ID NO:84)  | 0.200 |
| 11 | 324 | MCAYPGCNK (SEQ ID NO:142) | 0.200 |
| 12 | 251 | AAGSSSSVK (SEQ ID NO:28)  | 0.200 |
| 13 | 415 | SCRWPSCQK (SEQ ID NO:201) | 0.200 |
| 14 | 118 | SQASSGQAR (SEQ ID NO:216) | 0.120 |
| 15 | 292 | GVFRGIQDV (SEQ ID NO:103) | 0.120 |
| 16 | 137 | CLESQPAIR (SEQ ID NO:47)  | 0.080 |
| 17 | 425 | FARSDELVR (SEQ ID NO:75)  | 0.080 |
| 18 | 325 | CAYPGCNKR (SEQ ID NO:44)  | 0.080 |
| 19 | 312 | RSASETSEK (SEQ ID NO:190) | 0.060 |
| 20 | 65  | PPPPHSFI (SEQ ID NO:156)K | 0.060 |

TABLE IX

Results of BIMAS HLA Peptide Binding Prediction Analysis for Binding of Human WT1 Peptides to Human HLA A 3101

| Rank | Start Position | Subsequence Residue Listing | Score (Estimate of Half Time of Disassociation of a Molecule Containing This Subsequence) |
|---|---|---|---|
| 1  | 386 | KTCQRKFSR (SEQ ID NO:128) | 9.000 |
| 2  | 287 | RIHTHGVFR (SEQ ID NO:182) | 6.000 |
| 3  | 137 | CLESQPAIR (SEQ ID NO:47)  | 2.000 |
| 4  | 118 | SQASSGQAR (SEQ ID NO:216) | 2.000 |
| 5  | 368 | DQLKRHQRR (SEQ ID NO:60)  | 1.200 |
| 6  | 100 | FTGTAGACR (SEQ ID NO:84)  | 1.000 |
| 7  | 293 | VFRGIQDVR (SEQ ID NO:238) | 0.600 |
| 8  | 325 | CAYPGCNKR (SEQ ID NO:44)  | 0.600 |
| 9  | 169 | AQFPNHSFK (SEQ ID NO:36)  | 0.600 |
| 10 | 279 | PILCGAQYR (SEQ ID NO:155) | 0.400 |
| 11 | 436 | NMHQRNMTK (SEQ ID NO:148) | 0.400 |
| 12 | 425 | FARSDELVR (SEQ ID NO:75)  | 0.400 |

TABLE IX-continued

Results of BIMAS HLA Peptide Binding Prediction Analysis for Binding of Human WT1 Peptides to Human HLA A 3101

| Rank | Start Position | Subsequence Residue Listing | Score (Estimate of Half Time of Disassociation of a Molecule Containing This Subsequence) |
|---|---|---|---|
| 13 | 32 | AQWAPVLDF (SEQ ID NO:37) | 0.240 |
| 14 | 240 | QMNLGATLK (SEQ ID NO:168) | 0.200 |
| 15 | 354 | QCDFKDCER (SEQ ID NO:162) | 0.200 |
| 16 | 373 | HQRRHTGVK (SEQ ID NO:109) | 0.200 |
| 17 | 383 | FQCKTCQRK (SEQ ID NO:80) | 0.200 |
| 18 | 313 | SASETSEKR (SEQ ID NO:197) | 0.200 |
| 19 | 358 | KDCERRFSR (SEQ ID NO:118) | 0.180 |
| 20 | 391 | KFSRSDHLK (SEQ ID NO:120) | 0.180 |

TABLE X

Results of BIMAS HLA Peptide Binding Prediction Analysis for Binding of Human WT1 Peptides to Human HLA A 3302

| Rank | Start Position | Subsequence Residue Listing | Score (Estimate of Half Time of Disassociation of a Molecule Containing This Subsequence) |
|---|---|---|---|
| 1 | 337 | LSHLQMHSR (SEQ ID NO:141) | 15.000 |
| 2 | 409 | TSEKPFSCR (SEQ ID NO:232) | 15.000 |
| 3 | 364 | FSRSDQLKR (SEQ ID NO:83) | 15.000 |
| 4 | 137 | CLESQPAIR (SEQ ID NO:47) | 9.000 |
| 5 | 368 | DQLKRHQRR (SEQ ID NO:60) | 9.000 |
| 6 | 287 | RIHTHGVFR (SEQ ID NO:182) | 4.500 |
| 7 | 210 | TGSQALLLR (SEQ ID NO:223) | 3.000 |
| 8 | 425 | FARSDELVR (SEQ ID NO:75) | 3.000 |
| 9 | 313 | SASETSEKR (SEQ ID NO:197) | 3.000 |
| 10 | 293 | VFRGIQDVR (SEQ ID NO:238) | 3.000 |
| 11 | 354 | QCDFKDCER (SEQ ID NO:162) | 3.000 |
| 12 | 100 | FTGTAGACR (SEQ ID NO:84) | 3.000 |
| 13 | 118 | SQASSGQAR (SEQ ID NO:216) | 3.000 |
| 14 | 325 | CAYPGCNKR (SEQ ID NO:44) | 3.000 |
| 15 | 207 | DSCTGSQAL (SEQ ID NO:61) | 1.500 |
| 16 | 139 | ESQPAIRNQ (SEQ ID NO:72) | 1.500 |
| 17 | 299 | DVRRVPGVA (SEQ ID NO:63) | 1.500 |
| 18 | 419 | PSCQKKFAR (SEQ ID NO:159) | 1.500 |
| 19 | 272 | ESDNHTTPI (SEQ ID NO:71) | 1.500 |
| 20 | 4 | DVRDLNALL (SEQ ID NO:62) | 1.500 |

TABLE XI

Results of BIMAS HLA Peptide Binding Prediction Analysis for Binding of Human WT1 Peptides to Human HLA B14

| Rank | Start Position | Subsequence Residue Listing | Score (Estimate of Half Time of Disassociation of a Molecule Containing This Subsequence) |
|---|---|---|---|
| 1 | 362 | RRFSRSDQL (SEQ ID NO:187) | 1000.000 |
| 2 | 332 | KRYFKLSHL (SEQ ID NO:127) | 300.000 |
| 3 | 423 | KKFARSDEL (SEQ ID NO:122) | 150.000 |
| 4 | 390 | RKFSRSDHL (SEQ ID NO:183) | 150.000 |
| 5 | 439 | QRNMTKLQL (SEQ ID NO:173) | 20.000 |
| 6 | 329 | GCNKRYFKL (SEQ ID NO:90) | 10.000 |
| 7 | 10 | ALLPAVPSL (SEQ ID NO:34) | 10.000 |
| 8 | 180 | DPMGQQGSL (SEQ ID NO:59) | 9.000 |
| 9 | 301 | RRVPGVAPT (SEQ ID NO:189) | 6.000 |
| 10 | 126 | RMFPNAPYL (SEQ ID NO:185) | 5.000 |
| 11 | 371 | KRHQRRHTG (SEQ ID NO:126) | 5.000 |
| 12 | 225 | NLYQMTSQL (SEQ ID NO:147) | 5.000 |
| 13 | 144 | IRNQGYSTV (SEQ ID NO:117) | 4.000 |
| 14 | 429 | DELVRHHNM (SEQ ID NO:53) | 3.000 |
| 15 | 437 | MHQRNMTKL (SEQ ID NO:143) | 3.000 |
| 16 | 125 | ARMFPNAPY (SEQ ID NO:38) | 3.000 |

TABLE XI-continued

Results of BIMAS HLA Peptide Binding Prediction Analysis for Binding of Human WT1 Peptides to Human HLA B14

| Rank | Start Position | Subsequence Residue Listing | Score (Estimate of Half Time of Disassociation of a Molecule Containing This Subsequence) |
|---|---|---|---|
| 17 | 239 | NQMNLGATL (SEQ ID NO:151) | 3.000 |
| 18 | 286 | YRIHTHGVF (SEQ ID NO:252) | 3.000 |
| 19 | 174 | HSFKHEDPM (SEQ ID NO:110) | 3.000 |
| 20 | 372 | RHQRRHTGV (SEQ ID NO:181) | 3.000 |

TABLE XII

Results of BIMAS HLA Peptide Binding Prediction Analysis for Binding of Human WT1 Peptides to Human HLA B40

| Rank | Start Position | Subsequence Residue Listing | Score (Estimate of Half Time of Disassociation of a Molecule Containing This Subsequence) |
|---|---|---|---|
| 1 | 81 | AEPHEEQCL (SEQ ID NO:30) | 40.000 |
| 2 | 429 | DELVRHHNM (SEQ ID NO:53) | 24.000 |
| 3 | 410 | SEKPFSCRW (SEQ ID NO:207) | 20.000 |
| 4 | 318 | SEKRPFMCA (SEQ ID NO:208) | 15.000 |
| 5 | 233 | LECMTWNQM (SEQ ID NO:131) | 12.000 |
| 6 | 3 | SDVRDLNAL (SEQ ID NO:206) | 10.000 |
| 7 | 349 | GEKPYQCDF (SEQ ID NO:91) | 8.000 |
| 8 | 6 | RDLNALLPA (SEQ ID NO:177) | 5.000 |
| 9 | 85 | EEQCLSAFT (SEQ ID NO:65) | 4.000 |
| 10 | 315 | SETSEKRPF (SEQ ID NO:209) | 4.000 |
| 11 | 261 | TEGQSNHST (SEQ ID NO:221) | 4.000 |
| 12 | 23 | GCALPVSGA (SEQ ID NO:89) | 3.000 |
| 13 | 38 | LDFAPPGAS (SEQ ID NO:130) | 3.000 |
| 14 | 273 | SDNHTTPIL (SEQ ID NO:204) | 2.500 |
| 15 | 206 | TDSCTGSQA (SEQ ID NO:220) | 2.500 |
| 16 | 24 | CALPVSGAA (SEQ ID NO:43) | 2.000 |
| 17 | 98 | GQFTGTAGA (SEQ ID NO:99) | 2.000 |
| 18 | 30 | GAAQWAPVL (SEQ ID NO:86) | 2.000 |
| 19 | 84 | HEEQCLSAF (SEQ ID NO:107) | 2.000 |
| 20 | 26 | LPVSGAAQW (SEQ ID NO:138) | 2.000 |

TABLE XIII

Results of BIMAS HLA Peptide Binding Prediction Analysis for Binding of Human WT1 Peptides to Human HLA B60

| Rank | Start Position | Subsequence Residue Listing | Score (Estimate of Half Time of Disassociation of a Molecule Containing This Subsequence) |
|---|---|---|---|
| 1 | 81 | AEPHEEQCL (SEQ ID NO:30) | 160.000 |
| 2 | 3 | SDVRDLNAL (SEQ ID NO:206) | 40.000 |
| 3 | 429 | DELVRHHNM (SEQ ID NO:53) | 40.000 |
| 4 | 233 | LECMTWNQM (SEQ ID NO:131) | 22.000 |
| 5 | 273 | SDNHTTPIL (SEQ ID NO:204) | 20.000 |
| 6 | 209 | CTGSQALLL (SEQ ID NO:52) | 8.000 |
| 7 | 30 | GAAQWAPVL (SEQ ID NO:86) | 8.000 |
| 8 | 318 | SEKRPFMCA (SEQ ID NO:208) | 8.000 |
| 9 | 180 | DPMGQQGSL (SEQ ID NO:59) | 8.000 |
| 10 | 138 | LESQPAIRN (SEQ ID NO:132) | 5.280 |
| 11 | 239 | NQMNLGATL (SEQ ID NO:151) | 4.400 |
| 12 | 329 | GCNKRYFKL (SEQ ID NO:90) | 4.400 |
| 13 | 130 | NAPYLPSCL (SEQ ID NO:144) | 4.400 |
| 14 | 85 | EEQCLSAFT (SEQ ID NO:65) | 4.400 |
| 15 | 208 | SCTGSQALL (SEQ ID NO:202) | 4.000 |
| 16 | 207 | DSCTGSQAL (SEQ ID NO:61) | 4.000 |
| 17 | 218 | RTPYSSDNL (SEQ ID NO:194) | 4.000 |

TABLE XIII-continued

Results of BIMAS HLA Peptide Binding Prediction Analysis for Binding of Human WT1 Peptides to Human HLA B60

| Rank | Start Position | Subsequence Residue Listing | Score (Estimate of Half Time of Disassociation of a Molecule Containing This Subsequence) |
|---|---|---|---|
| 18 | 261 | TEGQSNHST (SEQ ID NO:221) | 4.000 |
| 19 | 18 | LGGGGGCAL (SEQ ID NO:134) | 4.000 |
| 20 | 221 | YSSDNLYQM (SEQ ID NO:253) | 2.200 |

TABLE XIV

Results of BIMAS HLA Peptide Binding Prediction Analysis for Binding of Human WT1 Peptides to Human HLA B61

| Rank | Start Position | Subsequence Residue Listing | Score (Estimate of Half Time of Disassociation of a Molecule Containing This Subsequence) |
|---|---|---|---|
| 1 | 318 | SEKRPFMCA (SEQ ID NO:208) | 20.000 |
| 2 | 429 | DELVRHHNM (SEQ ID NO:53) | 16.000 |
| 3 | 298 | QDVRRVPGV (SEQ ID NO:164) | 10.000 |
| 4 | 81 | AEPHEEQCL (SEQ ID NO:30) | 8.000 |
| 5 | 233 | LECMTWNQM (SEQ ID NO:131) | 8.000 |
| 6 | 6 | RDLNALLPA (SEQ ID NO:177) | 5.500 |
| 7 | 85 | EEQCLSAFT (SEQ ID NO:65) | 4.000 |
| 8 | 261 | TEGQSNHST (SEQ ID NO:221) | 4.000 |
| 9 | 206 | TDSCTGSQA (SEQ ID NO:220) | 2.500 |
| 10 | 295 | RGIQDVRRV (SEQ ID NO:179) | 2.200 |
| 11 | 3 | SDVRDLNAL (SEQ ID NO:206) | 2.000 |
| 12 | 250 | VAAGSSSSV (SEQ ID NO:236) | 2.000 |
| 13 | 29 | SGAAQWAPV (SEQ ID NO:211) | 2.000 |
| 14 | 315 | SETSEKRPF (SEQ ID NO:209) | 1.600 |
| 15 | 138 | LESQPAIRN (SEQ ID NO:132) | 1.200 |
| 16 | 244 | GATLKGVAA (SEQ ID NO:88) | 1.100 |
| 17 | 20 | GGGGCALPV (SEQ ID NO:92) | 1.100 |
| 18 | 440 | RNMTKLQLA (SEQ ID NO:186) | 1.100 |
| 19 | 23 | GCALPVSGA (SEQ ID NO:89) | 1.100 |
| 20 | 191 | QQYSVPPPV (SEQ ID NO:171) | 1.000 |

TABLE XV

Results of BIMAS HLA Peptide Binding Prediction Analysis for Binding of Human WT1 Peptides to Human HLA B62

| Rank | Start Position | Subsequence Residue Listing | Score (Estimate of Half Time of Disassociation of a Molecule Containing This Subsequence) |
|---|---|---|---|
| 1 | 146 | NQGYSTVTF (SEQ ID NO:150) | 211.200 |
| 2 | 32 | AQWAPVLDF (SEQ ID NO:37) | 96.000 |
| 3 | 263 | GQSNHSTGY (SEQ ID NO:100) | 96.000 |
| 4 | 88 | CLSAFTVHF (SEQ ID NO:48) | 96.000 |
| 5 | 17 | SLGGGGGCA (SEQ ID NO:215) | 9.600 |
| 6 | 239 | NQMNLGATL (SEQ ID NO:151) | 8.800 |
| 7 | 191 | QQYSVPPPV (SEQ ID NO:171) | 8.000 |
| 8 | 98 | GQFTGTAGA (SEQ ID NO:99) | 8.000 |
| 9 | 384 | QCKTCQRKF (SEQ ID NO:163) | 6.000 |
| 10 | 40 | FAPPGASAY (SEQ ID NO:74) | 4.800 |
| 11 | 227 | YQMTSQLEC (SEQ ID NO:251) | 4.800 |
| 12 | 187 | SLGEQQYSV (SEQ ID NO:214) | 4.400 |
| 13 | 86 | EQCLSAFTV (SEQ ID NO:69) | 4.400 |
| 14 | 152 | VTFDGTPSY (SEQ ID NO:244) | 4.400 |
| 15 | 101 | TGTAGACRY (SEQ ID NO:224) | 4.000 |
| 16 | 242 | NLGATLKGV (SEQ ID NO:146) | 4.000 |
| 17 | 92 | FTVHFSGQF (SEQ ID NO:85) | 4.000 |
| 18 | 7 | DLNALLPAV (SEQ ID NO:58) | 4.000 |
| 19 | 123 | GQARMFPNA (SEQ ID NO:98) | 4.000 |
| 20 | 280 | ILCGAQYRI (SEQ ID NO:116) | 3.120 |

TABLE XVI

Results of BIMAS HLA Peptide Binding Prediction Analysis for Binding of Human WT1 Peptides to Human HLA B7

| Rank | Start Position | Subsequence Residue Listing | Score (Estimate of Half Time of Disassociation of a Molecule Containing This Subsequence) |
|---|---|---|---|
| 1 | 180 | DPMGQQGSL (SEQ ID NO:59) | 240.000 |
| 2 | 4 | DVRDLNALL (SEQ ID NO:62) | 200.000 |
| 3 | 302 | RVPGVAPTL (SEQ ID NO:195) | 20.000 |
| 4 | 30 | GAAQWAPVL (SEQ ID NO:86) | 12.000 |
| 5 | 239 | NQMNLGATL (SEQ ID NO:151) | 12.000 |
| 6 | 130 | NAPYLPSCL (SEQ ID NO:144) | 12.000 |
| 7 | 10 | ALLPAVPSL (SEQ ID NO:34) | 12.000 |
| 8 | 299 | DVRRVPGVA (SEQ ID NO:63) | 5.000 |
| 9 | 208 | SCTGSQALL (SEQ ID NO:202) | 4.000 |
| 10 | 303 | VPGVAPTLV (SEQ ID NO:242) | 4.000 |
| 11 | 18 | LGGGGGCAL (SEQ ID NO:134) | 4.000 |
| 12 | 218 | RTPYSSDNL (SEQ ID NO:194) | 4.000 |
| 13 | 207 | DSCTGSQAL (SEQ ID NO:61) | 4.000 |
| 14 | 209 | CTGSQALLL (SEQ ID NO:52) | 4.000 |
| 15 | 329 | GCNKRYFKL (SEQ ID NO:90) | 4.000 |
| 16 | 235 | CMTWNQMNL (SEQ ID NO:49) | 4.000 |
| 17 | 441 | NMTKLQLAL (SEQ ID NO:149) | 4.000 |
| 18 | 126 | RMFPNAPYL (SEQ ID NO:185) | 4.000 |
| 19 | 225 | NLYQMTSQL (SEQ ID NO:147) | 4.000 |
| 20 | 143 | AIRNQGYST (SEQ ID NO:33) | 3.000 |

TABLE XVII

Results of BIMAS HLA Peptide Binding Prediction Analysis for Binding of Human WT1 Peptides to Human HLA B8

| Rank | Start Position | Subsequence Residue Listing | Score (Estimate of Half Time of Disassociation of a Molecule Containing This Subsequence) |
|---|---|---|---|
| 1 | 329 | GCNKRYFKL (SEQ ID NO:90) | 16.000 |
| 2 | 4 | DVRDLNALL (SEQ ID NO:62) | 12.000 |
| 3 | 316 | ETSEKRPFM (SEQ ID NO:73) | 3.000 |
| 4 | 180 | DPMGQQGSL (SEQ ID NO:59) | 1.600 |
| 5 | 208 | SCTGSQALL (SEQ ID NO:202) | 0.800 |
| 6 | 130 | NAPYLPSCL (SEQ ID NO:144) | 0.800 |
| 7 | 244 | GATLKGVAA (SEQ ID NO:88) | 0.800 |
| 8 | 30 | GAAQWAPVL (SEQ ID NO:86) | 0.800 |
| 9 | 299 | DVRRVPGVA (SEQ ID NO:63) | 0.400 |
| 10 | 420 | SCQKKFARS (SEQ ID NO:200) | 0.400 |
| 11 | 387 | TCQRKFSRS (SEQ ID NO:219) | 0.400 |
| 12 | 225 | NLYQMTSQL (SEQ ID NO:147) | 0.400 |
| 13 | 141 | QPAIRNQGY (SEQ ID NO:170) | 0.400 |
| 14 | 10 | ALLPAVPSL (SEQ ID NO:34) | 0.400 |
| 15 | 207 | DSCTGSQAL (SEQ ID NO:61) | 0.400 |
| 16 | 384 | QCKTCQRKF (SEQ ID NO:163) | 0.400 |
| 17 | 136 | SCLESQPAI (SEQ ID NO:198) | 0.300 |
| 18 | 347 | HTGEKPYQC (SEQ ID NO:112) | 0.300 |
| 19 | 401 | HTRTHTGKT (SEQ ID NO:114) | 0.200 |
| 20 | 332 | KRYFKLSHL (SEQ ID NO:127) | 0.200 |

TABLE XVIII

Results of BIMAS HLA Peptide Binding Prediction Analysis for Binding of Human WT1 Peptides to Human HLA B 2702

| Rank | Start Position | Subsequence Residue Listing | Score (Estimate of Half Time of Disassociation of a Molecule Containing This Subsequence) |
|---|---|---|---|
| 1 | 332 | KRYFKLSHL (SEQ ID NO:127) | 900.000 |
| 2 | 362 | RRFSRSDQL (SEQ ID NO:187) | 900.000 |
| 3 | 286 | YRIHTHGVF (SEQ ID NO:252) | 200.000 |
| 4 | 125 | ARMFPNAPY (SEQ ID NO:38) | 200.000 |

TABLE XVIII-continued

Results of BIMAS HLA Peptide Binding Prediction Analysis for Binding of Human WT1 Peptides to Human HLA B 2702

| Rank | Start Position | Subsequence Residue Listing | Score (Estimate of Half Time of Disassociation of a Molecule Containing This Subsequence) |
|---|---|---|---|
| 5 | 375 | RRHTGVKPF (SEQ ID NO:188) | 180.000 |
| 6 | 32 | AQWAPVLDF (SEQ ID NO:37) | 100.000 |
| 7 | 301 | RRVPGVAPT (SEQ ID NO:189) | 60.000 |
| 8 | 439 | QRNMTKLQL (SEQ ID NO:173) | 60.000 |
| 9 | 126 | RMFPNAPYL (SEQ ID NO:185) | 22.500 |
| 10 | 426 | ARSDELVRH (SEQ ID NO:39) | 20.000 |
| 11 | 146 | NQGYSTVTF (SEQ ID NO:150) | 20.000 |
| 12 | 144 | IRNQGYSTV (SEQ ID NO:117) | 20.000 |
| 13 | 389 | QRKFSRSDH (SEQ ID NO:172) | 20.000 |
| 14 | 263 | GQSNHSTGY (SEQ ID NO:100) | 20.000 |
| 15 | 416 | CRWPSCQKK (SEQ ID NO:50) | 20.000 |
| 16 | 191 | QQYSVPPPV (SEQ ID NO:171) | 10.000 |
| 17 | 217 | LRTPYSSDN (SEQ ID NO:140) | 10.000 |
| 18 | 107 | CRYGPFGPP (SEQ ID NO:51) | 10.000 |
| 19 | 98 | GQFTGTAGA (SEQ ID NO:99) | 10.000 |
| 20 | 239 | NQMNLGATL (SEQ ID NO:151) | 6.000 |

TABLE XIX

Results of BIMAS HLA Peptide Binding Prediction Analysis for Binding of Human WT1 Peptides to Human HLA B 2705

| Rank | Start Position | Subsequence Residue Listing | Score (Estimate of Half Time of Disassociation of a Molecule Containing This Subsequence) |
|---|---|---|---|
| 1 | 332 | KRYFKLSHL (SEQ ID NO:127) | 30000.000 |
| 2 | 362 | RRFSRSDQL (SEQ ID NO:187) | 30000.000 |
| 3 | 416 | CRWPSCQKK (SEQ ID NO:50) | 10000.000 |
| 4 | 439 | QRNMTKLQL (SEQ ID NO:173) | 2000.000 |
| 5 | 286 | YRIHTHGVF (SEQ ID NO:252) | 1000.000 |
| 6 | 125 | ARMFPNAPY (SEQ ID NO:38) | 1000.000 |
| 7 | 294 | FRGIQDVRR (SEQ ID NO:81) | 1000.000 |
| 8 | 432 | VRHHNMHQR (SEQ ID NO:243) | 1000.000 |
| 9 | 169 | AQFPNHSFK (SEQ ID NO:36) | 1000.000 |
| 10 | 375 | RRHTGVKPF (SEQ ID NO:188) | 900.000 |
| 11 | 126 | RMFPNAPYL (SEQ ID NO:185) | 750.000 |
| 12 | 144 | IRNQGYSTV (SEQ ID NO:117) | 600.000 |
| 13 | 301 | RRVPGVAPT (SEQ ID NO:189) | 600.000 |
| 14 | 32 | AQWAPVLDF (SEQ ID NO:37) | 500.000 |
| 15 | 191 | QQYSVPPPV (SEQ ID NO:171) | 300.000 |
| 16 | 373 | HQRRHTGVK (SEQ ID NO:109) | 200.000 |
| 17 | 426 | ARSDELVRH (SEQ ID NO:39) | 200.000 |
| 18 | 383 | FQCKTCQRK (SEQ ID NO:80) | 200.000 |
| 19 | 239 | NQMNLGATL( SEQ ID NO:151) | 200.000 |
| 20 | 389 | QRKFSRSDH (SEQ ID NO:172) | 200.000 |

TABLE XX

Results of BIMAS HLA Peptide Binding Predicition Analysis for Binding of Human WT1 Peptides to Human HLA B 3501

| Rank | Start Position | Subsequence Residue Listing | Score (Estimate of Half Time of Disassociation of a Molecule Containing This Subsequence) |
|---|---|---|---|
| 1 | 278 | TPILCGAQY (SEQ ID NO:227) | 40.000 |
| 2 | 141 | QPAIRNOGY (SEQ ID NO:170) | 40.000 |
| 3 | 219 | TPYSSDNLY (SEQ ID NO:231) | 40.000 |
| 4 | 327 | YPGCNKRYF (SEQ ID NO:250) | 20.000 |
| 5 | 163 | TPSHHAAQF (SEQ ID NO:228) | 20.000 |
| 6 | 180 | DPMGQQGSL (SEQ ID NO:59) | 20.000 |
| 7 | 221 | YSSDNLYQM (SEQ ID NO:253) | 20.000 |
| 8 | 26 | LPVSGAAQW (SEQ ID NO:138) | 10.000 |

TABLE XX-continued

Results of BIMAS HLA Peptide Binding Prediction Analysis for Binding of Human WT1 Peptides to Human HLA B 3501

| Rank | Start Position | Subsequence Residue Listing | Score (Estimate of Half Time of Disassociation of a Molecule Containing This Subsequence) |
|---|---|---|---|
| 9 | 174 | HSFKHEDPM (SEQ ID NO:110) | 10.000 |
| 10 | 82 | EPHEEQCLS (SEQ ID NO:68) | 6.000 |
| 11 | 213 | QALLLRTPY (SEQ ID NO:160) | 6.000 |
| 12 | 119 | QASSGQARM (SEQ ID NO:161) | 6.000 |
| 13 | 4 | DVRDLNALL (SEQ ID NO:62) | 6.000 |
| 14 | 40 | FAPPGASAY (SEQ ID NO:74) | 6.000 |
| 15 | 120 | ASSGQARMF (SEQ ID NO:40) | 5.000 |
| 16 | 207 | DSCTGSQAL (SEQ ID NO:61) | 5.000 |
| 17 | 303 | VPGVAPTLV (SEQ ID NO:242) | 4.000 |
| 18 | 316 | ETSEKRPFM (SEQ ID NO:73) | 4.000 |
| 19 | 152 | VTFDGTPSY (SEQ ID NO:244) | 4.000 |
| 20 | 412 | KPFSCRWPS (SEQ ID NO:123) | 4.000 |

TABLE XXI

Results of BIMAS HLA Peptide Binding Prediction Analysis for Binding of Human WT1 Peptides to Human HLA B 3701

| Rank | Start Position | Subsequence Residue Listing | Score (Estimate of Half Time of Disassociation of a Molecule Containing This Subsequence) |
|---|---|---|---|
| 1 | 3 | SDVRDLNAL (SEQ ID NO:206) | 40.000 |
| 2 | 273 | SDNHTTPIL (SEQ ID NO:204) | 40.000 |
| 3 | 81 | AEPHEEQCL (SEQ ID NO:30) | 10.000 |
| 4 | 298 | QDVRRVPGV (SEQ ID NO:164) | 8.000 |
| 5 | 428 | SDELVRHHN (SEQ ID NO:203) | 6.000 |
| 6 | 85 | EEQCLSAFT (SEQ ID NO:65) | 5.000 |
| 7 | 208 | SCTGSQALL (SEQ ID NO:202) | 5.000 |
| 8 | 4 | DVRDLNALL (SEQ ID NO:62) | 5.000 |
| 9 | 209 | CTGSQALLL (SEQ ID NO:52) | 5.000 |
| 10 | 38 | LDFAPPGAS (SEQ ID NO:130) | 4.000 |
| 11 | 223 | SDNLYQMTS (SEQ ID NO:205) | 4.000 |
| 12 | 179 | EDPMGQQGS (SEQ ID NO:64) | 4.000 |
| 13 | 206 | TDSCTGSQA (SEQ ID NO:220) | 4.000 |
| 14 | 6 | RDLNALLPA (SEQ ID NO:177) | 4.000 |
| 15 | 84 | HEEQCLSAF (SEQ ID NO:107) | 2.000 |
| 16 | 233 | LECMTWNQM (SEQ ID NO:131) | 2.000 |
| 17 | 429 | DELVRHHNM (SEQ ID NO:53) | 2.000 |
| 18 | 315 | SETSEKRPF (SEQ ID NO:209) | 2.000 |
| 19 | 349 | GEKPYQCDF (SEQ ID NO:91) | 2.000 |
| 20 | 302 | RVPGVAPTL (SEQ ID NO:195) | 1.500 |

TABLE XXII

Results of BIMAS HLA Peptide Binding Prediction Analysis for Binding of Human WT1 Peptides to Human HLA B 3801

| Rank | Start Position | Subsequence Residue Listing | Score (Estimate of Half Time of Disassociation of a Molecule Containing This Subsequence) |
|---|---|---|---|
| 1 | 437 | MHQRNMTKL (SEQ ID NO:143) | 36.000 |
| 2 | 434 | HHNMHQRNM (SEQ ID NO:108) | 6.000 |

TABLE XXII-continued

Results of BIMAS HLA Peptide Binding Prediction Analysis for Binding of Human WT1 Peptides to Human HLA B 3801

| Rank | Start Position | Subsequence Residue Listing | Score (Estimate of Half Time of Disassociation of a Molecule Containing This Subsequence) |
|---|---|---|---|
| 3 | 372 | RHQRRHTGV (SEQ ID NO:181) | 6.000 |
| 4 | 180 | DPMGQQGSL (SEQ ID NO:59) | 4.000 |
| 5 | 433 | RHHNMHQRN (SEQ ID NO:180) | 3.900 |
| 6 | 165 | SHHAAQFPN (SEQ ID NO:213) | 3.900 |
| 7 | 202 | CHTPTDSCT (SEQ ID NO:45) | 3.000 |
| 8 | 396 | DHLKTHTRT (SEQ ID NO:57) | 3.000 |
| 9 | 161 | GHTPSHHAA (SEQ ID NO:94) | 3.000 |
| 10 | 302 | RVPGVAPTL (SEQ ID NO:195) | 2.600 |
| 11 | 417 | RWPSCQKKF (SEQ ID NO:196) | 2.400 |
| 12 | 327 | YPGCNKRYF (SEQ ID NO:250) | 2.400 |
| 13 | 208 | SCTGSQALL (SEQ ID NO:202) | 2.000 |
| 14 | 163 | TPSHHAAQF (SEQ ID NO:228) | 2.000 |
| 15 | 120 | ASSGQARMF (SEQ ID NO:40) | 2.000 |
| 16 | 18 | LGGGGGCAL (SEQ ID NO:134) | 2.000 |
| 17 | 177 | KHEDPMGQQ (SEQ ID NO:121) | 1.800 |
| 18 | 83 | PHEEQCLSA (SEQ ID NO:154) | 1.800 |
| 19 | 10 | ALLPAVPSL (SEQ ID NO:34) | 1.300 |
| 20 | 225 | NLYQMTSQL (SEQ ID NO:147) | 1.300 |

TABLE XXIII

Results of BIMAS HLA Peptide Binding Prediction Analysis for Binding of Human WT1 Peptides to Human HLA B 3901

| Rank | Start Position | Subsequence Residue Listing | Score (Estimate of Half Time of Disassociation of a Molecule Containing This Subsequence) |
|---|---|---|---|
| 1 | 437 | MHQRNMTKL (SEQ ID NO:143) | 135.000 |
| 2 | 332 | KRYFKLSHL (SEQ ID NO:127) | 45.000 |
| 3 | 434 | HHNMHQRNM (SEQ ID NO:108) | 30.000 |
| 4 | 362 | RRFSRSDQL (SEQ ID NO:187) | 30.000 |
| 5 | 372 | RHQRRHTGV (SEQ ID NO:181) | 30.000 |
| 6 | 10 | ALLPAVPSL (SEQ ID NO:34) | 9.000 |
| 7 | 439 | QRNMTKLQL (SEQ ID NO:173) | 7.500 |
| 8 | 390 | RLFSRSDHL (SEQ ID NO:183) | 6.000 |
| 9 | 396 | DHLKTHTRT (SEQ ID NO:57) | 6.000 |
| 10 | 239 | NQMNLGATL (SEQ ID NO:151) | 6.000 |
| 11 | 423 | KKFARSDEL (SEQ ID NO:122) | 6.000 |
| 12 | 126 | RMFPNAPYL (SEQ ID NO:185) | 6.000 |
| 13 | 225 | NLYQMTSQL (SEQ ID NO:147) | 6.000 |
| 14 | 180 | DPMGQQGSL (SEQ ID NO:59) | 6.000 |
| 15 | 144 | IRNQGYSTV (SEQ ID NO:117) | 5.000 |
| 16 | 136 | SCLESQPAI (SEQ ID NO:198) | 4.000 |
| 17 | 292 | GVFRGIQDV (SEQ ID NO:103) | 3.000 |
| 18 | 302 | RVPGVAPTL (SEQ ID NO:195) | 3.000 |
| 19 | 208 | SCTGSQALL (SEQ ID NO:202) | 3.000 |
| 20 | 207 | DSCTGSQAL (SEQ ID NO:61) | 3.000 |

TABLE XXIV

Results of BIMAS HLA Peptide Binding Prediction Analysis for Binding of Human WT1 Peptides to Human HLA B 3902

| Rank | Start Position | Subsequence Residue Listing | Score (Estimate of Half Time of Disassociation of a Molecule Containing This Subsequence) |
|---|---|---|---|
| 1 | 239 | NQMNLGATL (SEQ ID NO:151) | 24.000 |

TABLE XXIV-continued

Results of BIMAS HLA Peptide Binding Prediction Analysis for Binding of Human WT1 Peptides to Human HLA B 3902

| Rank | Start Position | Subsequence Residue Listing | Score (Estimate of Half Time of Disassociation of a Molecule Containing This Subsequence) |
|---|---|---|---|
| 2 | 390 | RKFSRSDHL (SEQ ID NO:183) | 20.000 |
| 3 | 423 | KKFARSDEL (SEQ ID NO:122) | 20.000 |
| 4 | 32 | AQWAPVLDF (SEQ ID NO:37) | 5.000 |
| 5 | 146 | NQGYSTVTF (SEQ ID NO:150) | 5.000 |
| 6 | 130 | NAPYLPSCL (SEQ ID NO:144) | 2.400 |
| 7 | 225 | NLYQMTSQL (SEQ ID NO:147) | 2.400 |
| 8 | 30 | GAAQWAPVL (SEQ ID NO:86) | 2.400 |
| 9 | 441 | NMTKLQLAL (SEQ ID NO:149) | 2.400 |
| 10 | 302 | RVPGVAPTL (SEQ ID NO:195) | 2.400 |
| 11 | 126 | RMFPNAPYL (SEQ ID NO:185) | 2.000 |
| 12 | 218 | RTPYSSDNL (SEQ ID NO:194) | 2.000 |
| 13 | 209 | CTGSQALLL (SEQ ID NO:52) | 2.000 |
| 14 | 332 | KRYFKLSHL (SEQ ID NO:127) | 2.000 |
| 15 | 180 | DPMGQQGSL (SEQ ID NO:59) | 2.000 |
| 16 | 437 | MHQRNMTKL (SEQ ID NO:143) | 2.000 |
| 17 | 207 | DSCTGSQAL (SEQ ID NO:61) | 2.000 |
| 18 | 208 | SCTGSQALL (SEQ ID NO:202) | 2.000 |
| 19 | 329 | GCNKRYFKL (SEQ ID NO:90) | 2.000 |
| 20 | 10 | ALLPAVPSL (SEQ ID NO:34) | 2.000 |

TABLE XXV

Results of BIMAS HLA Peptide Binding Prediction Analysis for Binding of Human WT1 Peptides to Human HLA B 4403

| Rank | Start Position | Subsequence Residue Listing | Score (Estimate of Half Time of Disassociation of a Molecule Containing This Subsequence) |
|---|---|---|---|
| 1 | 315 | SETSEKRPF (SEQ ID NO:209) | 80.000 |
| 2 | 349 | GEKPYQCDF (SEQ ID NO:91) | 80.000 |
| 3 | 84 | HEEQCLSAF (SEQ ID NO:107) | 60.000 |
| 4 | 410 | SEKPFSCRW (SEQ ID NO:207) | 48.000 |
| 5 | 429 | DELVRHHNM (SEQ ID NO:53) | 24.000 |
| 6 | 278 | TPILCGAQY (SEQ ID NO:227) | 15.000 |
| 7 | 141 | QPAIRNQGY (SEQ ID NO:170) | 9.000 |
| 8 | 40 | FAPPGASAY (SEQ ID NO:74) | 9.000 |
| 9 | 213 | QALLLRTPY (SEQ ID NO:160) | 9.000 |
| 10 | 318 | SEKRPFMCA (SEQ ID NO:208) | 8.000 |
| 11 | 81 | AEPHEEQCL (SEQ ID NO:30) | 8.000 |
| 12 | 152 | VTFDGTPSY (SEQ ID NO:244) | 4.500 |
| 13 | 101 | TGTAGACRY (SEQ ID NO:224) | 4.500 |
| 14 | 120 | ASSGQARMF (SEQ ID NO:40) | 4.500 |
| 15 | 261 | TEGQSNHST (SEQ ID NO:221) | 4.000 |
| 16 | 85 | EEQCLSAFT (SEQ ID NO:65) | 4.000 |
| 17 | 233 | LECMTWNQM (SEQ ID NO:131) | 4.000 |
| 18 | 104 | AGACRYGPF (SEQ ID NO:31) | 4.000 |
| 19 | 3 | SDVRDLNAL (SEQ ID NO:206) | 3.000 |
| 20 | 185 | QGSLGEQQY (SEQ ID NO:166) | 3.000 |

TABLE XXVI

Results of BIMAS HLA Peptide Binding Prediction Analysis for Binding of Human WT1 Peptides to Human HLA B 5101

| Rank | Start Position | Subsequence Residue Listing | Score (Estimate of Half Time of Disassociation of a Molecule Containing This Subsequence) |
|---|---|---|---|
| 1 | 303 | VPGVAPTLV (SEQ ID NO:242) | 314.600 |
| 2 | 180 | DPMGQQGSL (SEQ ID NO:59) | 242.000 |
| 3 | 250 | VAAGSSSSV (SEQ ID NO:236) | 157.300 |
| 4 | 130 | NAPYLPSCL (SEQ ID NO:144) | 50.000 |
| 5 | 30 | GAAQWAPVL (SEQ ID NO:86) | 50.000 |
| 6 | 20 | GGGGCALPV (SEQ ID NO:92) | 44.000 |
| 7 | 64 | PPPPPHSFI (SEQ ID NO:157) | 40.000 |
| 8 | 29 | SGAAQWAPV (SEQ ID NO:211) | 40.000 |
| 9 | 18 | LGGGGGCAL (SEQ ID NO:134) | 31.460 |
| 10 | 295 | RGIQDVRRV (SEQ ID NO:179) | 22.000 |
| 11 | 119 | QASSGQARM (SEQ ID NO:161) | 18.150 |
| 12 | 418 | WPSCQKKFA (SEQ ID NO:246) | 12.100 |
| 13 | 82 | EPHEEQCLS (SEQ ID NO:68) | 12.100 |
| 14 | 110 | GPFGPPPPS (SEQ ID NO:96) | 11.000 |
| 15 | 272 | ESDNHTTPI (SEQ ID NO:71) | 8.000 |
| 16 | 306 | VAPTLVRSA (SEQ ID NO:237) | 7.150 |
| 17 | 280 | ILCGAQYRI (SEQ ID NO:116) | 6.921 |
| 18 | 219 | TPYSSDNLY (SEQ ID NO:231) | 6.600 |
| 19 | 128 | FPNAPYLPS (SEQ ID NO:79) | 6.500 |
| 20 | 204 | TPTDSCTGS (SEQ ID NO:230) | 6.050 |

TABLE XXVII

Results of BIMAS HLA Peptide Binding Prediction Analysis for Binding of Human WT1 Peptides to Human HLA B 5102

| Rank | Start Position | Subsequence Residue Listing | Score (Estimate of Half Time of Disassociation of a Molecule Containing This Subsequence) |
|---|---|---|---|
| 1 | 295 | RGIQDVRRV (SEQ ID NO:179) | 290.400 |
| 2 | 303 | VPGVAPTLV (SEQ ID NO:242) | 200.000 |
| 3 | 180 | DPMGQQGSL (SEQ ID NO:59) | 133.100 |
| 4 | 250 | VAAGSSSSV (SEQ ID NO:236) | 110.000 |
| 5 | 30 | GAAQWAPVL (SEQ ID NO:86) | 55.000 |
| 6 | 130 | NAPYLPSCL (SEQ ID NO:144) | 50.000 |
| 7 | 20 | GGGGCALPV (SEQ ID NO:92) | 44.000 |
| 8 | 29 | SGAAQWAPV (SEQ ID NO:211) | 44.000 |
| 9 | 64 | PPPPPHSFI (SEQ ID NO:157) | 40.000 |
| 10 | 119 | QASSGQARM (SEQ ID NO:161) | 36.300 |
| 11 | 110 | GPFGPPPPS (SEQ ID NO:96) | 27.500 |
| 12 | 412 | KPFSCRWPS (SEQ ID NO:123) | 25.000 |
| 13 | 18 | LGGGGGCAL (SEQ ID NO:134) | 24.200 |
| 14 | 24 | CALPVSGAA (SEQ ID NO:43) | 16.500 |
| 15 | 219 | TPYSSDNLY (SEQ ID NO:231) | 15.000 |
| 16 | 292 | GVFRGIQDV (SEQ ID NO:103) | 14.641 |
| 17 | 136 | SCLESQPAI (SEQ ID NO:198) | 14.520 |
| 18 | 418 | WPSCQKKFA (SEQ ID NO:246) | 12.100 |
| 19 | 269 | TGYESDNHT (SEQ ID NO:225) | 11.000 |
| 20 | 351 | KPYQCDFKD (SEQ ID NO:124) | 11.000 |

TABLE XXVIII

Results of BIMAS HLA Peptide Binding Prediction Analysis for Binding of Human WT1 Peptides to Human HLA B 5201

| Rank | Start Position | Subsequence Residue Listing | Score (Estimate of Half Time of Disassociation of a Molecule Containing This Subsequence) |
|---|---|---|---|
| 1 | 191 | QQYSVPPPV (SEQ ID NO:171) | 100.000 |
| 2 | 32 | AQWAPVLDF (SEQ ID NO:37) | 30.000 |
| 3 | 243 | LGATLKGVA (SEQ ID NO:133) | 16.500 |
| 4 | 303 | VPGVAPTLV (SEQ ID NO:242) | 13.500 |
| 5 | 86 | EQCLSAFTV (SEQ ID NO:69) | 12.000 |
| 6 | 295 | RGIQDVRRV (SEQ ID NO:179) | 10.000 |
| 7 | 98 | GQFTGTAGA (SEQ ID NO:99) | 8.250 |
| 8 | 292 | GVFRGIQDV (SEQ ID NO:103) | 8.250 |
| 9 | 29 | SGAAQWAPV (SEQ ID NO:211) | 6.000 |
| 10 | 146 | NQGYSTVTF (SEQ ID NO:150) | 5.500 |
| 11 | 20 | GGGGCALPV (SEQ ID NO:92) | 5.000 |
| 12 | 239 | NQMNLGATL (SEQ ID NO:151) | 4.000 |
| 13 | 64 | PPPPPHSFI (SEQ ID NO:157) | 3.600 |
| 14 | 273 | SDNHTTPIL (SEQ ID NO:204) | 3.300 |
| 15 | 286 | YRIHTHGVF (SEQ ID NO:252) | 3.000 |
| 16 | 269 | TGYESDNHT (SEQ ID NO:225) | 3.000 |
| 17 | 406 | TGKTSEKPF (SEQ ID NO:222) | 2.750 |
| 18 | 327 | YPGCNKRYF (SEQ ID NO:250) | 2.750 |
| 19 | 7 | DLNALLPAV (SEQ ID NO:58) | 2.640 |
| 20 | 104 | AGACRYGPF (SEQ ID NO:31) | 2.500 |

TABLE XXIX

Results of BIMAS HLA Peptide Binding Prediction Analysis for Binding of Human WT1 Peptides to Human HLA B 5801

| Rank | Start Position | Subsequence Residue Listing | Score (Estimate of Half Time of Disassociation of a Molecule Containing This Subsequence) |
|---|---|---|---|
| 1 | 230 | TSQLECMTW (SEQ ID NO:234) | 96.800 |
| 2 | 92 | FTVHFSGQF (SEQ ID NO:85) | 60.000 |
| 3 | 120 | ASSGQARMF (SEQ ID NO:40) | 40.000 |
| 4 | 168 | AAQFPNHSF (SEQ ID NO:29) | 20.000 |
| 5 | 408 | KTSEKPFSC (SEQ ID NO:129) | 12.000 |
| 6 | 394 | RSDHLKTHT (SEQ ID NO:192) | 9.900 |
| 7 | 276 | HTTPILCGA (SEQ ID NO:115) | 7.200 |
| 8 | 218 | RTPYSSDNL (SEQ ID NO:194) | 6.600 |
| 9 | 152 | VTFDGTPSY (SEQ ID NO:244) | 6.000 |
| 10 | 40 | FAPPGASAY (SEQ ID NO:74) | 6.000 |
| 11 | 213 | QALLLRTPY (SEQ ID NO:160) | 4.500 |
| 12 | 347 | HTGEKPYQC (SEQ ID NO:112) | 4.400 |
| 13 | 252 | AGSSSSVKW (SEQ ID NO:32) | 4.400 |
| 14 | 211 | GSQALLLRT (SEQ ID NO:102) | 4.356 |
| 15 | 174 | HSFKHEDPM (SEQ ID NO:110) | 4.000 |
| 16 | 317 | TSEKRPFMC (SEQ ID NO:233) | 4.000 |
| 17 | 26 | LPVSGAAQW (SEQ ID NO:138) | 4.000 |
| 18 | 289 | HTHGVFRGI (SEQ ID NO:113) | 3.600 |
| 19 | 222 | SSDNLYQMT (SEQ ID NO:217) | 3.300 |
| 20 | 96 | FSGQFTGTA (SEQ ID NO:82) | 3.300 |

TABLE XXX

Results of BIMAS HLA Peptide Binding Prediction Analysis for Binding of Human WT1 Peptides to Human HLA CW0301

| Rank | Start Position | Subsequence Residue Listing | Score (Estimate of Half Time of Disassociation of a Molecule Containing This Subsequence) |
|---|---|---|---|
| 1 | 10 | ALLPAVPSL (SEQ ID NO:34) | 100.000 |
| 2 | 332 | KRYFKLSHL (SEQ ID NO:127) | 48.000 |
| 3 | 126 | RMFPNAPYL (SEQ ID NO:185) | 36.000 |
| 4 | 3 | SDVRDLNAL (SEQ ID NO:206) | 30.000 |
| 5 | 239 | NQMNLGATL (SEQ ID NO:151) | 24.000 |
| 6 | 225 | NLYQMTSQL (SEQ ID NO:147) | 24.000 |
| 7 | 180 | DPMGQQGSL (SEQ ID NO:59) | 20.000 |
| 8 | 362 | RRFSRSDQL (SEQ ID NO:187) | 12.000 |
| 9 | 329 | GCNKRYFKL (SEQ ID NO:90) | 10.000 |
| 10 | 286 | YRIHTHGVF (SEQ ID NO:252) | 10.000 |
| 11 | 301 | RRVPGVAPT (SEQ ID NO:189) | 10.000 |
| 12 | 24 | CALPVSGAA (SEQ ID NO:43) | 10.000 |
| 13 | 136 | SCLESQPAI (SEQ ID NO:198) | 7.500 |
| 14 | 437 | MHQRNMTKL (SEQ ID NO:143) | 7.200 |
| 15 | 390 | RKFSRSDHL (SEQ ID NO:183) | 6.000 |
| 16 | 423 | KKFARSDEL (SEQ ID NO:122) | 6.000 |
| 17 | 92 | FTVHFSGQF (SEQ ID NO:85) | 5.000 |
| 18 | 429 | DELVRHHNM (SEQ ID NO:53) | 5.000 |
| 19 | 130 | NAPYLPSCL (SEQ ID NO:144) | 4.800 |
| 20 | 30 | GAAQWAPVL (SEQ ID NO:86) | 4.000 |

TABLE XXXI

Results of BIMAS HLA Peptide Binding Prediction Analysis for Binding of Human WT1 Peptides to Human HLA CW0401

| Rank | Start Position | Subsequence Residue Listing | Score (Estimate of Half Time of Disassociation of a Molecule Containing This Subsequence) |
|---|---|---|---|
| 1 | 356 | DFKDCERRF (SEQ ID NO:55) | 120.000 |
| 2 | 334 | YFKLSHLQM (SEQ ID NO:248) | 100.000 |
| 3 | 180 | DPMGQQGSL (SEQ ID NO:59) | 88.000 |
| 4 | 163 | TPSHHAAQF (SEQ ID NO:228) | 52.800 |
| 5 | 327 | YPGCNKRYF (SEQ ID NO:250) | 40.000 |
| 6 | 285 | QYRIHTHGV (SEQ ID NO:175) | 27.500 |
| 7 | 424 | KFARSDELV (SEQ ID NO:119) | 25.000 |
| 8 | 326 | AYPGCNKRY (SEQ ID NO:42) | 25.000 |
| 9 | 192 | QYSVPPPVY (SEQ ID NO:176) | 25.000 |
| 10 | 417 | RWPSCQKKF (SEQ ID NO:196) | 22.000 |

TABLE XXXI-continued

Results of BIMAS HLA Peptide Binding Prediction Analysis for Binding of Human WT1 Peptides to Human HLA CW0401

| Rank | Start Position | Subsequence Residue Listing | Score (Estimate of Half Time of Disassociation of a Molecule Containing This Subsequence) |
|---|---|---|---|
| 11 | 278 | TPILCGAQY (SEQ ID NO:227) | 12.000 |
| 12 | 10 | ALLPAVPSL (SEQ ID NO:34) | 11.616 |
| 13 | 141 | QPAIRNQGY (SEQ ID NO:170) | 11.000 |
| 14 | 303 | VPGVAPTLV (SEQ ID NO:242) | 11.000 |
| 15 | 219 | TPYSSDNLY (SEQ ID NO:231) | 10.000 |
| 16 | 39 | DFAPPGASA (SEQ ID NO:54) | 7.920 |
| 17 | 99 | QFTGTAGAC (SEQ ID NO:165) | 6.000 |
| 18 | 4 | DVRDLNALL (SEQ ID NO:62) | 5.760 |
| 19 | 70 | SFIKQEPSW (SEQ ID NO:210) | 5.500 |
| 20 | 63 | PPPPPPHSF (SEQ ID NO:158) | 5.280 |

TABLE XXXII

Results of BIMAS HLA Peptide Binding Prediction Analysis for Binding of Human WT1 Peptides to Human HLA CW0602

| Rank | Start Position | Subsequence Residue Listing | Score (Estimate of Half Time of Disassociation of a Molecule Containing This Subsequence) |
|---|---|---|---|
| 1 | 332 | KLRYFKLSHL (SEQ ID NO:127) | 9.680 |
| 2 | 239 | NQMNLGATL (SEQ ID NO:151) | 6.600 |
| 3 | 130 | NAPYLPSCL (SEQ ID NO:144) | 6.600 |
| 4 | 7 | DLNALLPAV (SEQ ID NO:58) | 6.000 |
| 5 | 441 | NMTKLQLAL (SEQ ID NO:149) | 6.000 |
| 6 | 225 | NLYQMTSQL (SEQ ID NO:147) | 6.000 |
| 7 | 4 | DVRDLNALL (SEQ ID NO:62) | 6.000 |
| 8 | 3 | SDVRDLNAL (SEQ ID NO:206) | 4.400 |
| 9 | 10 | ALLPAVPSL (SEQ ID NO:34) | 4.000 |
| 10 | 213 | QALLLRTPY (SEQ ID NO:160) | 3.300 |
| 11 | 319 | EKRPFMCAY (SEQ ID NO:67) | 3.000 |
| 12 | 30 | GAAQWAPVL (SEQ ID NO:86) | 2.200 |
| 13 | 242 | NLGATLKGV (SEQ ID NO:146) | 2.200 |
| 14 | 292 | GVFRGIQDV (SEQ ID NO:103) | 2.200 |
| 15 | 207 | DSCTGSQAL (SEQ ID NO:61) | 2.200 |
| 16 | 362 | RRFSRSDQL (SEQ ID NO:187) | 2.200 |
| 17 | 439 | QRNMTKLQL (SEQ ID NO:173) | 2.200 |

TABLE XXXII-continued

Results of BIMAS HLA Peptide Binding Prediction Analysis for Binding of Human WT1 Peptides to Human HLA CW0602

| Rank | Start Position | Subsequence Residue Listing | Score (Estimate of Half Time of Disassociation of a Molecule Containing This Subsequence) |
|---|---|---|---|
| 18 | 295 | RGIQDVRRV (SEQ ID NO:179) | 2.200 |
| 19 | 423 | KKFARSDEL (SEQ ID NO:122) | 2.200 |
| 20 | 180 | DPMGQQGSL (SEQ ID NO:59) | 2.200 |

TABLE XXXIII

Results of BIMAS HLA Peptide Binding Prediction Analysis for Binding of Human WT1 Peptides to Human HLA CW0702

| Rank | Start Position | Subsequence Residue Listing | Score (Estimate of Half Time of Disassociation of a Molecule Containing This Subsequence |
|---|---|---|---|
| 1 | 319 | EKRPFMCAY (SEQ ID NO:67) | 26.880 |
| 2 | 326 | AYPGCNKRY (SEQ ID NO:42) | 24.000 |
| 3 | 40 | FAPPGASAY (SEQ ID NO:74) | 14.784 |
| 4 | 192 | QYSVPPPVY (SEQ ID NO:176) | 12.000 |
| 5 | 278 | TPILCGAQY (SEQ ID NO:227) | 12.000 |
| 6 | 219 | TPYSSDNLY (SEQ ID NO:231) | 12.000 |
| 7 | 213 | QALLLRTPY (SEQ ID NO:160) | 8.800 |
| 8 | 125 | ARMFPNAPY (SEQ ID NO:38) | 8.000 |
| 9 | 327 | YPGCNKRYF (SEQ ID NO:250) | 6.600 |
| 10 | 152 | VTFDGTPSY (SEQ ID NO:244) | 5.600 |
| 11 | 141 | QPAIRNQGY (SEQ ID NO:170) | 4.800 |
| 12 | 345 | RKHTGEKPY (SEQ ID NO:184) | 4.000 |
| 13 | 185 | QGSLGEQQY (SEQ ID NO:166) | 4.000 |
| 14 | 101 | TGTAGACRY (SEQ ID NO:224) | 4.000 |
| 15 | 375 | RRHTGVKPF (SEQ ID NO:188) | 4.000 |
| 16 | 263 | GQSNHSTGY (SEQ ID NO:100) | 4.000 |
| 17 | 163 | TPSHHAAQF (SEQ ID NO:228) | 3.000 |
| 18 | 33 | QWAPVLDFA (SEQ ID NO:174) | 2.688 |
| 19 | 130 | NAPYLPSCL (SEQ ID NO:144) | 2.640 |
| 20 | 84 | HEEQCLSAF (SEQ ID NO:107) | 2.400 |

TABLE XXXIV

Results of BIMAS HLA Peptide Binding Prediction Analysis for Binding of Human WT1 Peptides to Mouse MHC Class I Db

| Rank | Start Position | Subsequence Residue Listing | Score (Estimate of Half Time of Disassociation of a Molecule Containing This Subsequence) |
|---|---|---|---|
| 1 | 235 | CMTWNQMNL (SEQ ID NO:49) | 5255.712 |
| 2 | 126 | RMFPNAPYL (SEQ ID NO:185) | 1990.800 |
| 3 | 221 | YSSDNLYQM (SEQ ID NO:253) | 930.000 |
| 4 | 228 | QMTSQLECM (SEQ ID NO:169) | 33.701 |
| 5 | 239 | NQMNLGATL (SEQ ID NO:151) | 21.470 |
| 6 | 441 | NMTKLQLAL (SEQ ID NO:149) | 19.908 |
| 7 | 437 | MHQRNMTKL (SEQ ID NO:143) | 19.837 |
| 8 | 136 | SCLESQPAI (SEQ ID NO:198) | 11.177 |
| 9 | 174 | HSFKHEDPM (SEQ ID NO:110) | 10.800 |
| 10 | 302 | RVPGVAPTL (SEQ ID NO:195) | 10.088 |
| 11 | 130 | NAPYLPSCL (SEQ ID NO:144) | 8.400 |
| 12 | 10 | ALLPAVPSL (SEQ ID NO:34) | 5.988 |
| 13 | 208 | SCTGSQALL (SEQ ID NO:202) | 4.435 |
| 14 | 209 | CTGSQALLL (SEQ ID NO:52) | 3.548 |
| 15 | 238 | WNQMNLGAT (SEQ ID NO:245) | 3.300 |
| 16 | 218 | RTPYSSDNL (SEQ ID NO:194) | 3.185 |
| 17 | 24 | CALPVSGAA (SEQ ID NO:43) | 2.851 |
| 18 | 18 | LGGGGGCAL (SEQ ID NO:134) | 2.177 |
| 19 | 142 | PAIRNQGYS (SEQ ID NO:152) | 2.160 |
| 20 | 30 | GAAQWAPVL (SEQ ID NO:86) | 1.680 |

TABLE XXXV

Results of BIMAS HLA Peptide Binding Prediction Analysis for Binding of Human WT1 Peptides to Mouse MHC Class I Dd

| Rank | Start Position | Subsequence Residue Listing | Score (Estimate of Half Time of Disassociation of a Molecule Containing This Subsequence) |
|---|---|---|---|
| 1 | 112 | FGPPPPSQA (SEQ ID NO:76) | 48.000 |
| 2 | 122 | SGQARMFPN (SEQ ID NO:212) | 36.000 |
| 3 | 104 | AGACRYGPF (SEQ ID NO:31) | 30.000 |
| 4 | 218 | RTPYSSDNL (SEQ ID NO:194) | 28.800 |
| 5 | 130 | NAPYLPSCL (SEQ ID NO:144) | 20.000 |
| 6 | 302 | RVPGVAPTL (SEQ ID NO:195) | 20.000 |
| 7 | 18 | LGGGGGCAL (SEQ ID NO:134) | 20.000 |
| 8 | 81 | AEPHEEQCL (SEQ ID NO:30) | 10.000 |
| 9 | 29 | SGAAQWAPV (SEQ ID NO:211) | 7.200 |

TABLE XXXV-continued

Results of BIMAS HLA Peptide Binding Prediction Analysis for Binding of Human WT1 Peptides to Mouse MHC Class I Dd

| Rank | Start Position | Subsequence | Residue Listing | Score (Estimate of Half Time of Disassociation of a Molecule Containing This Subsequence) |
|---|---|---|---|---|
| 10 | 423 | KKFARSDEL | (SEQ ID NO:122) | 7.200 |
| 11 | 295 | RGIQDVRRV | (SEQ ID NO:179) | 7.200 |
| 12 | 390 | RKFSRSDHL | (SEQ ID NO:183) | 6.000 |
| 13 | 332 | KRYFKLSHL | (SEQ ID NO:127) | 6.000 |
| 14 | 362 | RRFSRSDQL | (SEQ ID NO:187) | 6.000 |
| 15 | 417 | RWPSCQKKF | (SEQ ID NO:196) | 6.000 |
| 16 | 160 | YGHTPSHHA | (SEQ ID NO:249) | 6.000 |
| 17 | 20 | GGGGCALPV | (SEQ ID NO:92) | 6.000 |
| 18 | 329 | GCNKRYFKL | (SEQ ID NO:90) | 5.000 |
| 19 | 372 | RHQRRHTGV | (SEQ ID NO:181) | 4.500 |
| 20 | 52 | GGPAPPPAP | (SEQ ID NO:93) | 4.000 |

TABLE XXXVI

Results of BIMAS HLA Peptide Binding Prediction Analysis for Binding of Human WT1 Peptides to Mouse MHC Class I Kb

| Rank | Start Position | Subsequence | Residue Listing | Score (Estimate of Half Time of Disassociation of a Molecule Containing This Subsequence) |
|---|---|---|---|---|
| 1 | 329 | GCNKRYFKL | (SEQ ID NO:90) | 24.000 |
| 2 | 225 | NLYQMTSQL | (SEQ ID NO:147) | 10.000 |
| 3 | 420 | SCQKKFARS | (SEQ ID NO:200) | 3.960 |
| 4 | 218 | RTPYSSDNL | (SEQ ID NO:194) | 3.630 |
| 5 | 437 | MHQRNMTKL | (SEQ ID NO:143) | 3.600 |
| 6 | 387 | TCQRKFSRS | (SEQ ID NO:219) | 3.600 |
| 7 | 302 | RVPGVAPTL | (SEQ ID NO:195) | 3.300 |
| 8 | 130 | NAPYLPSCL | (SEQ ID NO:144) | 3.000 |
| 9 | 289 | HTHGVFRGI | (SEQ ID NO:113) | 3.000 |
| 10 | 43 | PGASAYGSL | (SEQ ID NO:153) | 2.400 |
| 11 | 155 | DGTPSYGHT | (SEQ ID NO:56) | 2.400 |
| 12 | 273 | SDNHTTPIL | (SEQ ID NO:204) | 2.200 |
| 13 | 126 | RMFPNAPYL | (SEQ ID NO:185) | 2.200 |
| 14 | 128 | FPNAPYLPS | (SEQ ID NO:79) | 2.000 |
| 15 | 3 | SDVRDLNAL | (SEQ ID NO:206) | 1.584 |
| 16 | 207 | DSCTGSQAL | (SEQ ID NO:61) | 1.584 |
| 17 | 332 | KRYFKLSHL | (SEQ ID NO:127) | 1.500 |
| 18 | 18 | LGGGGGCAL | (SEQ ID NO:134) | 1.320 |

TABLE XXXVI-continued

Results of BIMAS HLA Peptide Binding Prediction Analysis for Binding of Human WT1 Peptides to Mouse MHC Class I Kb

| Rank | Start Position | Subsequence Residue Listing | Score (Estimate of Half Time of Disassociation of a Molecule Containing This Subsequence) |
|---|---|---|---|
| 19 | 233 | LECMTWNQM (SEQ ID NO:131) | 1.320 |
| 20 | 441 | NMTKLQLAL (SEQ ID NO:149) | 1.200 |

TABLE XXXVII

Results of BIMAS HLA Peptide Binding Prediction Analysis for Binding of Human WT1 Peptides to Mouse MHC Class I Kd

| Rank | Start Position | Subsequence Residue Listing | Score (Estimate of Half Time of Disassociation of a Molecule Containing This Subsequence) |
|---|---|---|---|
| 1 | 285 | QYRIHTHGV (SEQ ID NO:175) | 600.000 |
| 2 | 424 | KFARSDELV (SEQ ID NO:119) | 288.000 |
| 3 | 334 | YFKLSHLQM (SEQ ID NO:248) | 120.000 |
| 4 | 136 | SCLESQPTI (SEQ ID NO:199) | 115.200 |
| 5 | 239 | NQMNLGATL (SEQ ID NO:151) | 115.200 |
| 6 | 10 | ALLPAVSSL (SEQ ID NO:35) | 115.200 |
| 7 | 47 | AYGSLGGPA (SEQ ID NO:41) | 86.400 |
| 8 | 180 | DPMGQQGSL (SEQ ID NO:59) | 80.000 |
| 9 | 270 | GYESDNHTA (SEQ ID NO:105) | 72.000 |
| 10 | 326 | AYPGCNKRY (SEQ ID NO:42) | 60.000 |
| 11 | 192 | QYSVPPPVY (SEQ ID NO:176) | 60.000 |
| 12 | 272 | ESDNHTAPI (SEQ ID NO:70) | 57.600 |
| 13 | 289 | HTHGVFRGI (SEQ ID NO:113) | 57.600 |
| 14 | 126 | DVRDLNALL (SEQ ID NO:62) | 57.600 |
| 15 | 4 | CTGSQALLL (SEQ ID NO:52) | 57.600 |
| 16 | 208 | SCTGSQALL (SEQ ID NO:202) | 48.000 |
| 17 | 441 | NMTKLQLAL (SEQ ID NO:149) | 48.000 |
| 18 | 207 | DSCTGSQAL (SEQ ID NO:61) | 48.000 |
| 19 | 130 | NAPYLPSCL (SEQ ID NO:144) | 48.000 |
| 20 | 235 | CMTWNQMNL (SEQ ID NO:49) | 48.000 |

TABLE XXXVIII

Results of BIMAS HLA Peptide Binding Prediction Analysis for
Binding of Human WT1 Peptides to Mouse MHC Class I Kk

| Rank | Start Position | Subsequence Residue Listing | Score (Estimate of Half Time of Disassociation of a Molecule Containing This Subsequence) |
|---|---|---|---|
| 1 | 81 | AEPHEEQCL (SEQ ID NO:30) | 40.000 |
| 2 | 85 | EEQCLSAFT (SEQ ID NO:65) | 40.000 |
| 3 | 429 | DELVRHHNM (SEQ ID NO:53) | 20.000 |
| 4 | 315 | SETSEKRPF (SEQ ID NO:209) | 20.000 |
| 5 | 261 | TEGQSNHST (SEQ ID NO:221) | 20.000 |
| 6 | 410 | SEKPFSCRW (SEQ ID NO:207) | 10.000 |
| 7 | 272 | ESDNHTTPI (SEQ ID NO:71) | 10.000 |
| 8 | 318 | SEKRPFMCA (SEQ ID NO:208) | 10.000 |
| 9 | 138 | LESQPAIRN (SEQ ID NO:132) | 10.000 |
| 10 | 233 | LECMTWNQM (SEQ ID NO:131) | 10.000 |
| 11 | 298 | QDVRRVPGV (SEQ ID NO:164) | 10.000 |
| 12 | 84 | HEEQCLSAF (SEQ ID NO:107) | 10.000 |
| 13 | 349 | GEKPYQCDF (SEQ ID NO:91) | 10.000 |
| 14 | 289 | HTHGVFRGI (SEQ ID NO:113) | 10.000 |
| 15 | 179 | EDPMGQQGS (SEQ ID NO:64) | 8.000 |
| 16 | 136 | SCLESQPAI (SEQ ID NO:198) | 5.000 |
| 17 | 280 | ILCGAQYRI (SEQ ID NO:116) | 5.000 |
| 18 | 273 | SDNHTTPIL (SEQ ID NO:204) | 5.000 |
| 19 | 428 | SDELVRHHN (SEQ ID NO:203) | 4.000 |
| 20 | 3 | SDVRDLNAL (SEQ ID NO:206) | 4.000 |

TABLE XXXIX

Results of BIMAS HLA Peptide Binding Prediction Analysis for
Binding of Human WT1 Peptides to Mouse MHC Class I Ld

| Rank | Start Position | Subsequence Residue Listing | Score (Estimate of Half Time of Disassociation of a Molecule Containing This Subsequence) |
|---|---|---|---|
| 1 | 163 | TPSHHAAQF (SEQ ID NO:228) | 360.000 |
| 2 | 327 | YPGCNKRYF (SEQ ID NO:250) | 300.000 |
| 3 | 180 | DPMGQQGSL (SEQ ID NO:59) | 150.000 |
| 4 | 26 | LPVSGAAQW (SEQ ID NO:138) | 93.600 |
| 5 | 278 | TPILCGAQY (SEQ ID NO:227) | 72.000 |
| 6 | 141 | QPAIRNQGY (SEQ ID NO:170) | 60.000 |
| 7 | 219 | TPYSSDNLY (SEQ ID NO:231) | 60.000 |
| 8 | 303 | VPGVAPTLV (SEQ ID NO:242) | 60.000 |
| 9 | 120 | ASSGQARMF (SEQ ID NO:40) | 50.000 |

TABLE XXXIX-continued

Results of BIMAS HLA Peptide Binding Prediction Analysis for Binding of Human WT1 Peptides to Mouse MHC Class I Ld

| Rank | Start Position | Subsequence Residue Listing | Score (Estimate of Half Time of Disassociation of a Molecule Containing This Subsequence) |
|---|---|---|---|
| 10 | 63 | PPPPPPHSF (SEQ ID NO:158) | 45.000 |
| 11 | 113 | GPPPPSQAS (SEQ ID NO:97) | 45.000 |
| 12 | 157 | TPSYGHTPS (SEQ ID NO:229) | 39.000 |
| 13 | 207 | DSCTGSQAL (SEQ ID NO:61) | 32.500 |
| 14 | 110 | GPFGPPPPS (SEQ ID NO:96) | 30.000 |
| 15 | 82 | EPHEEQCLS (SEQ ID NO:68) | 30.000 |
| 16 | 412 | KPFSCRWPS (SEQ ID NO:123) | 30.000 |
| 17 | 418 | WPSCQKKFA (SEQ ID NO:246) | 30.000 |
| 18 | 221 | YSSDNLYQM (SEQ ID NO:253) | 30.000 |
| 19 | 204 | TPTDSCTGS (SEQ ID NO:230) | 30.000 |
| 20 | 128 | FPNAPYLPS (SEQ ID NO:79) | 30.000 |

TABLE XL

Results of BIMAS HLA Peptide Binding Prediction Analysis for Binding of Human WT1 Peptides to Cattle HLA A20

| Rank | Start Position | Subsequence Residue Listing | Score (Estimate of Half Time of Disassociation of a Molecule Containing This Subsequence) |
|---|---|---|---|
| 1 | 350 | EKPYQCDFK (SEQ ID NO:66) | 1000.00 |
| 2 | 319 | EKRPFMCAY (SEQ ID NO:67) | 500.000 |
| 3 | 423 | KKFARSDEL (SEQ ID NO:122) | 500.000 |
| 4 | 345 | RKHTGEKPY (SEQ ID NO:184) | 500.000 |
| 5 | 390 | RKFSRSDHL (SEQ ID NO:183) | 500.000 |
| 6 | 137 | CLESQPAIR (SEQ ID NO:47) | 120.000 |
| 7 | 380 | VKPFQCKTC (SEQ ID NO:239) | 100.000 |
| 8 | 407 | GKTSEKPFS (SEQ ID NO:95) | 100.000 |
| 9 | 335 | FKLSHLQMH (SEQ ID NO:78) | 100.000 |
| 10 | 247 | LKGVAAGSS (SEQ ID NO:135) | 100.000 |
| 11 | 370 | LKRHQRRHT (SEQ ID NO:136) | 100.000 |
| 12 | 258 | VKWTEGQSN (SEQ ID NO:240) | 100.000 |
| 13 | 398 | LKTHTRTHT (SEQ ID NO:137) | 100.000 |
| 14 | 331 | NKRYFKLSH (SEQ ID NO:145) | 100.000 |
| 15 | 357 | FKDCERRFS (SEQ ID NO:77) | 100.000 |
| 16 | 385 | CKTCQRKFS (SEQ ID NO:46) | 100.000 |
| 17 | 294 | FRGIQDVRR (SEQ ID NO:81) | 80.000 |
| 18 | 368 | DQLKRHQRR (SEQ ID NO:60) | 80.000 |

TABLE XL-continued

Results of BIMAS HLA Peptide Binding Prediction Analysis for
Binding of Human WT1 Peptides to Cattle HLA A20

| Rank | Start Position | Subsequence Residue Listing | Score (Estimate of Half Time of Disassociation of a Molecule Containing This Subsequence) |
|---|---|---|---|
| 19 | 432 | VRHHNMHQR (SEQ ID NO:243) | 80.000 |
| 20 | 118 | SQASSGQAR (SEQ ID NO:216) | 80.000 |

TABLE XLI

Results of BIMAS HLA Peptide Binding Prediction Analysis for
Binding of Mouse WT1 Peptides to Mouse MHC Class I A 0201

| Rank | Start Position | Subsequence Residue Listing | Score (Estimate of Half Time of Disassociation of a Molecule Containing This Subsequence) |
|---|---|---|---|
| 1 | 126 | RMFPNAPYL (SEQ ID NO:293) | 313.968 |
| 2 | 187 | SLGEQQYSV (SEQ ID NO:299) | 285.163 |
| 3 | 10 | ALLPAVSSL (SEQ ID NO:255) | 181.794 |
| 4 | 225 | NLYQMTSQL (SEQ ID NO:284) | 68.360 |
| 5 | 292 | GVFRGIQDV (SEQ ID NO:270) | 51.790 |
| 6 | 93 | TLHFSGQFT (SEQ ID NO:302) | 40.986 |
| 7 | 191 | QQYSVPPPV (SEQ ID NO:290) | 22.566 |
| 8 | 280 | ILCGAQYRI (SEQ ID NO:274) | 17.736 |
| 9 | 441 | NMTKLHVAL (SEQ ID NO:285) | 15.428 |
| 10 | 235 | CMTWNQMNL (SEQ ID NO:258) | 15.428 |
| 11 | 7 | DLNALLPAV (SEQ ID NO:261) | 11.998 |
| 12 | 242 | NLGATLKGM (SEQ ID NO:283) | 11.426 |
| 13 | 227 | YQMTSQLEC (SEQ ID NO:307) | 8.573 |
| 14 | 239 | NQMNLGATL (SEQ ID NO:286) | 8.014 |
| 15 | 309 | TLVRSASET (SEQ ID NO:303) | 7.452 |
| 16 | 408 | KTSEKPFSC (SEQ ID NO:277) | 5.743 |
| 17 | 340 | LQMHSRKHT (SEQ ID NO:280) | 4.752 |
| 18 | 228 | QMTSQLECM (SEQ ID NO:289) | 4.044 |
| 19 | 37 | VLDFAPPGA (SEQ ID NO:304) | 3.378 |
| 20 | 302 | RVSGVAPTL (SEQ ID NO:295) | 1.869 |

TABLE XLII

Results of BIMAS HLA Peptide Binding Prediction Analysis for Binding of Mouse WT1 Peptides to Mouse MHC Class I Db

| Rank | Start Position | Subsequence Residue Listing | Score (Estimate of Half Time of Disassociation of a Molecule Containing This Subsequence) |
|---|---|---|---|
| 1 | 221 | YSSDNLYQM (SEQ ID NO:308) | 312.000 |
| 2 | 126 | RMFPNAPYL (SEQ ID NO:293) | 260.000 |
| 3 | 235 | CMTWNQMNL (SEQ ID NO:258) | 260.000 |
| 4 | 437 | MHQRNMTKL (SEQ ID NO:281) | 200.000 |
| 5 | 238 | WNQMNLGAT (SEQ ID NO:305) | 12.000 |
| 6 | 130 | NAPYLPSCL (SEQ ID NO:282) | 8.580 |
| 7 | 3 | SDVRDLNAL (SEQ ID NO:298) | 7.920 |
| 8 | 136 | SCLESQPTI (SEQ ID NO:296) | 7.920 |
| 9 | 81 | AEPHEEQCL (SEQ ID NO:254) | 6.600 |
| 10 | 10 | ALLPAVSSL (SEQ ID NO:255) | 6.600 |
| 11 | 218 | RTPYSSDNL (SEQ ID NO:294) | 6.000 |
| 12 | 441 | NMTKLHVAL (SEQ ID NO:285) | 3.432 |
| 13 | 228 | QMTSQLECM (SEQ ID NO:289) | 3.120 |
| 14 | 174 | HSFKHEDPM (SEQ ID NO:272) | 3.120 |
| 15 | 242 | NLGATLKGM (SEQ ID NO:283) | 2.640 |
| 16 | 261 | TEGQSNHGI (SEQ ID NO:301) | 2.640 |
| 17 | 225 | NLYQMTSQL (SEQ ID NO:284) | 2.640 |
| 18 | 207 | DSCTGSQAL (SEQ ID NO:263) | 2.600 |
| 19 | 119 | QASSGQARM (SEQ ID NO:288) | 2.600 |
| 20 | 18 | LGGGGGCGL (SEQ ID NO:279) | 2.600 |

TABLE XLIII

Results of BIMAS HLA Peptide Binding Prediction Analysis for Binding of Mouse WT1 Peptides to Mouse MHC Class I Kb

| Rank | Start Position | Subsequence Residue Listing | Score (Estimate of Half Time of Disassociation of a Molecule Containing This Subsequence) |
|---|---|---|---|
| 1 | 329 | GCNKRYFKL (SEQ ID NO:268) | 24.000 |
| 2 | 225 | NLYQMTSQL (SEQ ID NO:284) | 10.000 |
| 3 | 420 | SCQKKFARS (SEQ ID NO:297) | 3.960 |
| 4 | 218 | RTPYSSDNL (SEQ ID NO:294) | 3.630 |
| 5 | 437 | MHQRNMTKL (SEQ ID NO:281) | 3.600 |
| 6 | 387 | TCQRKFSRS (SEQ ID NO:300) | 3.600 |
| 7 | 289 | HTHGVFRGI (SEQ ID NO:273) | 3.000 |
| 8 | 130 | NAPYLPSCL (SEQ ID NO:282) | 3.000 |
| 9 | 43 | PGASAYGSL (SEQ ID NO:287) | 2.400 |

TABLE XLIII-continued

Results of BIMAS HLA Peptide Binding Prediction Analysis for Binding of Mouse WT1 Peptides to Mouse MHC Class I Kb

| Rank | Start Position | Subsequence Residue Listing | Score (Estimate of Half Time of Disassociation of a Molecule Containing This Subsequence) |
|---|---|---|---|
| 10 | 155 | DGAPSYGHT (SEQ ID NO:260) | 2.400 |
| 11 | 126 | RMFPNAPYL (SEQ ID NO:293) | 2.200 |
| 12 | 128 | FPNAPYLPS (SEQ ID NO:267) | 2.000 |
| 13 | 207 | DSCTGSQAL (SEQ ID NO:263) | 1.584 |
| 14 | 3 | SDVRDLNAL (SEQ ID NO:298) | 1.584 |
| 15 | 332 | KRYFKLSHL (SEQ ID NO:276) | 1.500 |
| 16 | 233 | LECMTWNQM (SEQ ID NO:278) | 1.320 |
| 17 | 18 | LGGGGGCGL (SEQ ID NO:279) | 1.320 |
| 18 | 242 | NLGATLKGM (SEQ ID NO:283) | 1.200 |
| 19 | 123 | GQARMFPN (SEQ ID NO:269)A | 1.200 |
| 20 | 441 | NMTKLHVAL (SEQ ID NO:285) | 1.200 |

TABLE XLIV

Results of BIMAS HLA Peptide Binding Prediction Analysis for Binding of Mouse WT1 Peptides to Mouse MHC Class I Kd

| Rank | Start Position | Subsequence Residue Listing | Score (Estimate of Half Time of Disassociation of a Molecule Containing This Subsequence) |
|---|---|---|---|
| 1 | 285 | QYRIHTHGV (SEQ ID NO:291) | 600.000 |
| 2 | 424 | KFARSDELV (SEQ ID NO:275) | 288.000 |
| 3 | 334 | YFKLSHLQM (SEQ ID NO:306) | 120.000 |
| 4 | 136 | SCLESQPTI (SEQ ID NO:296) | 115.200 |
| 5 | 239 | NQMNLGATL (SEQ ID NO:286) | 115.200 |
| 6 | 10 | ALLPAVSSL (SEQ ID NO:255) | 115.200 |
| 7 | 47 | AYGSLGGPA (SEQ ID NO:256) | 86.400 |
| 8 | 180 | DPMGQQGSL (SEQ ID NO:262) | 80.000 |
| 9 | 270 | GYESDNHTA (SEQ ID NO:271) | 72.000 |
| 10 | 192 | QYSVPPPVY (SEQ ID NO:292) | 60.000 |
| 11 | 326 | AYPGCNKRY (SEQ ID NO:257) | 60.000 |
| 12 | 289 | HTHGVFRGI (SEQ ID NO:273) | 57.600 |
| 13 | 4 | DVRDLNALL (SEQ ID NO:264) | 57.600 |
| 14 | 126 | RMFPNAPYL (SEQ ID NO:293) | 57.600 |
| 15 | 209 | CTGSQALLL (SEQ ID NO:259) | 48.000 |
| 16 | 86 | EQCLSAFTL (SEQ ID NO:265) | 48.000 |
| 17 | 302 | RVSGVAPTL (SEQ ID NO:295) | 48.000 |
| 18 | 218 | RTPYSSDNL (SEQ ID NO:294) | 48.000 |

TABLE XLIV-continued

Results of BIMAS HLA Peptide Binding Prediction Analysis for Binding of Mouse WT1 Peptides to Mouse MHC Class I Kd

| Rank | Start Position | Subsequence Residue Listing | Score (Estimate of Half Time of Disassociation of a Molecule Containing This Subsequence) |
|---|---|---|---|
| 19 | 272 | ESDNHTAPI (SEQ ID NO:266) | 48.000 |
| 20 | 225 | NLYQMTSQL (SEQ ID NO:284) | 48.000 |

TABLE XLV

Results of TSites Peptide Binding Prediction Analysis for Human WT1 Peptides Capable of Eliciting a Helper T cell Response

| Peptide | Sequence | |
|---|---|---|
| p6–23 | RDLNALLPAVPSLGGGG | (SEQ ID NO:1) |
| p30–35 | GAAQWA | (SEQ ID NO:309) |
| p45–56 | ASAYGSLGGPAP | (SEQ ID NO:310) |
| p91–105 | AFTVHFSGQFTGTAG | (SEQ ID NO:311) |
| p117–139 | PSQASSGQARMFPNAPYLPSCLE | (SEQ ID NO:2) |
| p167–171 | HAAQF | (SEQ ID NO:312) |
| p202–233 | CHTPTDSCTGSQALLLRTPYSSDN-LYQMTSQL | (SEQ ID NO:313) |
| p244–262 | GATLKGVAAGSSSSVKWTE | (SEQ ID NO:4) |
| p287–318 | RIHTHGVFRGIQDVR-RVPGVAPTLVRSASETS | (SEQ ID NO:314) |
| p333–336 | RYFK | (SEQ ID NO:315) |
| p361–374 | ERRFSRSDQLKRHQ | (SEQ ID NO:316) |
| p389–410 | QRKFSRSDHLKTHTRTHTGKTS | (SEQ ID NO:317) |
| p421–441 | CQKKFARSDELVRHHNMHQRN | (SEQ ID NO:318) |

Certain CTL peptides (shown in Table XLVI) were selected for further study. For each peptide in Table XLVI, scores obtained using BIMAS HLA peptide binding prediction analysis are provided.

TABLE XLVI

WT1 Peptide Sequences and HLA Peptide Binding Predictions

| Peptide | Sequence | Comments |
|---|---|---|
| p329–337 GCNKRYFKL | (SEQ ID Nos:90 and 268) | Score 24,000 |
| p225–233 NLYQMTSQL | (SEQ ID Nos:147 and 284) | binds also to class II and HLA A2, Kd, score 10,000 |
| p235–243 CMTWNQMNL | (SEQ ID Nos:49 and 258) | binds also to HLA A2, score 5,255, 712 |
| p126–I34 RMFPNAPYL | (SEQ ID Nos:185 and 293) | binds also to Kd, class II and HLA A2, score 1,990,800 |
| p221–229 YSSDNLYQM | (SEQ ID Nos:253 and 308) | binds also to Ld, score 312,000 |
| p228–236 QMTSQLECM | (SEQ ID Nos:169 and 289) | score 3,120 |
| p239–247 NQMNLGATL | (SEQ ID Nos:151 and 286) | binds also to HLA A 0201, Kd, score 8,015 |
| mouse p136–144 SCLESQPTI | (SEQ ID NO:296) | binds also to Kd, 1mismatch to human |
| human p136–144 SCLESQPAI | (SEQ ID NO:198) | score 7,920 |

TABLE XLVI-continued

WT1 Peptide Sequences and HLA Peptide Binding Predictions

| Peptide | | Sequence | Comments |
|---|---|---|---|
| mouse p10–18 | ALLPAVSSL | (SEQ ID NO:255) | binds also to Kd, HLA A2, 1 mismatch to human |
| human p10–18 | ALLPAVPSL | (SEQ ID NO:34) | score 6,600 |

Peptide binding to C57B1/6 murine MHC was confirmed using the leukemia cell line RMA-S, as described by Ljunggren et al., Nature 346:476–480, 1990. In brief, RMA-S cells were cultured for 7 hours at 26° C. in complete medium supplemented with 1% FCS. A total of $10^6$ RMA-S cells were added into each well of a 24-well plate and incubated either alone or with the designated peptide (25 ug/ml) for 16 hours at 26° C. and additional 3 hours at 37° C. in complete medium. Cells were then washed three times and stained with fluorescein isothiocyanate-conjugated anti $D^b$ or anti-$K^b$ antibody (PharMingen, San Diego, Calif.). Labeled cells were washed twice, resuspended and fixed in 500 ul of PBS with 1% paraformaldehyde and analyzed for fluorescence intensity in a flow cytometer (Becton-Dickinson FACSCalibur®). The percentage of increase of $D^b$ or $K^b$ molecules on the surface of the RMA-S cells was measured by increased mean fluorescent intensity of cells incubated with peptide compared with that of cells incubated in medium alone.

Mice were immunized with the peptides capable of binding to murine class I MHC. Following immunization, spleen cells were stimulated in vitro and tested for the ability to lyse targets incubated with WT1 peptides. CTL were evaluated with a standard chromium release assay (Chen et al., Cancer Res. 54:1065–1070, 1994). 106 target cells were incubated at 37° C. with 150 µCi of sodium $^{51}$Cr for 90 minutes, in the presence or absence of specific peptides. Cells were washed three times and resuspended in RPMI with 5% fetal bovine serum. For the assay, $10^4$ $^{51}$Cr-labeled target cells were incubated with different concentrations of effector cells in a final volume of 200 µl in U-bottomed 96-well plates. Supernatants were removed after 4 to 7 hours at 37° C., and the percentage specific lysis was determined by the formula:

% specific lysis=100×(experimental release–spontaneous release)/(maximum release–spontaneous release).

Figure 9A:
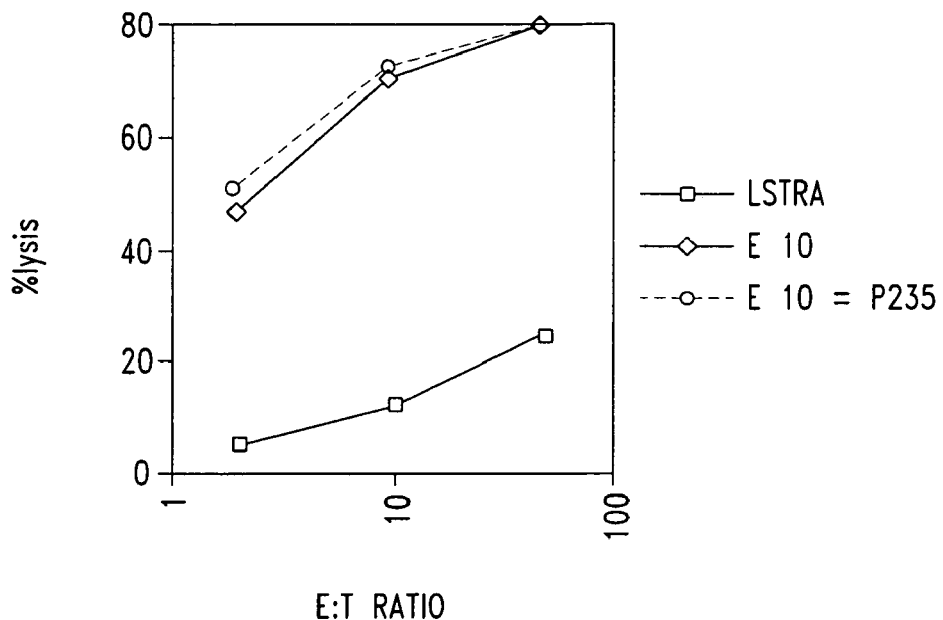
FIGS. 9A and 9B are graphs illustrating the elicitation of WT1 peptide-specific CTL in mice immunized with WT1 peptides.
Figure 9B:
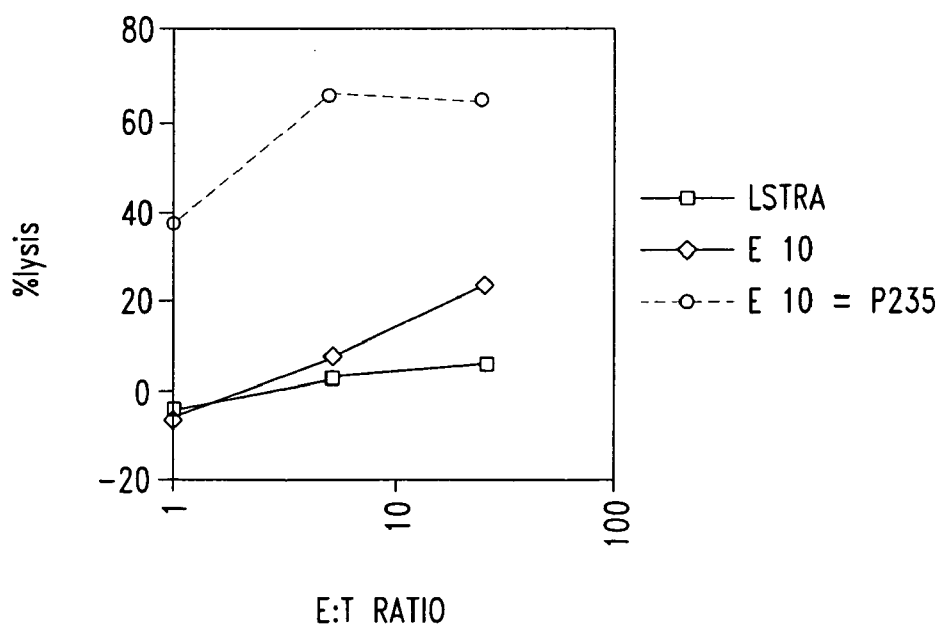
Figure 10A:
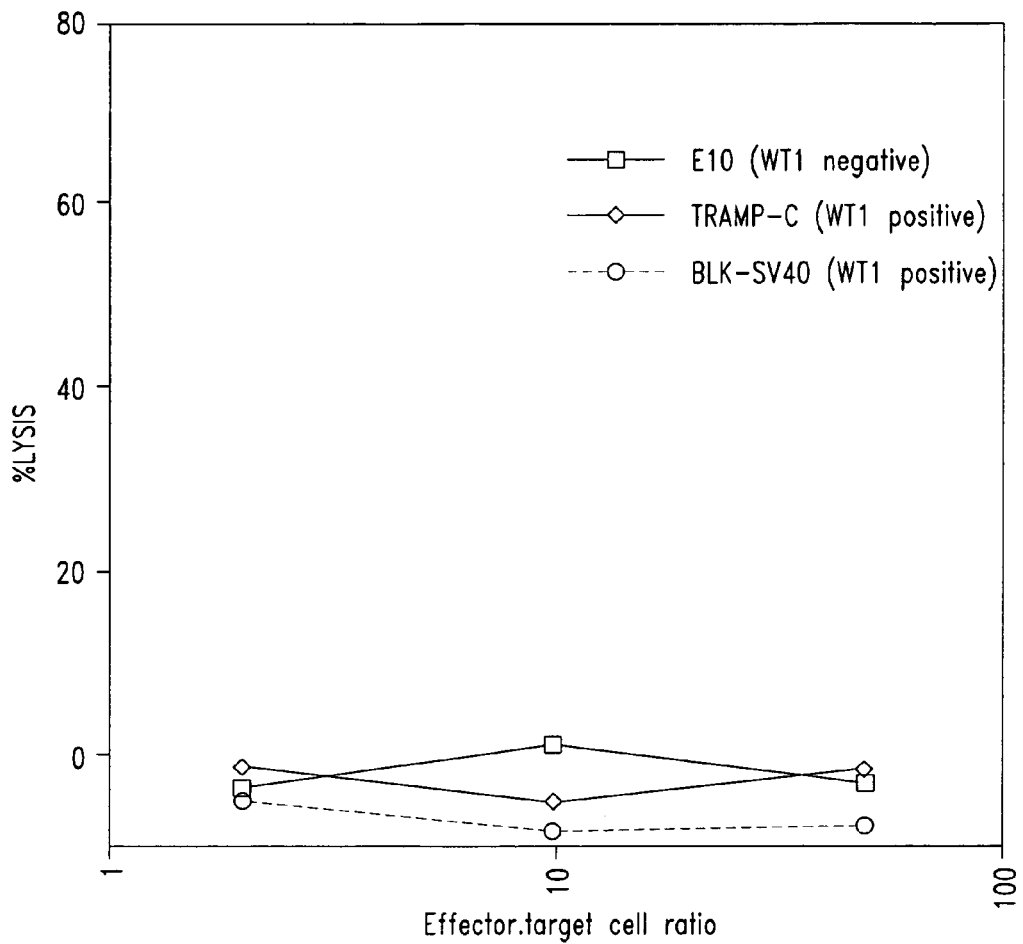
FIGS. 10A–10D are graphs illustrating the elicitation of WT1 specific CTL, which kill WT1 positive tumor cell lines but do not kill WT1 negative cell lines, following vaccination of B6 mice with WT1 peptide P117.
Figure 10B:
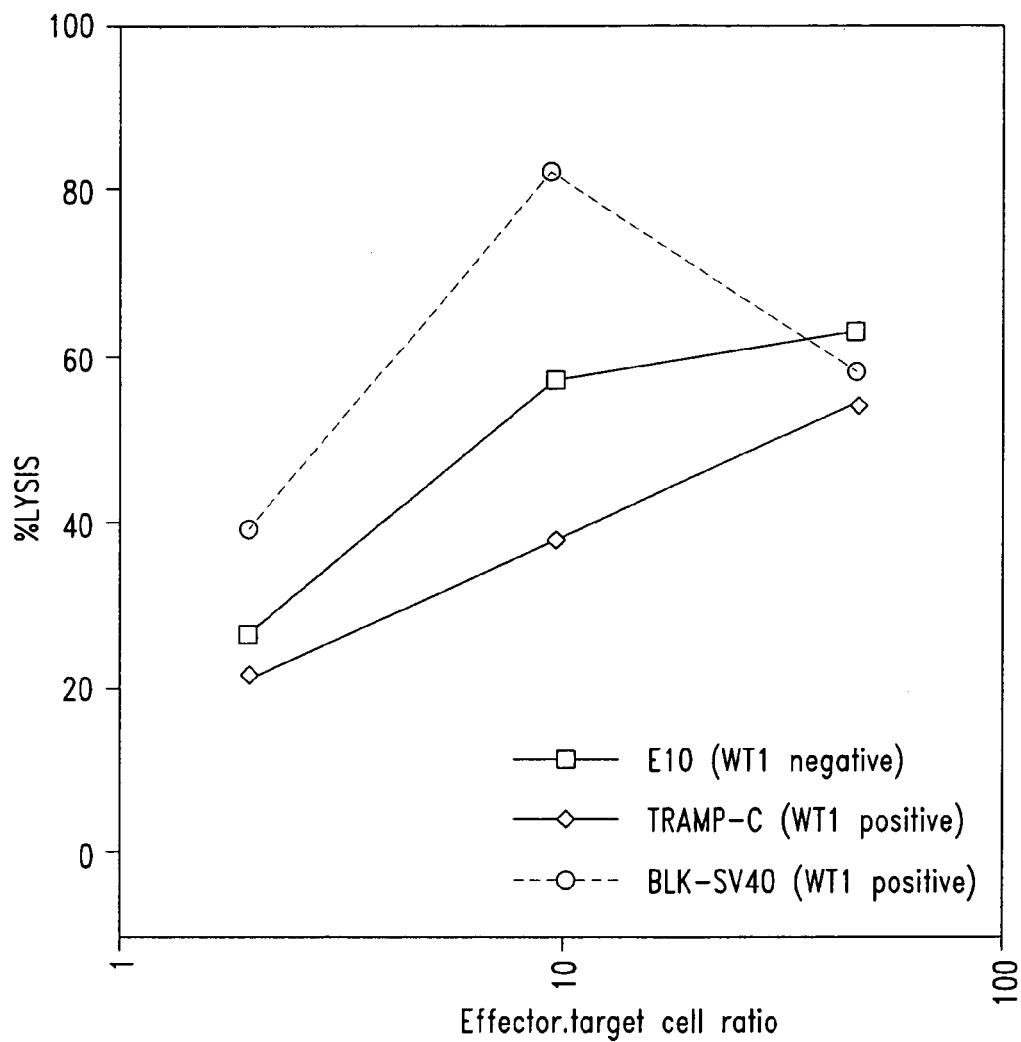
Figure 10C:
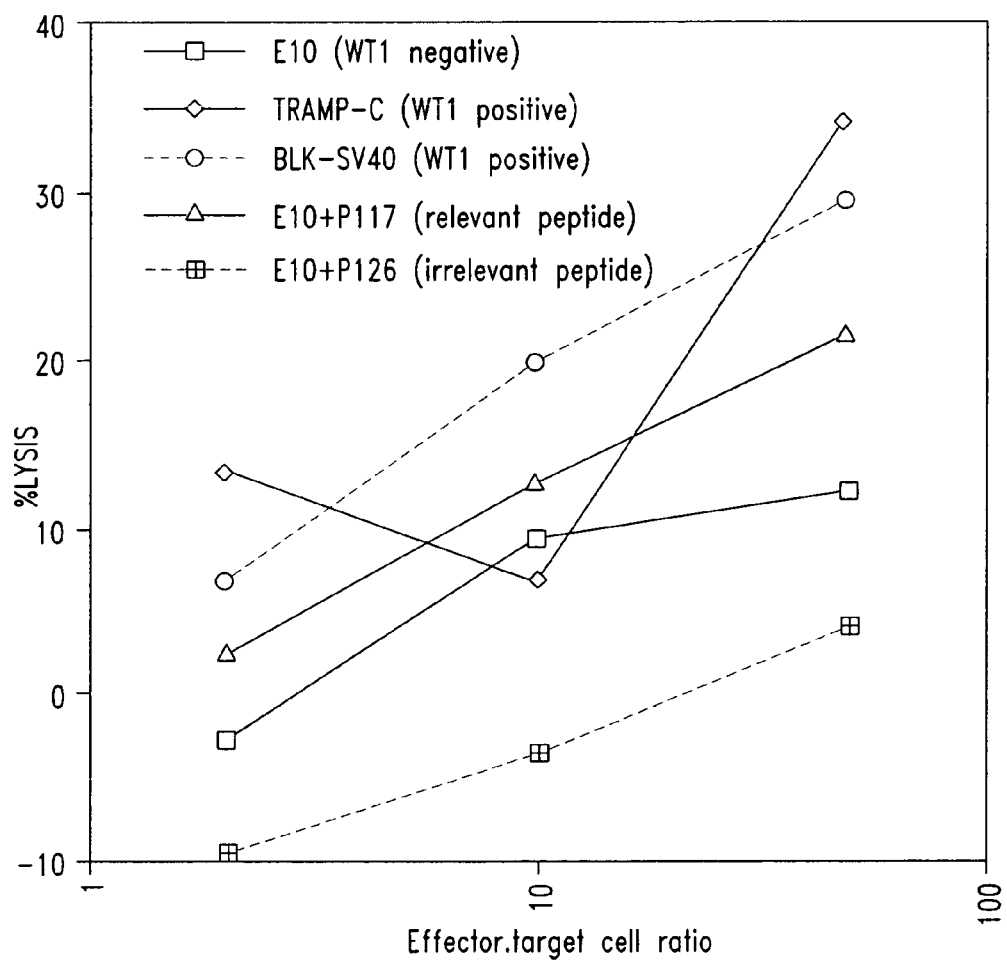
Figure 10D:
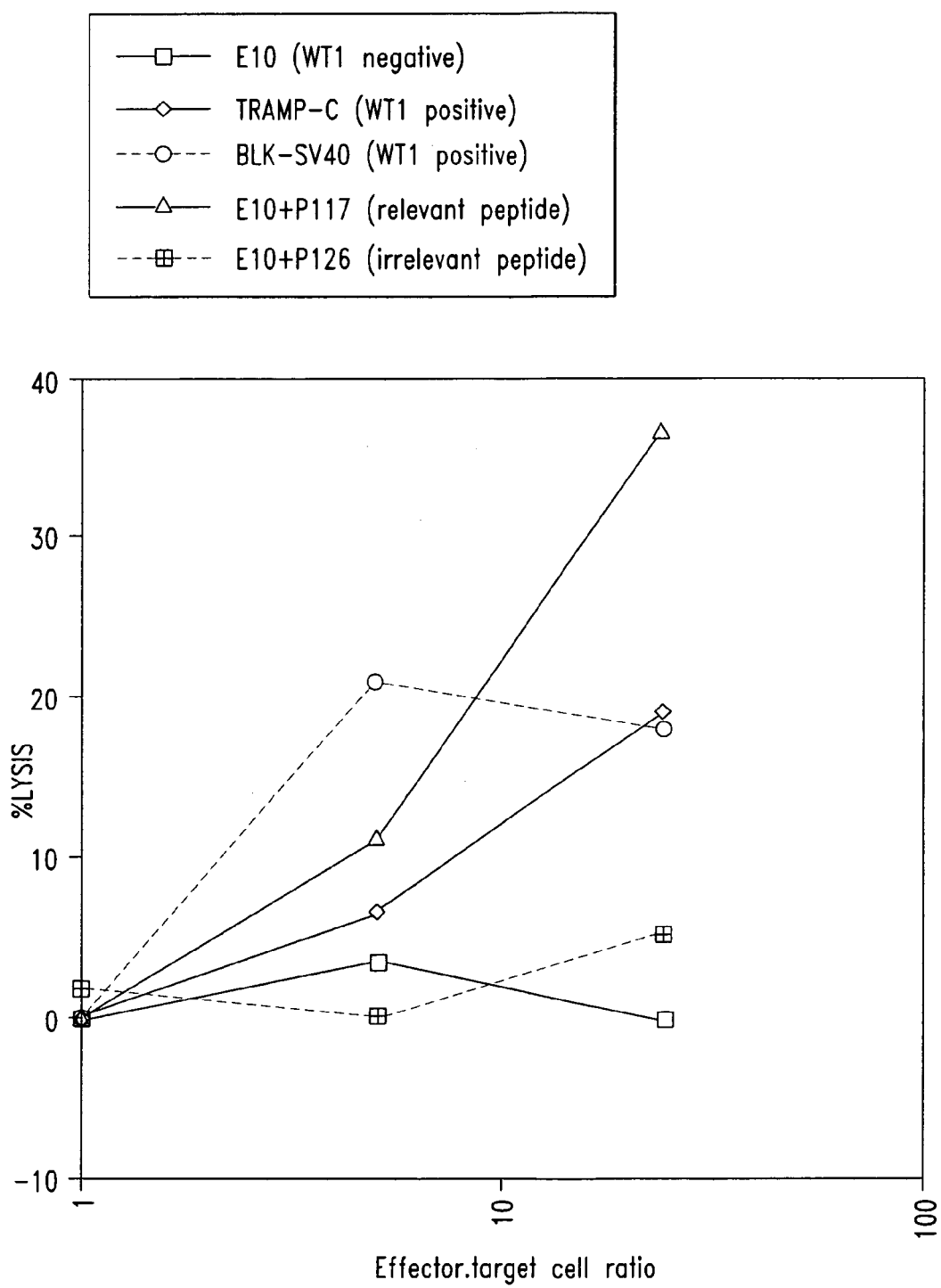

The results, presented in Table XLVII, show that some WT1 peptides can bind to class I MHC molecules, which is essential for generating CTL. Moreover, several of the peptides were able to elicit peptide specific CTL (FIGS. 9A and 9B), as determined using chromium release assays. Following immunization to CTL peptides p10–18 human, p136–144 human, p136–144 mouse and p235–243, peptide specific CTL lines were generated and clones were established. These results indicate that peptide specific CTL can kill malignant cells expressing WT1.

TABLE XLVII

Binding of WT1 CTL Peptides to mouse B6 class I antigens

| Peptide | Binding Affinity to Mouse MUC Class I |
|---|---|
| Positive control | 91% |
| negative control | 0.5.–1.3% |
| p235–243 | 33.6% |
| p136–144 mouse | 27.9% |
| p136–144 human | 52% |
| p10–18: human | 2.2% |
| p225–233 | 5.8% |
| p329–337 | 1.2% |
| p126–134 | 0.9% |
| p221–229 | 0.8% |
| p228–236 | 1.2% |
| p239–247 | 1% |

Example 5

Use of a WT1 Polypeptide to Elicit WT1 Specific CTL in Mice

This Example illustrates the ability of a representative WT1 polypeptide to elicit CTL immunity capable of killing WT1 positive tumor cell lines.

P117–139, a peptide with motifs appropriate for binding to class I and class II MHC, was identified as described above using TSITES and BIMAS HLA peptide binding prediction analyses. Mice were immunized as described in Example 3. Following immunization, spleen cells were stimulated in vitro and tested for the ability to lyse targets incubated with WT1 peptides, as well as WT1 positive and negative tumor cells. CTL were evaluated with a standard chromium release assay. The results, presented in FIGS. 10A–10D, show that P117 can elicit WT1 specific CTL capable of killing WT1 positive tumor cells, whereas no killing of WT1 negative cells was observed. These results demonstrate that peptide specific CTL in fact kill malignant cells expressing WT1 and that vaccine and T cell therapy are effective against malignancies that express WT1.

Similar immunizations were performed using the 9-mer class I MHC binding peptides p136–144, p225–233, p235–243 as well as the 23-mer peptide p117–139. Following immunization, spleen cells were stimulated in vitro with each of the 4 peptides and tested for ability to lyse targets incubated with WT1 peptides. CTL were generated specific for p136–144, p235–243 and p117–139, but not for p225–233. CTL data for p235–243 and p117–139 are presented in FIGS. 11A and 11B. Data for peptides p136–144 and p225–233 are not depicted.

CTL lysis demands that the target WT1 peptides are endogenously processed and presented in association with tumor cell class I MHC molecules. The above WT1 peptide specific CTL were tested for ability to lyse WT1 positive versus negative tumor cell lines. CTL specific for p235–243 lysed targets incubated with the p235–243 peptides, but failed to lyse cell lines that expressed WT1 proteins (FIG. 11A). By marked contrast, CTL specific for p117–139 lysed targets incubated with p117–139 peptides and also lysed malignant cells expressing WT1 (FIG. 11B). As a negative control, CTL specific for p117–139 did not lyse WT1 negative EL-4 (also referred to herein as E10).

Specificity of WT1 specific lysis was confirmed by cold target inhibition (FIGS. 12A–12B). Effector cells were plated for various effector: target ratios in 96-well U-bottom plates. A ten-fold excess (compared to hot target) of the indicated peptide-coated target without $^{51}$Cr labeling was added. Finally, $10^4$ $^{51}$Cr-labeled target cells per well were added and the plates incubated at 37° C. for 4 hours. The total volume per well was 200 µl.

Lysis of TRAMP-C by p117–139 specific CTL was blocked from 58% to 36% by EL-4 incubated with the relevant peptide p117–139, but not with EL-4 incubated with an irrelevant peptide (FIG. 12A). Similarly, lysis of BLK-SV40 was blocked from 18% to 0% by EL-4 incubated with the relevant peptide p117–139 (FIG. 12B). Results validate that WT1 peptide specific CTL specifically kill malignant cells by recognition of processed WT1.

Figure 13A:
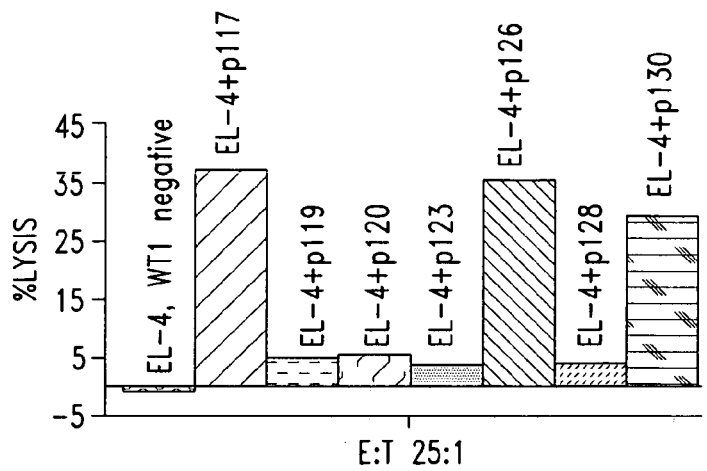
FIGS. 13A–13C are histograms depicting an evaluation of the 9mer CTL epitope within p117–139. The p117–139 tumor specific CTL line was tested against peptides within aa117–139 containing or lacking an appropriate H-2$^b$ class I binding motif and following restimulation with p126–134 or p130–138. The bars represent the mean % specific lysis in chromium release assays performed in triplicate with an E:T ratio of 25:1.

Several segments with putative CTL motifs are contained within p117–139. To determine the precise sequence of the CTL epitope all potential 9-mer peptides within p117–139 were synthesized (Table XLVIII). Two of these peptides (p126–134 and p130–138) were shown to bind to H-2b class I molecules (Table XLVIII). CTL generated by immunization with p117–139 lysed targets incubated with p126–134 and p130–138, but not the other 9-mer peptides within p117–139 (FIG. 13A).

Figure 13B:
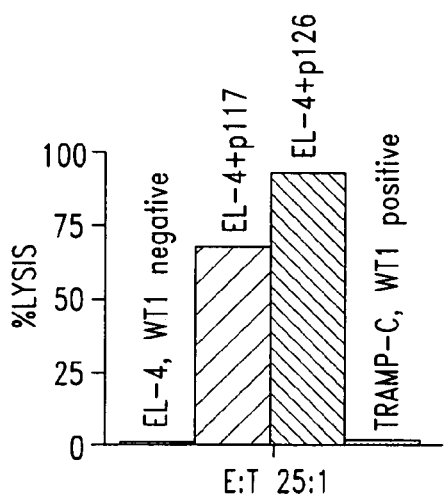
Figure 13C:
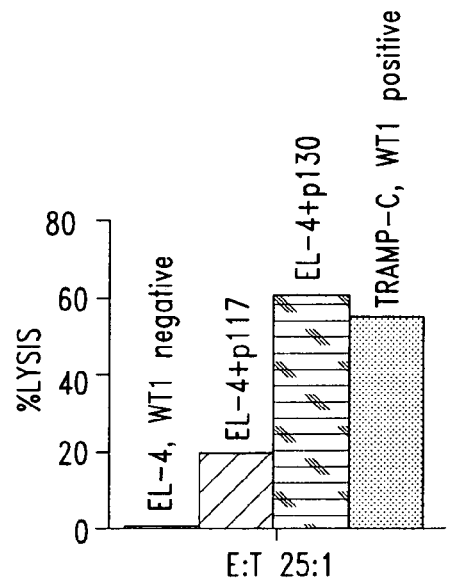
Figure 14:
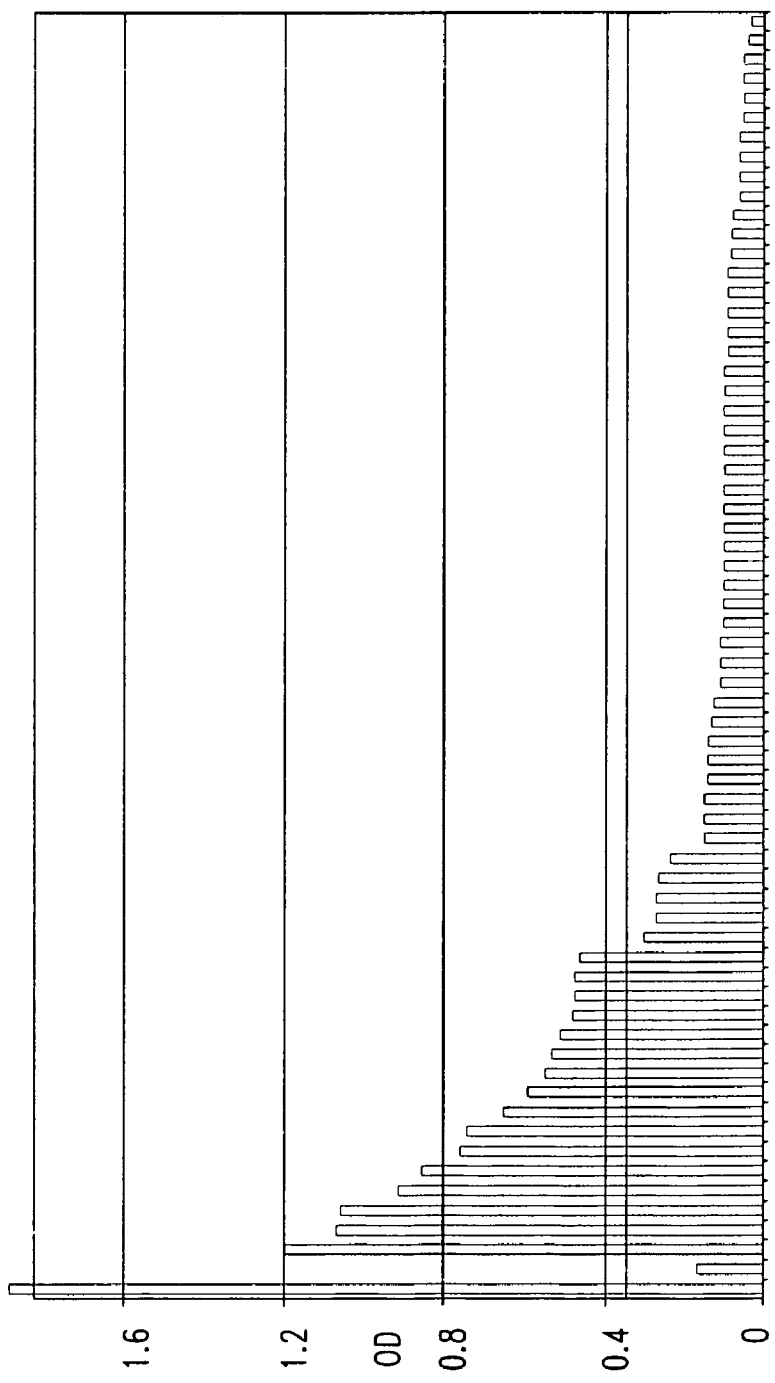
FIG. 14 depicts serum antibody reactivity to WT1 in 63 patients with AML. Reactivity of serum antibody to WT1/N-terminus protein was evaluated by ELISA in patients with AML. The first and second lanes represent the positive and negative controls, respectively. The first and second lanes represent the ositive and negative controls, respectively. Commercially obtained WT1 specific antibody WT180 was used for the positive control. The next 63 lanes represent results using sera from each individual patient. The OD values depicted were from ELISA using a 1:500 serum dilution. The figure includes cumulative data from 3 separate experiments.
Figure 15:
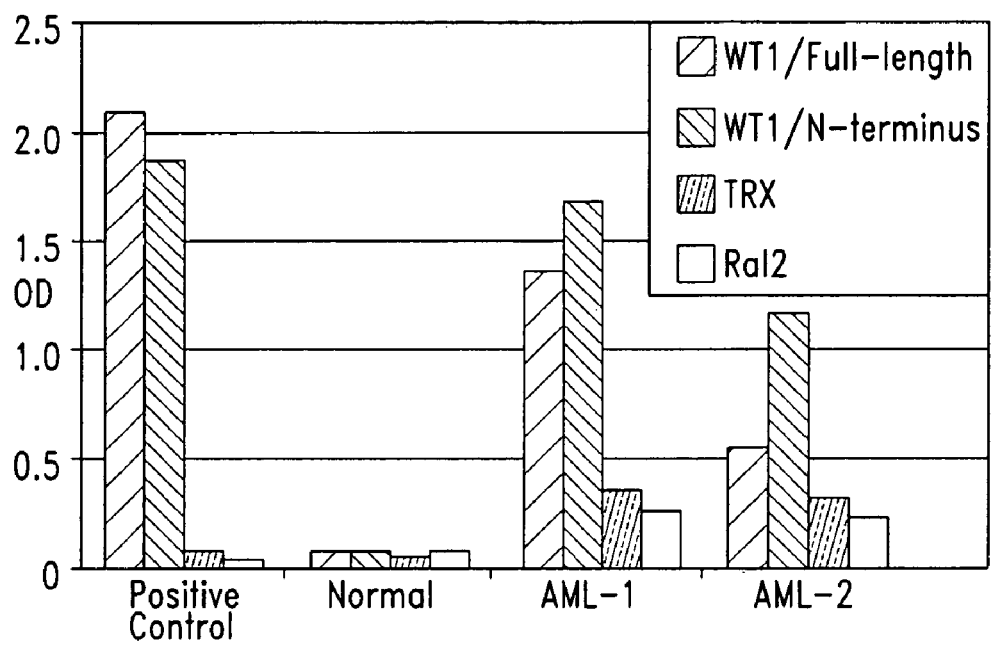
FIG. 15 depicts serum antibody reactivity to WT1 proteins and control proteins in 2 patients with AML. Reactivity of serum antibody to WT1/full-length, WT1N-terminus, TRX and Ra12 proteins was evaluated by ELISA in 2 patients with AML. The OD values depicted were from ELISA using a 1:500 serum dilution. AML-1 and AML-2 denote serum from 2 of the individual patients in FIG. 1 with demonstrated antibody reactivity to WT1/full-length. The WT1 full-length protein was expressed as a fusion protein with Ra12. The WT1/N-terminus protein was expressed as a fusion protein with TRX. The control Ra12 and TRX proteins were purified in a similar manner. The results confirm that the serum antibody reactivity against the WT1 fusion proteins is directed against the WT1 portions of the protein.

The p117–139 specific CTL line was restimulated with either p126–134 or p130–138. Following restimulation with p126–134 or p130–138, both T cell lines demonstrated peptide specific lysis, but only p130–138 specific CTL showed lysis of a WT1 positive tumor cell line (FIGS. 13B and 13C). Thus, p130–138 appears to be the naturally processed epitope.

TABLE XLVIII

Binding of WT1 CTL 9mer Peptides within p117–139 to mouse B6 class I antigens

| Peptide | Binding Affinity to Mouse MHC Class I |
|---|---|
| P117–125 PSQASSGQA (SEQ ID NO:221) | 2% |
| P118–126 SQASSGQAR (SEQ ID NO:216) | 2% |
| P119–127 QASSGQARM (SEQ ID Nos:161 and 288) | 2% |
| P120–128 ASSGQARMF (SEQ ID NO:40) | 1% |
| P121–129 SSGQARMFP (SEQ ID NO:222) | 1% |
| P122–130 SGQARMFPN (SEQ ID NO:212) | 1% |
| P123–131 GQARMFPNA (SEQ ID Nos:98 and 269) | 1% |
| P124–132 QARMFPNAP (SEQ ID NO:223) | 1% |

TABLE XLVIII-continued

Binding of WT1 CTL 9mer Peptides within p117–139 to mouse B6 class I antigens

| Peptide | Binding Affinity to Mouse MHC Class I |
|---|---|
| P125–133 APMFPNAPY (SEQ ID NO:38) | 1% |
| P126–134 RMFPNAPYL (SEQ ID Nos:185 and 293) | 79% |
| P127–135 MFPNAPYLP (SEQ ID NO:224) | 2% |
| P128–136 FPNAPYLPS (SEQ ID Nos:79 and 267) | 1% |
| P129–137 PNAPYLPSC (SEQ ID NO:225) | 1% |
| P130–138 NAPYLPSCL (SEQ ID Nos:144 and 282) | 79% |
| P131–139 APYLPSCLE (SEQ ID NO:226) | 1% |

Example 6

Identification of WT1 Specific mRNA in Mouse Tumor Cell Lines

This Example illustrates the use of RT-PCR to detect WT1 specific mRNA in cells and cell lines.

Mononuclear cells were isolated by density gradient centrifugation, and were immediately frozen and stored at −80° C. until analyzed by RT-PCR for the presence of WT1 specific mRNA. RT-PCR was generally performed as described by Fraizer et al., *Blood* 86:4704–4706, 1995. Total RNA was extracted from $10^7$ cells according to standard procedures. RNA pellets were resuspended in 25 µL diethylpyrocarbonate treated water and used directly for reverse transcription. The zinc-finger region (exons 7 to 10) was amplified by PCR as a 330 bp mouse cDNA. Amplification was performed in a thermocycler during one or, when necessary, two sequential rounds of PCR. AmpliTaq DNA Polymerase (Perkin Elmer Cetus, Norwalk, Conn.), 2.5 mM MgCl$_2$ and 20 pmol of each primer in a total reaction volume of 50 µl were used. Twenty µL aliquots of the PCR products were electrophoresed on 2% agarose gels stained with ethidium bromide. The gels were photographed with Polaroid film (Polaroid 667, Polaroid Ltd., Hertfordshire, England). Precautions against cross contamination were taken following the recommendations of Kwok and Higuchi, *Nature* 339:237–238, 1989. Negative controls included the cDNA- and PCR-reagent mixes with water instead of cDNA in each experiment. To avoid false negatives, the presence of intact RNA and adequate cDNA generation was evaluated for each sample by a control PCR using β-actin primers. Samples that did not amplify with these primers were excluded from analysis.

Primers for amplification of WT1 in mouse cell lines were: P115: 1458–1478: 5' CCC AGG CTG CAA TAA GAG ATA 3' (forward primer; SEQ ID NO:21); and P116: 1767–1787: 5' ATG TTG TGA TGG CGG ACC AAT 3' (reverse primer; SEQ ID NO:22) (see Inoue et al, *Blood* 88:2267–2278, 1996; Fraizer et al., *Blood* 86:4704–4706, 1995).

Beta Actin primers used in the control reactions were: 5' GTG GGG CGC CCC AGG CAC CA 3' (sense primer; SEQ ID NO:23); and 5' GTC CTT AAT GTC ACG CAC GAT TTC 3' (antisense primer; SEQ ID NO:24)

Primers for use in amplifying human WT1 include: P117: 954–974: 5' GGC ATC TGA GAC CAG TGA GAA 3' (SEQ ID NO:25); and P118: 1434–1414: 5' GAG AGT CAG ACT TGA AAG CAGT 3' (SEQ ID NO:5). For nested RT-PCR, primers may be: P119: 1023–1043: 5' GCT GTC CCA CTT ACA GAT GCA 3' (SEQ ID NO:26); and P120: 1345–1365: 5' TCA AAG CGC CAG CTG GAG TTT 3' (SEQ ID NO:27).

Table XLVIII shows the results of WT1 PCR analysis of mouse tumor cell lines. Within Table IV, (+++) indicates a strong WT1 PCR amplification product in the first step RT PCR, (++) indicates a WT1 amplification product that is detectable by first step WT1 RT PCR, (+) indicates a product that is detectable only in the second step of WT1 RT PCR, and (−) indicates WT1 PCR negative.

TABLE XLIX

Detection of WT1 mRNA in Mouse Tumor Cell Lines

| Cell Line | WT1 mRNA |
|---|---|
| K562 (human leukemia; ATCC): Positive control; (Lozzio and Lozzio, Blood 45:321–334, 1975) | +++ |
| TRAMPC (SV40 transformed prostate, B6); Foster et al., Cancer Res. 57:3325–3330, 1997 | +++ |
| BLK-SV40 HD2 (SV40-transf. fibroblast, B6; ATCC); Nature 276:510–511, 1978 | ++ |
| CTLL (T-cell, B6; ATCC); Gillis, Nature 268:154–156, 1977) | + |
| FM (FBL-3 subline, leukemia, B6); Glynn and Fefer, Cancer Res. 28:434–439, 1968 | + |
| BALB 3T3 (ATCC); Aaroston and Todaro, J. Cell. Physiol. 72:141–148, 1968 | + |
| S49.1 (Lymphoma, T-cell like, B/C; ATCC); Horibata and Harris, Exp. Cell. Res. 60:61, 1970 | + |
| BNL CL.2 (embryonic liver, B/C; ATCC); Nature 276:510–511, 1978 | + |
| MethA (sarcoma, B/C); Old et al., Ann. NY Acad. Sci. 101:80–106, 1962 | − |
| P3.6.2.8.1 (myeloma, B/C; ATCC); Proc. Nati. Acad. Sci. USA 66:344, 1970 | − |
| P2N (leukemia, DBA/2; ATCC); Melling et al., J. Immunol. 117:1267–1274, 1976 | − |
| BCL1 (lymphoma, B/C; ATCC); Slavin and Strober, Nature 272:624–626, 1977 | − |
| LSTRA (lymphoma, B/C); Glynn et al., Cancer Res. 28:434–439, 1968 | − |
| E10/EL-4 (lymphoma, B6); Glynn et al., Cancer Res. 28:434–439, 1968 | − |

Example 7

Expression in *E. coli* of WT-1 Trx Fusion Construct

The truncated open reading frame of WT-1 (WT-1B) was PCR amplified with the following primers:

```
Forward Primer starting at amino acid 2
P-37                              (SEQ ID NO.347)
5'ggctccgacgtgcgggacctg 3' Tm 64° C.

Reverse Primer creating EcoRI site after stop
co-
don
P-23                              (SEQ ID NO.348)
5'gaattctcaaagcgccagctggagtttggt 3' Tm 63° C.
```

The PCR was performed under the following conditions:

```
10 µl 10X Pfu buffer
1 µl 10 mM dNTPs
2 µl 10 µM each oligo
83 µL sterile water
1.5 µl Pfu DNA polymerase (Stratagene,
La Jolla, CA)
50 ng DNA (pPDM FL WT-1)
96° C. 2 minutes
96° C. 20 seconds       63° C.         72° C.
                        15 seconds     3 minutes ×
                                       40 cycles
72° C. 4 minutes
```

The PCR product was digested with EcoRI restriction enzyme, gel purified and then cloned into pTrx 2H vector (a modified pET28 vector with a Trx fusion on the N-terminal and two His tags surrounding the Trx fusion. After the Trx fusion there exists protease cleavage sites for thrombin and enterokinase). The pTrx2H construct was digested with StuI and EcoRI restriction enzymes. The correct constructs were confirmed by DNA sequence analysis and then transformed into BL21 (DE3) pLys S and BL21 (DE3) CodonPlus expression host cells.

Example 8

Expression in *E. coli* of WT-1 a His Tag Fusion Constructs

The N-terminal open reading frame of WT-1 (WT-1A) was PCR amplified with the following primers:

```
Forward Primer starting at amino acid 2
P-37                              (SEQ ID NO.349)
5'ggctccgacgtgcgggacctg 3' Tm 64° C.

Reverse Primer creating EcoRI site after an
arti-
ficial stop codon put after amino acid 249.
PDM-335                           (SEQ ID NO.345)
5'gaattctcaaagcgccagctggagtttggt 3' Tm 64° C.
```

The PCR was performed under the following conditions:

```
10 µl 10X Pfu buffer
1 µl 10 mM dNTPs
2 µl 10 µM each oligo
83 µL sterile water
1.5 µl Pfu DNA polymerase (Stratagene,
La Jolla, CA)
50 ng DNA (pPDM FL WT-1)
96° C. 2 minutes
96° C. 20 seconds       63° C.         72° C.
                        15 seconds     1 minute 20
                                       seconds ×
                                       40 cycles
72° C. 4 minutes
```

The PCR product was digested with EcoRI restriction enzyme, gel purified and then cloned into pPDM, a modified pET28 vector with a His tag in frame, which had been digested with Eco72I and EcoRI restriction enzymes. The PCR product was also transformed into pTrx 2H vector. The pTrx2H construct was digested with StuI and EcoRI restriction enzymes. The correct constructs were confirmed by DNA sequence analysis and then transformed into BL21 (DE3) pLys S and BL21 (DE3) CodonPlus expression host cells.

Example 9

Expression in *E. coli* of WT-1 B His Tag Fusion Constructs

The truncated open reading frame of WT-1 (WT-1A) was PCR amplified with the following primers:

```
Forward Primer starting at amino acid 250
PDM-346                              (SEQ ID NO.350)
5'cacagcacagggtacgagagc 3' Tm 58° C.

Reverse Primer creating EcoRI site after stop
co-
don
P-23                                 (SEQ ID NO.347)
5'gaattctcaaagcgccagctggagtttggt 3' Tm 63° C.
```

The PCR was performed under the following conditions:

```
10 µl 10X Pfu buffer
1 µl 10 mM dNTPs
2 µl 10 µM each oligo
83 µL sterile water
1.5 µl Pfu DNA polymerase (Stratagene, La Jolla, CA)
50 ng DNA (pPDM FL WT-1)
96° C. 2 minutes
```

-continued

| 96° C. 20 seconds | 63° C. 15 seconds | 72° C. 1 minute 30 seconds × 40 cycles |
|---|---|---|
| 72° C. 4 minutes | | |

The PCR product was digested with EcoRI restriction enzyme, gel purified and then cloned into pPDM, a modified pET28 vector with a His tag in frame, which had been digested with Eco72I and EcoRI restriction enzymes. The PCR product was also transformed into pTrx 2H vector. The pTrx 2H construct was digested with StuI and EcoRI restriction enzymes. The correct constructs were confirmed by DNA sequence analysis and then transformed into BL21 (DE3) pLys S and BL21 (DE3) CodonPlus expression host cells.

For Examples 7–9, the following SEQ ID NOs. are disclosed:

SEQ ID NO. 327 is the determined cDNA sequence for Trx_WT-1_B

SEQ ID NO. 328 is the determined cDNA sequence for Trx_WT-1_A

SEQ ID NO. 329 is the determined cDNA sequence for Trx_WT-1

SEQ ID NO. 330 is the determined cDNA sequence for WT-1_A

SEQ ID NO. 331 is the determined cDNA sequence for WT-1_B

SEQ ID NO. 332 is the predicted amino acid sequence encoded by SEQ ID No. 327

SEQ ID NO. 333 is the predicted amino acid sequence encoded by SEQ ID No. 328

SEQ ID NO. 334 is the predicted amino acid sequence encoded by SEQ ID No. 329

SEQ ID NO. 335 is the predicted amino acid sequence encoded by SEQ ID No. 330

SEQ ID NO. 336 is the predicted amino acid sequence encoded by SEQ ID No. 331

Example 10

Truncated Forms of WT-1 Expressed in *E. coli*

Three reading frames of WT-1 were amplified by PCR using the following primers:

For WT-1 Tr2:

```
For WT-1 Tr2:
PDM-441 (SEQ ID NO. 353) 5' cacgaagaacagtgcctgagcgcattcac 3'
Tm 63° C.

PDM-442 (SEQ ID NO. 354) 5' ccggcgaattcatcagtataaattgtcactgc 3'
TM 62° C.

For WT-1 Tr3:
PDM-443 (SEQ ID NO. 355) 5' caggctttgctgctgaggacgccc 3'
Tm 64° C.

PDM-444 (SEQ ID NO. 356) 5' cacggagaattcatcactggtatggtttctcacc
Tm 64° C.

For WT-1 Tr4:
PDM-445 (SEQ ID NO. 357) 5' cacagcaggaagcacactggtgagaaac 3'
Tm 63° C.

PDM-446 (SEQ ID NO. 358) 5' ggatatctgcagaattctcaaagcgccagc 3'
TM 63° C.
```

The PCR was performed under the following conditions:

```
10 µl 10X Pfu buffer
1 µl 10 mM dNTPs
2 µl 10 µM each oligo
83 µL sterile water
1.5 µl Pfu DNA polymerase (Stratagene, La Jolla, CA)
50 ng DNA (pPDM FL WT-1)
96° C. 2 minutes
```

| 96° C. 20 seconds | 63° C. 15 seconds | 72° C. 20 seconds × 40 cycles |
|---|---|---|
| 72° C. 4 minutes | | |

The PCR products were digested with EcoRI and cloned into pPDM His (a modified pET28 vector with a His tag in frame on the 5' end) which has been digested with Eco72I and EcoRI. The constructs were confirmed to be correct through sequence analysis and transformed into BL21 pLys S and BL21 CodonPlus cells or BLR pLys S and BLR CodonPlus cells.

Example 11

**WT-1 C (Amino Acids 76–437) and WT-1 D (Amino Acids 91–437) Expression in *E. coli***

The WT-1 C reading frame was amplified by PCR using the following primers:

```
PDM-504 (SEQ ID NO. 359) 5' cactccttcatcaaacaggaac 3'        Tm 61° C.

PDM-446 (SEQ ID NO. 360) 5' ggatatctgcagaattctcaaagcgccagc 3' Tm 63° C.
```

The PCR was performed under the following conditions:

10 µl 10X Pfu buffer
1 µl 10 mM dNTPs
2 µl 10 µM each oligo
83 µL sterile water
1.5 µl Pfu DNA polymerase (Stratagene, La Jolla, CA)
50 ng DNA (pPDM FL WT-1)
96° C. 2 minutes
96° C. 20 seconds   63° C. 15 seconds   72° C. 2 minutes × 40 cycles
72° C. 4 minutes The PCR product was digested with EcoRI and cloned into pPDM His which had been digested with Eco72I and EcoRI. The sequence was confirmed through sequence analysis and then transformed into BLR pLys S and BLR which is co-transformed with CodonPlus RP.

Example 12

Synthetic Production of WT-1 TR-1 by Annealing Overlapping Oligos

This example was performed to determine the effect of changing proline codon usage on expression.

The following pairs of oligos were annealed:

```
1. PDM-505 (SEQ ID NO. 361) 5' ggttccgacgtgcgggacctgaacgcactgctg 3'

PDM-506 (SEQ ID NO. 362) 5' ctgccggcagcagtgcgttcaggtcccgcacgtcggaacc 3'

2. PDM-507 (SEQ ID NO. 363) 5' ccggcagttccatccctgggtggcggtggaggctg 3'

PDM-508 (SEQ ID NO. 364) 5' cggcagtgcgcagcctccaccgccacccagggatggaa 3'

3. PDM-509 (SEQ ID NO. 365) 5' cgcactgccggttagcggtgcagcacagtgggctc 3'

PDM-510 (SEQ ID NO. 366) 5' cagaactggagcccactgtgctgcaccgctaac 3'

4. PDM-511 (SEQ ID NO. 367) 5' cagttctggacttcgcaccgcctggtgcatccgcatac 3'

PDM-512 (SEQ ID NO. 368) 5' cagggaaccgtatgcggatgcaccaggcggtgcgaagtc 3'

5. PDM-513 (SEQ ID NO. 369) 5' ggttccctgggtggtccagcacctccgcccgcaacgcc 3'

PDM-514 (SEQ ID NO. 370) 5' ggcggtgggggcgttgcgggcggaggtgctggaccacc 3'

6. PDM-515 (SEQ ID NO. 371) 5' cccaccgcctccaccgccccgcactccttcatcaaacag 3'

PDM-516 (SEQ ID NO. 372) 5' ctaggttcctgtttgatgaaggagtgcgggggcggtgga 3'

7. PDM-517 (SEQ ID NO. 373) 5' gaacctagctgggtggtgcagaaccgcacgaagaaca 3'

PDM-518 (SEQ ID NO. 374) 5' ctcaggcactgttcttcgtgcggttctgcaccacccag 3'

8. PDM-519 (SEQ ID NO. 375) 5' gtgcctgagcgcattctgagaattctgcagat 3'

PDM-520 (SEQ ID NO. 376) 5' gtgtgatggatatctgcagaattctcagaatgcg 3'
```

Each oligo pair was separately combined then annealed. The pairs were then ligated together and one μl of ligation mix was used for PCR conditions below:

```
10 μl 10X Pfu buffer
1 μl 10 mM dNTPs
2 μl 10 μM each oligo
83 μL sterile water
1.5 μl Pfu DNA polymerase (Stratagene,
La Jolla, CA)
96° C. 2 minutes
96° C. 20 seconds       63° C.       72° C.
                        15 seconds   30 seconds ×
                                     40 cycles
72° C. 4 minutes
```

The PCR product was digested with EcoRI and cloned into pPDM His which had been digested with Eco72I and EcoRI. The sequence was confirmed and then transformed into BLR pLys S and BLR which is co-transformed with CodonPlus RP.

For examples 10–12, the following SEQ ID NOs. are disclosed:

SEQ ID NO:337 is the determined cDNA sequence for WT-1_Tr1SEQ ID NO:338 is the determined cDNA sequence for WT-1_Tr2

SEQ ID NO:339 is the determined cDNA sequence for WT-1_Tr3

SEQ ID NO:340 is the determined cDNA sequence for WT-1_Tr4

SEQ ID NO:341 is the determined cDNA sequence for WT-1_C

SEQ ID NO:342 is the predicted amino acid sequence encoded by SEQ ID NO:337

SEQ ID NO:343 is the predicted amino acid sequence encoded by SEQ ID NO:338

SEQ ID NO:344 is the predicted amino acid sequence encoded by SEQ ID NO:339

SEQ ID NO:345 is the predicted amino acid sequence encoded by SEQ ID NO:340

SEQ ID NO:346 is the predicted amino acid sequence encoded by SEQ ID NO:341

The WT-1 C sequence represents a polynucleotide having the coding regions of TR2, TR3 and TR4.

SEQ ID NO. 328 is the determined cDNA sequence for Trx_WT-1_A

The WT-1 TR-1 synthetic sequence represents a polynucleotide in which alternative codons for proline were substituted for the native codons, producing a polynucleotide capable of expressing WT-1 TR-1 in *E. coli*.

Example 13

Evaluation of the Systemic Histopathological and Toxicological Effects of WT1 Immunization in Mice The purpose of this example is to analyze the immunogenicity and potential systemic histopathological and toxicological effects of WT1 protein immunization in a multiple dose titration in mice.

The experimental design for immunization of mice with WT1 protein is outlined in Table L.

TABLE L

Experimental Design of WT1 Immunization in Mice

| Histology Group | Corixa Group | Treatment Description | Dose Level | Total No. (Females) |
|---|---|---|---|---|
| 1 | 0 | No treatment | 0 | 4 |
| 2 | 1.1 | MPL-SE (adjuvants alone), 6×, 1 week apart | 10 ug | 4 |
| 3 | 1.2 | MPL-SE, 3×, 2 weeks apart | 10 ug | 4 |
| 4 | 2.1 | Ral2-WT1 + MPL-SE, 6× | 25 ug | 4 |
| 5 | 2.2 | Ral2-WT1 + MPL-SE, 3× | 25 ug | 4 |
| 6 | 3.1 | Ral2-WT1 + MPL-SE, 6× | 100 ug | 4 |
| 7 | 3.2 | Ral2-WT1 + MPL-SE, 3× | 100 ug | 4 |
| 8 | 4.1 | Ral2-WT1 + MPL-SE, 6× | 1000 ug | 4 |
| 9 | 4.2 | Ral2-WT1 + MPL-SE, 3× | 1000 ug | 4 |

Figure 20A:
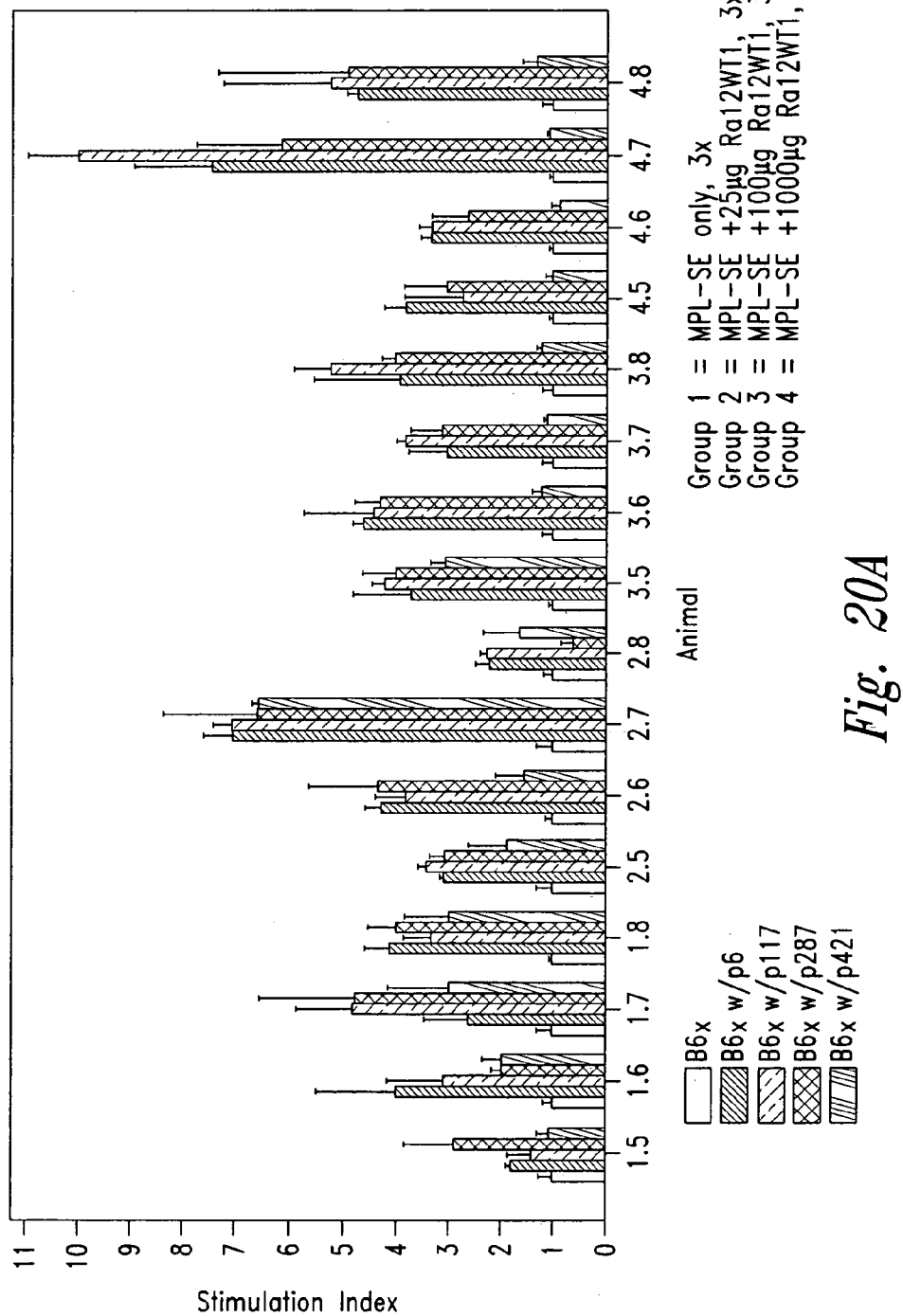
FIGS. 20A and B is a bar graph of the proliferative T-cell responses in mice immunized with WT1 protein.

Vaccination to WT1 protein using MPL-SE as adjuvant, in a multiple dose titration study (doses ranging from 25 μg, 100 μg to 1000 μg WT1 protein) in female C57/B6 mice elicited a strong WT1-specific antibody response (FIG. 19) and cellular T-cell responses (FIG. 20).

No systemic histopathological or toxicological effects of immunization with WT1 protein was observed. No histological evidence for toxicity was seen in the following tissues: adrenal gland, brain, cecum, colon, duodenum, eye, femur and marrow, gall bladder, heart, ileum, jejunum, kidney, larynx, lacrimal gland, liver, lung, lymph node, muscle, esophagus, ovary, pancreas, parathyroid, salivary gland, sternum and marrow, spleen, stomach, thymus, trachea, thyroid, urinary bladder and uterus.

Special emphasis was put on evaluation of potential hematopoietic toxicity. The myeloid/erythroid ratio in sternum and femur marrow was normal. All evaluable blood cell counts and blood chemistry (BUN, creatinine, bilirubin, albumin, globulin) were within the normal range (Table LI).

Given that existent immunity to WT1 is present in some patients with leukemia and that vaccination to WT1 protein can elicit WT1 specific Ab and cellular T-cell responses in mice without toxicity to normal tissues, these experiments validate WT1 as a tumor/leukemia vaccine.

TABLE LI

WT1 Dose Titration Study Clinical Chemistry and Hematology Analysis

| Animal # Normal | K/uL WBC 5.4–16.0 | M/uL RBC 6.7–12.5 | g/dl Hg. 10.2–16.6 | % HCT 32–54 | fL MCV 31–62 | pg MCH 9.2–20.8 | % MCHC 22.0–35.5 |
|---|---|---|---|---|---|---|---|
| Group 1 | | | | | | | |
| 1 (0) | 5.6 | 8.41 | 12.8 | 43.5 | 53 | 15.2 | 29.4 |
| 2 (0) | 5.5 | 9.12 | 13.4 | 47.5 | 53 | 14.7 | 28.2 |
| 3 (0) | 7.5 | 9.22 | 13.5 | 48 | 54 | 14.7 | 28.1 |
| 4 (0) | 3.9 | 9.27 | 13.6 | 46 | 52 | 14.7 | 29.6 |
| Mean | 5.6 | 9.0 | 13.3 | 46.3 | 53.0 | 14.8 | 28.8 |
| STD | 1.5 | 0.4 | 0.4 | 2.0 | 0.8 | 0.3 | 0.8 |
| Group 2 | | | | | | | |
| 5 (1.5) | 6.6 | 9 | 13.1 | 46 | 54 | 14.5 | 28.5 |
| 6 (1.6) | 5.2 | 8.58 | 12.6 | 44 | 53 | 14.7 | 28.6 |
| 7 (1.7) | 7.8 | 9.21 | 13.6 | 46 | 53 | 14.7 | 29.6 |
| 8 (1.8) | 6.3 | NA | NA | 41 | NA | NA | NA |
| Mean | 6.5 | 8.9 | 13.1 | 44.3 | 53.3 | 14.6 | 28.9 |
| STD | 1.1 | 0.3 | 0.5 | 2.4 | 0.6 | 0.1 | 0.6 |
| Group 3 | | | | | | | |
| 9 (2.5) | 8.3 | 9.16 | 13.6 | 50.3 | 55 | 14.9 | 27.1 |
| 10 (2.6) | 5 | 8.78 | 13 | 44.2 | 50 | 14.8 | 29.3 |
| 11 (2.7) | 4 | 8.94 | 13.2 | 48.3 | 54 | 14.7 | 27.3 |
| 12 (2.8) | 8.2 | NA | NA | 41 | NA | NA | NA |
| Mean | 6.4 | 9.0 | 13.3 | 46.0 | 53.0 | 14.8 | 27.9 |
| STD | 2.2 | 0.2 | 0.3 | 4.2 | 2.6 | 0.1 | 1.2 |
| Group 4 | | | | | | | |
| 13 (3.5) | 6.1 | 8.82 | 13.1 | 46 | 54 | 14.9 | 28.5 |
| 14 (3.6) | 6.1 | 8.64 | 12.9 | 46 | 54 | 15 | 28 |
| 15 (3.7) | 9.3 | 8.93 | 13.2 | 48 | 55 | 14.8 | 27.5 |
| 16 (3.8) | 4.8 | 8.19 | 12.6 | 44 | 55 | 15.3 | 28.6 |
| Mean | 6.6 | 8.6 | 13.0 | 46.0 | 54.5 | 15.0 | 28.2 |
| STD | 1.9 | 0.3 | 0.3 | 1.6 | 0.6 | 0.2 | 0.5 |
| Group 5 | | | | | | | |
| 17 (4.5) | 3.1 | 8.48 | 12.6 | 46 | 54 | 14.9 | 27.5 |
| 18 (4.6) | 5.7 | 9.12 | 13.7 | 48 | 54 | 15 | 28.5 |
| 19 (4.7) | 5.3 | 8.58 | 13 | 44.5 | 55 | 15.2 | 29.2 |
| 20 (4.8) | 5.3 | NA | NA | 40 | NA | NA | NA |
| Mean | 4.9 | 8.7 | 13.1 | 44.6 | 54.3 | 15.0 | 28.4 |
| STD | 1.2 | 0.3 | 0.6 | 3.4 | 0.6 | 0.2 | 0.9 |
| Group 6 | | | | | | | |
| 21 (1.1) | 3.5 | 9.36 | 13.5 | 37.6 | 40 | 14.4 | 35.9 |
| 22 (1.2) | 6.9 | 8.93 | 13.6 | 37.3 | 42 | 15.3 | 36.6 |
| 23 (1.3) | 3.6 | 8.3 | 12.5 | 35.3 | 43 | 15.1 | 35.5 |
| 24 (1.4) | NA | NA | NA | NA | NA | NA | NA |
| Mean | 4.7 | 8.9 | 13.2 | 36.7 | 41.7 | 14.9 | 36.0 |
| STD | 1.9 | 0.5 | 0.6 | 1.3 | 1.5 | 0.5 | 0.6 |
| Group 7 | | | | | | | |
| 25 (2.1) | 4 | NA | NA | 40 | NA | NA | NA |
| 26 (2.2) | 7.4 | 9.12 | 13.2 | 38.5 | 42 | 14.5 | 34.3 |
| 27 (2.3) | 4.5 | 8.19 | 12.1 | 34.5 | 42 | 14.8 | 35.1 |
| 28 (2.4) | 5.8 | 8.25 | 12.3 | 34.1 | 41 | 14.9 | 36.1 |
| Mean | 5.4 | 8.5 | 12.5 | 36.8 | 41.7 | 14.7 | 35.2 |
| STD | 1.5 | 0.5 | 0.6 | 2.9 | 0.6 | 0.2 | 0.9 |
| Group 8 | | | | | | | |
| 29 (3.1) | 5.1 | 8.53 | 12.6 | 34.9 | 41 | 14.7 | 36 |
| 30 (3.2) | 7.6 | 8.42 | 13 | 36.1 | 43 | 15.4 | 35.9 |
| 31 (3.3) | 3.4 | 8.45 | 12.6 | 34.9 | 41 | 14.9 | 36.1 |
| 32 (3.4) | 6.1 | 8.11 | 12.3 | 34.8 | 43 | 15.2 | 35.5 |
| Mean | 5.6 | 8.4 | 12.6 | 35.2 | 42.0 | 15.1 | 35.9 |
| STD | 1.8 | 0.2 | 0.3 | 0.6 | 1.2 | 0.3 | 0.3 |
| Group 9 | | | | | | | |
| 33 (4.1) | NA | NA | NA | NA | NA | NA | NA |
| 34 (4.2) | 4.5 | 8.63 | 12.8 | 36.2 | 42 | 14.8 | 35.2 |
| 35 (4.3) | 3.9 | 8.85 | 13 | 36.6 | 41 | 14.7 | 35.6 |
| 36 (4.4) | 4.7 | 8.14 | 12.3 | 33.8 | 42 | 15.1 | 36.3 |
| Mean | 4.4 | 8.5 | 12.7 | 35.5 | 41.7 | 14.9 | 35.7 |
| STD | 0.4 | 0.4 | 0.4 | 1.5 | 0.6 | 0.2 | 0.6 |

TABLE LI-continued

WT1 Dose Titration Study Clinical Chemistry and Hematology Analysis

| Animal # Normal | yes/no Plt. clump no | K/uL Platelets 150–1500 | Abs. Baso 0.0–0.15 | Abs. Eos 0.0–0.51 | Abs. Bands 0.0–0.32 | Abs. Polys 8.0–42.9 | Abs. Lymph 8.0–18.0 | Abs. Mono 0.0–1.5 |
|---|---|---|---|---|---|---|---|---|
| Group 1 | | | K/uL | K/uL | K/uL | K/uL | K/uL | K/uL |
| 1 (0) | yes | 726 | 0 | 56 | 0 | 336 | 5208 | 0 |
| 2 (0) | no | 860 | 0 | 0 | 0 | 55 | 5445 | 0 |
| 3 (0) | no | 875 | 0 | 375 | 0 | 525 | 6525 | 75 |
| 4 (0) | yes | 902 | 0 | 0 | 0 | 156 | 3744 | 0 |
| Mean | | 840.8 | 0.0 | 107.8 | 0.0 | 268.0 | 5230.5 | 18.8 |
| STD | | 78.4 | 0.0 | 180.1 | 0.0 | 207.0 | 1144.8 | 37.5 |
| Group 2 | | | | | | | | |
| 5 (1.5) | no | 1193 | 0 | 132 | 0 | 792 | 5214 | 462 |
| 6 (1.6) | no | 1166 | 0 | 52 | 0 | 624 | 4472 | 52 |
| 7 (1.7) | no | 1087 | 0 | 234 | 0 | 1170 | 6396 | 0 |
| 8 (1.8) | yes | NA | 0 | 126 | 0 | 126 | 5922 | 126 |
| Mean | | 1148.7 | 0.0 | 136.0 | 0.0 | 678.0 | 5501.0 | 160.0 |
| STD | | 55.1 | 0.0 | 74.8 | 0.0 | 433.1 | 840.5 | 207.9 |
| Group 3 | | | | | | | | |
| 9 (2.5) | no | 705 | 0 | 166 | 0 | 664 | 7387 | 83 |
| 10 (2.6) | no | 1140 | 0 | 150 | 0 | 500 | 4350 | 0 |
| 11 (2.7) | no | 952 | 0 | 120 | 0 | 680 | 3200 | 0 |
| 12 (2.8) | yes | NA | 0 | 164 | 0 | 656 | 7216 | 164 |
| Mean | | 932.3 | 0.0 | 150.0 | 0.0 | 625.0 | 5538.3 | 61.8 |
| STD | | 218.2 | 0.0 | 21.2 | 0.0 | 83.9 | 2090.6 | 78.6 |
| Group 4 | | | | | | | | |
| 13 (3.5) | no | 785 | 0 | 488 | 0 | 732 | 4636 | 244 |
| 14 (3.6) | yes | 973 | 0 | 0 | 0 | 488 | 5307 | 305 |
| 15 (3.7) | yes | 939 | 0 | 465 | 0 | 558 | 7812 | 465 |
| 16 (3.8) | yes | 1622 | 0 | 192 | 0 | 480 | 4080 | 48 |
| Mean | | 1079.8 | 0.0 | 286.3 | 0.0 | 564.5 | 5458.8 | 265.5 |
| STD | | 370.6 | 0.0 | 233.4 | 0.0 | 117.0 | 1647.1 | 172.4 |
| Group 5 | | | | | | | | |
| 17 (4.5) | no | 892 | 0 | 31 | 0 | 620 | 2449 | 0 |
| 18 (4.6) | yes | 966 | 57 | 114 | 0 | 855 | 4674 | 0 |
| 19 (4.7) | yes | 883 | 0 | 53 | 0 | 742 | 4452 | 53 |
| 20 (4.8) | yes | NA | 0 | 106 | 0 | 53 | 5141 | 0 |
| Mean | | 913.7 | 14.3 | 76.0 | 0.0 | 567.5 | 4179.0 | 13.3 |
| STD | | 45.5 | 28.5 | 40.4 | 0.0 | 356.2 | 1188.5 | 26.5 |
| Group 6 | | | | | | | | |
| 21 (1.1) | yes | 784 | 0 | 35 | 0 | 385 | 2870 | 210 |
| 22 (1.2) | yes | 806 | 0 | 69 | 0 | 207 | 6486 | 138 |
| 23 (1.3) | yes | 790 | 0 | 180 | 0 | 396 | 2988 | 36 |
| 24 (1.4) | NA | NA | NA | NA | NA | NA | NA | NA |
| Mean | | 793.3 | 0.0 | 94.7 | 0.0 | 329.3 | 4114.7 | 128.0 |
| STD | | 11.4 | 0.0 | 75.8 | 0.0 | 106.1 | 2054.5 | 87.4 |
| Group 7 | | | | | | | | |
| 25 (2.1) | yes | NA | 0 | 80 | 0 | 200 | 3720 | 0 |
| 26 (2.2) | yes | 753 | 0 | 0 | 0 | 518 | 6734 | 148 |
| 27 (2.3) | yes | 725 | 0 | 90 | 0 | 225 | 4140 | 45 |
| 28 (2.4) | yes | 792 | 0 | 232 | 0 | 754 | 4814 | 0 |
| Mean | | 756.7 | 0.0 | 100.5 | 0.0 | 424.3 | 4852.0 | 48.3 |
| STD | | 33.7 | 0.0 | 96.5 | 0.0 | 263.0 | 1333.1 | 69.8 |
| Group 8 | | | | | | | | |
| 29 (3.1) | yes | 784 | 0 | 153 | 0 | 561 | 4233 | 153 |
| 30 (3.2) | yes | 512 | 0 | 152 | 0 | 304 | 6992 | 152 |
| 31 (3.3) | yes | 701 | 0 | 0 | 0 | 238 | 3094 | 68 |
| 32 (3.4) | yes | 631 | 0 | 305 | 0 | 305 | 5368 | 122 |
| Mean | | 657.0 | 0.0 | 152.5 | 0.0 | 352.0 | 4921.8 | 123.8 |
| STD | | 115.1 | 0.0 | 124.5 | 0.0 | 142.8 | 1663.3 | 39.9 |
| Group 9 | | | | | | | | |
| 33 (4.1) | NA | NA | NA | NA | NA | NA | NA | NA |
| 34 (4.2) | yes | 724 | 0 | 125 | 0 | 540 | 3780 | 45 |
| 35 (4.3) | yes | 758 | 0 | 117 | 0 | 429 | 3315 | 39 |
| 36 (4.4) | yes | 808 | 0 | 47 | 0 | 329 | 4089 | 235 |
| Mean | | 763.3 | 0.0 | 96.3 | 0.0 | 432.7 | 3728.0 | 106.3 |
| STD | | 42.3 | 0.0 | 42.9 | 0.0 | 105.5 | 389.6 | 111.5 |

TABLE LI-continued

WT1 Dose Titration Study Clinical Chemistry and Hematology Analysis

| Animal # Normal | mg/dl BUN 13.9–28.3 | mg/dl Creatinine 0.3–1.0 | g/dl T. protein 4.0–8.6 | g/dl Albumin 2.5–4.8 | g/dl Globulin 1.5–3.8 | mg/dl T. Bilirubin 0.10–0.90 |
|---|---|---|---|---|---|---|
| Group 1 | | | | | | |
| 1 (0) | NA | NA | NA | NA | NA | NA |
| 2 (0) | 28 | 0.5 | 4.9 | 3.7 | 1.2 | 0.3 |
| 3 (0) | 25 | 0.5 | 4.9 | 3.8 | 1.1 | 0.2 |
| 4 (0) | 27 | 0.5 | 4.7 | 3.7 | 1 | 0.2 |
| Mean | 26.7 | 0.5 | 4.8 | 3.7 | 1.1 | 0.2 |
| STD | 1.5 | 0.0 | 0.1 | 0.1 | 0.1 | 0.1 |
| Group 2 | | | | | | |
| 5 (1.5) | 34 | 0.5 | 4.6 | 3.6 | 1 | 0.2 |
| 6 (1.6) | 31 | 0.4 | 4.6 | 3.3 | 1.3 | 0.2 |
| 7 (1.7) | 34 | 0.6 | 4.9 | 4 | 0.9 | 0.3 |
| 8 (1.8) | NA | NA | NA | NA | NA | NA |
| Mean | 33.0 | 0.5 | 4.7 | 3.6 | 1.1 | 0.2 |
| STD | 1.7 | 0.1 | 0.2 | 0.4 | 0.2 | 0.1 |
| Group 3 | | | | | | |
| 9 (2.5) | NA | NA | NA | NA | NA | NA |
| 10 (2.6) | 33 | 0.5 | 4.6 | 3.6 | 1 | 0.3 |
| 11 (2.7) | NA | NA | NA | NA | NA | NA |
| 12 (2.8) | 31 | 0.5 | 4.8 | 3.7 | 1.1 | 0.2 |
| Mean | 32.0 | 0.5 | 4.7 | 3.7 | 1.1 | 0.3 |
| STD | 1.4 | 0.0 | 0.1 | 0.1 | 0.1 | 0.1 |
| Group 4 | | | | | | |
| 13 (3.5) | 32 | 0.7 | 4.6 | 3.4 | 1.2 | 0.2 |
| 14 (3.6) | 34 | 0.4 | 4.8 | 3.8 | 1 | 0.2 |
| 15 (3.7) | 30 | 0.4 | 4.7 | 3.4 | 1.3 | 0.2 |
| 16 (3.8) | 24 | 0.3 | 5.1 | 3.8 | 1.3 | 0.2 |
| Mean | 30.0 | 0.5 | 4.8 | 3.6 | 1.2 | 0.2 |
| STD | 4.3 | 0.2 | 0.2 | 0.2 | 0.1 | 0.0 |
| Group 5 | | | | | | |
| 17 (4.5) | 22 | 0.4 | 4.6 | 3.3 | 1.3 | 0.2 |
| 18 (4.6) | 31 | 0.5 | 4.9 | 3.7 | 1.2 | 0.2 |
| 19 (4.7) | 23 | 0.6 | 4.8 | 3.6 | 1.2 | 0.2 |
| 20 (4.8) | 28 | 0.5 | 4.5 | 3.4 | 1.1 | 0.2 |
| Mean | 26.0 | 0.5 | 4.7 | 3.5 | 1.2 | 0.2 |
| STD | 4.2 | 0.1 | 0.2 | 0.2 | 0.1 | 0.0 |
| Group 6 | | | | | | |
| 21 (1.1) | 28 | 0.3 | 5.1 | 3.4 | 1.7 | 0.2 |
| 22 (1.2) | 36 | 0.3 | 5.1 | 3.8 | 1.3 | 0.2 |
| 23 (1.3) | 32 | 0.4 | 4.9 | 3.5 | 1.4 | 0.1 |
| 24 (1.4) | NA | NA | NA | NA | NA | NA |
| Mean | 32.0 | 0.3 | 5.0 | 3.6 | 1.5 | 0.2 |
| STD | 4.0 | 0.1 | 0.1 | 0.2 | 0.2 | 0.1 |
| Group 7 | | | | | | |
| 25 (2.1) | 32 | 0.2 | 5 | 3.4 | 1.6 | 0.2 |
| 26 (2.2) | 24 | 0.3 | 4.2 | 2.8 | 1.4 | 0.1 |
| 27 (2.3) | 28 | 0.3 | 4.8 | 3.2 | 1.6 | 0.2 |
| 28 (2.4) | 27 | 0.3 | 5 | 3.4 | 1.6 | 0.1 |
| Mean | 27.8 | 0.3 | 4.8 | 3.2 | 1.6 | 0.2 |
| STD | 3.3 | 0.0 | 0.4 | 0.3 | 0.1 | 0.1 |
| Group 8 | | | | | | |
| 29 (3.1) | 32 | 0.3 | 4.9 | 3.3 | 1.6 | 0.2 |
| 30 (3.2) | NA | NA | NA | NA | NA | NA |
| 31 (3.3) | 18 | 0.3 | 4.8 | 3.1 | 1.7 | 0.2 |
| 32 (3.4) | 26 | 0.2 | 4.2 | 2.9 | 1.3 | 0 |
| Mean | 25.3 | 0.3 | 4.6 | 3.1 | 1.5 | 0.1 |
| STD | 7.0 | 0.1 | 0.4 | 0.2 | 0.2 | 0.1 |
| Group 9 | | | | | | |
| 33 (4.1) | 25 | 0.2 | 4.1 | 2.7 | 1.4 | 0.3 |
| 34 (4.2) | NA | NA | NA | NA | NA | NA |
| 35 (4.3) | 23 | 0.2 | 4.7 | 3.1 | 1.6 | 0.2 |
| 36 (4.4) | 29 | 0.3 | 4.7 | 3.2 | 1.5 | 0.3 |

TABLE LI-continued

WT1 Dose Titration Study Clinical Chemistry and Hematology Analysis

| Mean | 25.7 | 0.2 | 4.5 | 3.0 | 1.5 | 0.3 |
| --- | --- | --- | --- | --- | --- | --- |
| STD | 3.1 | 0.1 | 0.3 | 0.3 | 0.1 | 0.1 |

Abbreviations: WBC: white blood cells; RBC: red blood cells; Hg.: hemoglobin; HCT: hematocrit; MCV: Mean corpuscular volume; MCH: mean corpuscular hemoglobin; MCHC: mean corpuscular hemoglobin concentration; Plt.: platelets; Abs.: Absolute; Baso: basophils; Eos: eosinophils; Abs. Bands: immature neutrophils; Polys: polymorphonuclear cells; Lymph: lymphocytes; Mono: monocytes; BUN: blood urea nitrogen Example 14

Elicitation of Human WT1-specific T-cell Responses by Whole Gene in vitro Priming This example demonstrates that WT1 specific T-cell responses can be generated from the blood of normal individuals.

Figure 23:
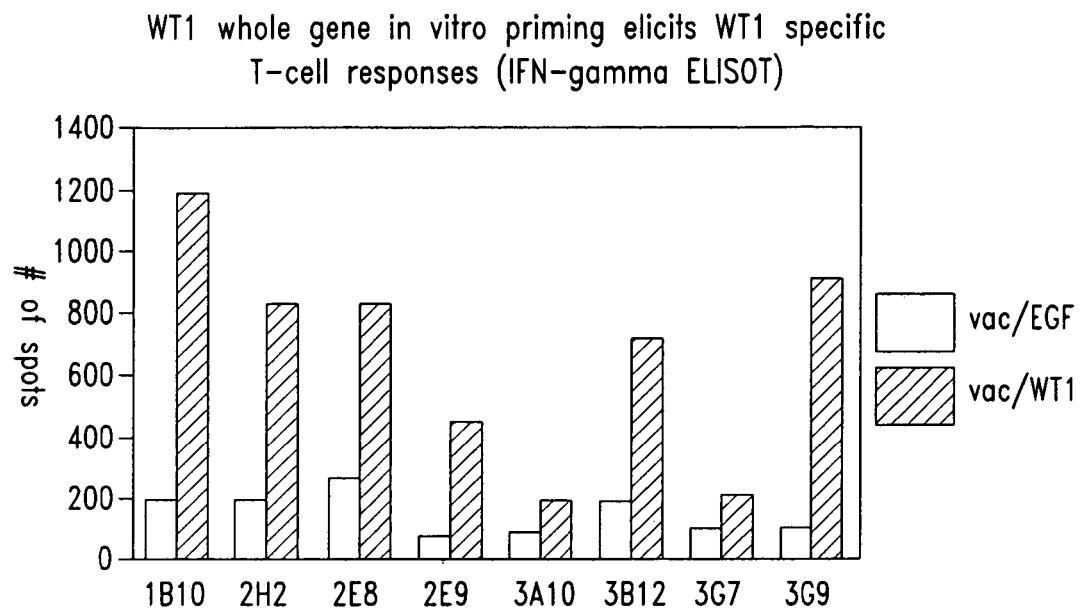
FIG. 23 is a graph of an IFN-gamma ELISPOT assay showing that WT1 whole gene in vitro priming elicits WT1 specific T-cell responses.

Dendritic cells (DC) were differentiated from monocyte cultures derived from PBMC of normal donors by growth for 4–10 days in RPMI medium containing 10% human serum, 50 ng/ml GMCSF and 30 ng/ml IL-4. Following culture, DC were infected 16 hours with recombinant WT1-expressing vaccinia virus at an M.O.I. of 5, or for 3 days with recombinant WT1-expressing adenovirus at an M.O.I. of 10 (FIGS. 21 and 22). Vaccinia virus was inactivated by U.V. irradiation. CD8+ T-cells were isolated by positive selection using magnetic beads, and priming cultures were initiated in 96-well plates. Cultures were restimulated every 7–10 days using autologous dendritic cells adeno or vaccinia infected to express WT1. Following 3–6 stimulation cycles, CD8+ lines could be identified that specifically produced interferon-gamma when stimulated with autologous-WT1-expressing dendritic cells or fibroblasts. The WT1-specific activity of these lines could be maintained following additional stimulation cycles. These lines were demonstrated to specifically recognize adeno or vaccinia WT1 infected autologous dendritic cells but not adeno or vaccinia EGFP-infected autologous dendritic cells by Elispot assays (FIG. 23).

Example 15

Formulation of RA12-WT1 For Injection: Use of Excipients to Stabilize Lyophilized Product This example describes the formulation that allows the complete solubilization of lyophilized Ra12-WT1.

The following formulation allowed for the recombinant protein Ra12-WT1 to be dissolved into an aqueous medium after being lyophilized to dryness:

Recombinant Ra12-WT1 concentration: 0.5–1.0 mg/ml; Buffer: 10–20 mM Ethanolamine, pH 10.0; 1.0–5.0 mM Cysteine; 0.05% Tween-80 (Polysorbate-80); Sugar: 10% Trehalose (T5251, Sigma, Mo.) 10% Maltose (M9171, Sigma, Mo.) 10% Sucrose (S7903, Sigma, MO) 10% Fructose (F2543, Sigma, MO) 10% Glucose (G7528, Sigma, MO).

The lyophilized protein with the sugar excipient was found to dissolve significantly more than without the sugar excipient. Analysis by coomassie stained SDS-PAGE showed no signs of remaining solids in the dissolved material.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed:

1. A polypeptide consisting of the amino acid sequence of SEQ ID NO:335.

2. A composition comprising the polypeptide of claim 1 in combination with a pharmaceutically acceptable carrier or excipient.

3. A composition comprising the polypeptide of claim 1 in combination with a non-specific immune response enhancer.

4. The composition according to claim 3 wherein the non-specific immune response enhancer preferentially enhances a T cell response in a patient.

5. The composition according to claim 3, wherein the immune response enhancer comprises a microsphere.

* * * * *

UNITED STATES PATENT AND TRADEMARK OFFICE
CERTIFICATE OF CORRECTION

PATENT NO.       : 7,144,581 B2
APPLICATION NO.  : 09/785019
DATED            : December 5, 2006
INVENTOR(S)      : Alexander Gaiger et al.

It is certified that error appears in the above-identified patent and that said Letters Patent is hereby corrected as shown below:

Column 1
Line 4, "This invention was made in part with government support under NIH SBIR Phase I grant number IR43 CA81752-01A1. The Government may have certain rights in this invention" should read --This invention was made with U.S. government support under Grant Numbers IR43 CA81752-01A1 and NIH/NCI R37CA30558 awarded by the National Institutes of Health. The U.S. government has certain rights in this invention--.

Signed and Sealed this

Sixteenth Day of November, 2010

David J. Kappos
*Director of the United States Patent and Trademark Office*